(12) United States Patent
Cho et al.

(10) Patent No.: US 11,634,414 B2
(45) Date of Patent: *Apr. 25, 2023

(54) HETEROCYCLIC COMPOUND AND ORGANIC LIGHT-EMITTING ELEMENT INCLUDING SAME

(71) Applicant: LG CHEM, LTD., Seoul (KR)

(72) Inventors: Seongmi Cho, Daejeon (KR); Wanpyo Hong, Daejeon (KR); Dong Hoon Lee, Daejeon (KR); Jungoh Huh, Daejeon (KR); Min Woo Jung, Daejeon (KR); Jungha Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 508 days.

This patent is subject to a terminal disclaimer.

(21) Appl. No.: 16/633,538

(22) PCT Filed: Aug. 2, 2018

(86) PCT No.: PCT/KR2018/008771
§ 371 (c)(1),
(2) Date: Jan. 23, 2020

(87) PCT Pub. No.: WO2019/027263
PCT Pub. Date: Feb. 7, 2019

(65) Prior Publication Data
US 2020/0190070 A1  Jun. 18, 2020

(30) Foreign Application Priority Data

Aug. 2, 2017 (KR) .................. 10-2017-0098081
Aug. 1, 2018 (KR) .................. 10-2018-0089915

(51) Int. Cl.
| | | |
|---|---|---|
| *C07D 311/96* | (2006.01) | |
| *C07D 335/04* | (2006.01) | |
| *C07D 407/14* | (2006.01) | |
| *C07D 409/14* | (2006.01) | |
| *H01L 51/00* | (2006.01) | |
| *C07D 491/048* | (2006.01) | |
| *C07D 487/04* | (2006.01) | |
| *C07D 495/04* | (2006.01) | |
| *H01L 51/50* | (2006.01) | |

(52) U.S. Cl.
CPC ......... *C07D 407/14* (2013.01); *C07D 409/14* (2013.01); *C07D 487/04* (2013.01); *C07D 491/048* (2013.01); *C07D 495/04* (2013.01); *H01L 51/0067* (2013.01); *H01L 51/0072* (2013.01); *H01L 51/0073* (2013.01); *H01L 51/0074* (2013.01); *H01L 51/5072* (2013.01); *H01L 51/5092* (2013.01); *H01L 51/5096* (2013.01)

(58) Field of Classification Search
CPC .. C07D 311/96; C07D 335/04; C07D 407/14; C07D 409/14; C07D 487/04; C07D 491/048; C07D 495/04; H01L 51/0067; H01L 51/0072; H01L 51/0073; H01L 51/0074; H01L 51/5072; H01L 51/5092; H01L 51/5096; H01L 51/5012; H01L 51/5016

See application file for complete search history.

(56) References Cited

U.S. PATENT DOCUMENTS

| | | | |
|---|---|---|---|
| 9,722,187 B2 | 8/2017 | Jeong et al. | |
| 10,505,128 B2 | 12/2019 | Chung et al. | |
| 2009/0153031 A1 | 6/2009 | Kai et al. | |
| 2016/0118599 A1 | 4/2016 | Jeong et al. | |
| 2017/0213988 A1 | 7/2017 | Park et al. | |
| 2017/0222157 A1 | 8/2017 | Jatsch et al. | |
| 2018/0337341 A1 | 11/2018 | Heo et al. | |

(Continued)

FOREIGN PATENT DOCUMENTS

| | | |
|---|---|---|
| CN | 101233127 A | 7/2008 |
| CN | 101440082 | 5/2009 |

(Continued)

OTHER PUBLICATIONS

English translation of the description of WIPO Publication WO-2019027189-A1. (Year: 2022).*

(Continued)

*Primary Examiner* — Joseph R Kosack
*Assistant Examiner* — Sagar Patel
(74) *Attorney, Agent, or Firm* — Dentons US LLP

(57) ABSTRACT

Provided is a hetero-cyclic compound of Chemical Formula 1:

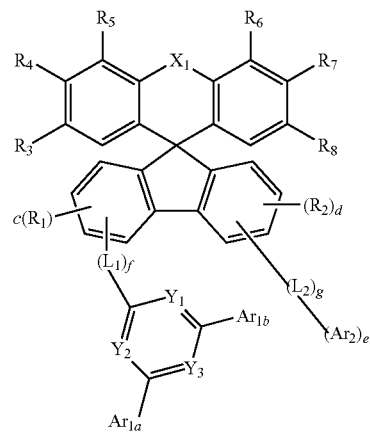

and an organic light emitting device comprising the same.

9 Claims, 2 Drawing Sheets

(56) References Cited

U.S. PATENT DOCUMENTS

2019/0386227 A1* 12/2019 Lee .................... H01L 51/0071
2020/0227646 A1* 7/2020 Jung .................... C07D 335/04
2021/0336155 A1* 10/2021 Huh .................... H01L 51/0058

FOREIGN PATENT DOCUMENTS

| CN | 103435597 | 12/2013 | | |
|---|---|---|---|---|
| CN | 106536485 | 3/2017 | | |
| KR | 10-20140009019 | 1/2014 | | |
| KR | 10-20140103393 | 8/2014 | | |
| KR | 10-20150034612 | 4/2015 | | |
| KR | 10-1593368 | 2/2016 | | |
| KR | 10-20160016050 | 2/2016 | | |
| KR | 10-20160047670 | 5/2016 | | |
| KR | 10-2016-0102949 | 8/2016 | | |
| KR | 10-20170032414 | 3/2017 | | |
| KR | 101755986 | 7/2017 | | |
| KR | 10-20180046150 | 5/2018 | | |
| WO | 2016001097 | 1/2016 | | |
| WO | 2016-023458 | 2/2016 | | |
| WO | 2017-018795 A2 | 2/2017 | | |
| WO | 2017116625 | 7/2017 | | |
| WO | WO-2019027189 A1 * | 2/2019 | ............. | H01L 51/00 |
| WO | WO-2019190248 A1 * | 10/2019 | ........... | C07D 209/82 |

OTHER PUBLICATIONS

English translation of the description of WIPO Publication WO-2019190248-A1. (Year: 2022).*
Liu et al., "Progress of blue light-emitting organic electroluminescet materials containing 1,3,4-oxadiazole ring and related devices," [J].Chemical Industry and Engineering Progrep, 25(8):895— (2006). Abstract only.

* cited by examiner

【FIG. 1】
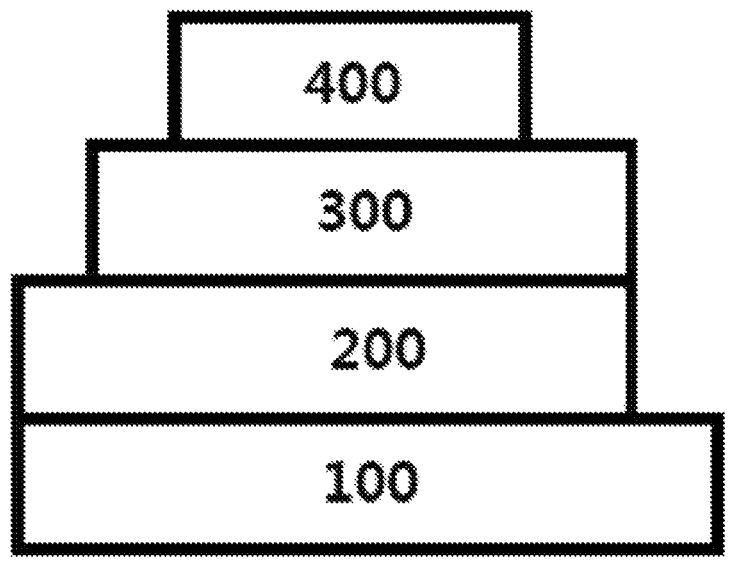
【FIG. 2】
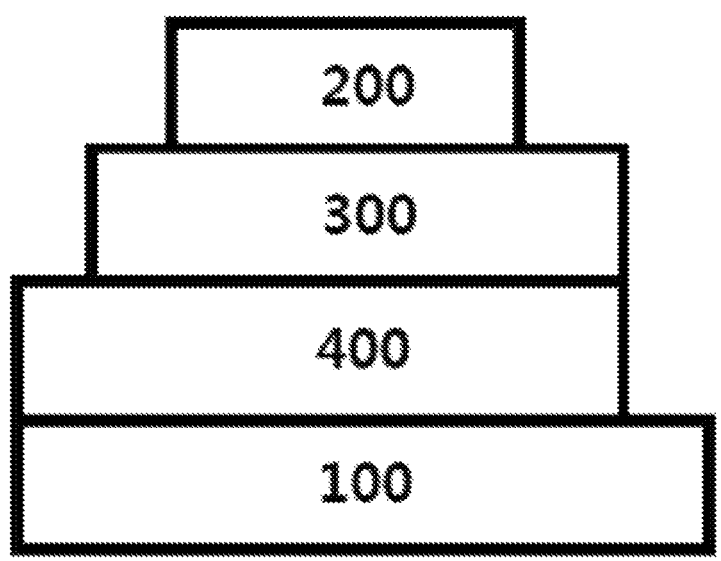

[FIG. 3]
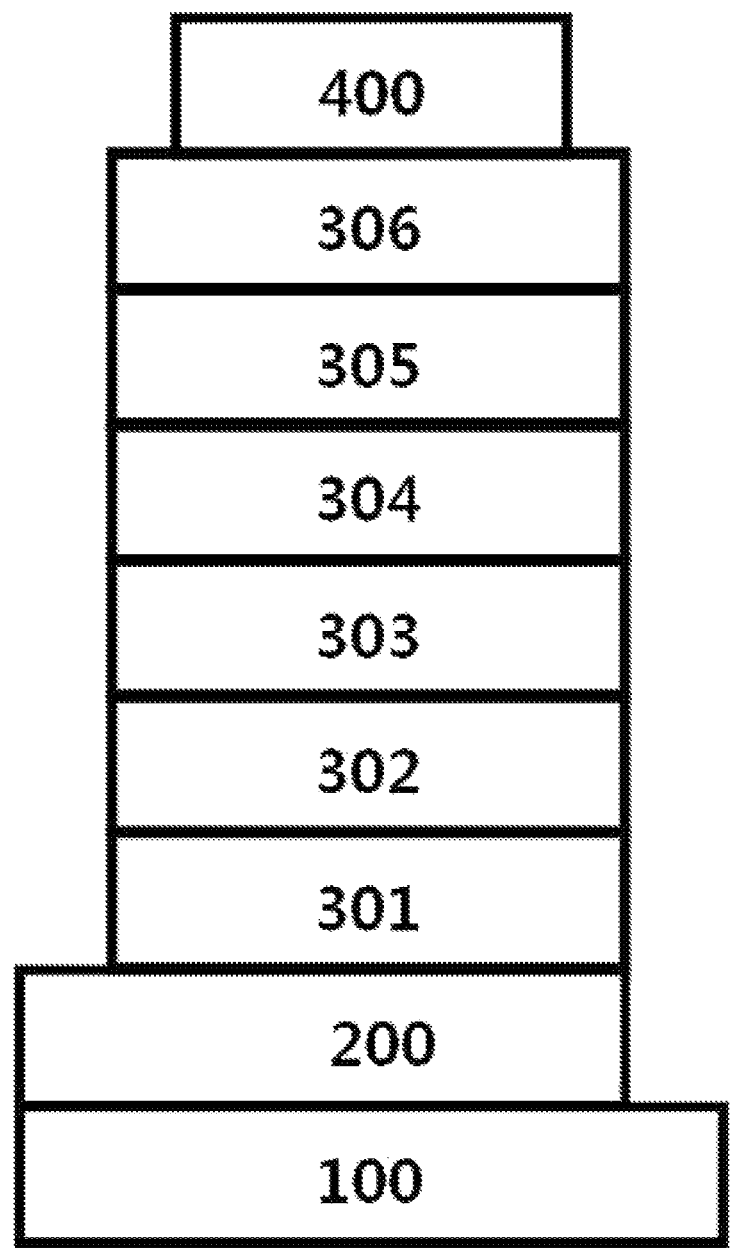

HETEROCYCLIC COMPOUND AND ORGANIC LIGHT-EMITTING ELEMENT INCLUDING SAME

CROSS-REFERENCE TO RELATED APPLICATIONS

This application is a National Stage Application of International Application No. PCT/KR2018/008771 filed on Aug. 2, 2018, which claims priority to and the benefits of Korean Patent Application No. 10-2017-0098081, filed with the Korean Intellectual Property Office on Aug. 2, 2017, and Korean Patent Application No. 10-2018-0089915, filed with the Korean Intellectual Property Office on Aug. 1, 2018, the entire contents of which are incorporated herein by reference.

TECHNICAL FIELD

The present application relates to a hetero-cyclic compound and an organic light emitting device comprising the same.

BACKGROUND

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film can be formed in a single layer or a multilayer as necessary.

A material of the organic thin film can have a light emitting function as necessary. For example, as a material of the organic thin film, compounds capable of forming a light emitting layer themselves alone can be used, or compounds capable of performing a role of a host or a dopant of a host-dopant-based light emitting layer can also be used. In addition thereto, compounds capable of performing roles of hole injection, hole transfer, electron blocking, hole blocking, electron transfer, electron injection and the like can also be used as a material of the organic thin film.

Development of an organic thin film material has been continuously required for enhancing performance, lifetime or efficiency of an organic light emitting device.

BRIEF DESCRIPTION

Technical Problem

Researches for an organic light emitting device comprising a compound capable of satisfying conditions required for materials usable in an organic light emitting device, for example, a proper energy level, electrochemical stability, thermal stability and the like, and having a chemical structure that can perform various roles required in an organic light emitting device depending on substituents have been required.

The present specification is directed to providing a hetero-cyclic compound and an organic light emitting device comprising the same.

Technical Solution

One embodiment of the present specification provides a hetero-cyclic compound of the following Chemical Formula 1:

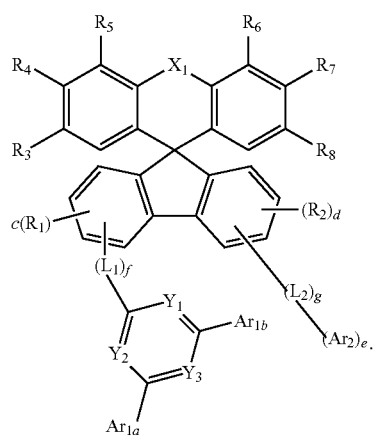

Chemical Formula 1

In Chemical Formula 1:

$X_1$ is O or S;

$L_1$ and $L_2$ are the same as or different from each other, and each independently is a direct bond; a substituted or unsubstituted $C_6$ to $C_{60}$ arylene group; or a substituted or unsubstituted $C_2$ to $C_{60}$ heteroarylene group;

two or more of $Y_1$ to $Y_3$ are N, and the rest is $CR_9$;

$Ar_{1a}$ and $Ar_{1b}$ are the same as or different from each other, and each independently is a substituted or unsubstituted $C_6$ to $C_{60}$ aryl group or a substituted or unsubstituted $C_2$ to $C_{60}$ heteroaryl group;

$Ar_2$ is the following Chemical Formula 2 or 3:

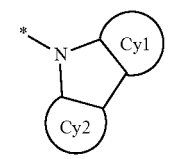

Chemical Formula 2

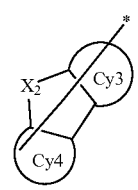

Chemical Formula 3

Cy1 to Cy4 are the same as or different from each other, and each independently is a substituted or unsubstituted $C_6$ to $C_{60}$ aromatic hydrocarbon ring; or a substituted or unsubstituted $C_2$ to $C_{60}$ aromatic heterorring;

$X_2$ is O, S, $NR_{10}$ or $CR_{11}R_{12}$;

$R_1$ to $R_8$ and $R_{10}$ to $R_{12}$ are the same as or different from each other, and each independently is hydrogen, deuterium, a halogen group, a cyano group, a nitro group, an amino group, a substituted or unsubstituted $C_1$ to $C_{60}$ alkyl group, a substituted or unsubstituted $C_1$ to $C_{60}$ haloalkyl group, a substituted or unsubstituted $C_1$ to $C_{60}$ alkoxy group, a substituted or unsubstituted $C_1$ to $C_{60}$ haloalkoxy group, a substituted or unsubstituted $C_3$ to $C_{60}$ cycloalkyl group, a substituted or unsubstituted $C_2$ to $C_{60}$ alkenyl group, a substituted or unsubstituted $C_6$ to $C_{60}$ aryl group, a substituted or unsubstituted $C_6$ to $C_{60}$ aryloxy group, or a substituted or unsubstituted $C_2$ to $C_{60}$ heteroaryl group;

$R_9$ is hydrogen or deuterium;

\* is a site bonding to $L_2$ of Chemical Formula 1;

c and d are each an integer of 0 to 3;

e is an integer of 1 or 2;

f and g are each an integer of 1 to 3;

when c is 2 or greater, $R_1$s are the same as or different from each other;

when d is 2 or greater, $R_2$s are the same as or different from each other;

when e is 2, $Ar_2$s are the same as or different from each other;

when f is 2 or greater, $L_1$s are the same as or different from each other; and when g is 2 or greater, $L_2$s are the same as or different from each other.

Another embodiment of the present specification provides an organic light emitting device comprising an anode, a cathode, and one or more organic material layers provided between the anode and the cathode, wherein one or more layers of the organic material layers comprise the hetero-cyclic compound described above.

Advantageous Effects

A hetero-cyclic compound according to one embodiment of the present specification can be used as a material of an organic material layer of an organic light emitting device. The hetero-cyclic compound can be used as a material of a light emitting layer, an electron transfer layer, an electron injection layer or the like in an organic light emitting device. Particularly, the hetero-cyclic compound of Chemical Formula 1 can be used as a material of an electron transfer layer or a light emitting layer in an organic light emitting device.

In addition, using the hetero-cyclic compound of Chemical Formula 1 in an organic light emitting device lowers a driving voltage of the device, enhances light efficiency, and can enhance lifetime properties of the device by thermal stability of the compound.

DESCRIPTION OF DRAWINGS

FIG. 1 to FIG. 3 are diagrams each schematically illustrating a lamination structure of an organic light emitting device according to one embodiment of the present specification.

REFERENCE NUMERALS

100: Substrate
200: Anode
300: Organic Material Layer
301: Hole Injection Layer
302: Hole Transfer Layer
303: Light Emitting Layer
304: Hole Blocking Layer
305: Electron Transfer Layer
306: Electron Injection Layer
400: Cathode

DETAILED DESCRIPTION

Hereinafter, the present specification will be described in detail.

One embodiment of the present specification provides a hetero-cyclic compound of Chemical Formula 1.

According to one embodiment of the present specification, the hetero-cyclic compound of Chemical Formula 1 can exhibit long lifetime and high efficiency properties by having a core structure as above. In addition, long lifetime and high efficiency properties can be obtained by the N-containing monocyclic ring and the substituent of $Ar_2$ substituting a benzene ring that is not adjacent to $X_1$ of the core structure, compared to when the N-containing monocyclic ring and the substituent $Ar_2$ substituting a benzene ring adjacent to $X_1$ of the core structure.

The hetero-cyclic compound according to one embodiment of the present specification is a compound of Chemical Formula 1. More specifically, the hetero-cyclic compound of Chemical Formula 1 is capable of being used as a material of an organic material layer of an organic light emitting device with such a core structure and structural characteristics of the substituents described above.

Examples of the substituents in the present specification will be described below, however, the substituents are not limited thereto.

In the present specification, "substituted or unsubstituted" means being substituted with one or more substituents selected from the group consisting of deuterium, a halogen group, a cyano group, a $C_1$ to $C_{60}$ alkyl group, a $C_2$ to $C_{60}$ alkenyl group, a $C_2$ to $C_{60}$ alkynyl group, a $C_3$ to $C_{60}$ cycloalkyl group, a $C_2$ to $C_{60}$ heterocycloalkyl group, a $C_6$ to $C_{60}$ aryl group, a $C_2$ to $C_{60}$ heteroaryl group, a $C_1$ to $C_{20}$ alkylamine group, a $C_6$ to $C_{60}$ arylamine group, and a $C_2$ to $C_{60}$ heteroarylamine group, or being unsubstituted, or being substituted with a substituent bonding two or more of the above-mentioned substituents, or being substituted, or being substituted with a substituent linking two or more substituents selected from among the above-mentioned substituents, or being unsubstituted. For example, "a substituent linking two or more substituents" can comprise a biphenyl group. In other words, a biphenyl group can be an aryl group, or can be interpreted as a substituent linking two phenyl groups. The additional substituents can be further substituted.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents can be the same as or different from each other.

In the present specification, the halogen group can be fluorine, chlorine, bromine or iodine.

In the present specification, the alkyl group comprises linear or branched having 1 to 60 carbon atoms, and can be further substituted with other substituents. The number of carbon atoms of the alkyl group can be from 1 to 60, specifically from 1 to 40 and more specifically from 1 to 6. Specific examples thereof can comprise a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group and the like, but are not limited thereto.

In the present specification, the alkenyl group comprises linear or branched having 2 to 60 carbon atoms, and can be further substituted with other substituents. The number of carbon atoms of the alkenyl group can be from 2 to 60, specifically from 2 to 40 and more specifically from 2 to 20. Specific examples thereof can comprise a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl) vinyl-1-yl group, a 2,2-bis(diphenyl-1-yl)vinyl-1-yl group, a stilbenyl group, a styrenyl group and the like, but are not limited thereto.

In the present specification, the cycloalkyl group comprises monocyclic or multicyclic having 3 to 60 carbon atoms, and can be further substituted with other substituents. Herein, the multicyclic means a group in which the cycloalkyl group is directly linked to or fused with other cyclic groups. Herein, the other cyclic groups can be a cycloalkyl group, but can also be different types of cyclic groups such as a heterocycloalkyl group, an aryl group and a heteroaryl group. The number of carbon groups of the cycloalkyl group can be from 3 to 60, specifically from 3 to 40 and more specifically from 5 to 20. Specific examples thereof can comprise a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the aryl group comprises monocyclic or multicyclic having 6 to 60 carbon atoms, and can be further substituted with other substituents. Herein, the multicyclic means a group in which the aryl group is directly linked to or fused with other cyclic groups. Herein, the other cyclic groups can be an aryl group, but can also be different types of cyclic groups such as a cycloalkyl group, a heterocycloalkyl group and a heteroaryl group. The aryl group comprises a spiro group. The number of carbon atoms of the aryl group can be from 6 to 60, specifically from 6 to 40 and more specifically from 6 to 25. Specific examples of the aryl group can comprise a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the heteroaryl group comprises O, S, Se, N or Si as a heteroatom, comprises monocyclic or multicyclic having 2 to 60 carbon atoms, and can be further substituted with other substituents. Herein, the multicyclic means a group in which the heteroaryl group is directly linked to or fused with other cyclic groups. Herein, the other cyclic groups can be a heteroaryl group, but can also be different types of cyclic groups such as a cycloalkyl group, a heterocycloalkyl group and an aryl group. The number of carbon atoms of the heteroaryl group can be from 2 to 60, specifically from 2 to 40 and more specifically from 3 to 25. Specific examples of the heteroaryl group can comprise a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a quinozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b] carbazolyl group, an indolinyl group, a 10,11-dihydrodibenzo[b,f]azepine group, a 9,10-dihydroacridinyl group, a phenanthrazinyl group, a phenothia-thiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl, a pyrazolo[1,5-c]-quinazolinyl group, a pyrido[1,2-b]indazolyl group, a pyrido-[1,2-a]imidazo[1,2-e]indolinyl group, a 5,11-dihydroindeno[1,2-b]carbazolyl group and the like, but are not limited thereto.

In the present specification, the amine group can be selected from the group consisting of a monoalkylamine group; a monoarylamine group; a monoheteroarylamine group; —NH$_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group can comprise a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. Descriptions on the aryl group provided above can be applied thereto except for each being a divalent.

In the present specification, the heteroarylene group means the heteroaryl group having two bonding sites, that is, a divalent group. Descriptions on the heteroaryl group provided above can be applied thereto except for each being a divalent.

In the present specification, the aromatic hydrocarbon ring means an aromatic ring comprising carbon.

In the present specification, the aromatic heteroring means an aromatic ring comprising one or more of heteroatoms.

According to one embodiment of the present specification, Chemical Formula 2 can be any one of the following structural formulae:

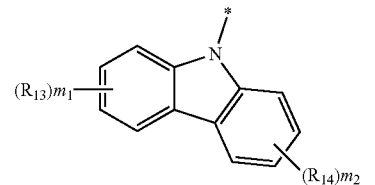

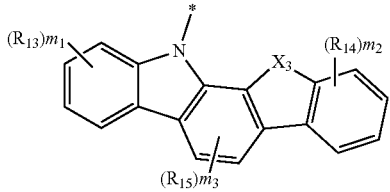

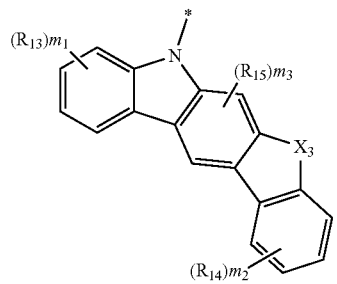

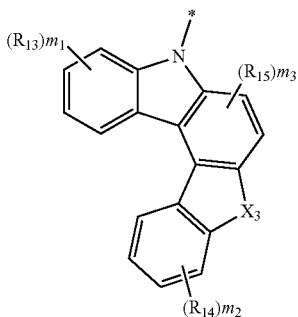

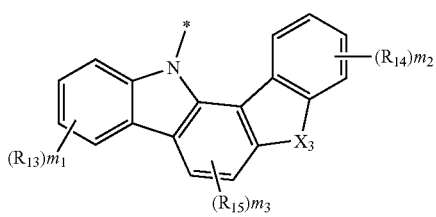

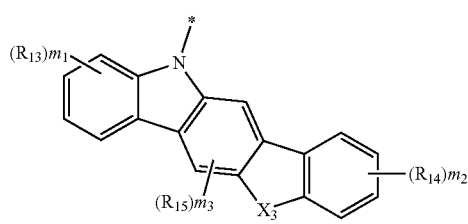

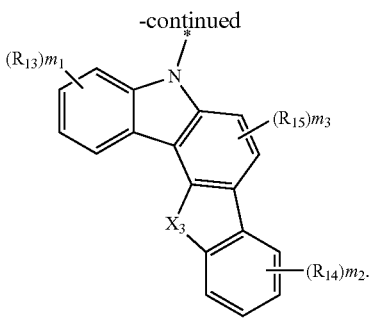

In the structural formulae:

$X_3$ is O, S, $NR_{16}$ or $CR_{17}R_{18}$;

* is a site bonding to $L_2$ of Chemical Formula 1;

$R_{13}$ to $R_{18}$ are the same as or different from each other, and each independently is hydrogen, deuterium, a halogen group, a cyano group, a nitro group, an amino group, a substituted or unsubstituted $C_1$ to $C_{60}$ alkyl group, a substituted or unsubstituted $C_1$ to $C_{60}$ haloalkyl group, a substituted or unsubstituted $C_1$ to $C_{60}$ alkoxy group, a substituted or unsubstituted $C_1$ to $C_{60}$ haloalkoxy group, a substituted or unsubstituted $C_3$ to $C_{60}$ cycloalkyl group, a substituted or unsubstituted $C_2$ to $C_{60}$ alkenyl group, a substituted or unsubstituted $C_6$ to $C_{60}$ aryl group, a substituted or unsubstituted $C_6$ to $C_{60}$ aryloxy group, or a substituted or unsubstituted $C_2$ to $C_{60}$ heteroaryl group;

m1 and m2 are each an integer of 0 to 4;

m3 is an integer of 0 to 2;

when m1 is 2 or greater, the $R_{13}$s are the same as or different from each other;

when m2 is 2 or greater, the $R_{14}$s are the same as or different from each other; and when m3 is 2, the $R_{15}$s are the same as or different from each other.

According to one embodiment of the present specification, Chemical Formula 3 can be any one of the following structural formulae:

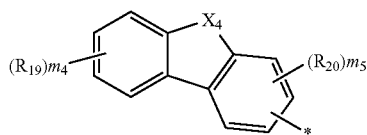

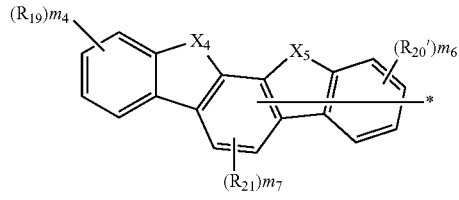

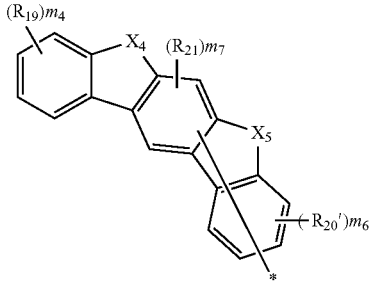

-continued

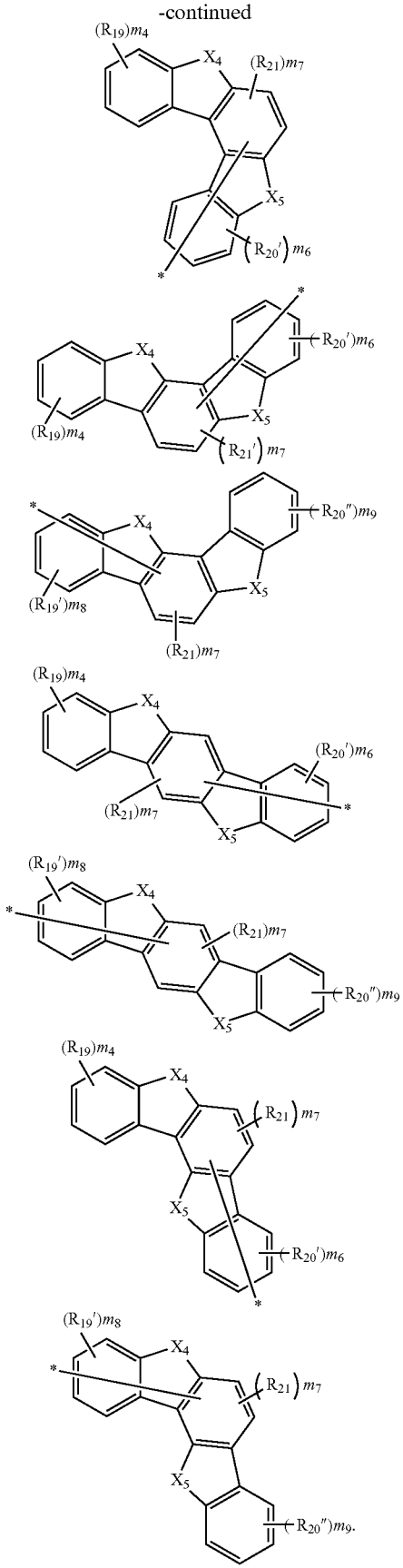

In the structural formulae:

* is a site bonding to $L_2$ of Chemical Formula 1;

$X_4$ and $X_5$ are the same as or different from each other, and each independently is O, S, $NR_{22}$ or $CR_{23}R_{24}$;

$R_{19}$ to $R_{24}$, $R_{19}'$, $R_{20}'$ and $R_{20}''$ are the same as or different from each other, and each independently is hydrogen, deuterium, a halogen group, a cyano group, a nitro group, an amino group, a substituted or unsubstituted $C_1$ to $C_{60}$ alkyl group, a substituted or unsubstituted $C_1$ to $C_{60}$ haloalkyl group, a substituted or unsubstituted $C_1$ to $C_{60}$ alkoxy group, a substituted or unsubstituted $C_1$ to $C_{60}$ haloalkoxy group, a substituted or unsubstituted $C_3$ to $C_{60}$ cycloalkyl group, a substituted or unsubstituted $C_2$ to $C_{60}$ alkenyl group, a substituted or unsubstituted $C_6$ to $C_{60}$ aryl group, a substituted or unsubstituted $C_6$ to $C_{60}$ aryloxy group, or a substituted or unsubstituted $C_2$ to $C_{60}$ heteroaryl group; m4, m6, m8 and m9 are each an integer of 0 to 4;

m5 is an integer of 0 to 3;

m7 is an integer of 0 to 2;

when m4 is 2 or greater, the $R_{19}$s are the same as or different from each other;

when m5 is 2 or greater, the $R_{20}$s are the same as or different from each other;

when m6 is 2 or greater, the $R_{20}'$s are the same as or different from each other;

when m7 is 2, the $R_{21}$s are the same as or different from each other;

when m8 is 2 or greater, the $R_{19}'$s are the same as or different from each other;

when m9 is 2 or greater, the $R_{20}''$s are the same as or different from each other;

m6+m7≤5, and m7+m8≤5.

According to one embodiment of the present specification, Chemical Formula 1 can be any one of the following Chemical Formulae 4 to 11:

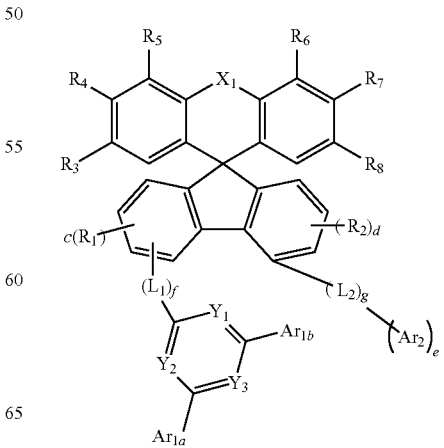

Chemical Formula 4

Chemical Formula 5
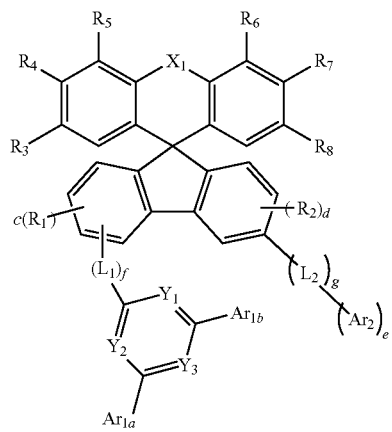
Chemical Formula 6
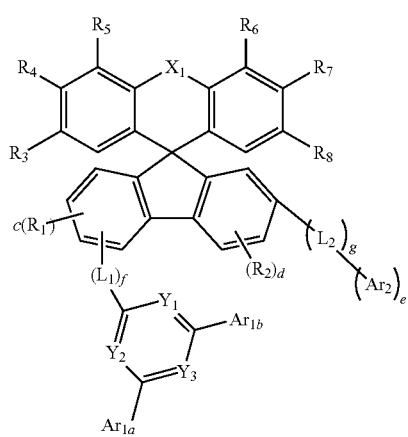
Chemical Formula 7
Chemical Formula 8
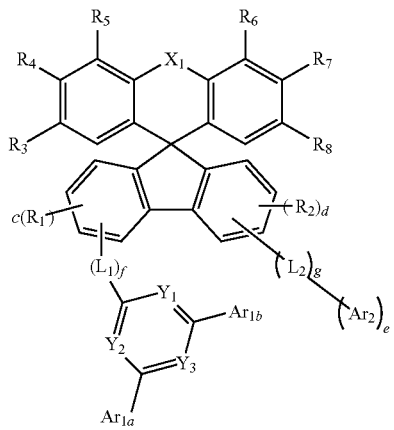
Chemical Formula 9
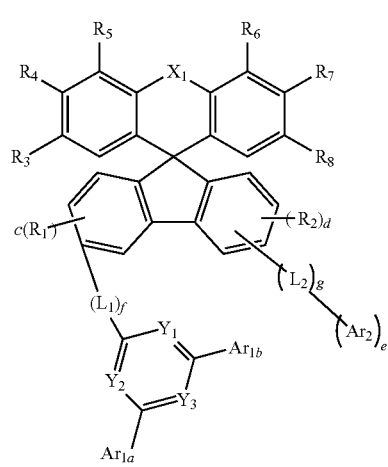
Chemical Formula 10
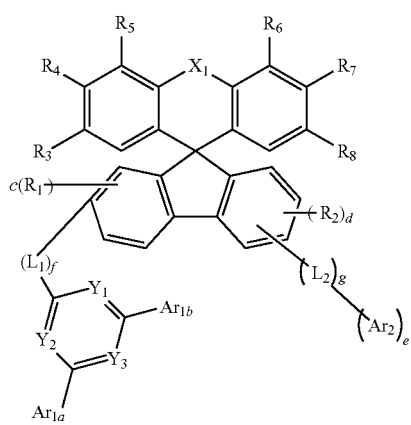

Chemical Formula 11

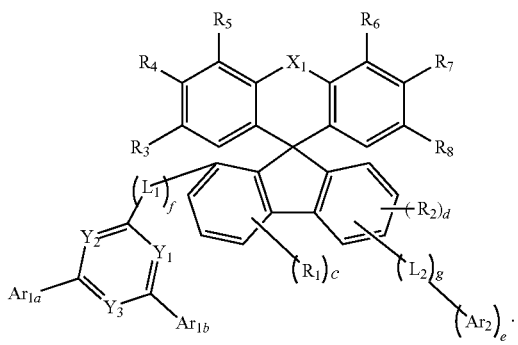

In Chemical Formulae 4 to 11:

$R_1$ to $R_8$, $L_1$, $L_2$, $Ar_{1a}$, $Ar_{1b}$, $Ar_2$, $X_1$, $Y_1$ to $Y_3$ and c to g have the same definitions as in Chemical Formula 1.

In the present specification, substituents of the above-described structural formulae can be more specifically described as follows.

According to one embodiment of the present specification, in Chemical Formula 1, $X_1$ is O or S.

According to another embodiment of the present specification, in Chemical Formula 1, $X_1$ is O.

According to one embodiment of the present specification, in Chemical Formula 1, $L_1$ and $L_2$ are the same as or different from each other, and each independently is a direct bond, a substituted or unsubstituted $C_6$ to $C_{60}$ arylene group, or a substituted or unsubstituted $C_2$ to $C_{60}$ heteroarylene group.

According to another embodiment of the present specification, in Chemical Formula 1, $L_1$ and $L_2$ are the same as or different from each other, and each independently is a direct bond or a substituted or unsubstituted $C_6$ to $C_{60}$ arylene group.

According to another embodiment of the present specification, in Chemical Formula 1, $L_1$ and $L_2$ are the same as or different from each other, and each independently is a direct bond or a substituted or unsubstituted phenylene group.

According to another embodiment of the present specification, in Chemical Formula 1, $L_1$ and $L_2$ are the same as or different from each other, and each independently is a direct bond or a phenylene group.

According to another embodiment of the present specification, in Chemical Formula 1, $L_1$ is a direct bond.

According to another embodiment of the present specification, in Chemical Formula 1, $L_2$ is a direct bond or a phenylene group.

According to one embodiment of the present specification, in Chemical Formula 1, two or more of $Y_1$ to $Y_3$ are N, and the remaining are $CR_9$.

According to another embodiment of the present specification, in Chemical Formula 1, $Y_1$ and $Y_2$ are N, and $Y_3$ is $CR_9$.

According to another embodiment of the present specification, in Chemical Formula 1, $Y_1$ and $Y_3$ are N, and $Y_2$ is $CR_9$.

According to another embodiment of the present specification, in Chemical Formula 1, $Y_2$ and $Y_3$ are N, and $Y_1$ is $CR_9$.

According to another embodiment of the present specification, in Chemical Formula 1, $Y_1$ to $Y_3$ are N. According to one embodiment of the present specification, in Chemical Formula 1, $Ar_{1a}$ and $Ar_{1b}$ are the same as or different from each other, and each independently is a substituted or unsubstituted $C_6$ to $C_{60}$ aryl group; or a substituted or unsubstituted $C_2$ to $C_{60}$ heteroaryl group.

According to another embodiment of the present specification, in Chemical Formula 1, $Ar_{1a}$ and $Ar_{1b}$ are the same as or different from each other, and each independently is a substituted or unsubstituted $C_6$ to $C_{20}$ aryl group or a substituted or unsubstituted $C_5$ to $C_{30}$ heteroaryl group.

According to another embodiment of the present specification, in Chemical Formula 1, $Ar_{1a}$ and $Ar_{1b}$ are the same as or different from each other, and each independently is a substituted or unsubstituted $C_6$ to $C_{60}$ aryl group.

According to another embodiment of the present specification, in Chemical Formula 1, $Ar_{1a}$ and $Ar_{1b}$ are the same as or different from each other, and each independently is a substituted or unsubstituted $C_6$ to $C_{20}$ aryl group.

According to another embodiment of the present specification, in Chemical Formula 1, $Ar_{1a}$ and $Ar_b$ are the same as or different from each other, and each independently is a substituted or unsubstituted phenyl group, a substituted or unsubstituted biphenyl group, a substituted or unsubstituted terphenyl group, a substituted or unsubstituted naphthalene group, a substituted or unsubstituted anthracene group, a substituted or unsubstituted phenanthrene group, or a substituted or unsubstituted fluorene group.

According to another embodiment of the present specification, in Chemical Formula 1, $Ar_{1a}$ and $Ar_{1b}$ are the same as or different from each other, and each independently is a substituted or unsubstituted phenyl group, a substituted or unsubstituted biphenyl group, or a substituted or unsubstituted naphthalene group.

According to another embodiment of the present specification, in Chemical Formula 1, $Ar_{1a}$ and $Ar_b$ are the same as or different from each other, and each independently is a substituted or unsubstituted phenyl group.

According to another embodiment of the present specification, in Chemical Formula 1, $Ar_{1a}$ and $Ar_{1b}$ are the same as or different from each other, and each independently is a phenyl group that is unsubstituted or substituted with an alkyl group having 2 to 12 carbon atoms.

According to another embodiment of the present specification, in Chemical Formula 1, $Ar_{1a}$ and $Ar_{1b}$ are the same as or different from each other, and each independently is a phenyl group that is unsubstituted or substituted with an alkyl group having 2 to 6 carbon atoms.

According to another embodiment of the present specification, in Chemical Formula 1, $Ar_{1a}$ and $Ar_{1b}$ are the same as or different from each other, and each independently is a phenyl group that is unsubstituted or substituted with a t-butyl group.

According to another embodiment of the present specification, in Chemical Formula 1, $Ar_{1a}$ and $Ar_{1b}$ are the same as or different from each other, and each independently is a phenyl group that is unsubstituted or substituted with a t-butyl group; a biphenyl group; or a naphthalene group.

According to another embodiment of the present specification, in Chemical Formula 1, $Ar_{1a}$ and $Ar_{1b}$ are the same as or different from each other, and each independently is a phenyl group that is unsubstituted or substituted with a t-butyl group or a biphenyl group.

According to one embodiment of the present specification, in Chemical Formulae 2 and 3, Cy1 to Cy4 are the same as or different from each other, and each independently is a substituted or unsubstituted $C_6$ to $C_{60}$ aromatic hydrocarbon ring or a substituted or unsubstituted $C_2$ to $C_{60}$ aromatic heteroring.

According to one embodiment of the present specification, in Chemical Formulae 2 and 3, Cy1 to Cy4 are the same as or different from each other, and each independently is a substituted or unsubstituted $C_6$ to $C_{20}$ aromatic hydrocarbon ring or a substituted or unsubstituted $C_2$ to $C_{20}$ aromatic heteroring.

According to another embodiment of the present specification, in Chemical Formulae 2 and 3, Cy1 to Cy4 are the same as or different from each other, and each independently is a benzene unsubstituted or substituted with one or more substituents selected from the group consisting of a substituted or unsubstituted $C_1$ to $C_{60}$ alkyl group, a substituted or unsubstituted $C_1$ to $C_{60}$ alkoxy group, and a substituted or unsubstituted $C_6$ to $C_{60}$ aryl group; naphthalene unsubstituted or substituted with one or more substituents selected from the group consisting of a substituted or unsubstituted $C_1$ to $C_{60}$ alkyl group, a substituted or unsubstituted $C_1$ to $C_{60}$ alkoxy group, and a substituted or unsubstituted $C_6$ to $C_{60}$ aryl group; fluorene unsubstituted or substituted with one or more substituents selected from the group consisting of a substituted or unsubstituted $C_1$ to $C_{60}$ alkyl group, a substituted or unsubstituted $C_1$ to $C_{60}$ alkoxy group, and a substituted or unsubstituted $C_6$ to $C_{60}$ aryl group; dibenzofuran; dibenzothiophene; or carbazole unsubstituted or substituted with one or more substituents selected from the group consisting of a substituted or unsubstituted $C_1$ to $C_{60}$ alkyl group, a substituted or unsubstituted $C_1$ to $C_{60}$ alkoxy group, and a substituted or unsubstituted $C_6$ to $C_{60}$ aryl group.

According to another embodiment of the present specification, in Chemical Formulae 2 and 3, Cy1 to Cy4 are the same as or different from each other, and each independently is a benzene unsubstituted or substituted with one or more substituents selected from the group consisting of a substituted or unsubstituted $C_1$ to $C_{60}$ alkyl group, a substituted or unsubstituted $C_1$ to $C_{60}$ alkoxy group, and a substituted or unsubstituted $C_6$ to $C_{60}$ aryl group; fluorene unsubstituted or substituted with a substituted or unsubstituted $C_1$ to $C_{60}$ alkyl group; dibenzofuran; dibenzothiophene; or carbazole unsubstituted or substituted with a substituted or unsubstituted $C_6$ to $C_{60}$ aryl group.

According to another embodiment of the present specification, in Chemical Formulae 2 and 3, Cy1 to Cy4 are the same as or different from each other, and each independently is a benzene unsubstituted or substituted with one or more substituents selected from the group consisting of a $C_1$ to $C_{60}$ alkyl group, a $C_1$ to $C_{60}$ alkoxy group, and a $C_6$ to $C_{60}$ aryl group; fluorene unsubstituted or substituted with a $C_1$ to $C_{60}$ alkyl group; dibenzofuran; dibenzothiophene; or carbazole unsubstituted or substituted with a $C_6$ to $C_{60}$ aryl group.

According to another embodiment of the present specification, in Chemical Formulae 2 and 3, Cy1 to Cy4 are the same as or different from each other, and each independently is a benzene unsubstituted or substituted with a methoxy group or a phenyl group; fluorene unsubstituted or substituted with a methyl group; dibenzofuran; dibenzothiophene; or carbazole unsubstituted or substituted with a phenyl group.

According to another embodiment of the present specification, in Chemical Formulae 2 and 3, Cy1 to Cy4 are the same as or different from each other, and each independently is a benzene that is unsubstituted or substituted with a methoxy group or a phenyl group; fluorene substituted with a methyl group; dibenzofuran; dibenzothiophene; or carbazole substituted with a phenyl group.

According to one embodiment of the present specification, in Chemical Formulae 1 to 3, $R_1$ to $R_8$ and $R_{10}$ to $R_{12}$ are the same as or different from each other, and each independently is hydrogen; deuterium; a halogen group; a cyano group; a nitro group; an amino group; a substituted or unsubstituted $C_1$ to $C_{60}$ alkyl group; a substituted or unsubstituted $C_1$ to $C_{60}$ haloalkyl group; a substituted or unsubstituted $C_1$ to $C_{60}$ alkoxy group; a substituted or unsubstituted $C_1$ to $C_{60}$ haloalkoxy group; a substituted or unsubstituted $C_3$ to $C_{60}$ cycloalkyl group; a substituted or unsubstituted $C_2$ to $C_{60}$ alkenyl group; a substituted or unsubstituted $C_6$ to $C_{60}$ aryl group; a substituted or unsubstituted $C_6$ to $C_{60}$ aryloxy group; or a substituted or unsubstituted $C_2$ to $C_{60}$ heteroaryl group comprising one or more heteroatoms selected from the group consisting of N, O and S.

According to another embodiment of the present specification, in Chemical Formulae 1 to 3, $R_1$ to $R_8$ and $R_{10}$ to $R_{12}$ are the same as or different from each other, and each independently is hydrogen, deuterium, a cyano group, a substituted or unsubstituted $C_1$ to $C_{60}$ alkyl group, or a substituted or unsubstituted $C_6$ to $C_{60}$ aryl group.

According to another embodiment of the present specification, in Chemical Formulae 1 to 3, $R_1$ to $R_8$ and $R_{10}$ to $R_{12}$ are the same as or different from each other, and each independently is hydrogen, deuterium, a cyano group, a substituted or unsubstituted methyl group, or a substituted or unsubstituted phenyl group.

According to another embodiment of the present specification, in Chemical Formulae 1 to 3, $R_1$ to $R_8$ are hydrogen or a cyano group.

According to another embodiment of the present specification, in Chemical Formulae 1 to 3, $R_1$ is hydrogen or a cyano group.

According to another embodiment of the present specification, in Chemical Formulae 1 to 3, $R_2$ to $R_8$ are hydrogen.

According to another embodiment of the present specification, $R_9$ is hydrogen.

According to another embodiment of the present specification, in Chemical Formulae 1 to 3, $R_{10}$ is a substituted or unsubstituted $C_6$ to $C_{20}$ aryl group.

According to another embodiment of the present specification, in Chemical Formulae 1 to 3, $R_{10}$ is a substituted or unsubstituted phenyl group.

According to another embodiment of the present specification, in Chemical Formulae 1 to 3, $R_{10}$ is a phenyl group.

According to another embodiment of the present specification, in Chemical Formulae 1 to 3, $R_{11}$ and $R_{12}$ are the same as or different from each other, and each independently is a substituted or unsubstituted $C_1$ to $C_{20}$ alkyl group.

According to another embodiment of the present specification, in Chemical Formulae 1 to 3, $R_{11}$ and $R_{12}$ are the same as or different from each other, and each independently is a substituted or unsubstituted $C_1$ to $C_4$ alkyl group.

According to another embodiment of the present specification, in Chemical Formulae 1 to 3, $R_{11}$ and $R_{12}$ are the same as or different from each other, and each independently is a substituted or unsubstituted methyl group.

According to another embodiment of the present specification, in Chemical Formulae 1 to 3, $R_{11}$ and $R_{12}$ are a methyl group.

According to one embodiment of the present specification, in Chemical Formula 1, c and d are each an integer of 0 to 3.

According to one embodiment of the present specification, in Chemical Formula 1, e is an integer of 1 or 2.

According to another embodiment of the present specification, in Chemical Formula 1, e is 1.

According to another embodiment of the present specification, in Chemical Formula 1, e is 2.

According to another embodiment of the present specification, f and g are each 1 or 2.

According to one embodiment of the present specification, $X_3$ is O.

According to another embodiment of the present specification, $X_3$ is S.

According to another embodiment of the present specification, $X_3$ is $NR_{16}$.

According to another embodiment of the present specification, $X_3$ is $NR_{17}R_{18}$.

According to one embodiment of the present specification, $R_{13}$ to $R_{15}$ are the same as or different from each other, and each independently is hydrogen, a substituted or unsubstituted $C_1$ to $C_{60}$ alkoxy group, or a substituted or unsubstituted $C_6$ to $C_{60}$ aryl group.

According to one embodiment of the present specification, $R_{13}$ to $R_{15}$ are the same as or different from each other, and each independently is hydrogen, a substituted or unsubstituted methoxy group, or a substituted or unsubstituted phenyl group.

According to one embodiment of the present specification, $R_{13}$ to $R_{15}$ are hydrogen, a methoxy group, or a phenyl group.

According to one embodiment of the present specification, $R_{16}$ is a substituted or unsubstituted $C_6$ to $C_{60}$ aryl group.

According to one embodiment of the present specification, $R_{16}$ is a substituted or unsubstituted $C_6$ to $C_{20}$ aryl group.

According to one embodiment of the present specification, $R_{16}$ is a substituted or unsubstituted phenyl group.

According to one embodiment of the present specification, $R_{16}$ is a phenyl group.

According to one embodiment of the present specification, $R_{17}$ and $R_{18}$ are the same as or different from each other, and each independently is a substituted or unsubstituted $C_1$ to $C_{60}$ alkyl group.

According to one embodiment of the present specification, $R_{17}$ and $R_{18}$ are the same as or different from each other, and each independently is a substituted or unsubstituted $C_1$ to $C_{20}$ alkyl group.

According to one embodiment of the present specification, $R_{17}$ and $R_{18}$ are the same as or different from each other, and each independently is a substituted or unsubstituted $C_1$ to $C_4$ alkyl group.

According to one embodiment of the present specification, $R_{17}$ and $R_{18}$ are the same as or different from each other, and each independently is a substituted or unsubstituted methyl group.

According to one embodiment of the present specification, $R_{17}$ and $R_{18}$ are a methyl group.

According to one embodiment of the present specification, $R_{19}$ to $R_{21}$, $R_{19}'$, $R_{20}'$ and $R_{20}''$ are the same as or different from each other, and each independently is hydrogen, a substituted or unsubstituted $C_1$ to $C_{60}$ alkoxy group, or a substituted or unsubstituted $C_6$ to $C_{60}$ aryl group.

According to one embodiment of the present specification, $R_{19}$ to $R_{21}$, $R_{19}'$, $R_{20}'$ and $R_{20}''$ are the same as or different from each other, and each independently is hydrogen, a substituted or unsubstituted methoxy group, or a substituted or unsubstituted phenyl group.

According to one embodiment of the present specification, $R_{19}$ to $R_{21}$, $R_{19}'$, $R_{20}'$ and $R_{20}''$ are the same as or different from each other, and each independently is hydrogen, a methoxy group, or a phenyl group.

According to one embodiment of the present specification, $R_{22}$ is a substituted or unsubstituted $C_6$ to $C_{60}$ aryl group.

According to one embodiment of the present specification, $R_{22}$ is a substituted or unsubstituted $C_6$ to $C_{20}$ aryl group.

According to one embodiment of the present specification, $R_{22}$ is a substituted or unsubstituted phenyl group.

According to one embodiment of the present specification, $R_{22}$ is a phenyl group.

According to one embodiment of the present specification, $R_{23}$ and $R_{24}$ are the same as or different from each other, and each independently is a substituted or unsubstituted $C_1$ to $C_{60}$ alkyl group.

According to one embodiment of the present specification, $R_{23}$ and $R_{24}$ are the same as or different from each other, and each independently is a substituted or unsubstituted $C_1$ to $C_{20}$ alkyl group.

According to one embodiment of the present specification, $R_{23}$ and $R_{24}$ are the same as or different from each other, and each independently is a substituted or unsubstituted $C_1$ to $C_4$ alkyl group.

According to one embodiment of the present specification, $R_{23}$ and $R_{24}$ are the same as or different from each other, and each independently is a substituted or unsubstituted methyl group.

According to one embodiment of the present specification, $R_{23}$ and $R_{24}$ are a methyl group.

According to one embodiment of the present application, Chemical Formula 1 can be any one of the following compounds, but is not limited thereto:

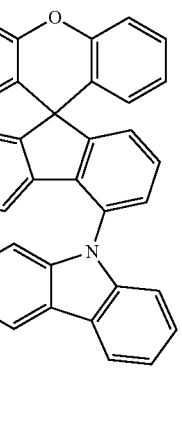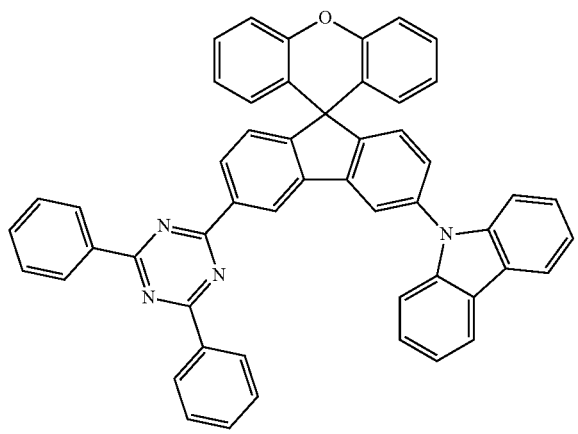

-continued
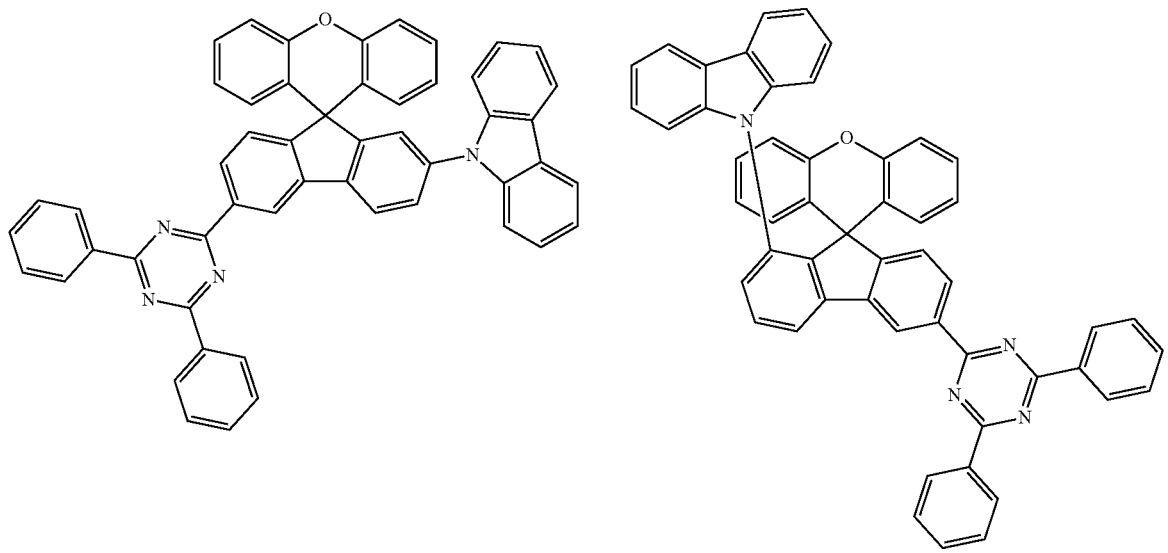
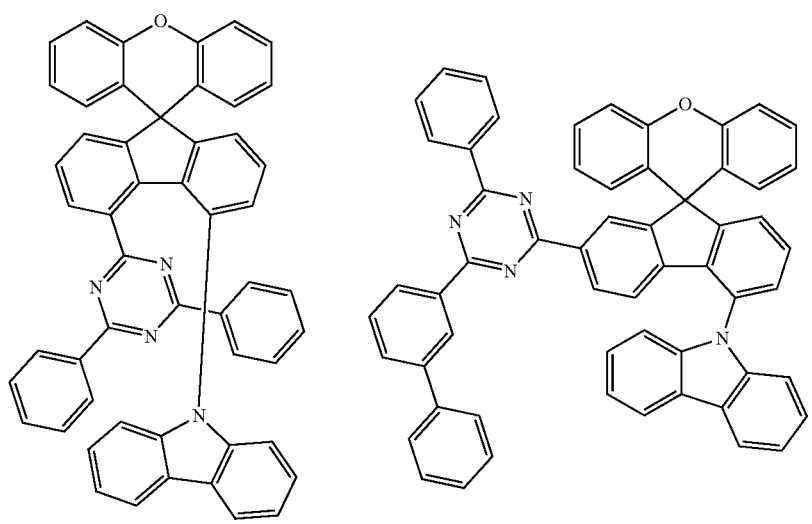
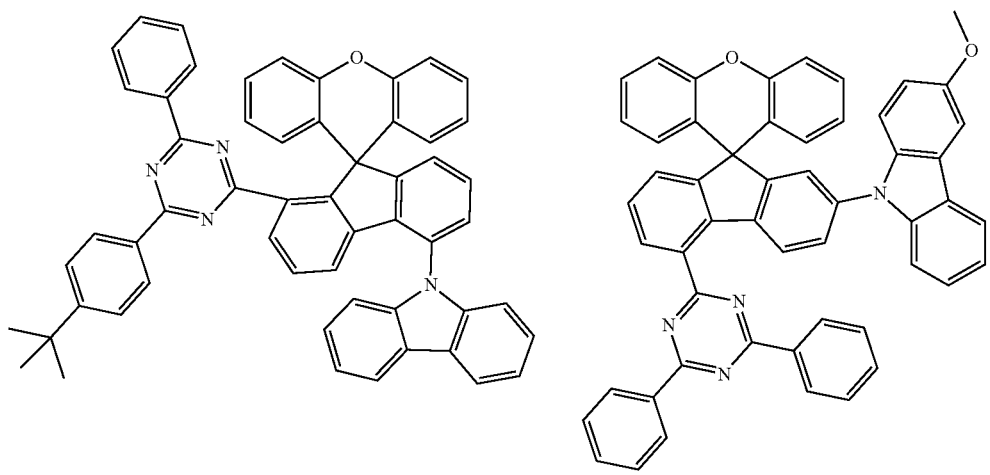

21
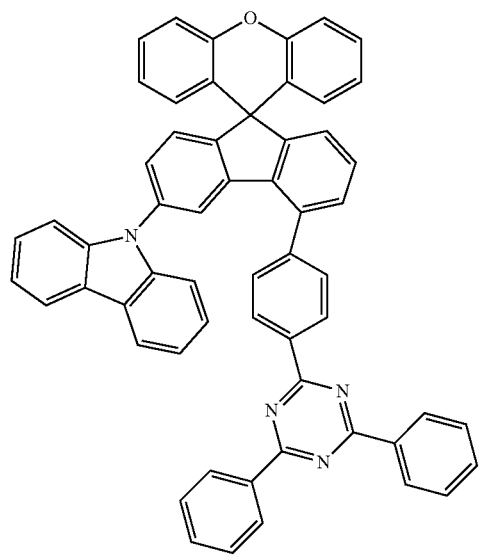
22
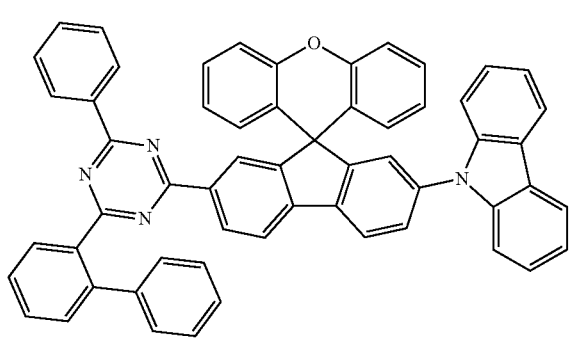
-continued
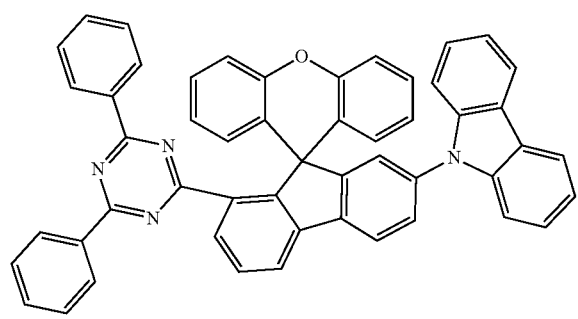
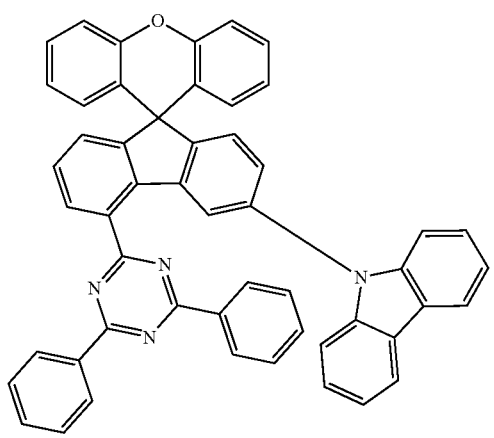
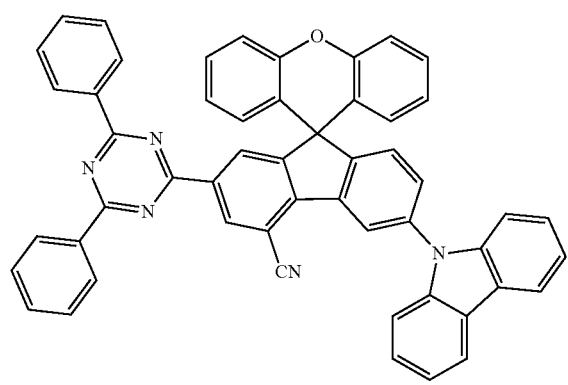
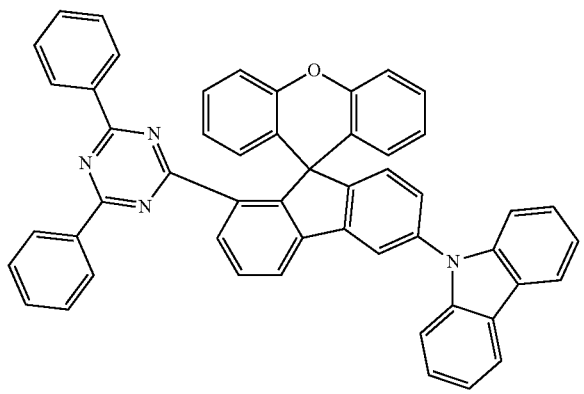

-continued
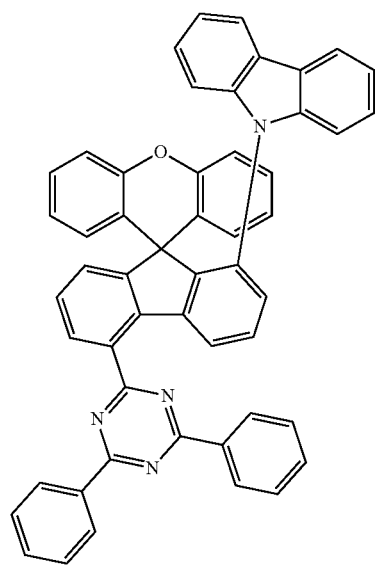
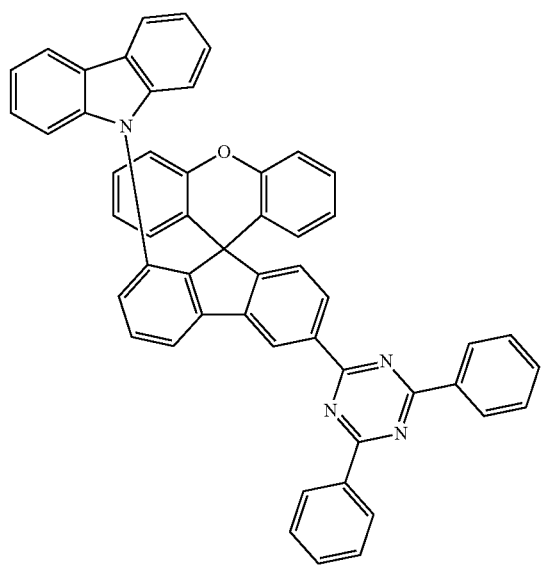
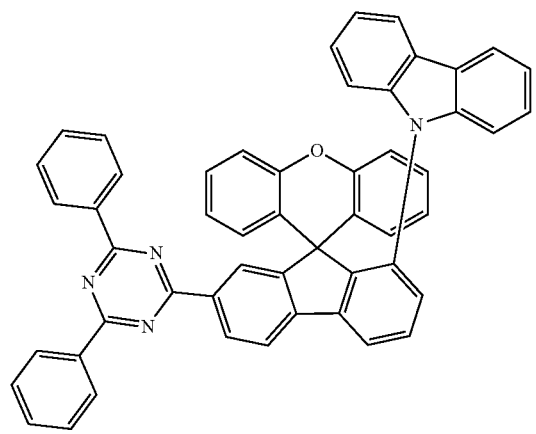
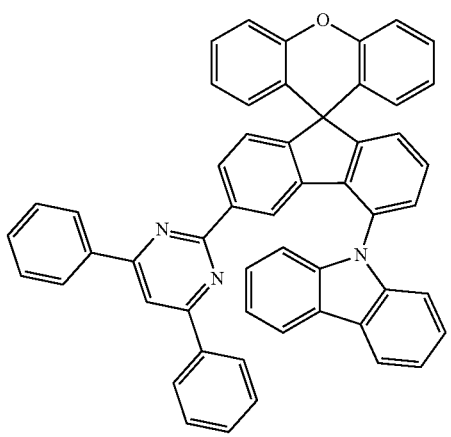
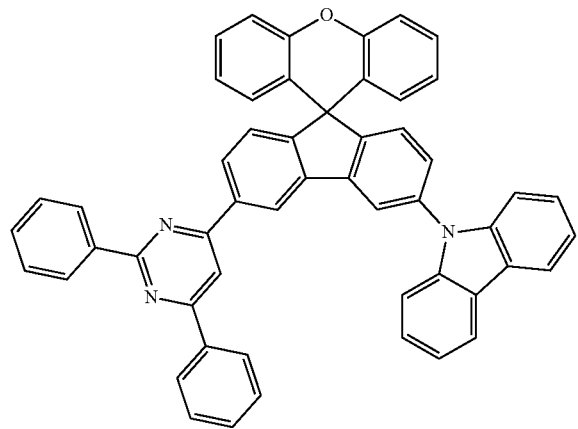
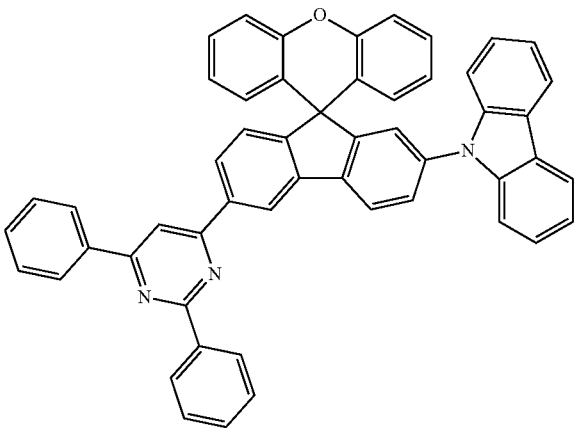

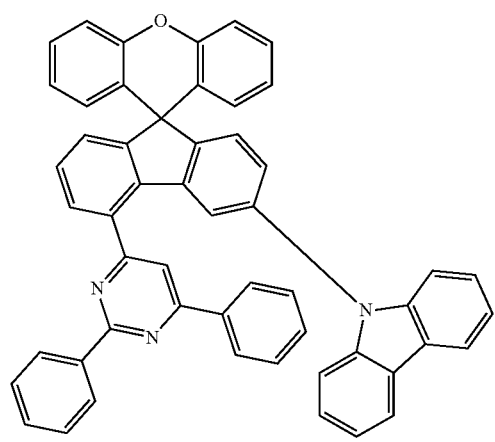
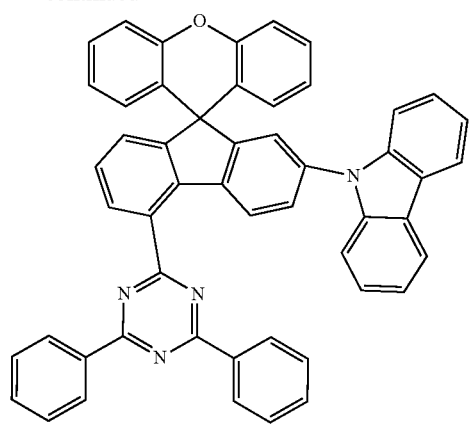
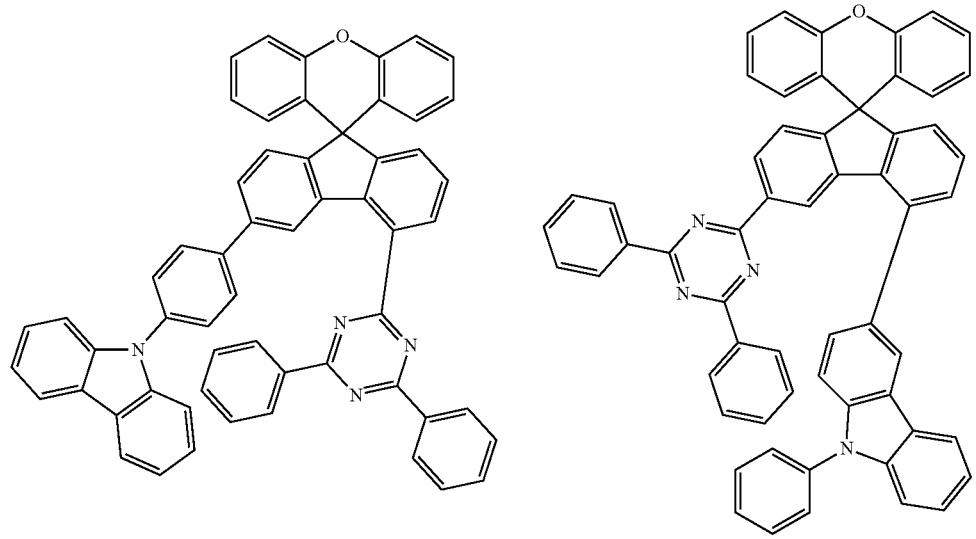
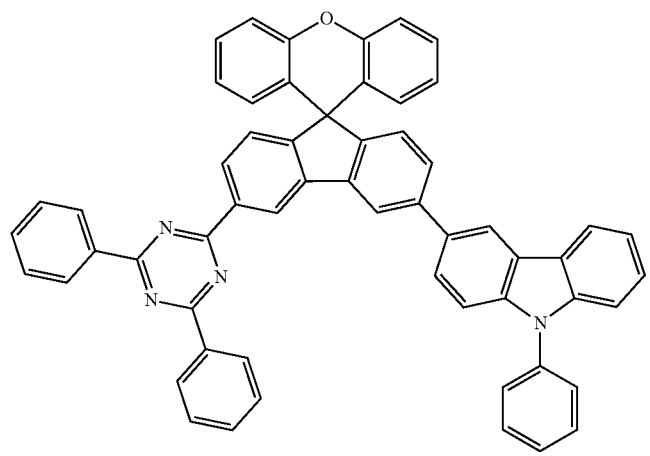

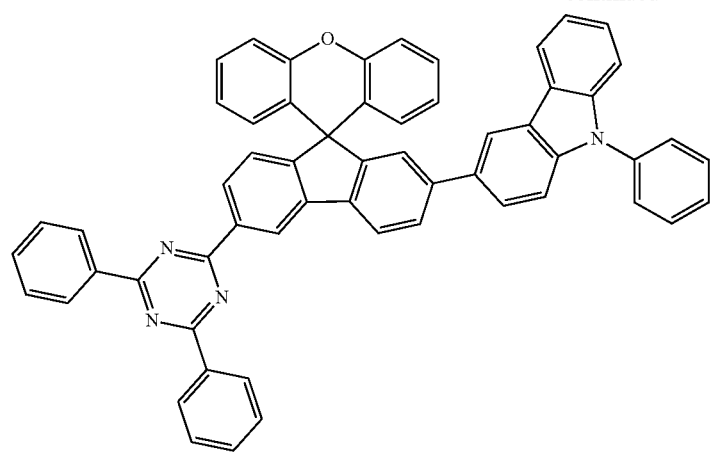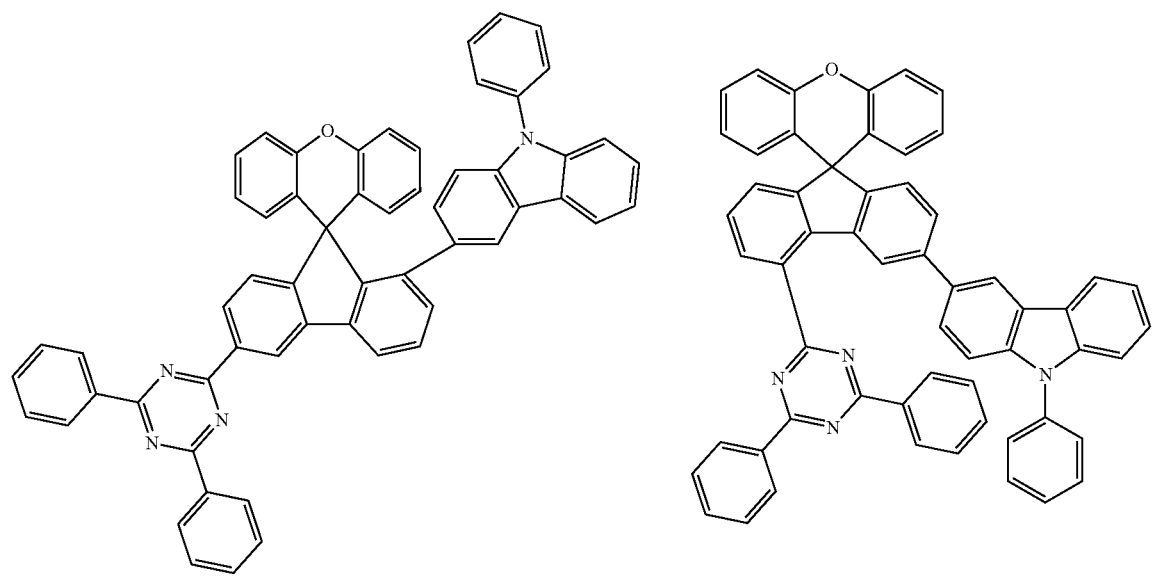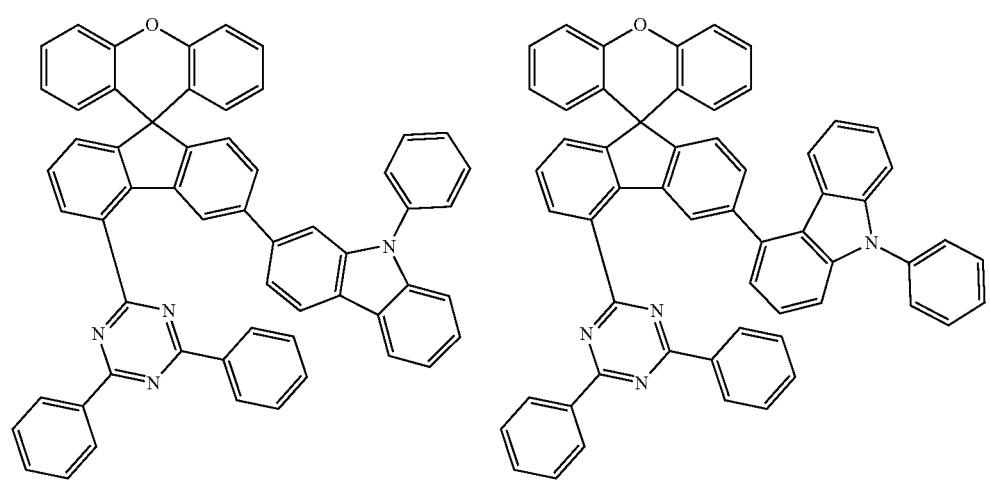

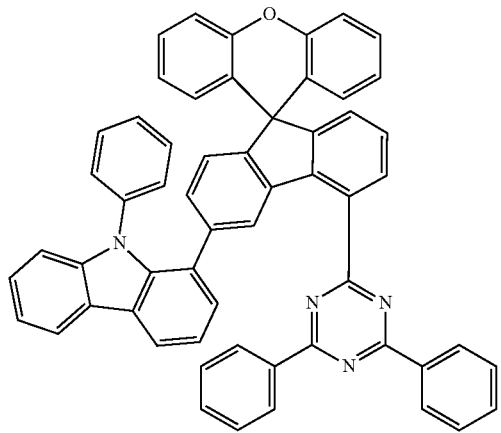
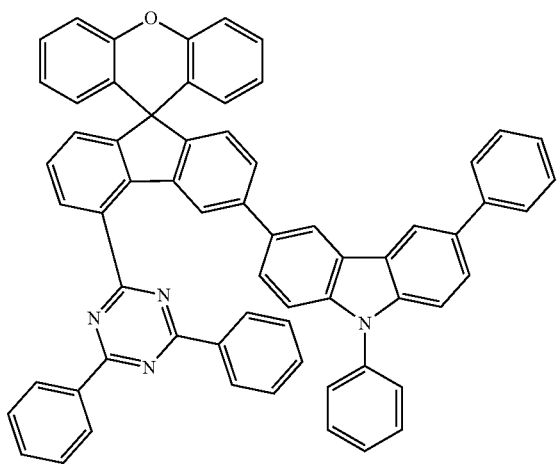
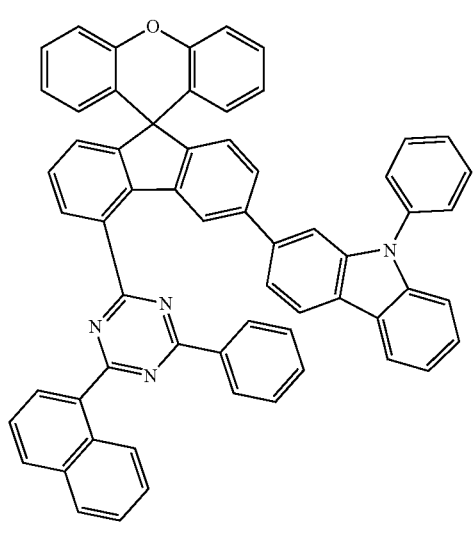
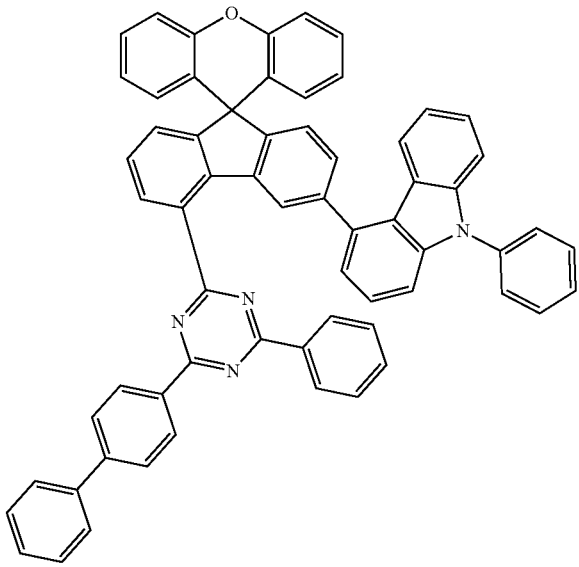
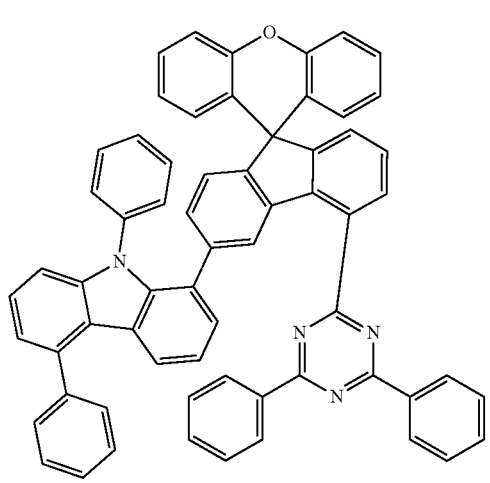
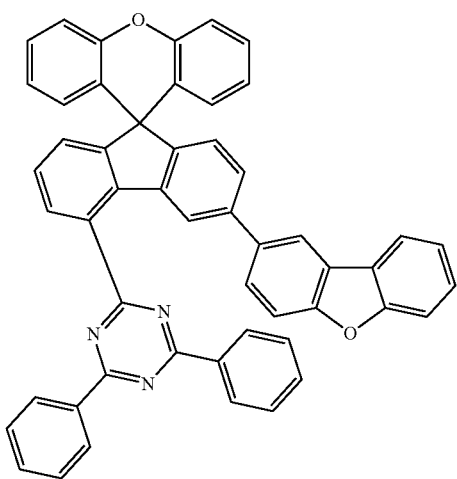

31
32
-continued
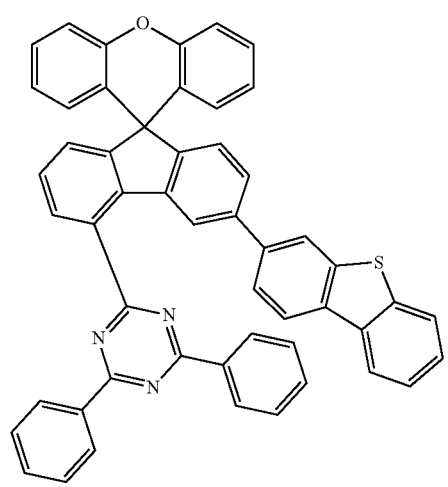
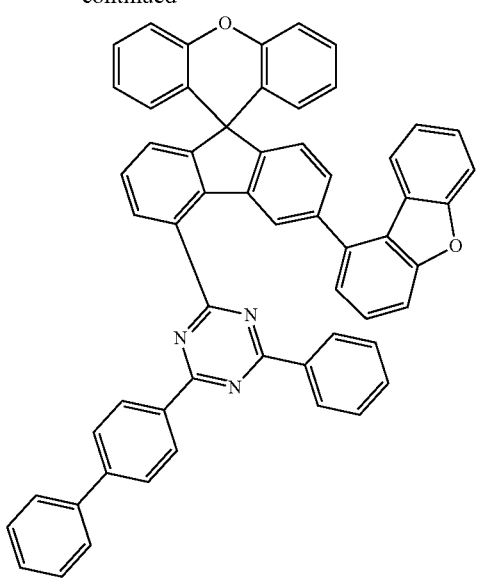
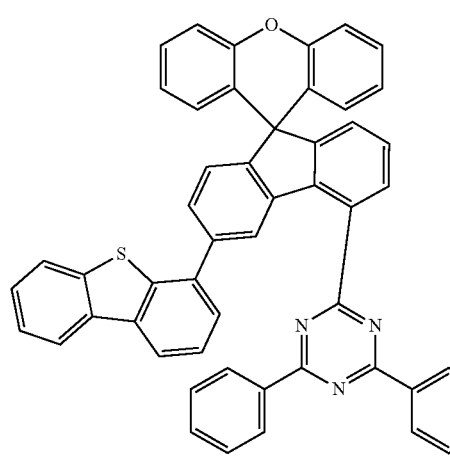
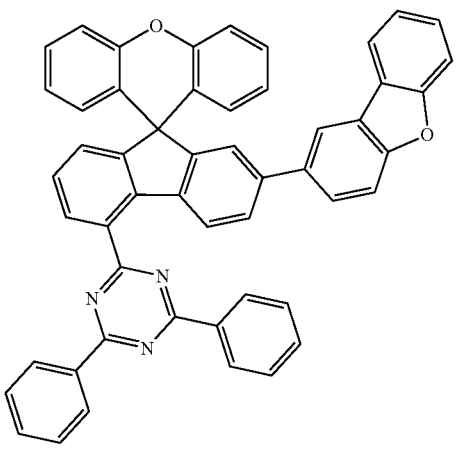
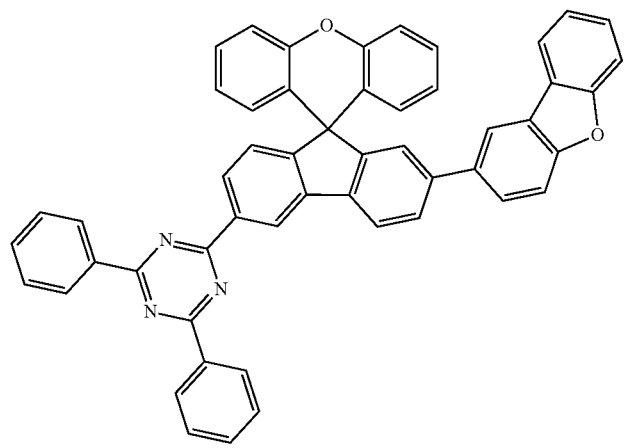

-continued
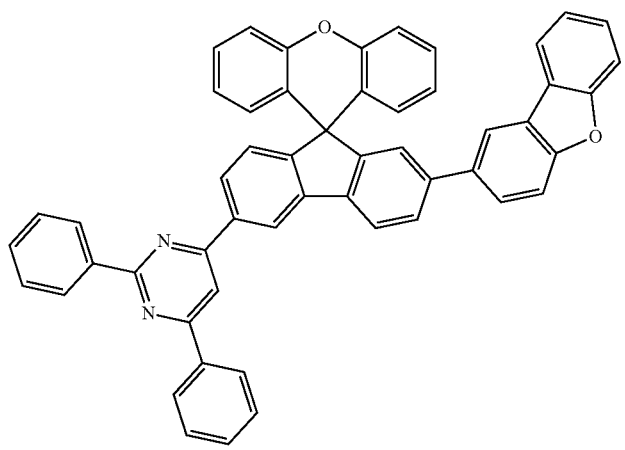
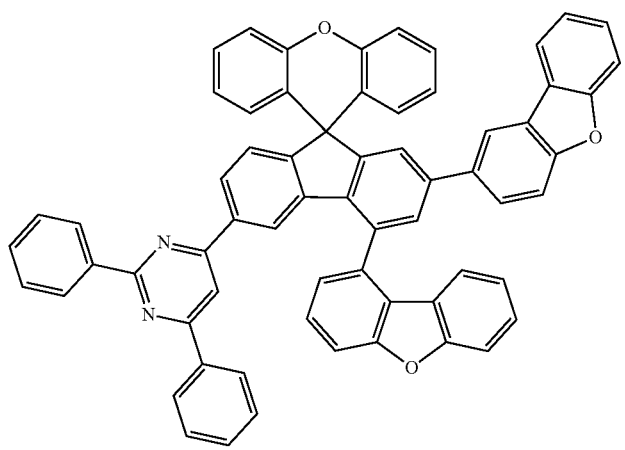
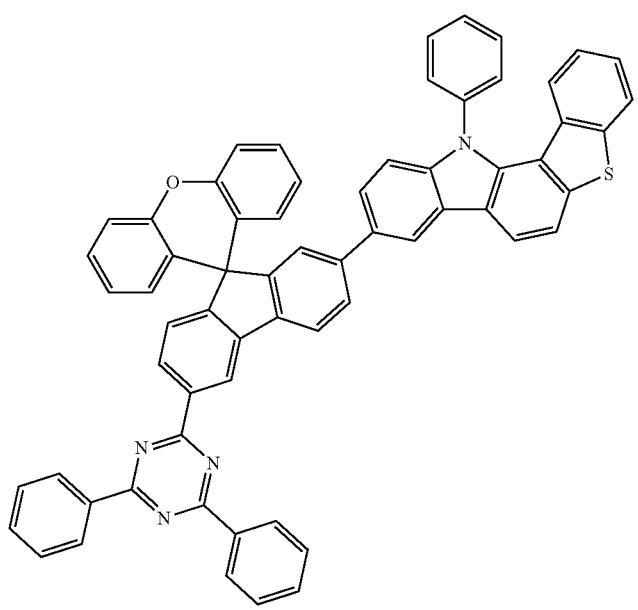

35
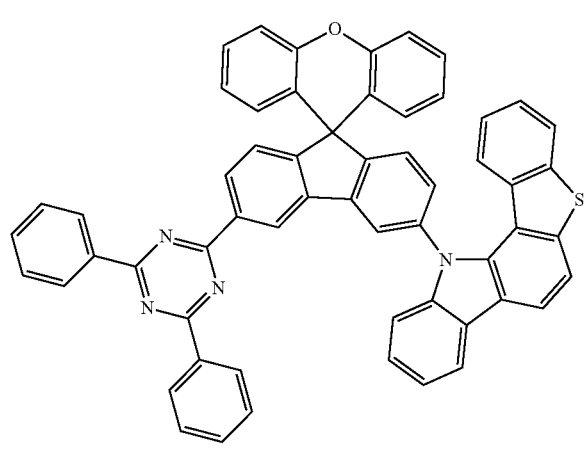
36
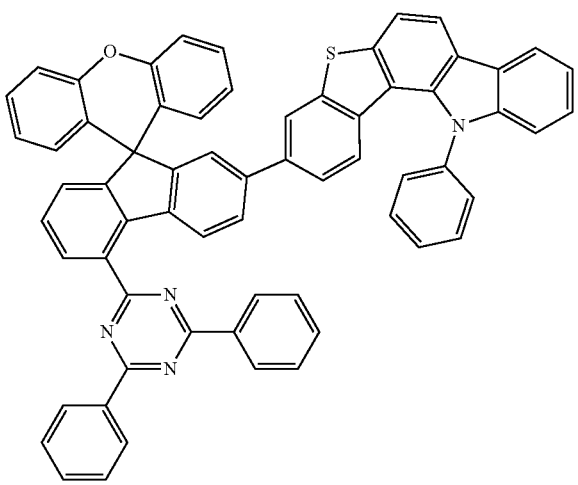
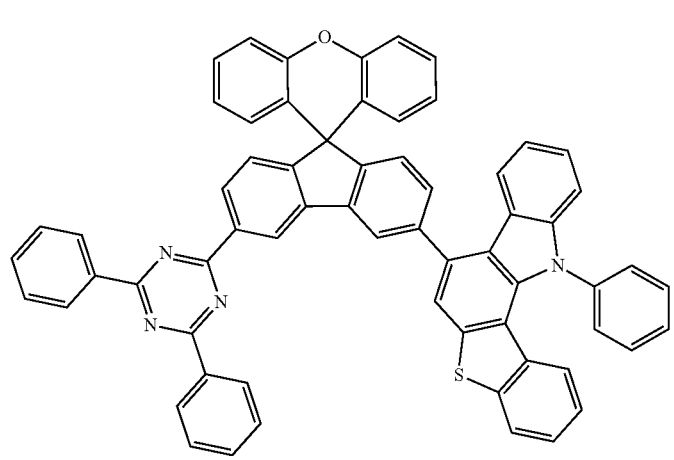
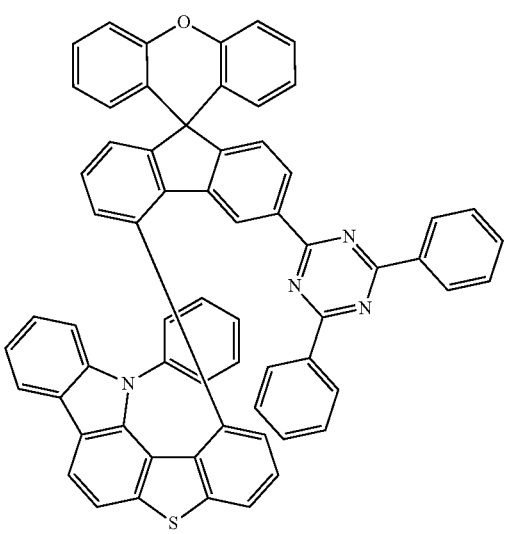
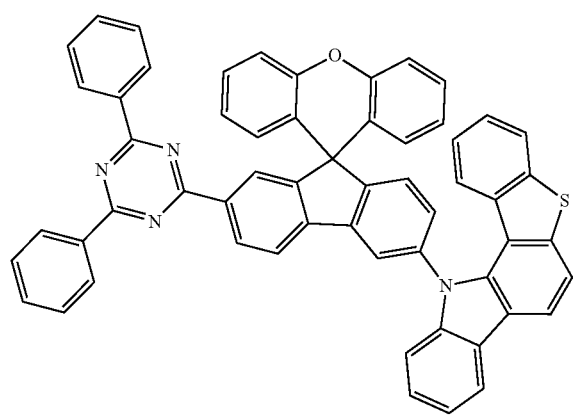

-continued
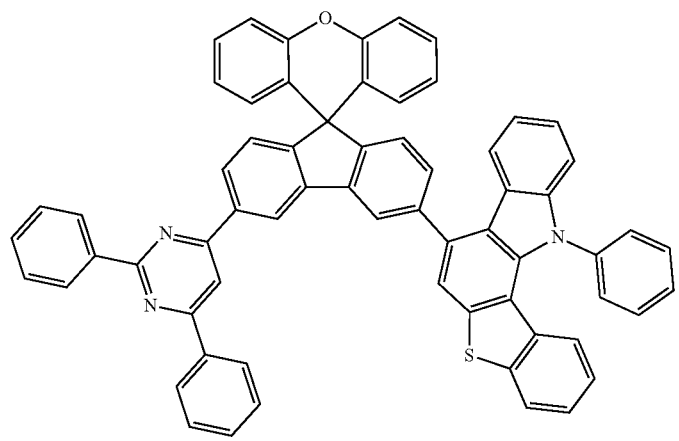
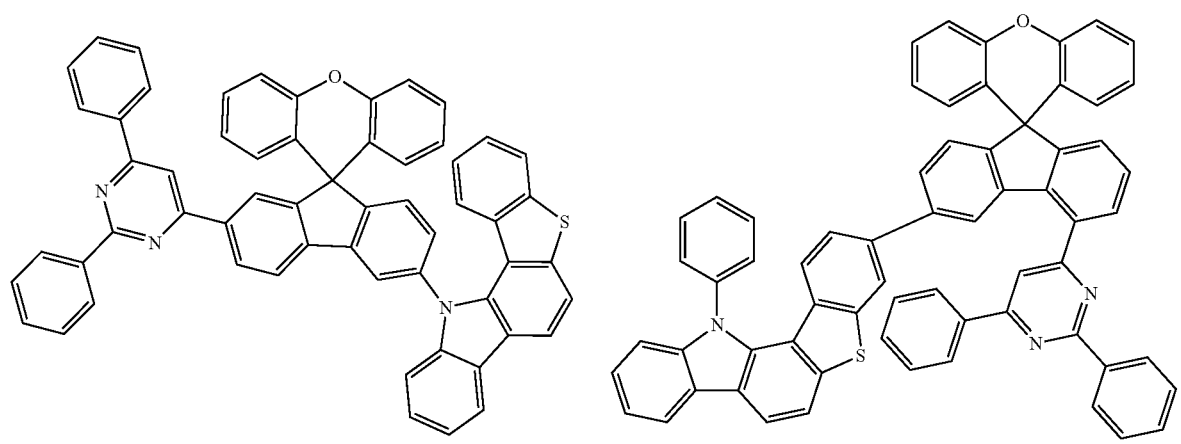
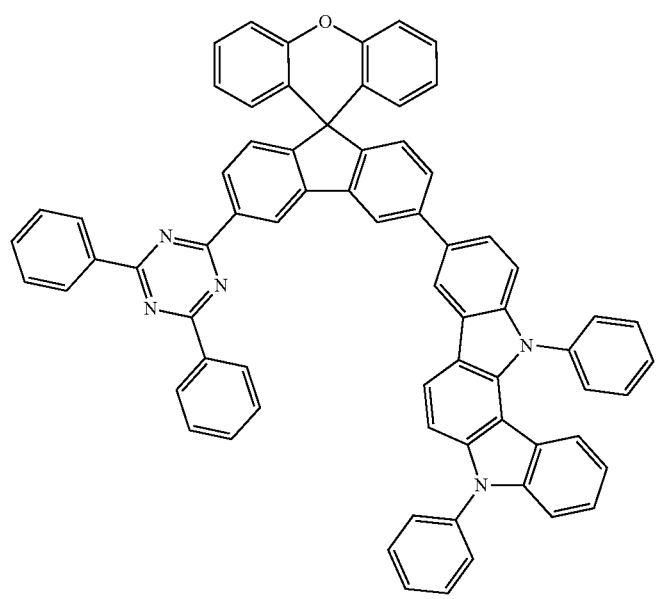

-continued
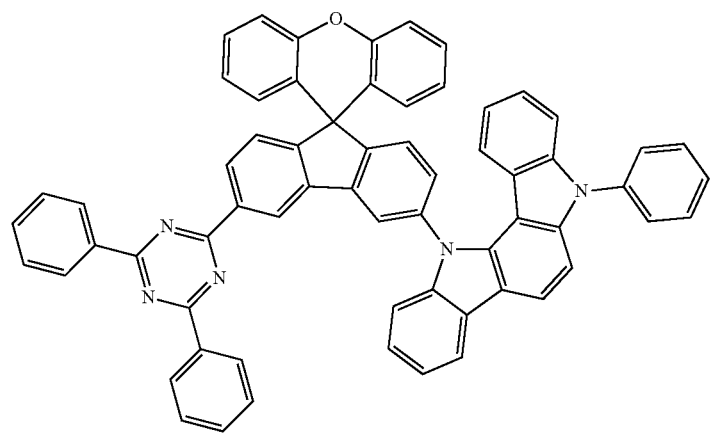
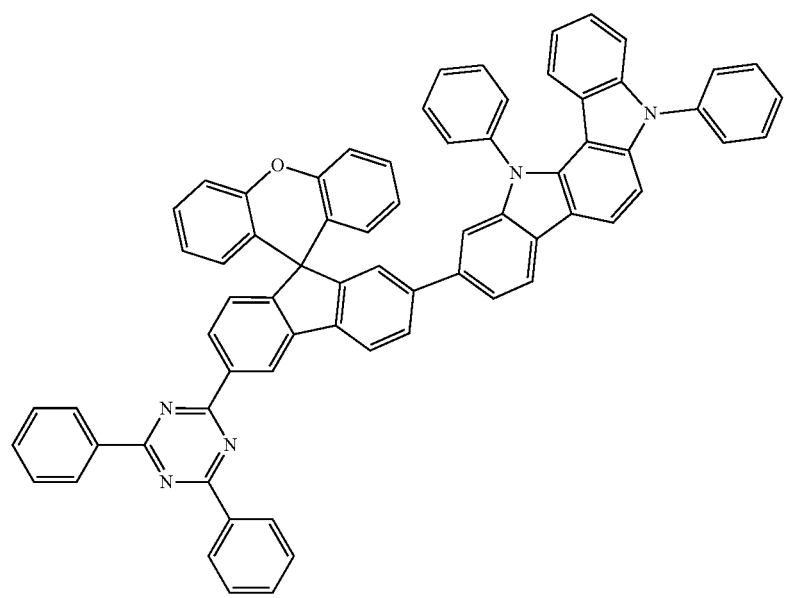
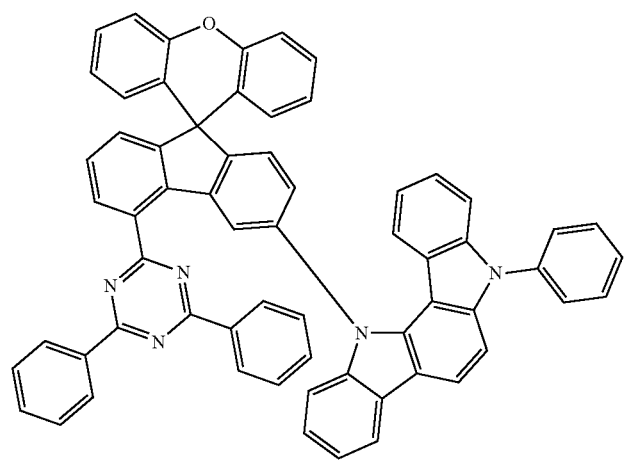

-continued
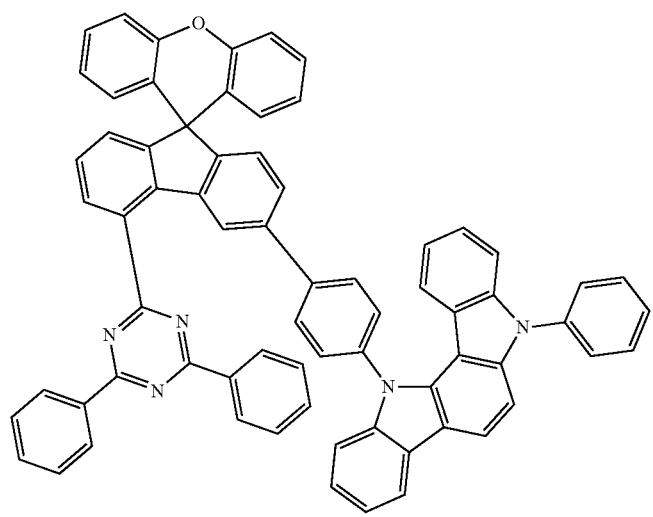
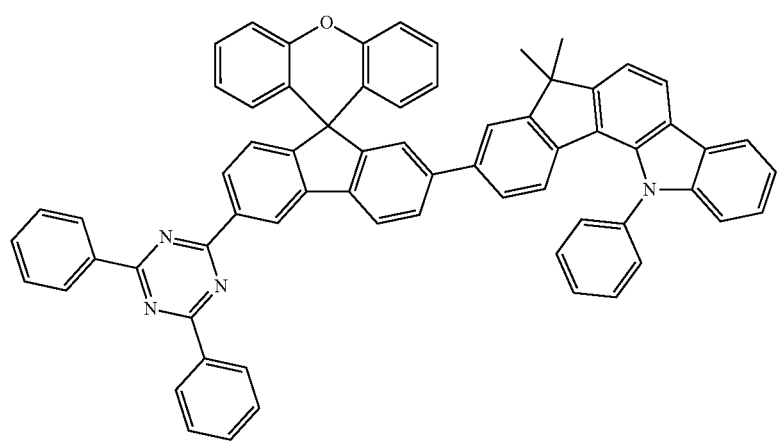
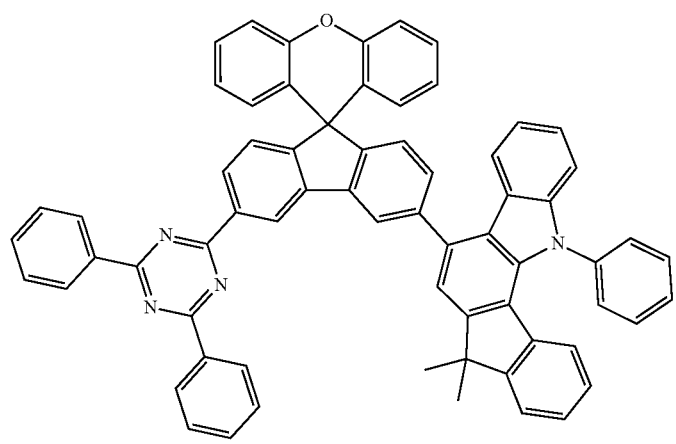

-continued
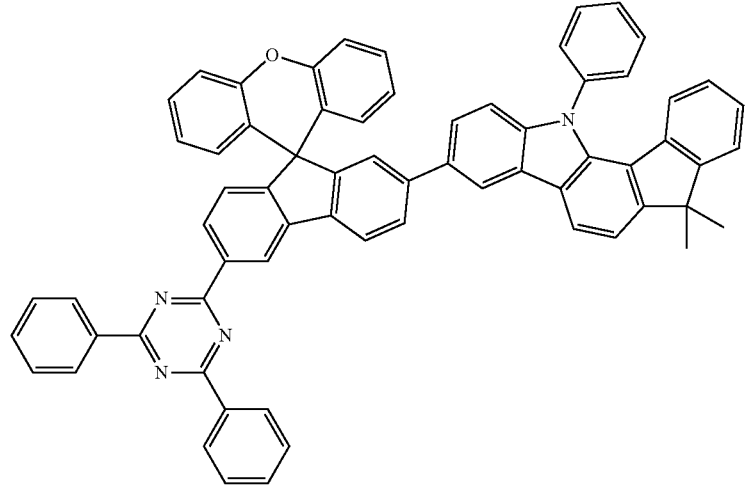
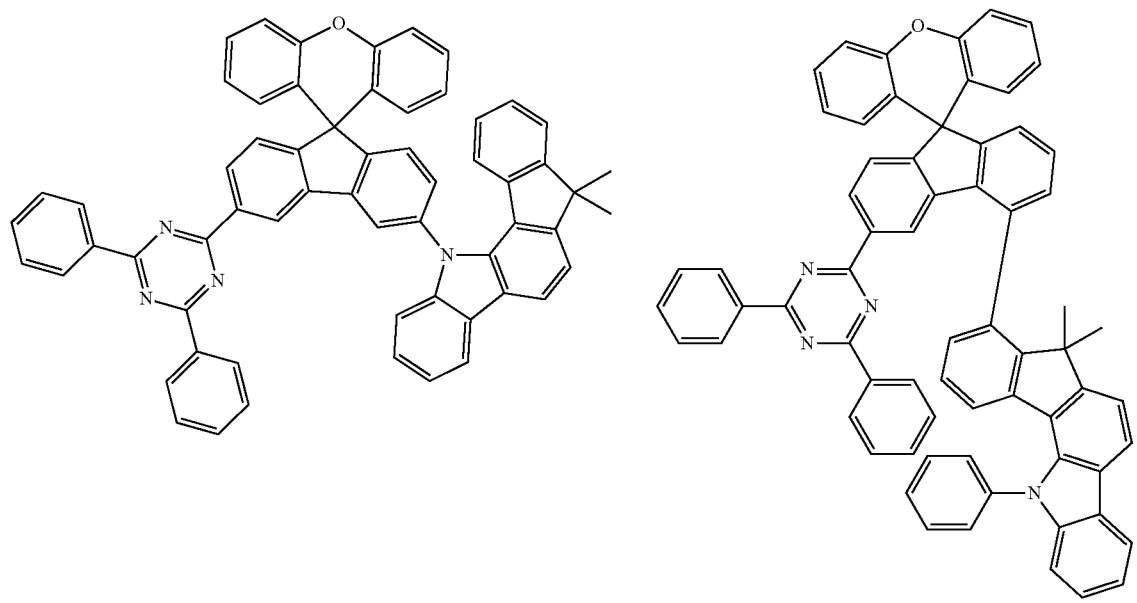
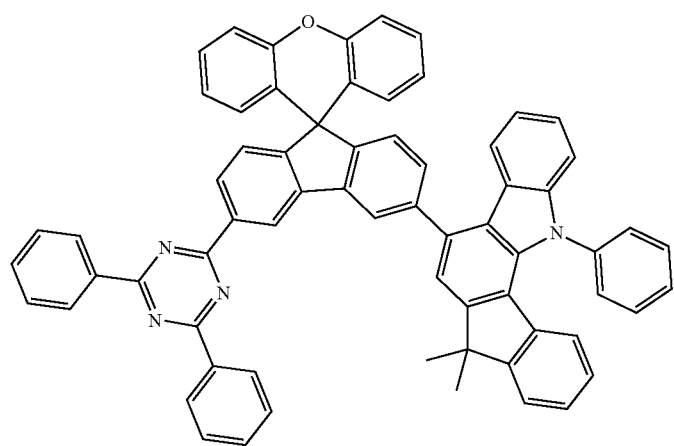

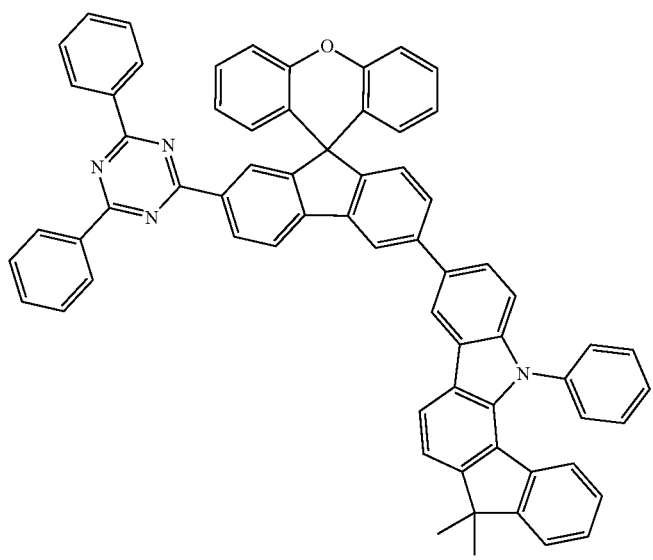
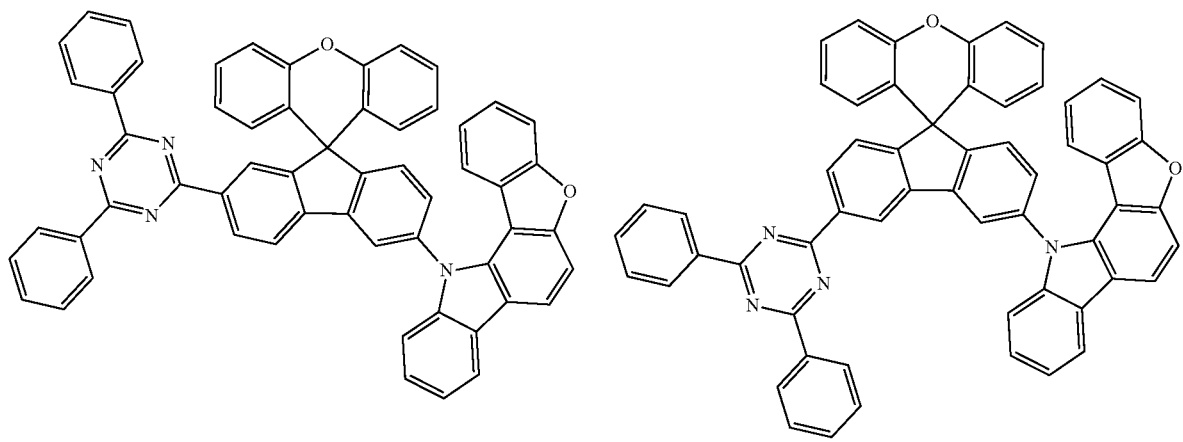
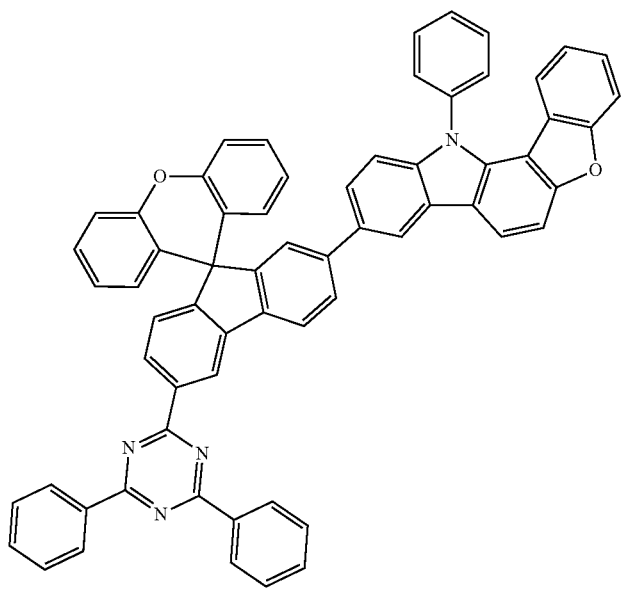

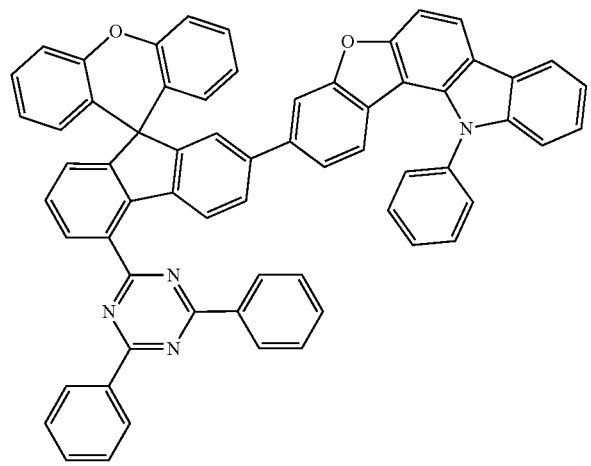
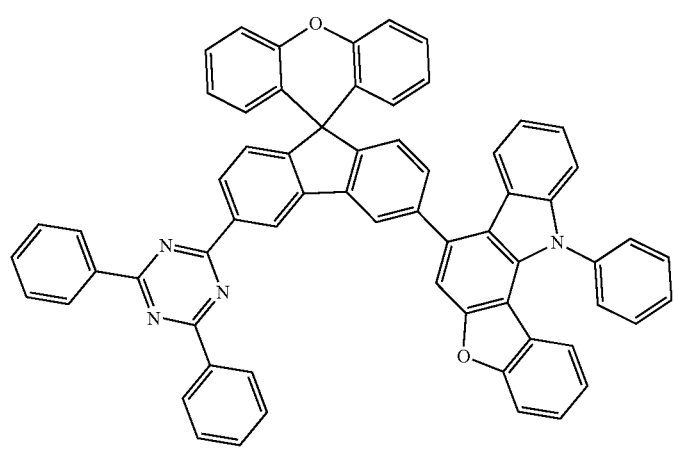
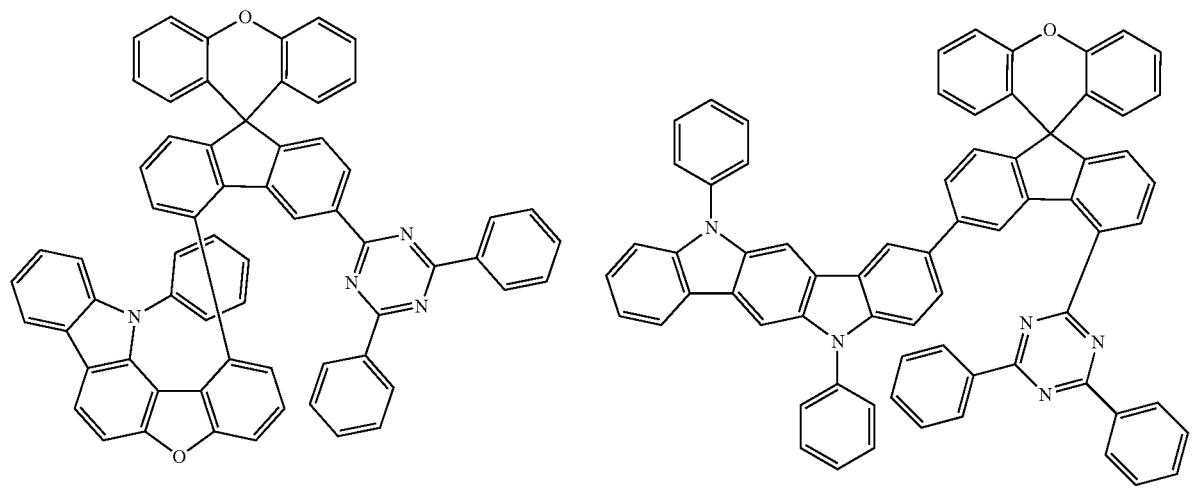

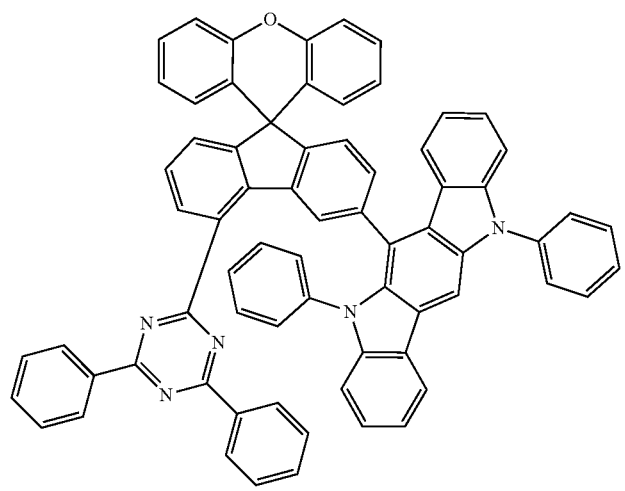
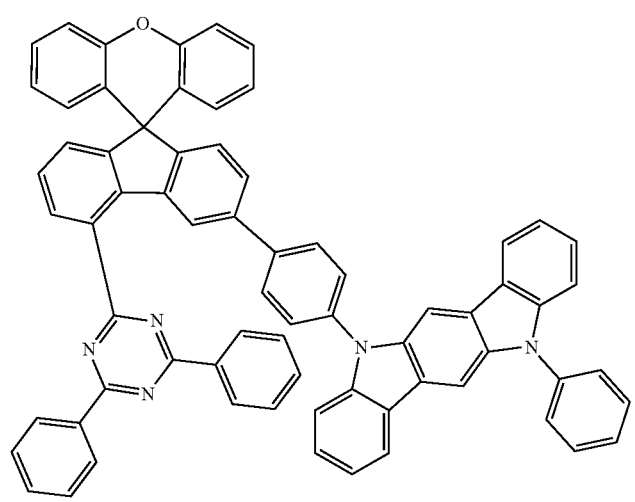
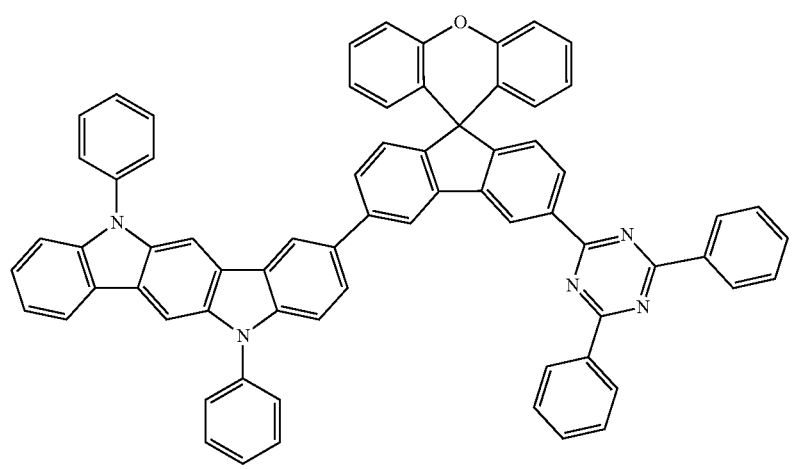

-continued
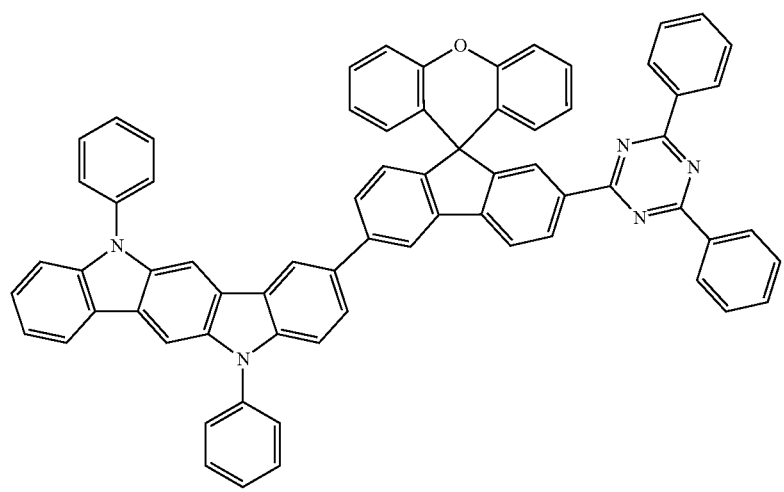
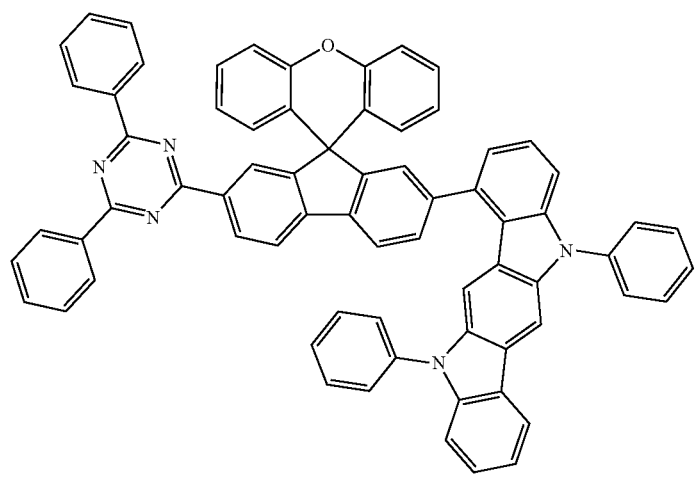
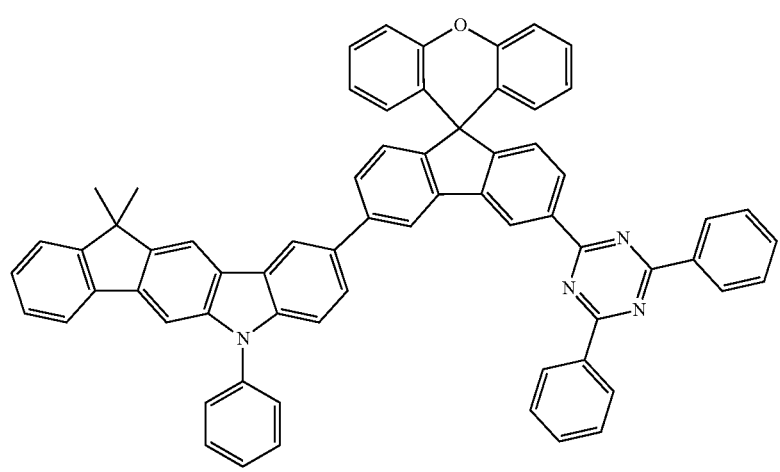

53 54
-continued
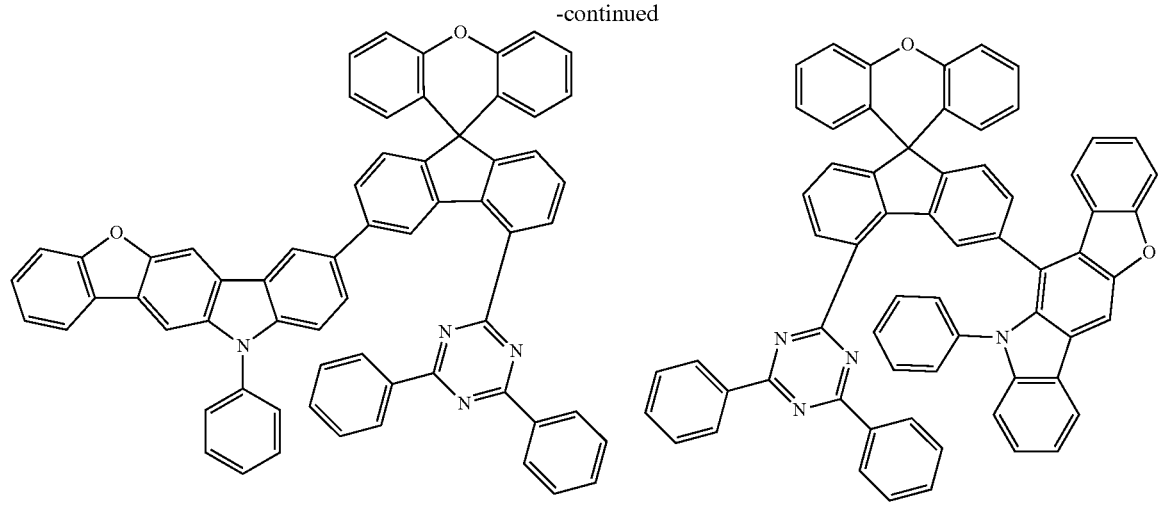
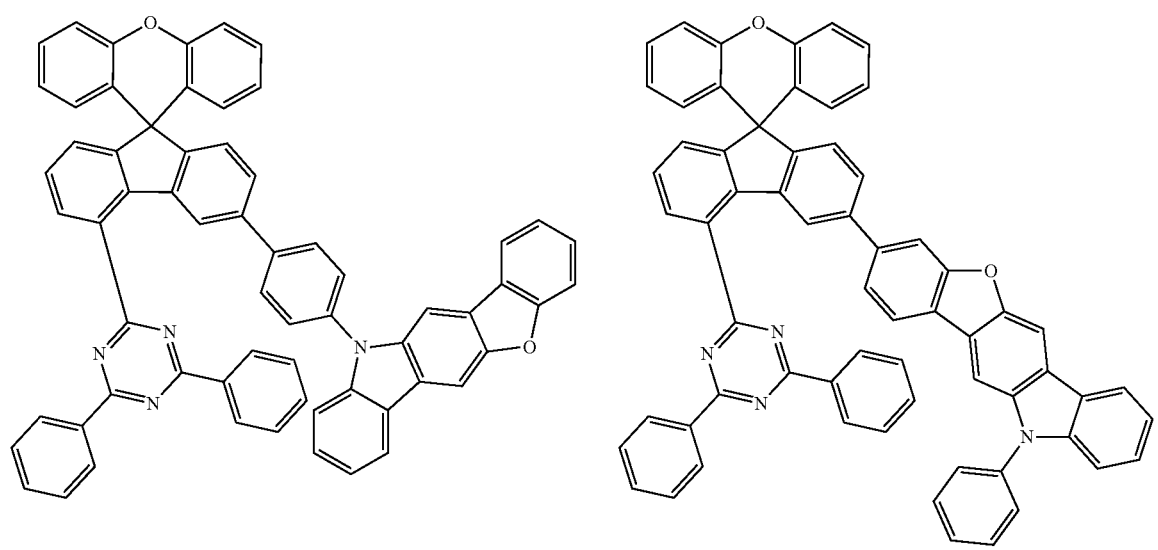
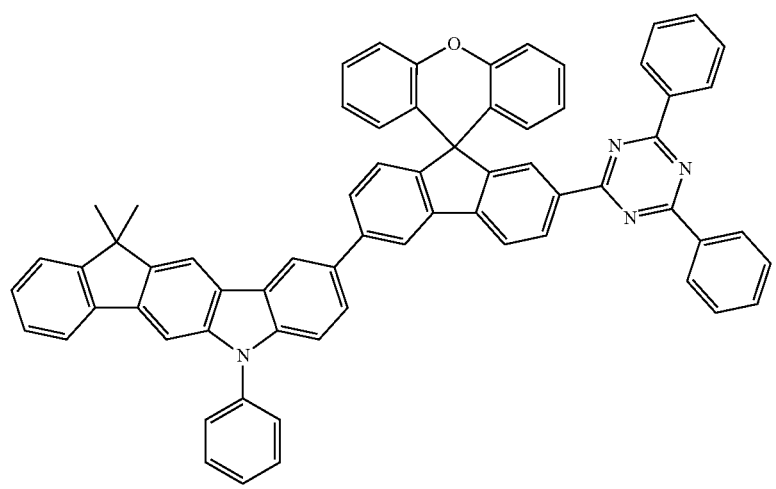

-continued
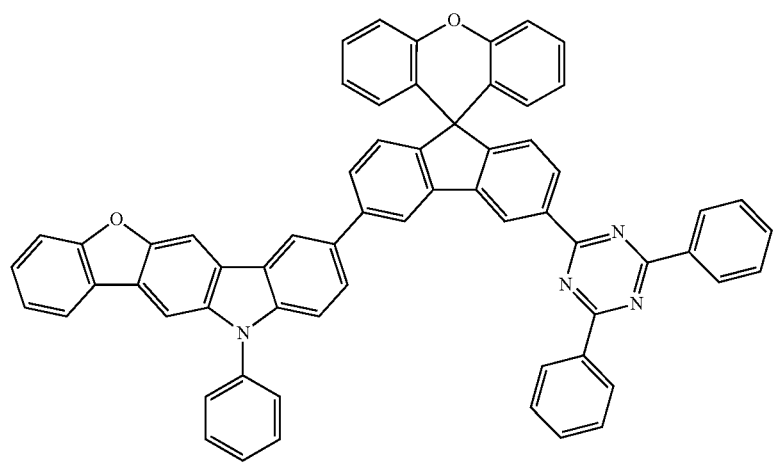
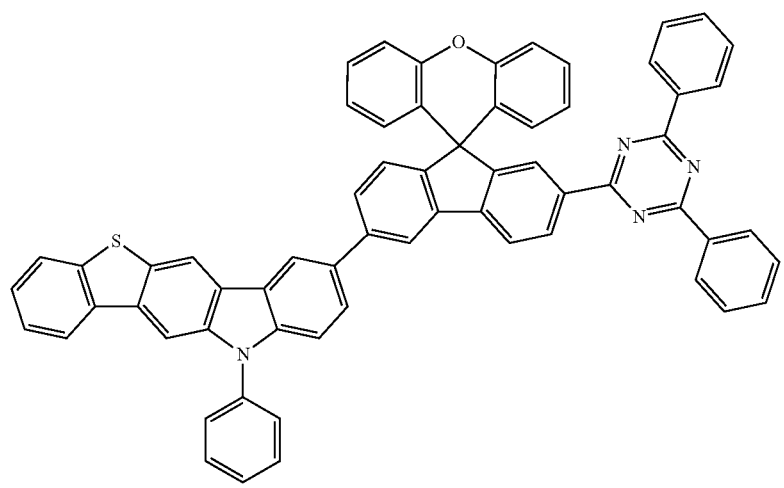
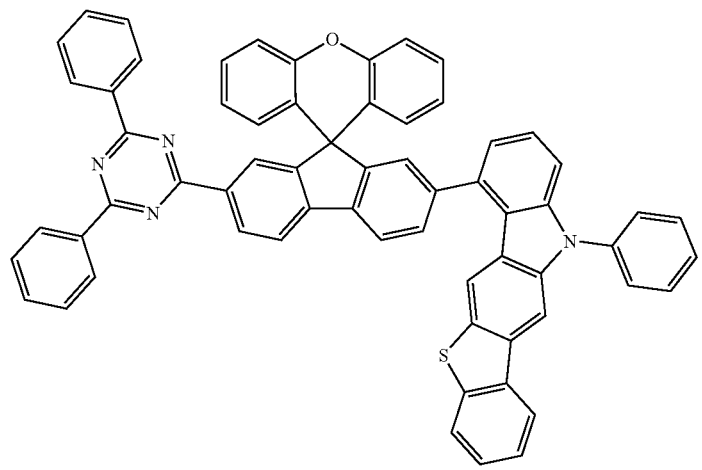

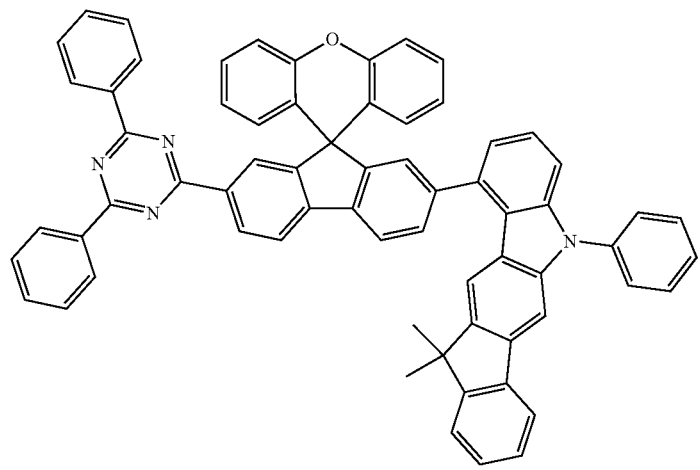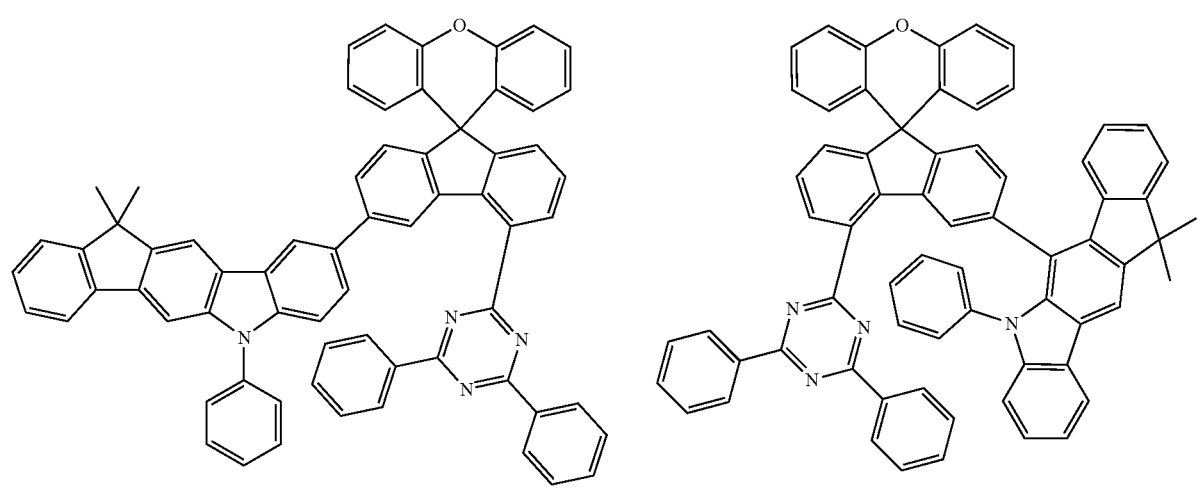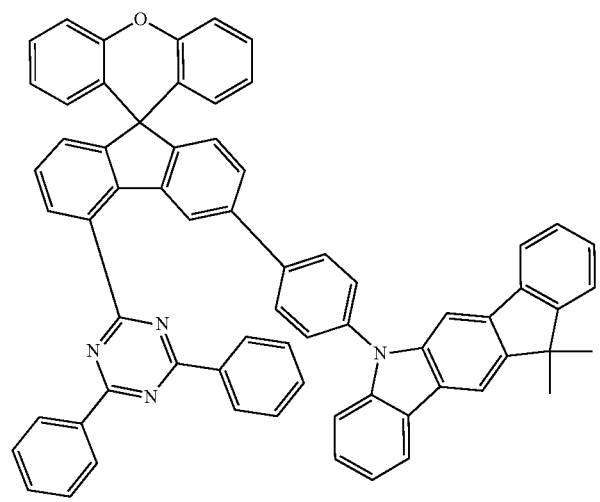

-continued
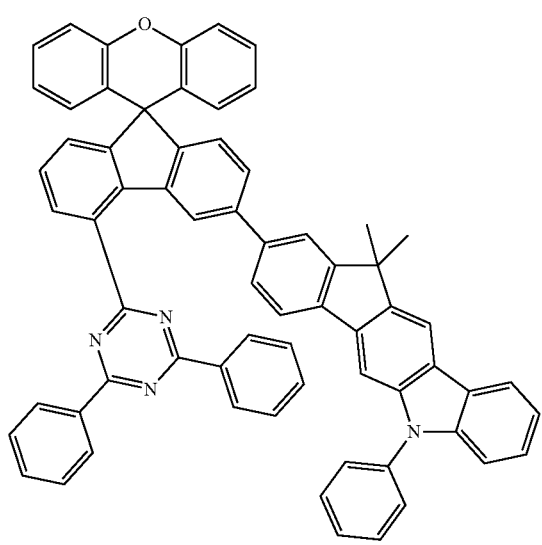
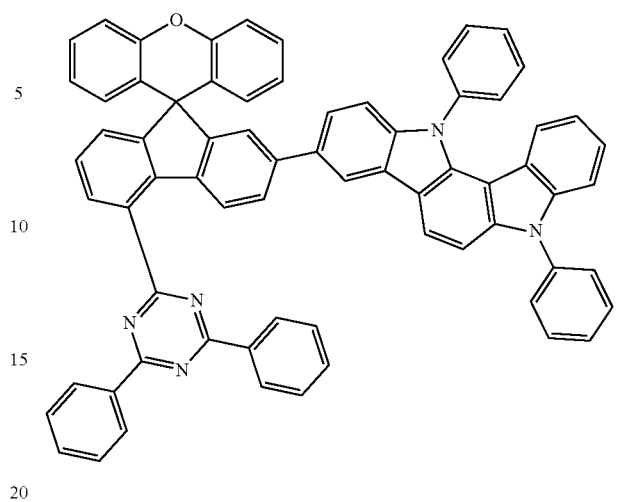
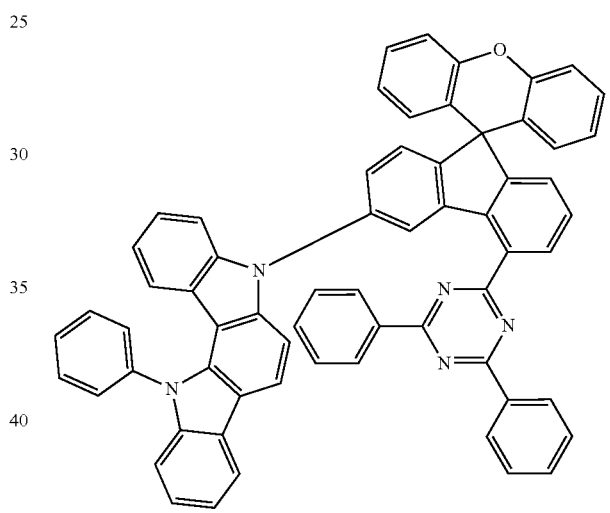
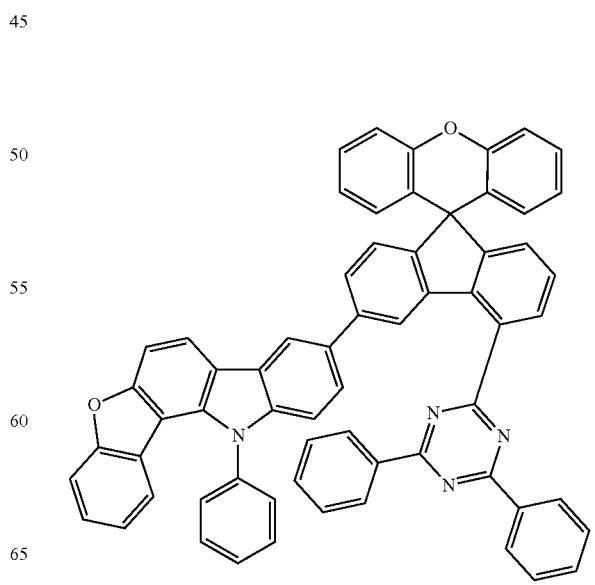

61
-continued
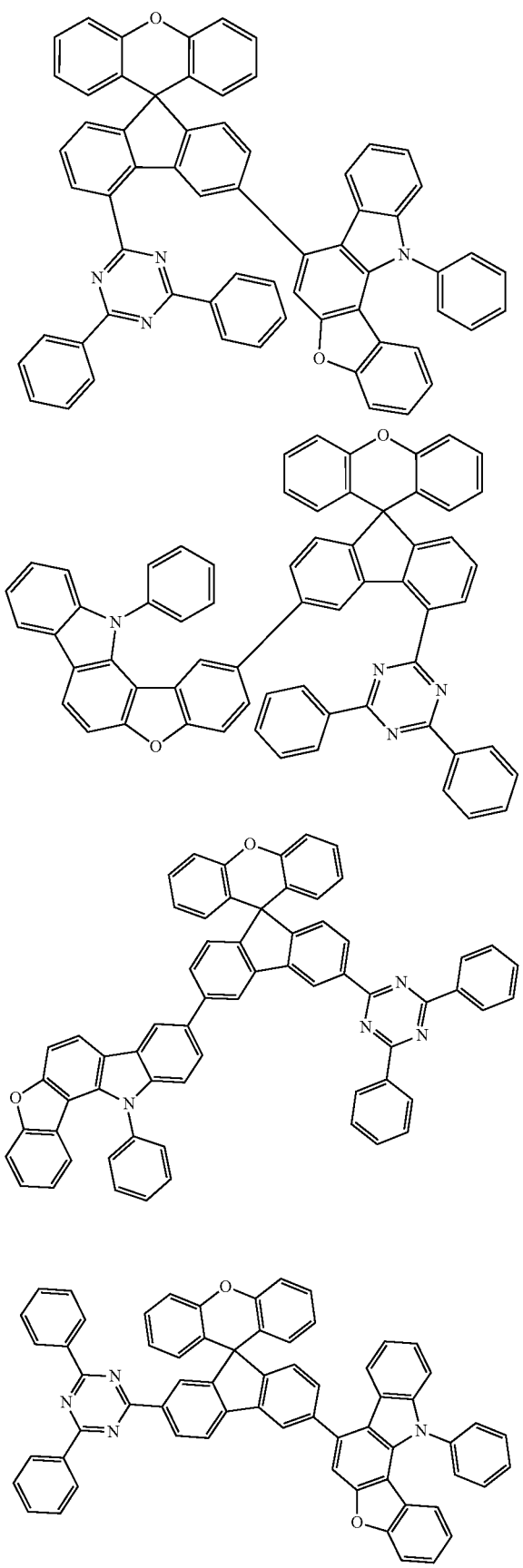
62
-continued
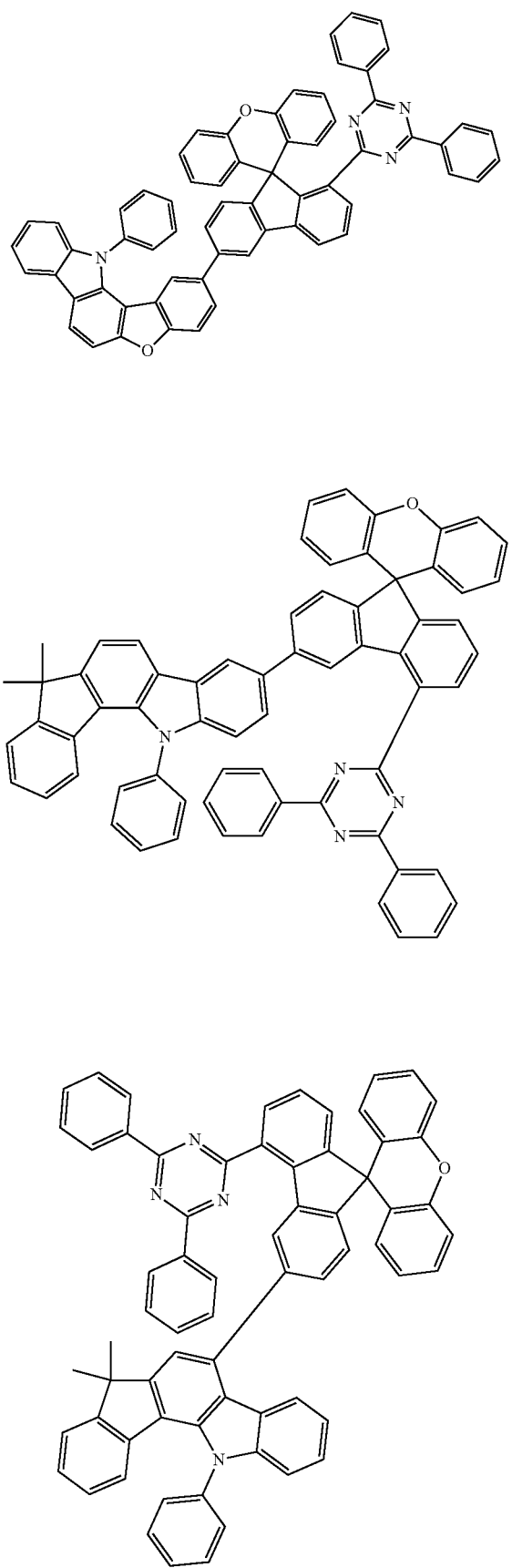

63
-continued
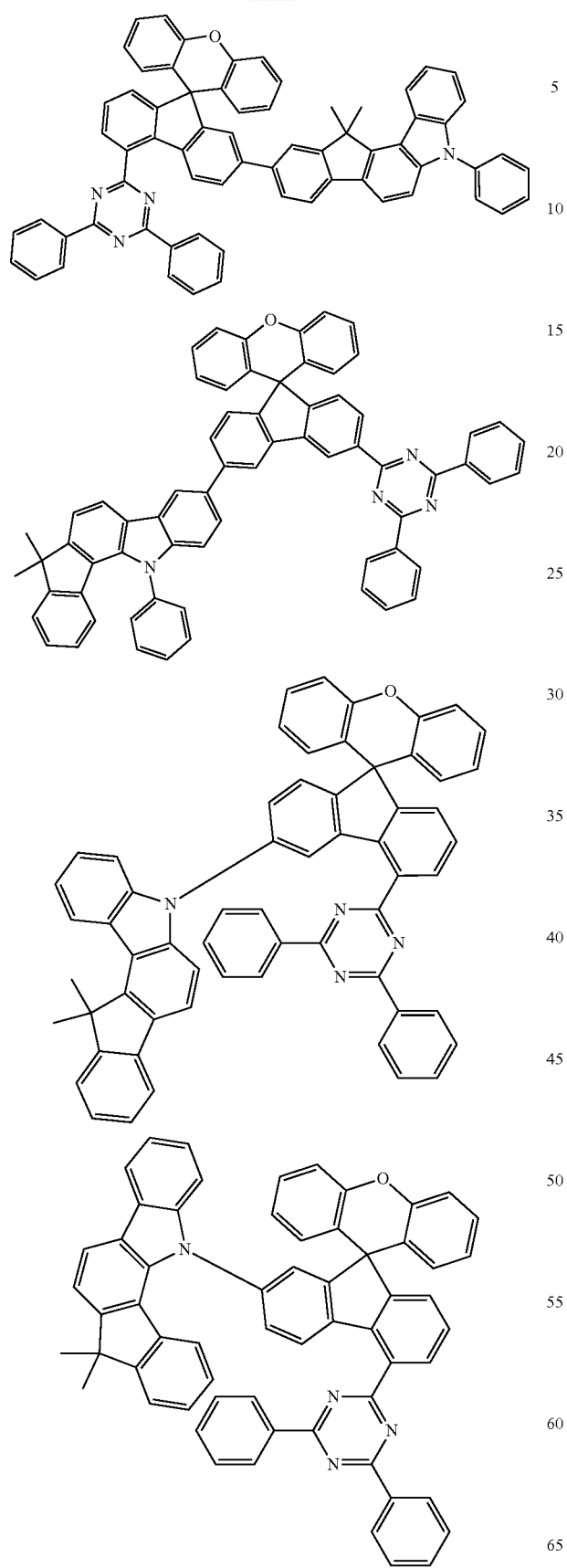
64
-continued

65
-continued
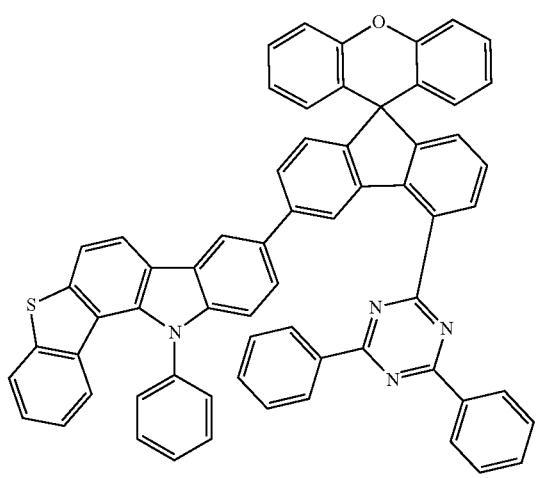
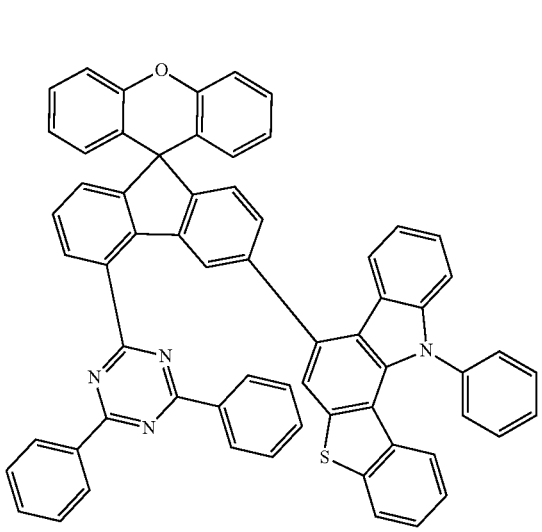
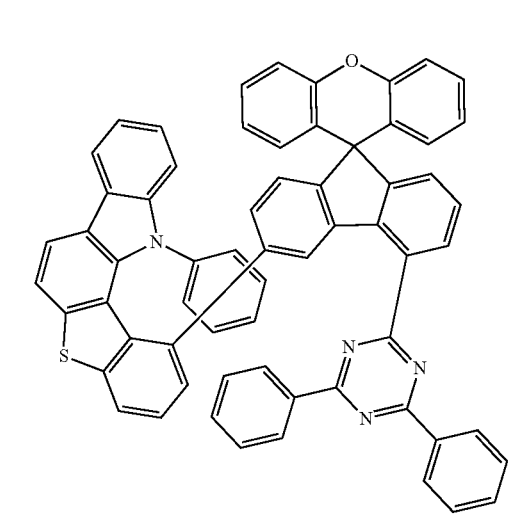
66
-continued
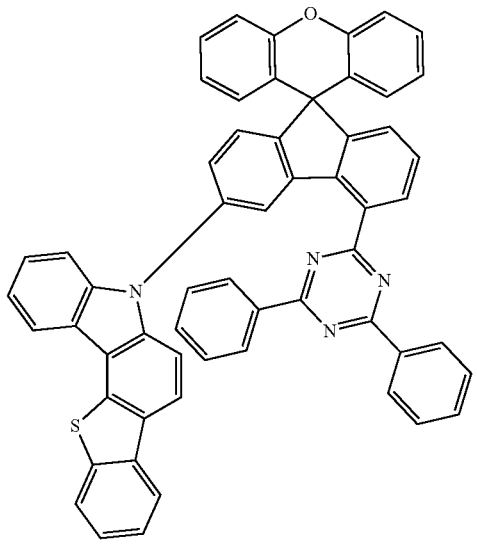
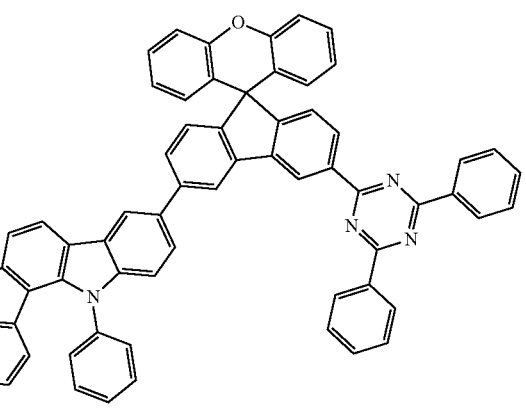
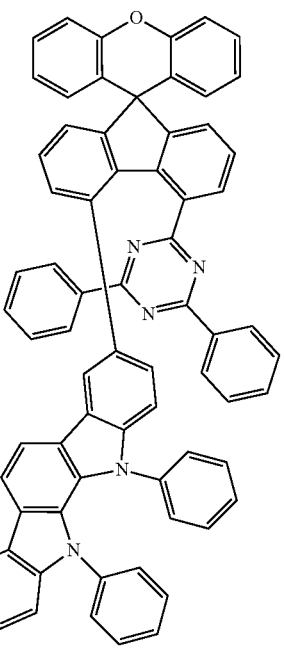

67
-continued
68
-continued
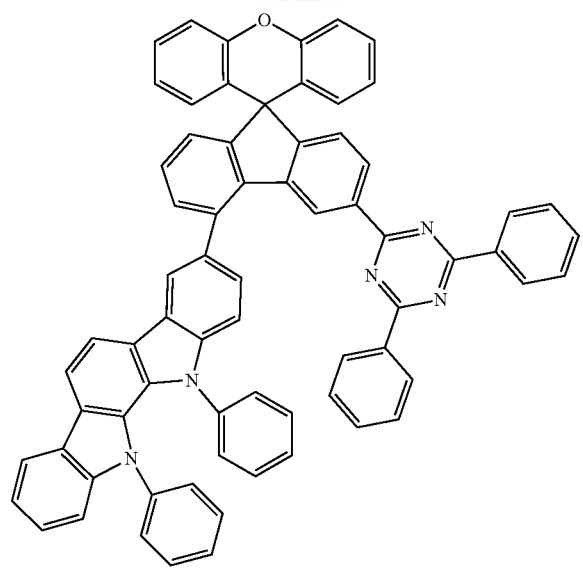
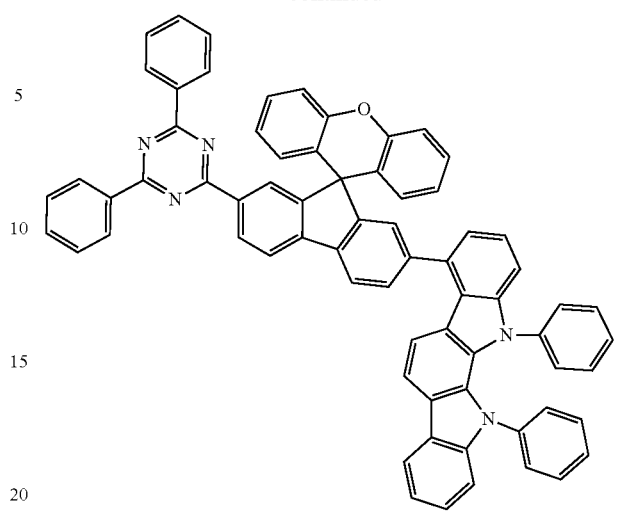
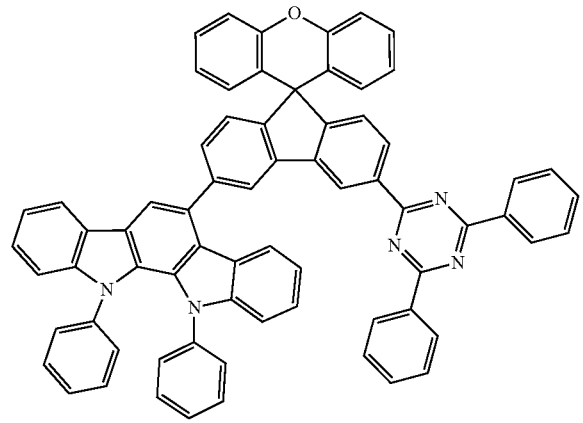
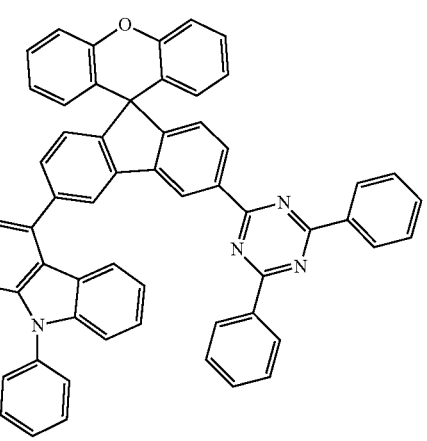

69
-continued
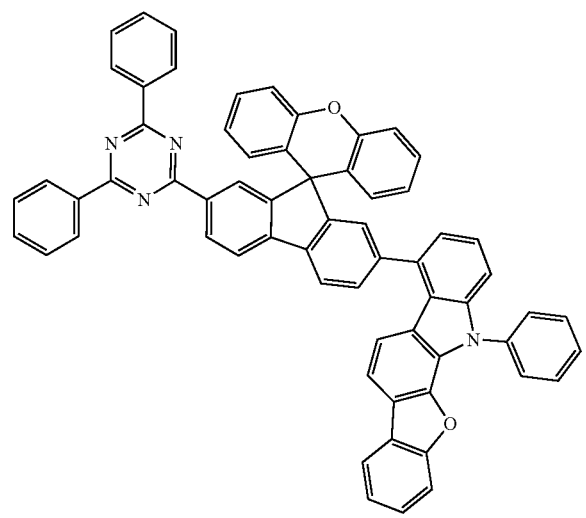
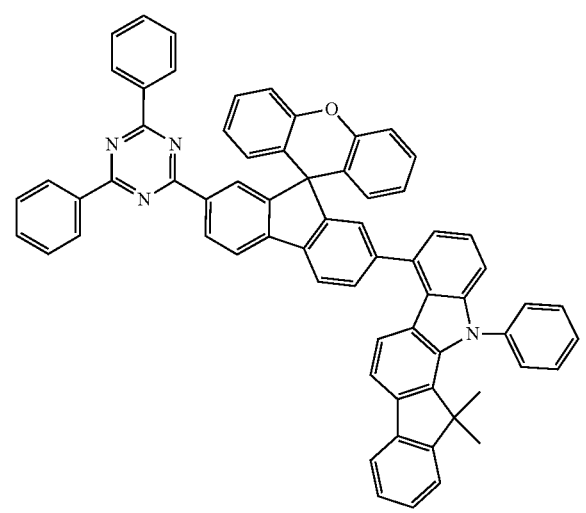
70
-continued
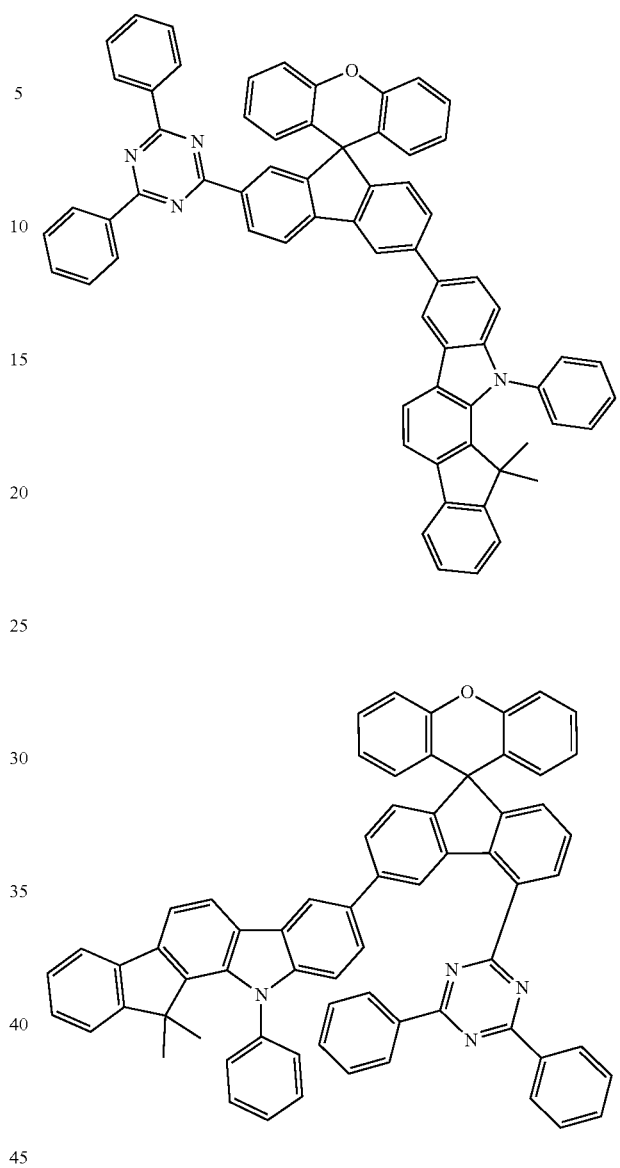
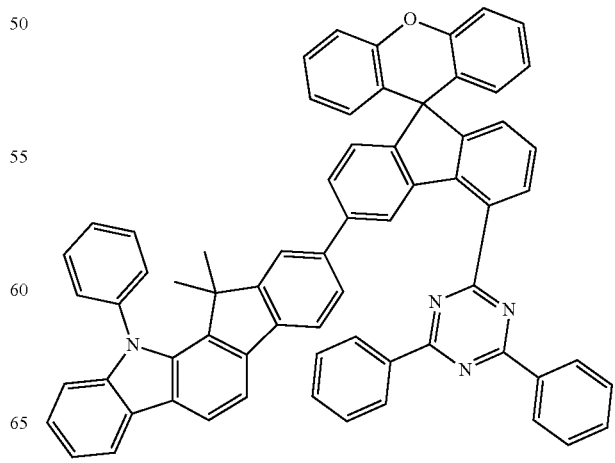

71
-continued
72
-continued
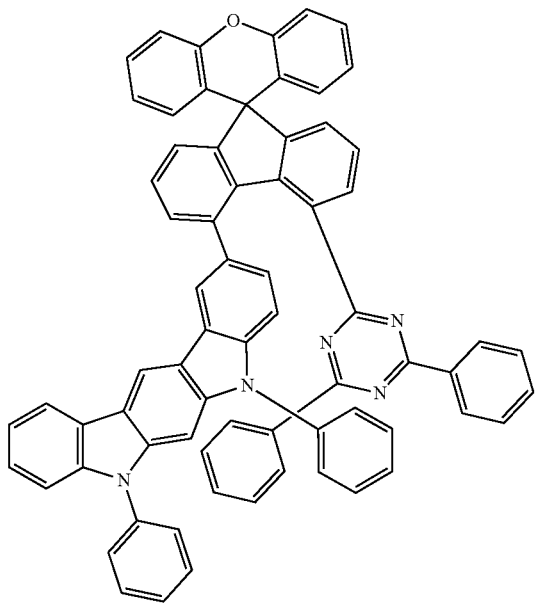
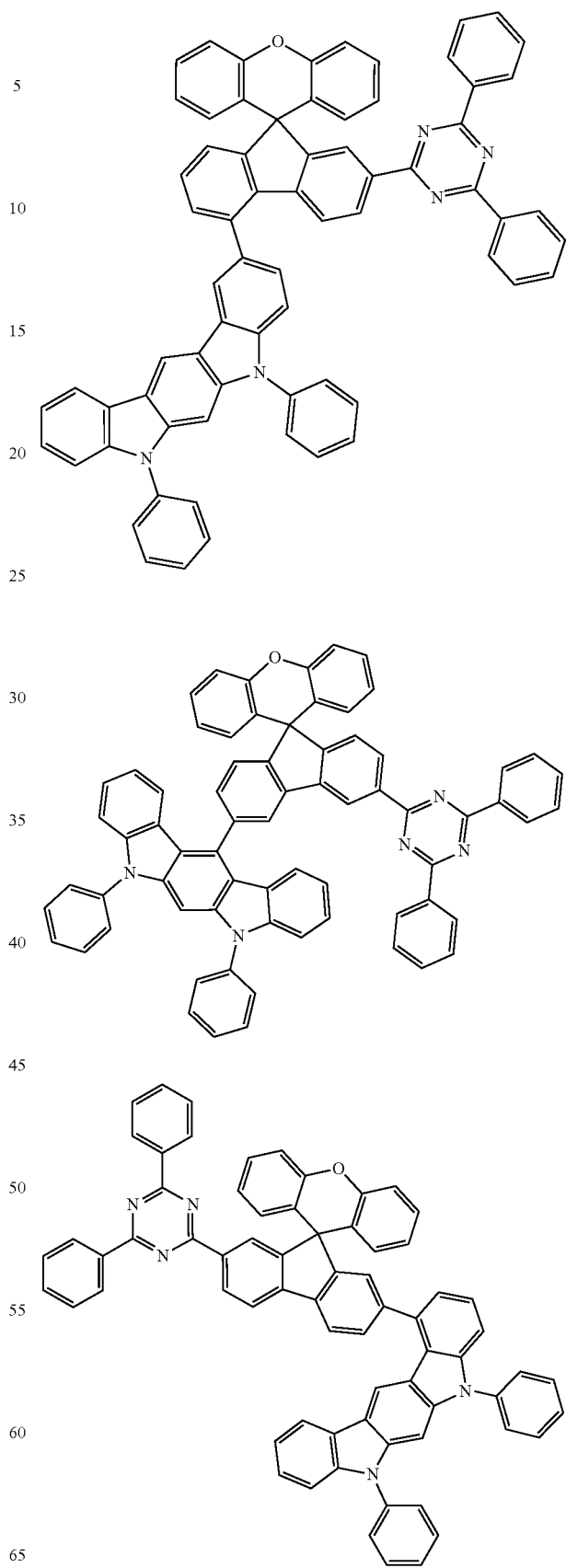

73
-continued
74
-continued
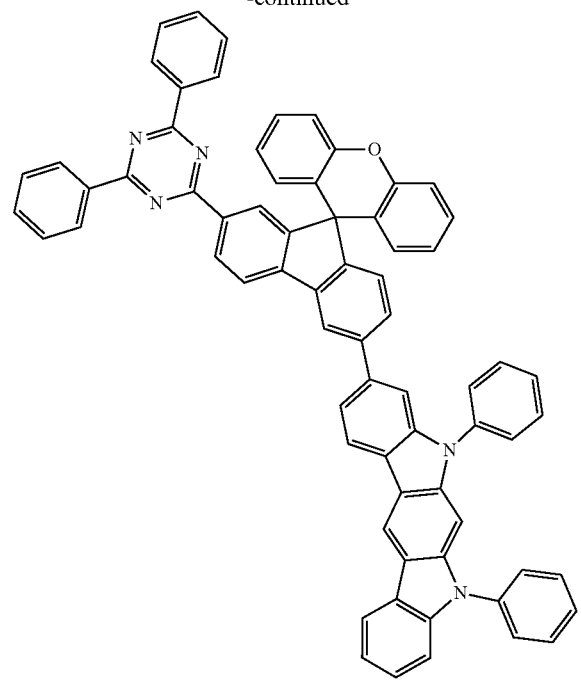
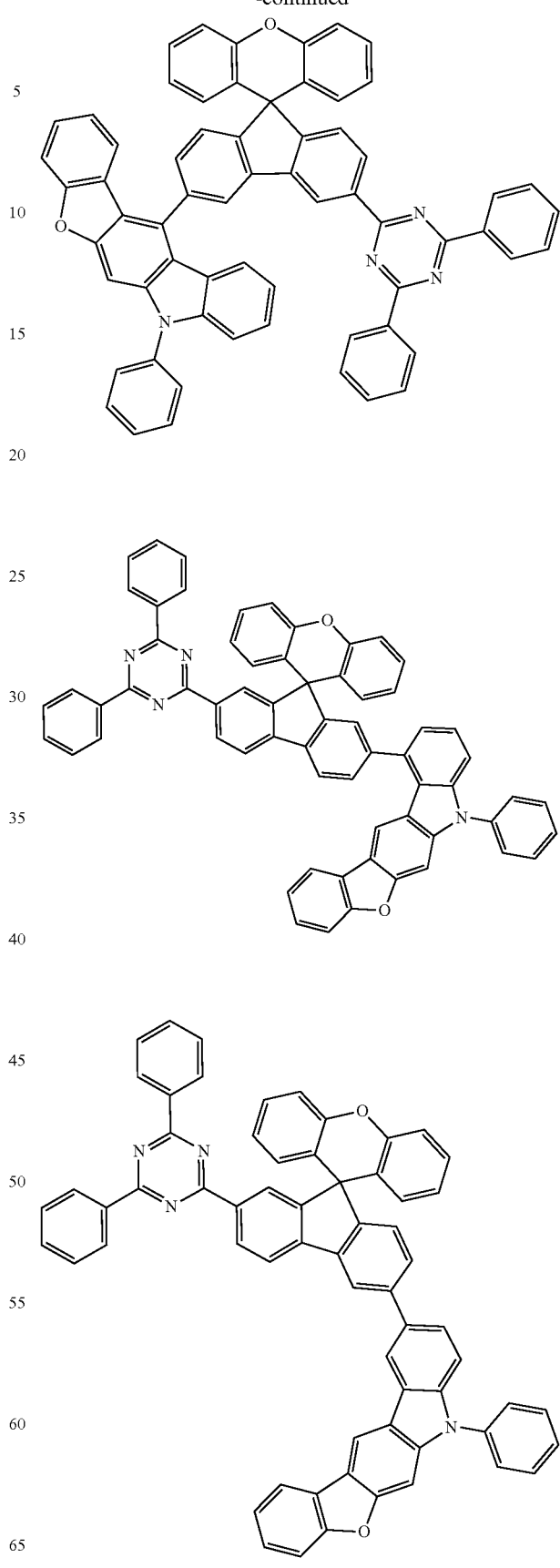

75
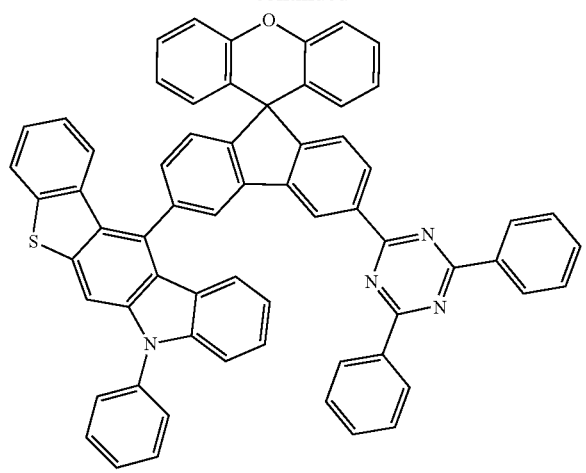
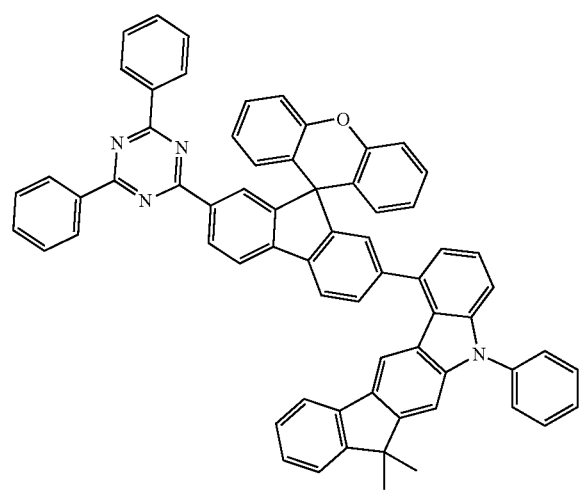
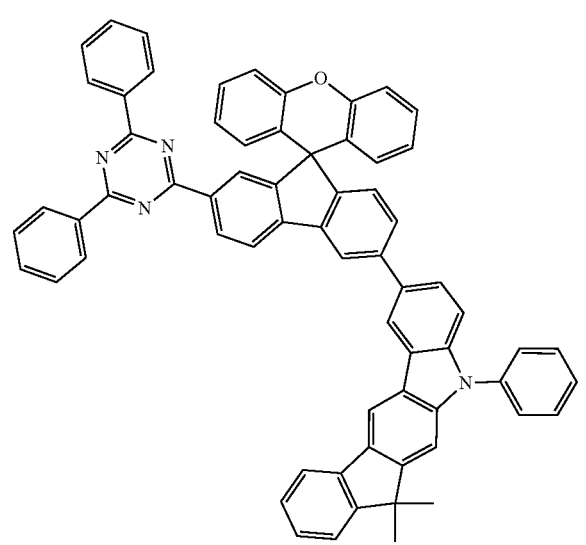
76
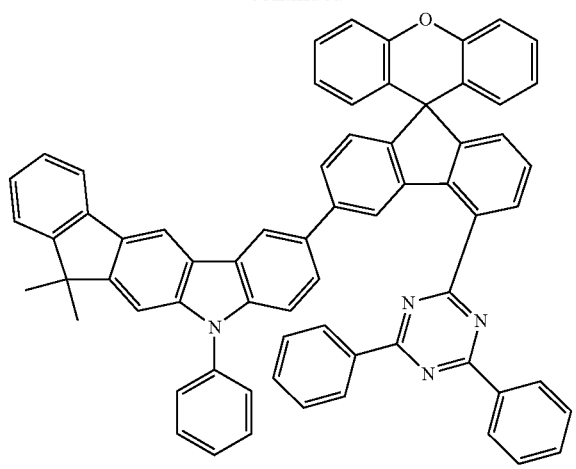
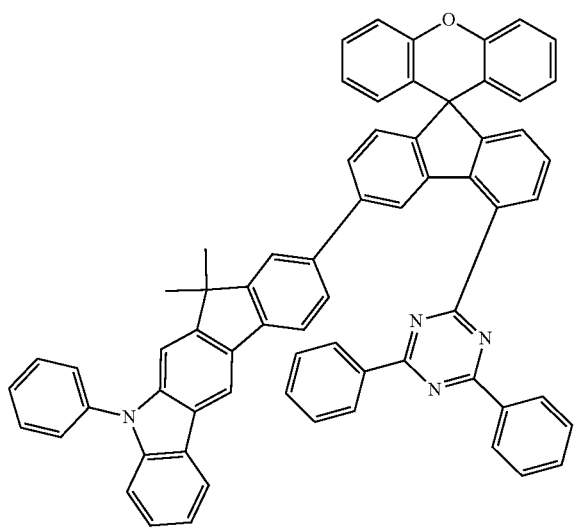

77
-continued
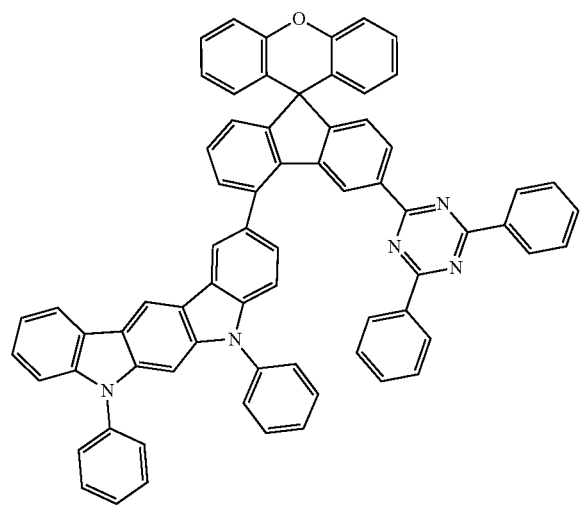
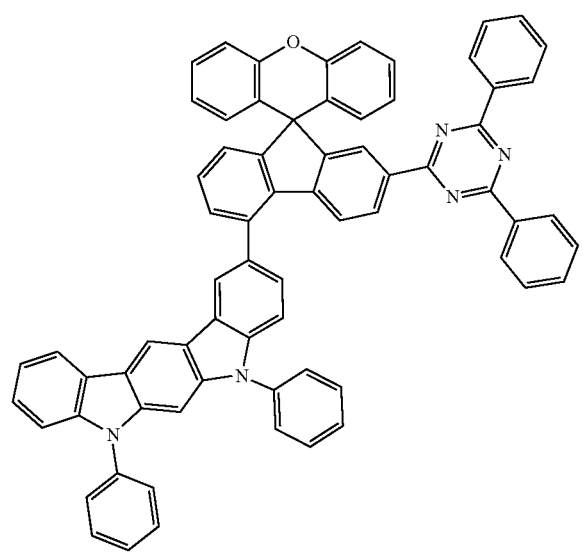
78
-continued
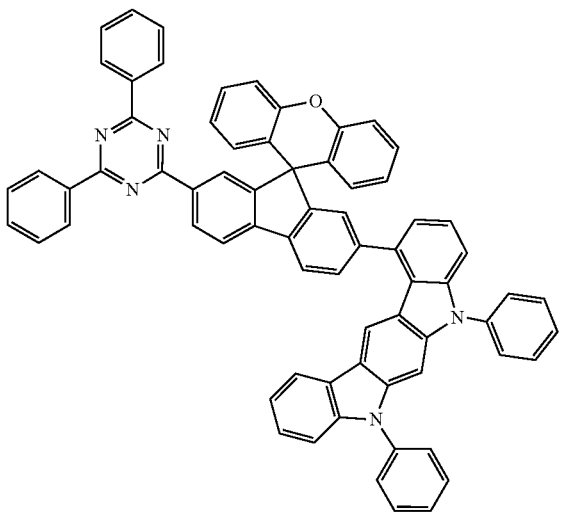
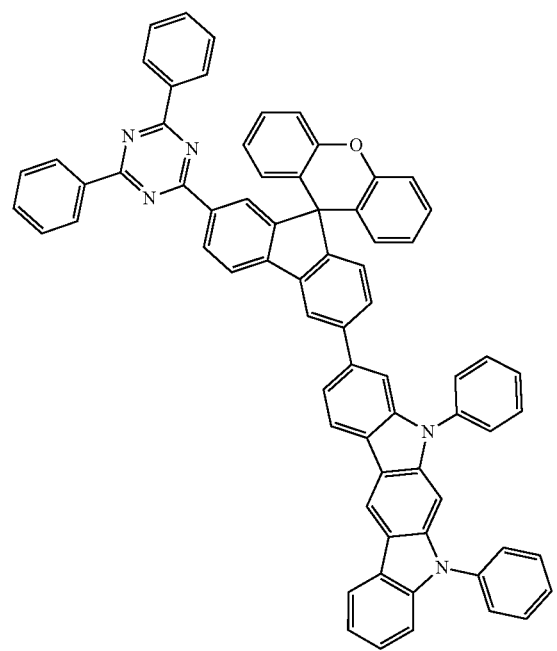

79
-continued
80
-continued
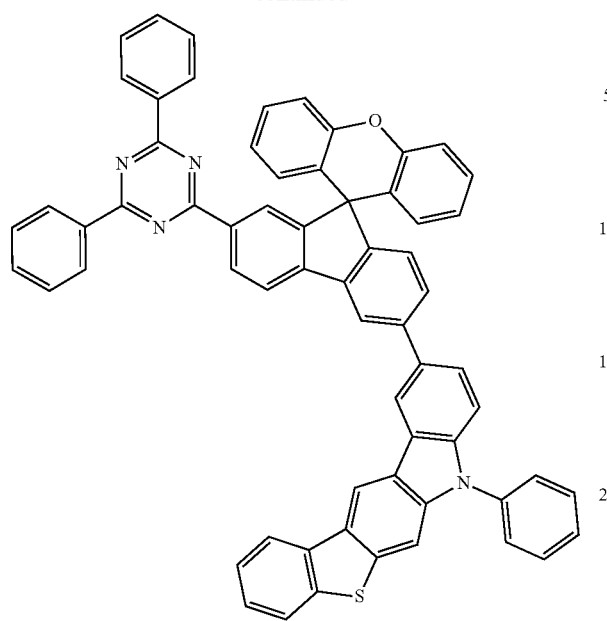
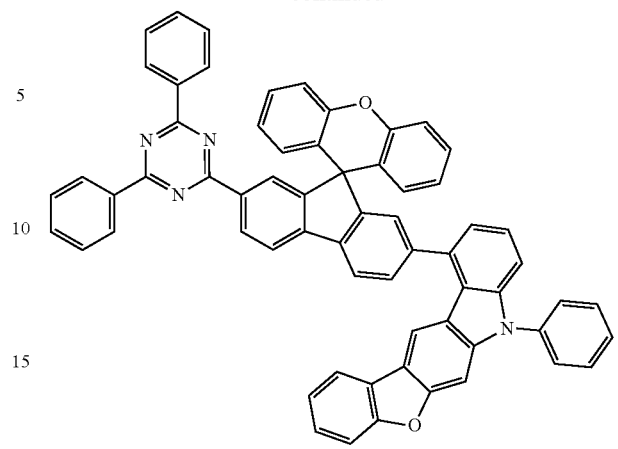
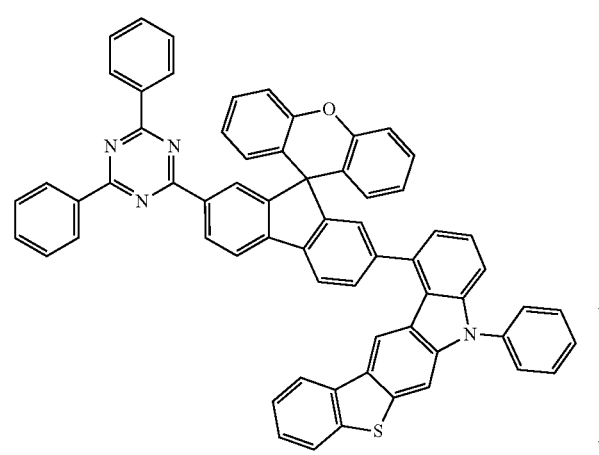
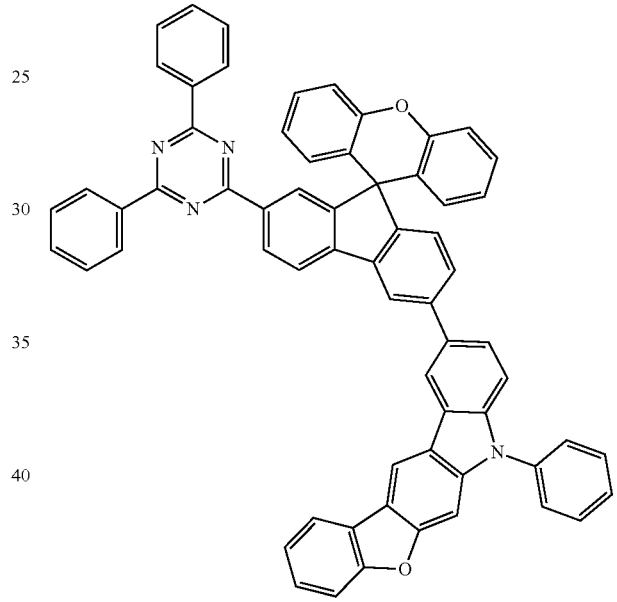
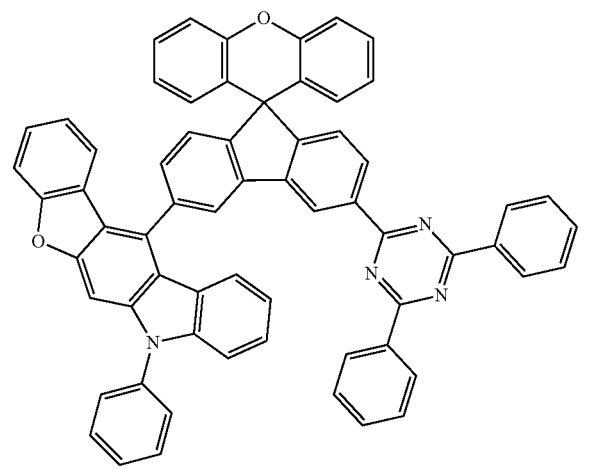
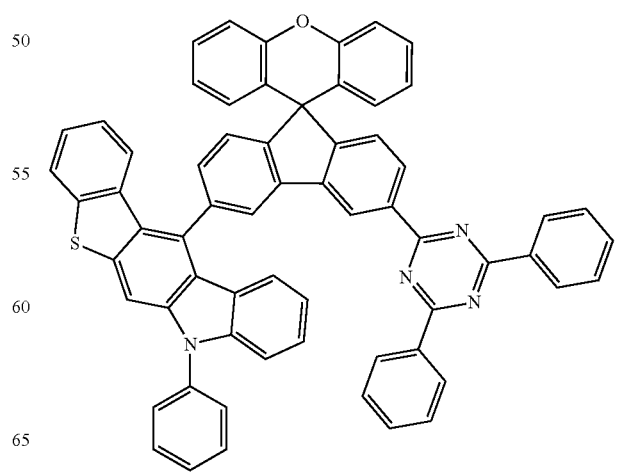

81
-continued
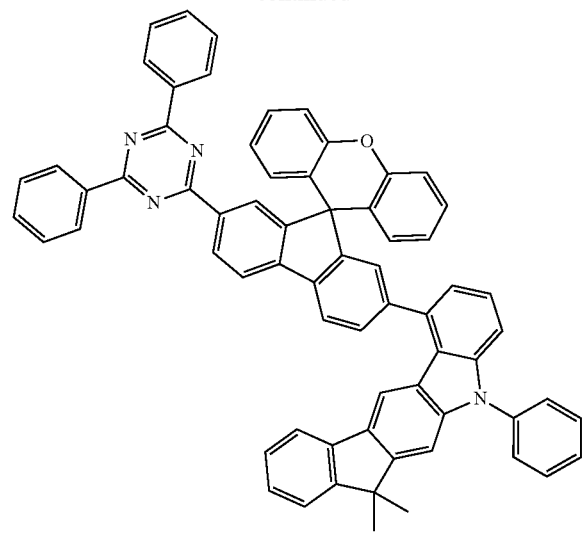
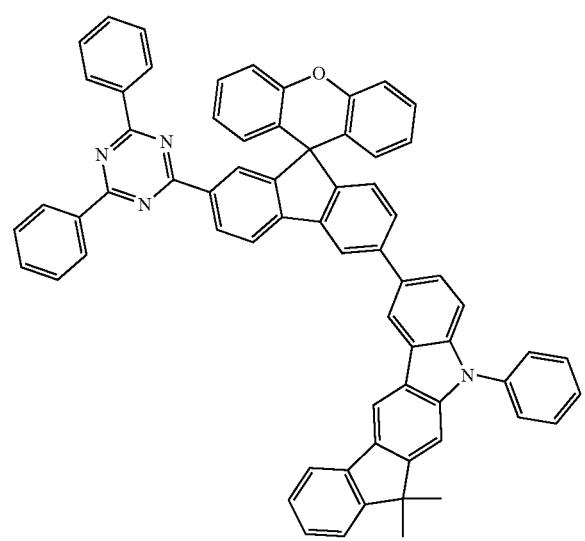
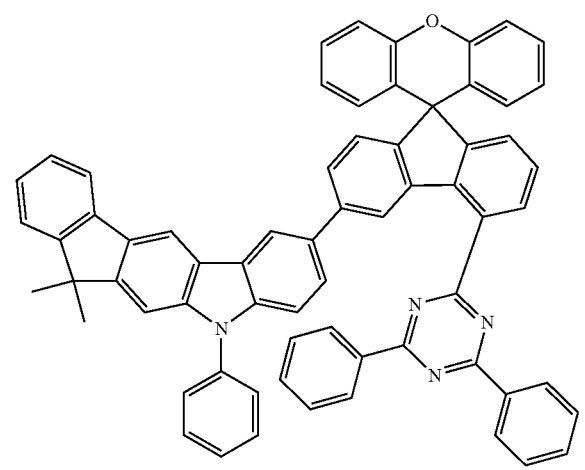
82
-continued
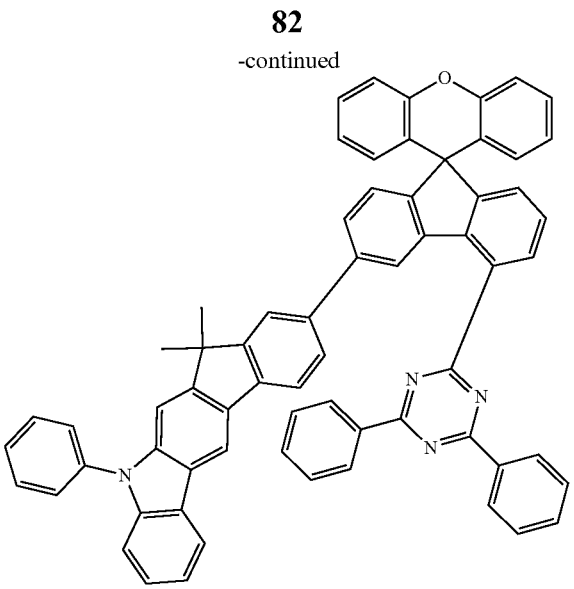
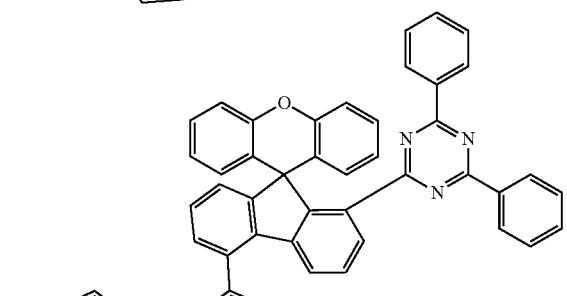
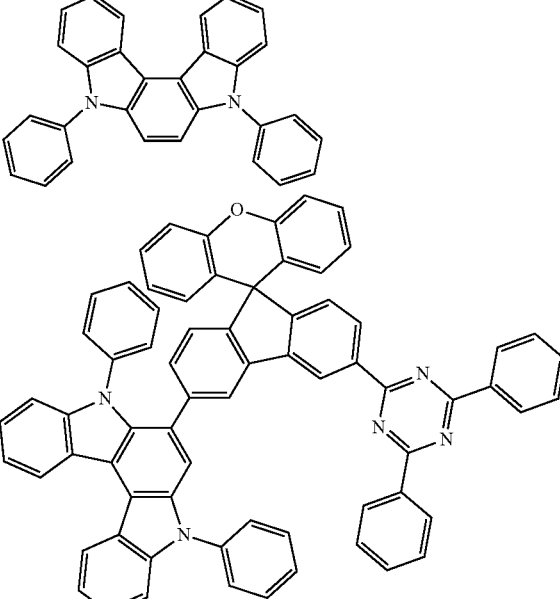
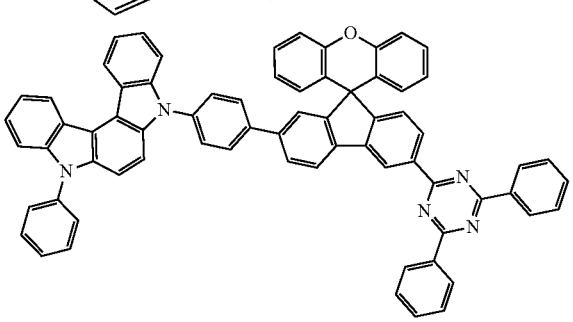

83
-continued
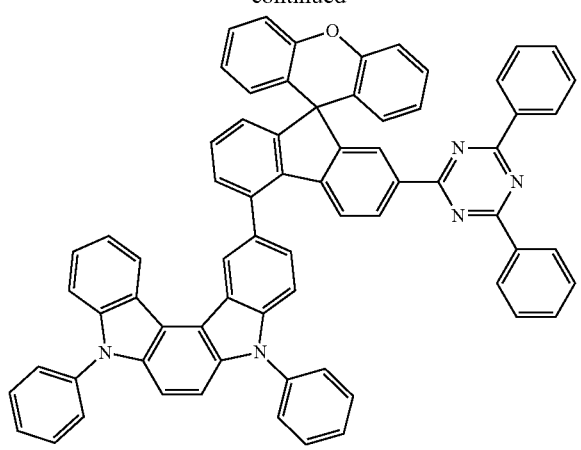
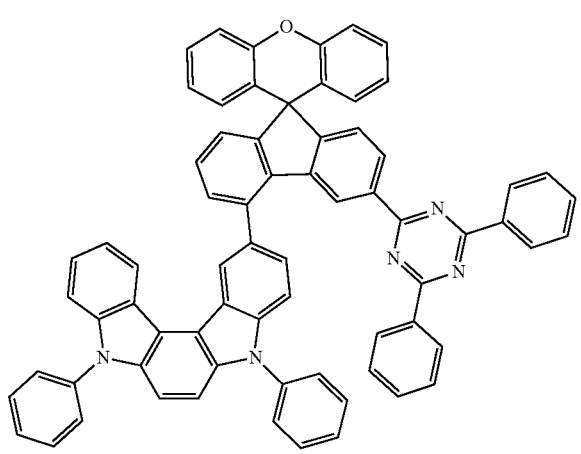
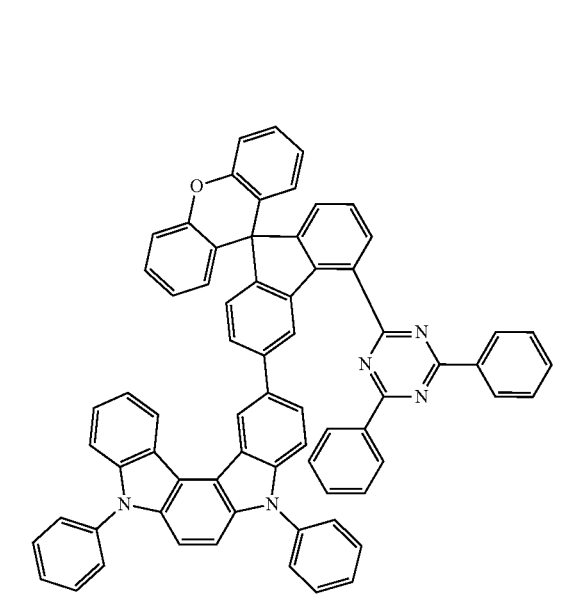
84
-continued
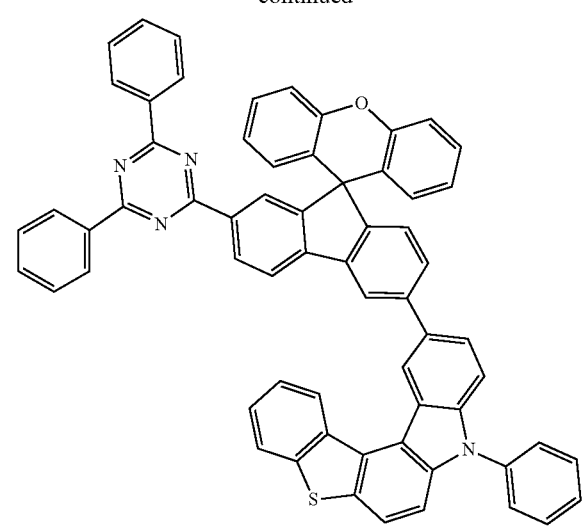
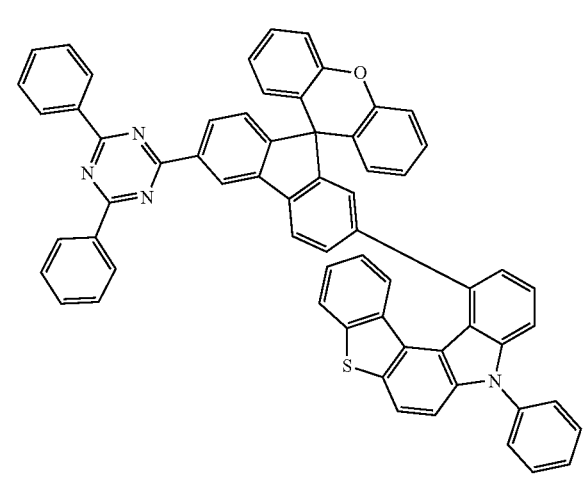
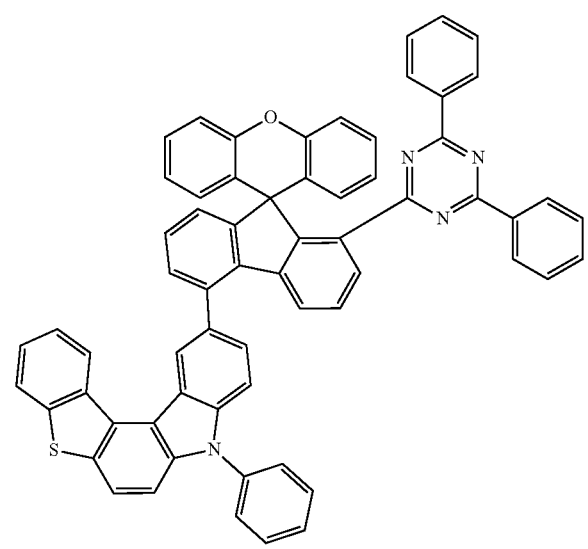

85
-continued
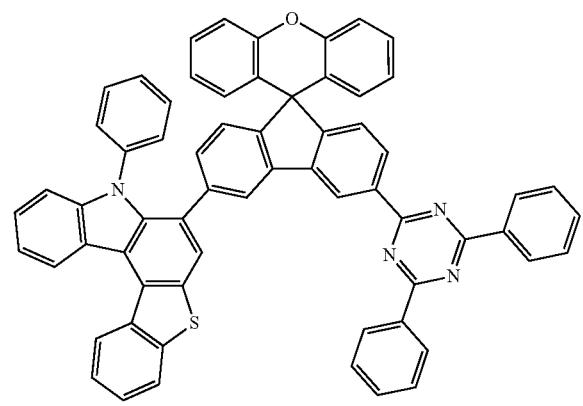
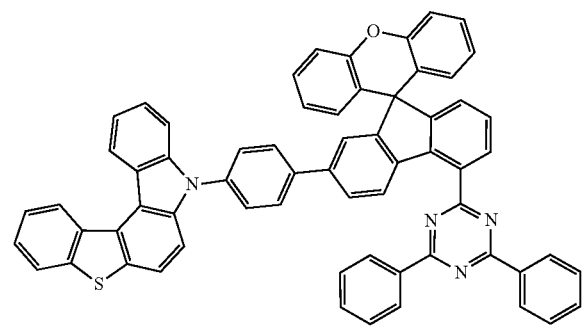
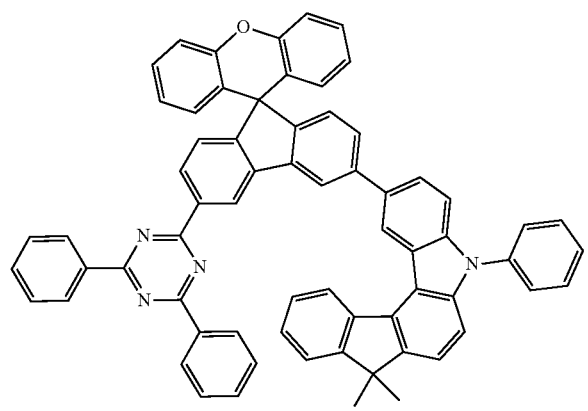
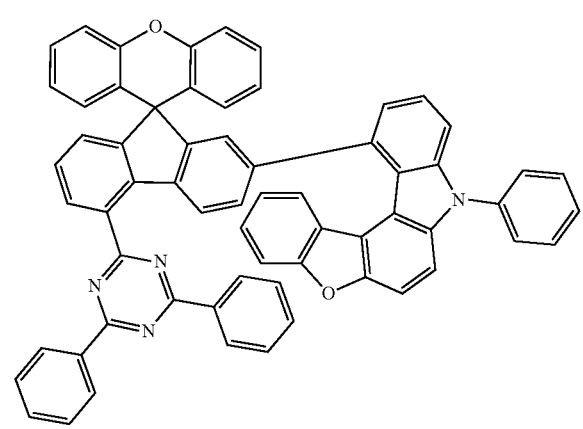
86
-continued
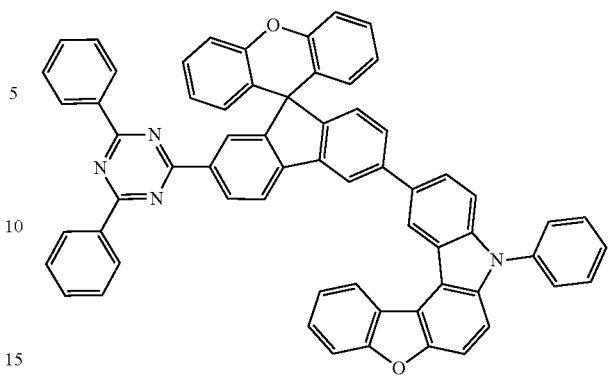
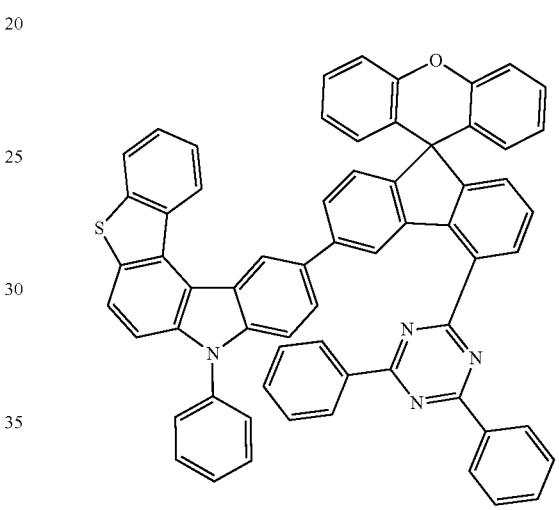
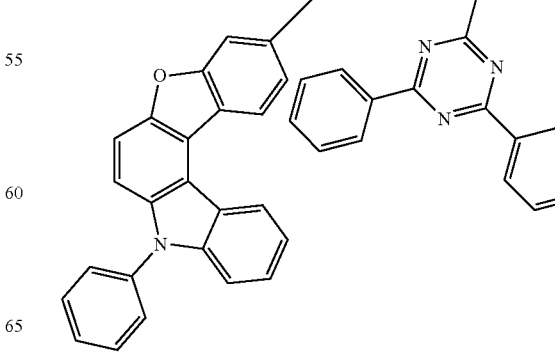

-continued

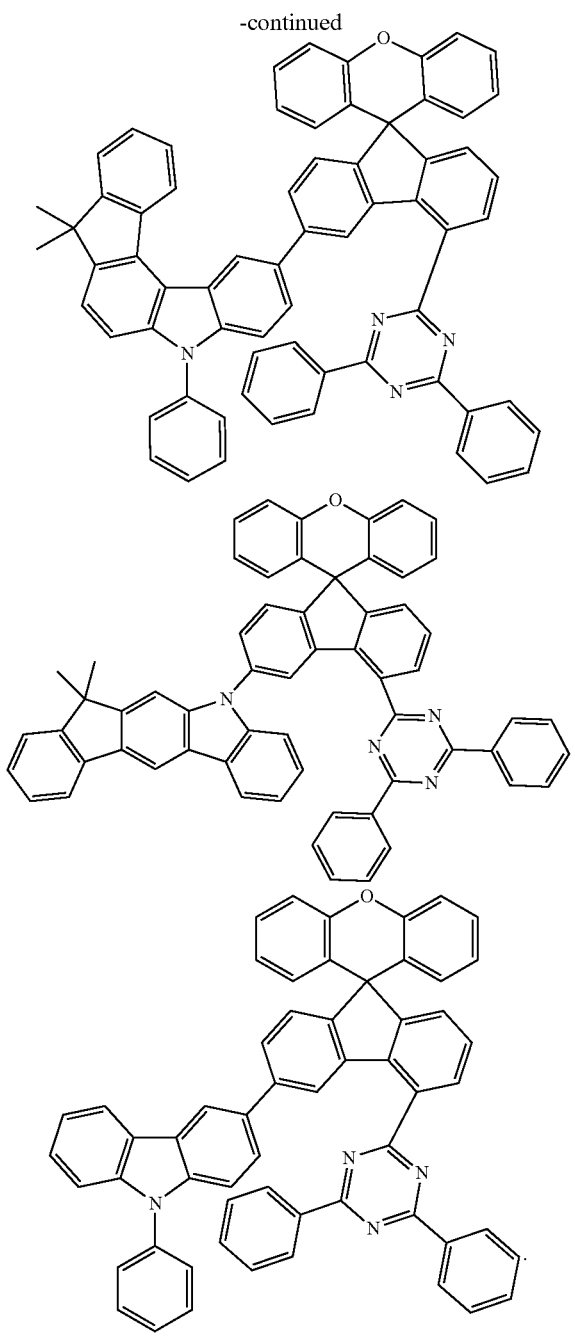

In the present specification, by introducing various substituents to the structure of Chemical Formula 1, compounds having unique properties of the introduced substituents can be synthesized. For example, by introducing substituents normally used as a light emitting layer material and an electron transfer layer material used when manufacturing an organic light emitting device to the core structure, materials satisfying conditions required for each organic material layer can be synthesized.

In addition, by introducing various substituents to the structure of Chemical Formula 1, the energy band gap can be finely controlled, and meanwhile, properties at interfaces between organic materials are enhanced, and material applications can become diverse.

The hetero-cyclic compound according to one embodiment of the present specification can be prepared through a multistep chemical reaction. Some intermediate compounds are prepared first, and the compound of Chemical Formula 1 can be prepared from the intermediate compounds. More specifically, the hetero-cyclic compound according to one embodiment of the present specification can be prepared based on preparation examples to be described below.

Another embodiment of the present specification provides an organic light emitting device comprising the hetero-cyclic compound of Chemical Formula 1.

The organic light emitting device according to one embodiment of the present specification can be manufactured using common organic light emitting device manufacturing methods and materials except that one or more organic material layers are formed using the hetero-cyclic compound described above.

The hetero-cyclic compound can be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

Specifically, the organic light emitting device according to one embodiment of the present specification comprises an anode, a cathode, and one or more organic material layers provided between the anode and the cathode, wherein one or more layers of the organic material layers comprise the hetero-cyclic compound of Chemical Formula 1.

FIG. 1 to FIG. 3 illustrate a lamination order of electrodes and organic material layers of an organic light emitting device according to one embodiment of the present specification. However, the scope of the present specification is not limited to these diagrams, and structures of organic light emitting devices known in the art can also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate can also be obtained.

The organic light emitting device according to the present specification can be manufactured using materials and methods known in the art except that one or more layers of the organic material layers comprise the hetero-cyclic compound of Chemical Formula 1.

The organic material layer of the organic light emitting device of the present specification can be formed in a single layer structure, but can be formed in a multilayer structure in which two or more organic material layers are laminated. For example, the organic light emitting device of the present disclosure can have a structure comprising a hole injection layer, a hole transfer layer, a layer carrying out hole transfer and hole injection at the same time, an electron blocking layer, a light emitting layer, an electron transfer layer, an electron injection layer, a layer carrying out electron transfer and electron injection at the same time, and the like, as the organic material layer. However, the structure of the organic light emitting device is not limited thereto, and can comprise less or more numbers of organic material layers.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present specification is not limited to such a lamination structure, and as necessary, layers other than the light emitting layer may not be included, and other necessary functional layers can be further included. For example, an electron blocking layer (307) can be further included between the hole transfer layer (302) and the light emitting layer (303).

In one embodiment of the present specification, the hetero-cyclic compound of Chemical Formula 1 can form one or more layers of the organic material layers of the organic light emitting device alone. However, as necessary, the hetero-cyclic compound of Chemical Formula 1 can be mixed with other materials to form the organic material layers.

In one embodiment of the present specification, the organic material layer comprises at least one of a hole blocking layer, an electron injection layer and an electron transfer layer, and at least one of the hole blocking layer, the electron injection layer and the electron transfer layer comprises the hetero-cyclic compound.

In one embodiment of the present specification, the organic material layer can comprise an electron transfer layer or an electron injection layer, and the electron transfer layer or the electron injection layer comprises the hetero-cyclic compound.

In one embodiment of the present specification, the organic material layer can comprise a hole injection layer or a hole transfer layer, and the hole injection layer or the hole transfer layer comprises the hetero-cyclic compound.

In one embodiment of the present specification, the organic material layer comprises a light emitting layer, and the light emitting layer comprises the hetero-cyclic compound.

In one embodiment of the present specification, the organic material layer comprises a light emitting layer, and the light emitting layer can comprise the above-described compound as a host of the light emitting layer. As one example, the hetero-cyclic compound of Chemical Formula 1 can be used as a material of a phosphorescent host of the light emitting layer in the organic light emitting device.

In the organic light emitting device according to one embodiment of the present specification, materials other than the hetero-cyclic compound of Chemical Formula 1 are illustrated below, however, these are for illustrative purposes only and not for limiting the scope of the present specification, and can be replaced by materials known in the art.

The anode is an electrode injecting holes, and as the anode material, materials having large work function are normally preferred so that hole injection to an organic material layer is smooth. Specific examples of the anode material that can be used in the present disclosure can comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

The cathode is an electrode injecting electrons, and as the cathode material, materials having small work function are normally preferred so that electron injection to an organic material layer is smooth. Specific examples of the cathode material can comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials can be used, and for example, phthalocyanine compounds such as copper phthalocyanine disclosed in U.S. Pat. No. 4,356,429, or starburst-type amine derivatives such as tris(4-carbazoyl-9-yl-phenyl)amine (TCTA), 4,4',4"-tri[phenyl(m-tolyl)amino]-triphenylamine (m-MTDATA) or 1,3,5-tris[4-(3-methylphenyl-phenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrenesulfonate), polyaniline/camphor sulfonic acid or polyaniline/poly(4-styrene-sulfonate) that are conductive polymers having solubility, and the like, can be used.

As the hole transfer material, pyrazoline derivatives, arylamine-based derivatives, stilbene derivatives, triphenyldiamine derivatives and the like can be used, and low molecular or high molecular materials can also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, can be used, and high molecular materials can also be used as well as low molecular materials.

As examples of the electron injection material, LiF is typically used in the art, however, the present application is not limited thereto.

As the light emitting material, red, green or blue light emitting materials can be used, and as necessary, two or more light emitting materials can be mixed and used. Herein, two or more light emitting materials can be used by being deposited as individual sources of supply or by being premixed and deposited as one source of supply. In addition, fluorescent materials can also be used as the light emitting material, however, phosphorescent materials can also be used. As the light emitting material, materials emitting light by bonding electrons and holes injected from an anode and a cathode, respectively, can be used alone, however, materials having a host material and a dopant material involved in light emission together can also be used.

When mixing light emitting material hosts, same series hosts can be mixed and used, or different series hosts can be mixed and used. For example, any two or more types of materials among n-type host materials or p-type host materials can be selected, and used as a host material of a light emitting layer.

The organic light emitting device according to one embodiment of the present specification can be a top-emission type, a bottom-emission type or a dual-emission type depending on the materials used.

Methods for preparing the compound of Chemical Formula 1 and manufacturing of an organic light emitting device using the same will be specifically described in the following examples. However, the following examples are for illustrative purposes only, and the scope of the present disclosure is not limited thereby.

The compound of the present disclosure was prepared using a Buchwald-Hartwig coupling reaction, a Heck coupling reaction, a Suzuki coupling reaction and the like as a typical reaction, and evaluations on the device were progressed after purifying and the sublimation purifying all the compounds.

<Synthesis Example 1> Synthesis of Compound 1
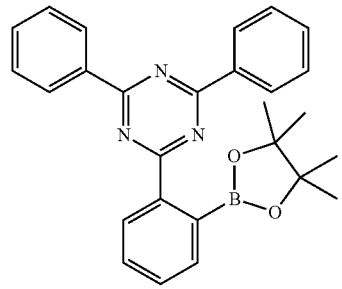
1A
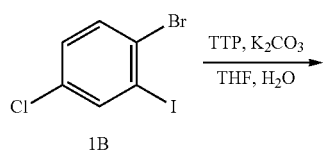
1B
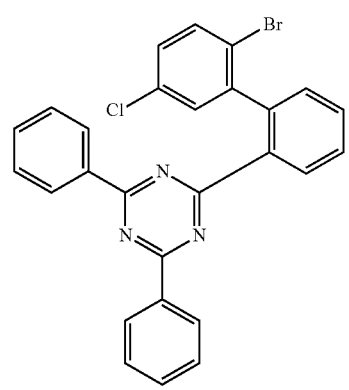
1C
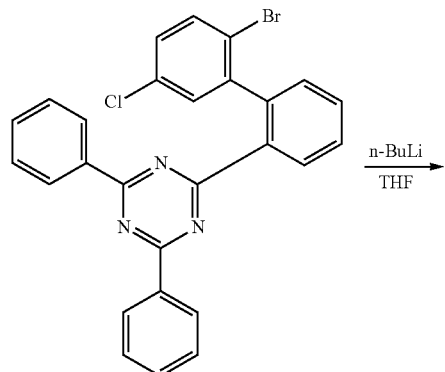
1C
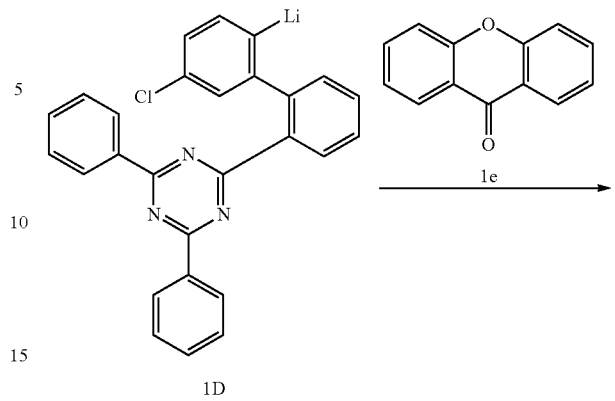
1D
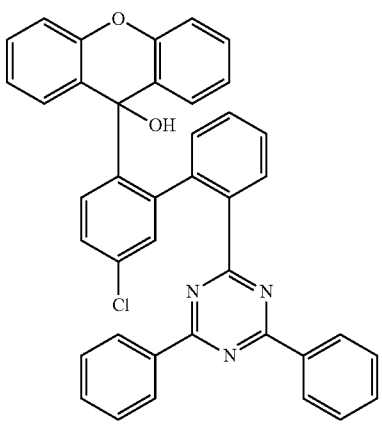
1F
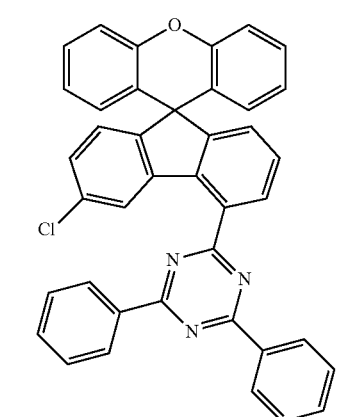
1G -continued

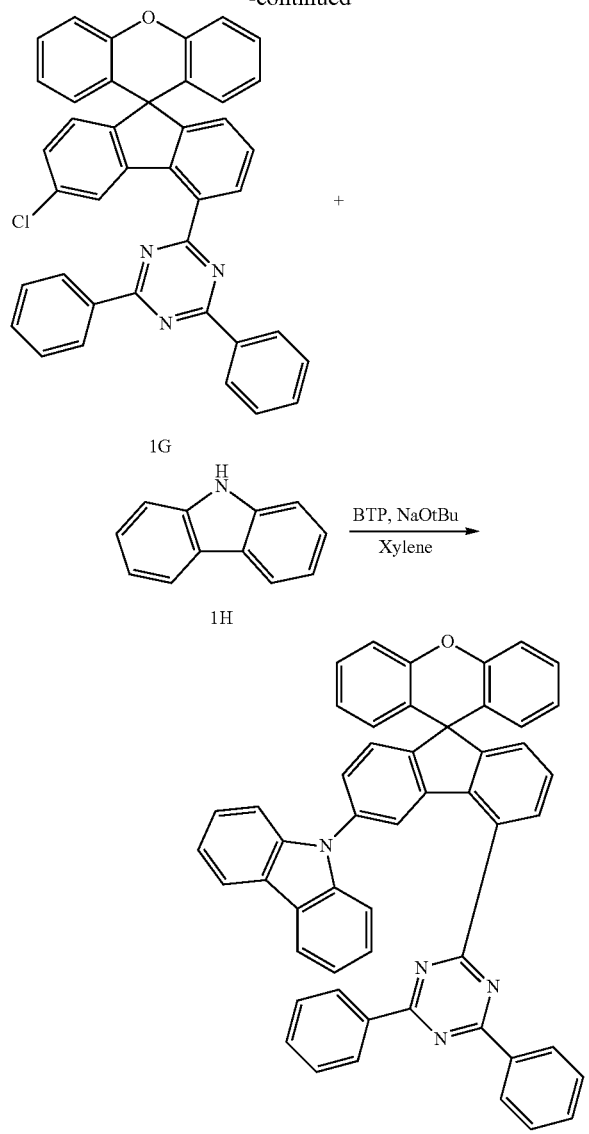

1) Preparation of Chemical Formula 1C

While adding Chemical Formula 1A (50 g, 115 mmol) and Chemical Formula 1B (36 g, 115 mmol) to tetrahydrofuran (THF) (300 ml) and stirring the result under nitrogen atmosphere, potassium carbonate (48 g, 345 mmol) dissolved in water was added thereto.

After that, the result was heated, and tetrakis(triphenylphosphine)palladium(0) (4 g, 3 mmol) was slowly added thereto under reflux. After that, the result was reacted for approximately 9 hours, and the reaction was terminated. After the reaction was terminated, the temperature was lowered to room temperature (25° C.), and the organic layer was separated and then distilled. After that, the distillate was extracted twice with chloroform and water, then the organic layer was vacuum distilled again, and purified using column chromatography (chloroform:hexane) to prepare Chemical Formula 1C (44 g, yield: 77%). MS: [M+H]+=498

2) Preparation of Chemical Formula 1G

Chemical Formula 1C (30.0 g, 60 mmol) was introduced to anhydrous tetrahydrofuran (THF) (500 ml), and cooled to −78° C. After that, while stirring the result, n-butyllithium (29 mL, 72 mmol) was slowly added dropwise thereto over 30 minutes, the result was reacted for 1 hour, the temperature was raised to room temperature (25° C.), and the result was reacted for 1 hour to synthesize Chemical Formula 1D.

After the reaction, the result was cooled back to −78° C., and Chemical Formula 1e (11.8 g, 60 mmol) was added in a solid state a little at a time. After that, the temperature was slowly raised, and after reacting for 2 hours, the reaction was terminated by pouring water thereinto, then the water layer and the organic layer were separated, and the organic layer was vacuum distilled to obtain Chemical Formula 1F.

This was introduced into acetic acid (500 ml) again, and while stirring the result, 1 to 2 drops of sulfuric acid was introduced thereto as a catalyst, and the result was refluxed. After reacting for 2 hours, the produced solids were filtered, the filtered material was dissolved in chloroform again, then neutralized and extracted using water saturated with calcium carbonate, and the organic layer was dried using magnesium sulfate.

After that, the organic layer was vacuum distilled, and recrystallized using ethanol. The produced solids were filtered and then dried to prepare Chemical Formula 1G (21 g, yield: 57%). MS: [M+H]+=598

3) Preparation of Final Compound 1

Chemical Formula 1G (10 g, 17 mmol) and Chemical Formula 1H (3.4 g, 20 mmol) were introduced into xylene (100 ml) under nitrogen atmosphere, and the result was stirred and refluxed. After that, sodium tertiary butoxide (3 g, 33 mmol) was introduced thereto, and after sufficiently stirring the result, bis(tritert-butylphosphine)palladium (0.3 g, 0.5 mmol) was introduced thereinto. The result was stirred and refluxed for 12 hours. When the reaction was completed, the temperature was lowered to room temperature (25° C.), and then the produced solids were filtered. The filtered solids were dissolved in chloroform, washed twice with water, then the organic material layer was separated, anhydrous magnesium sulfate was added thereto, and the result was stirred, then filtered, and the filtrate was vacuum distilled. The concentrate was purified through silica column using chloroform and hexane to prepare final Compound 1 (5 g, yield: 39%), a white solid compound. MS: [M+H]+=729

<Synthesis Example 2> Synthesis of Compound 2

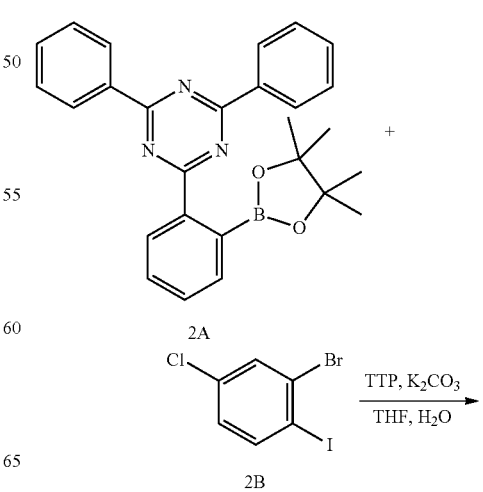

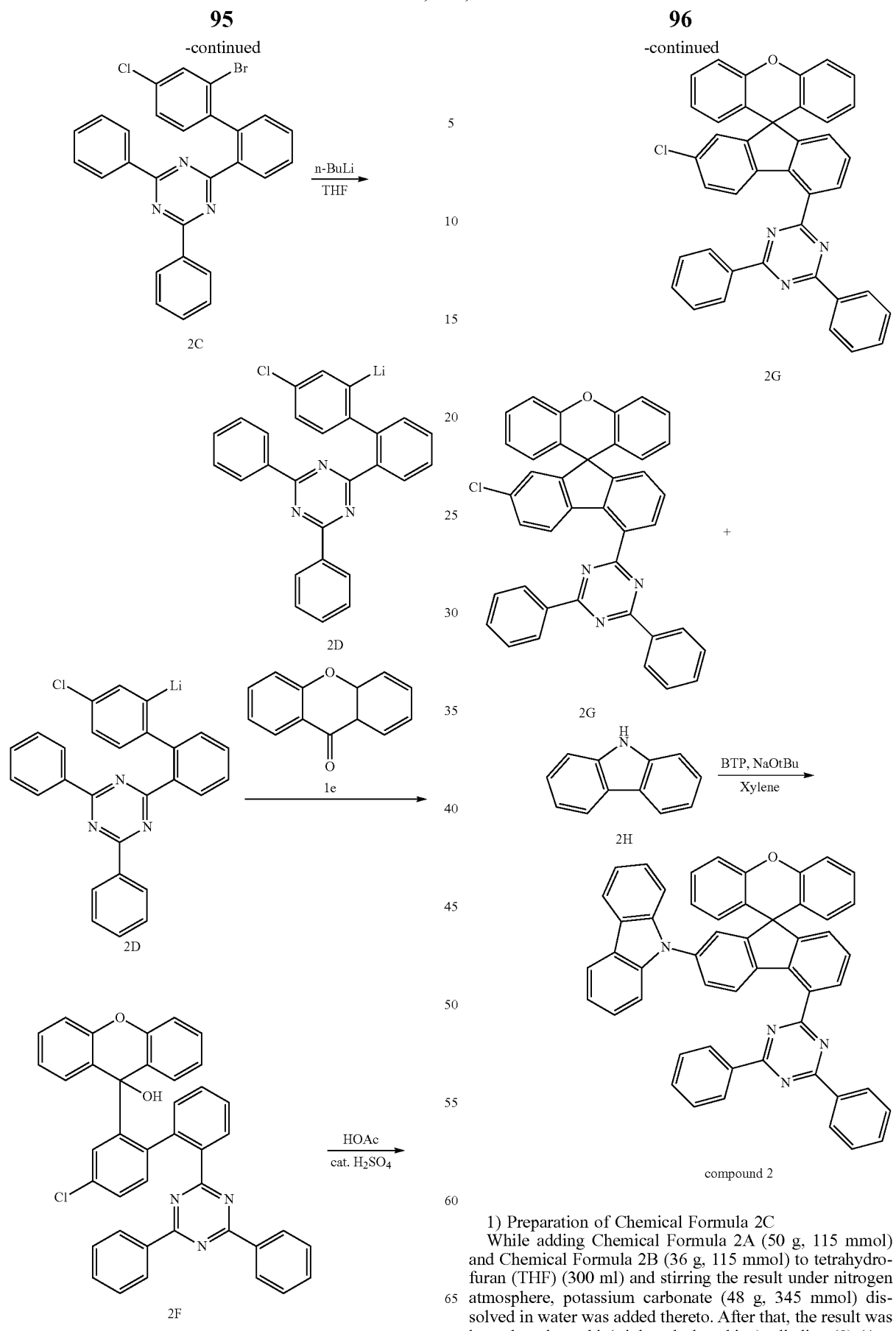
1) Preparation of Chemical Formula 2C
While adding Chemical Formula 2A (50 g, 115 mmol) and Chemical Formula 2B (36 g, 115 mmol) to tetrahydrofuran (THF) (300 ml) and stirring the result under nitrogen atmosphere, potassium carbonate (48 g, 345 mmol) dissolved in water was added thereto. After that, the result was heated, and tetrakis(triphenyl-phosphine)palladium(0) (4 g, 3 mmol) was slowly added thereto under reflux. After that, the result was reacted for approximately 9 hours, and the reaction was terminated. After the reaction was terminated, the temperature was lowered to room temperature (25° C.), and the organic layer was separated and then distilled. After that, the distillate was extracted twice with chloroform and water, then the organic layer was vacuum distilled again, and purified using column chromatography (chloroform:hexane) to prepare Chemical Formula 2C (58 g, yield: 84%). MS: [M+H]+=498

2) Preparation of Chemical Formula 2G

Chemical Formula 2C (30.0 g, 60 mmol) was introduced into anhydrous tetrahydrofuran (THF) (500 ml), and cooled to −78° C. After that, while stirring the result, n-butyllithium (29 mL, 72 mmol) was slowly added dropwise thereto over 30 minutes, the result was reacted for 1 hour, the temperature was raised to room temperature (25° C.), and the result was reacted for 1 hour to synthesize Chemical Formula 2D.

After the reaction, the result was cooled back to −78° C., and Chemical Formula 1e (11.8 g, 60 mmol) was added in a solid state a little at a time. After that, the temperature was slowly raised, and after reacting for 2 hours, the reaction was terminated by pouring water thereinto, then the water layer and the organic layer were separated, and the organic layer was vacuum distilled to obtain Chemical Formula 2F.

This was introduced into acetic acid (500 ml) again, and while stirring the result, 1 to 2 drops of sulfuric acid was introduced thereto as a catalyst, and the result was refluxed. After reacting for 2 hours, the produced solids were filtered, the filtered material was dissolved in chloroform again, then neutralized and extracted using water saturated with calcium carbonate, and the organic layer was dried using magnesium sulfate. After that, the organic layer was vacuum distilled, and recrystallized using ethanol. The produced solids were filtered and then dried to prepare Chemical Formula 2G (24 g, yield: 66%). MS: [M+H]+=598

3) Preparation of Final Compound 2

Chemical Formula 2G (10 g, 17 mmol) and Chemical Formula 2H (3.4 g, 20 mmol) were introduced into xylene (100 ml) under nitrogen atmosphere, and the result was stirred and refluxed. After that, sodium tertiary butoxide (3 g, 33 mmol) was introduced thereto, and after sufficiently stirring the result, bis(tritert-butylphosphine)palladium (0.3 g, 0.5 mmol) was introduced thereto. The result was stirred and refluxed for 12 hours.

When the reaction was completed, the temperature was lowered to room temperature (25° C.), and then the produced solids were filtered. The filtered solids were dissolved in chloroform, washed twice with water, then the organic material layer was separated, anhydrous magnesium sulfate was added thereto, and the result was stirred, then filtered, and the filtrate was vacuum distilled. The concentrate was purified through silica column using chloroform and hexane to prepare final Compound 2 (7 g, yield: 58%), a white solid compound.

MS: [M+H]+=729

<Synthesis Example 3> Synthesis of Compound 3

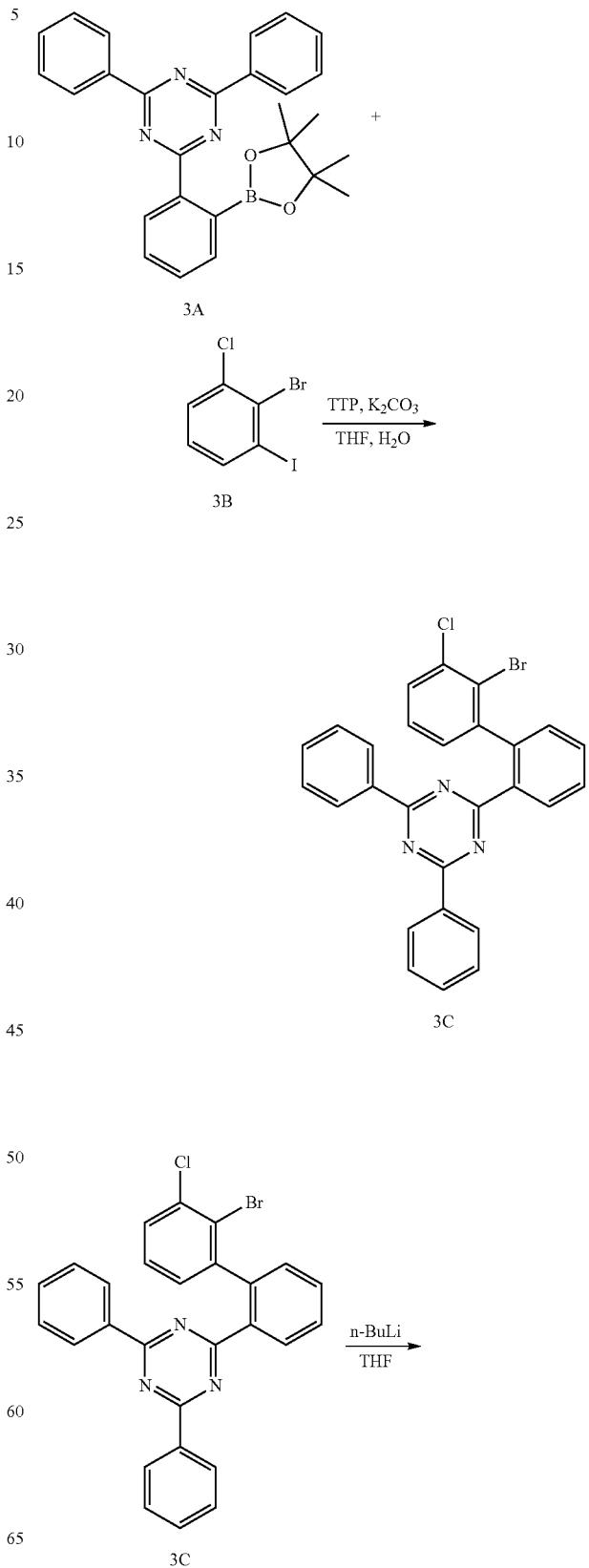

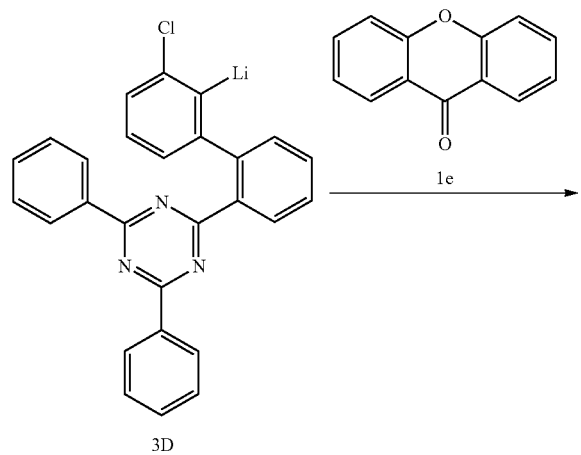

3D

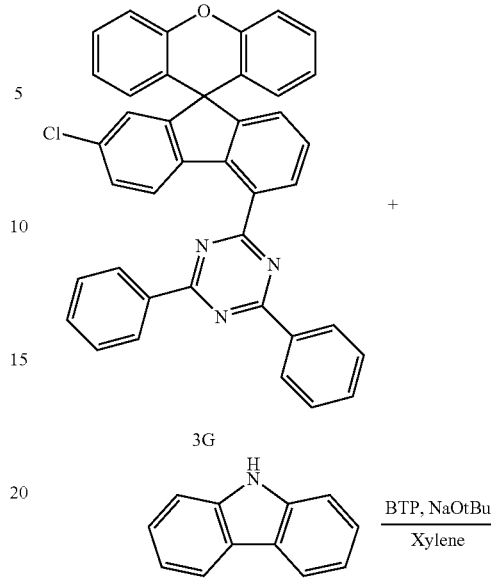

3G

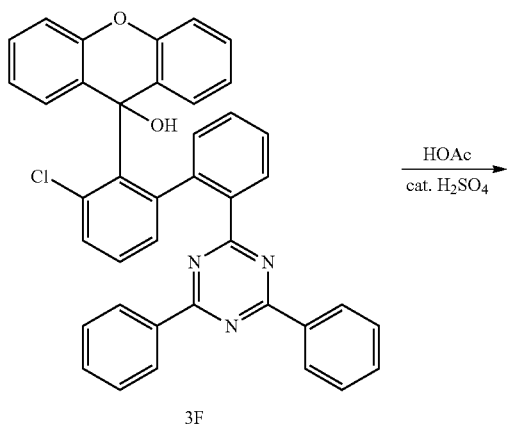

3F

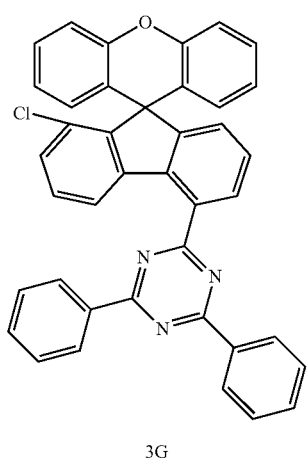

3G

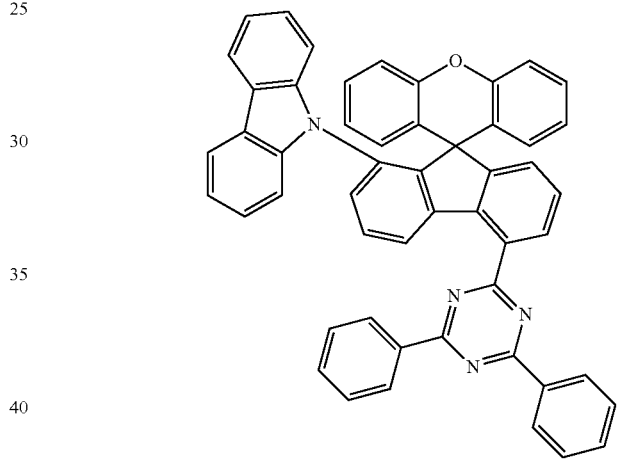

compound 3

1) Preparation of Chemical Formula 3C

While adding Chemical Formula 3A (50 g, 115 mmol) and Chemical Formula 3B (36 g, 115 mmol) to tetrahydrofuran (THF) (300 ml) and stirring the result under nitrogen atmosphere, potassium carbonate (48 g, 345 mmol) dissolved in water was added thereto. After that, the result was heated, and tetrakis(triphenyl-phosphine)palladium(0) (4 g, 3 mmol) was slowly added thereto under reflux. After that, the result was reacted for approximately 9 hours, and the reaction was terminated. After the reaction was terminated, the temperature was lowered to room temperature (25° C.), and the organic layer was separated and then distilled. After that, the distillate was extracted twice with chloroform and water, then the organic layer was vacuum distilled again, and purified using column chromatography (chloroform:hexane) to prepare Chemical Formula 3C (48 g, 70%). MS: [M+H]+=498

2) Preparation of Chemical Formula 3G

Chemical Formula 3C (30.0 g, 60 mmol) was introduced into anhydrous tetrahydrofuran (THF) (500 ml), and cooled to −78° C. After that, while stirring the result, n-butyllithium (29 mL, 72 mmol) was slowly added dropwise thereto over 30 minutes, the result was reacted for 1 hour, the temperature was raised to room temperature (25° C.), and the result was reacted for 1 hour to synthesize Chemical Formula 3D.

After the reaction, the result was cooled back to −78° C., and Chemical Formula 1e (11.8 g, 60 mmol) was added in a solid state a little at a time. After that, the temperature was slowly raised, and after reacting for 2 hours, the reaction was terminated by pouring water thereinto, then the water layer and the organic layer were separated, and the organic layer was vacuum distilled to obtain Chemical Formula 3F. This was introduced into acetic acid (500 ml) again, and while stirring the result, 1 to 2 drops of sulfuric acid was introduced thereto as a catalyst, and the result was refluxed. After reacting for 2 hours, the produced solids were filtered, the filtered material was dissolved in chloroform again, then neutralized and extracted using water saturated with calcium carbonate, and the organic layer was dried using magnesium sulfate. After that, the organic layer was vacuum distilled, and recrystallized using ethanol. The produced solids were filtered and then dried to prepare Chemical Formula 3G (21 g, yield: 57%). MS: [M+H]+=598

3) Preparation of Compound 3

Chemical Formula 3G (10 g, 17 mmol) and Chemical Formula 3H (3.4 g, 20 mmol) were introduced into xylene (100 ml) under nitrogen atmosphere, and the result was stirred and refluxed. After that, sodium tertiary butoxide (3 g, 33 mmol) was introduced thereto, and after sufficiently stirring the result, bis(tritert-butylphosphine)palladium (0.3 g, 0.5 mmol) was introduced thereto. The result was stirred and refluxed for 12 hours. When the reaction was completed, the temperature was lowered to room temperature (25° C.), and then the produced solids were filtered. The filtered solids were dissolved in chloroform, washed twice with water, then the organic material layer was separated, anhydrous magnesium sulfate was added thereto, and the result was stirred, then filtered, and the filtrate was vacuum distilled. The concentrate was purified through silica column using chloroform and hexane to prepare final Compound 3 (5 g, yield: 40%), a white solid compound.

MS: [M+H]+=729

<Synthesis Example 4> Synthesis of Compound 4

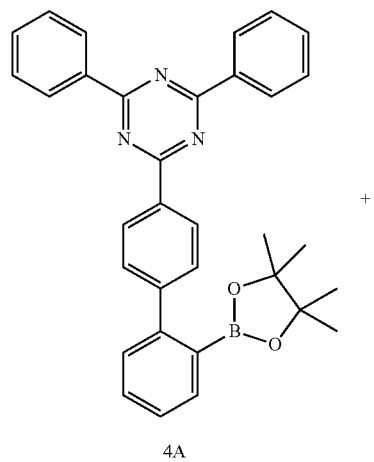

4A

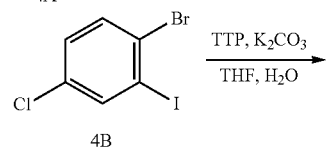

4B

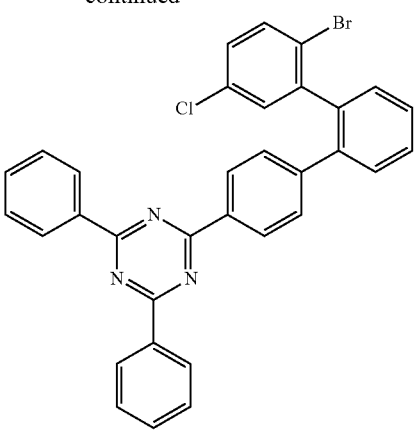

4C

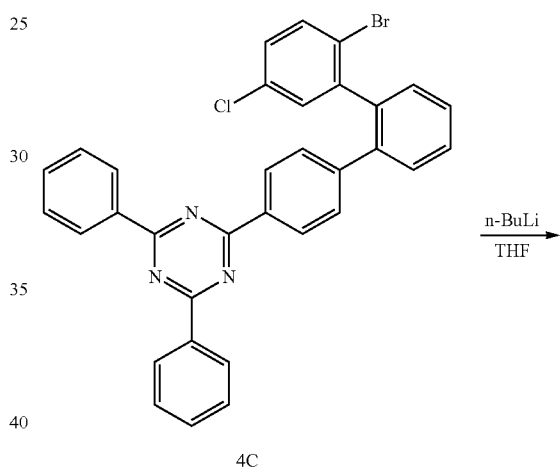

4C

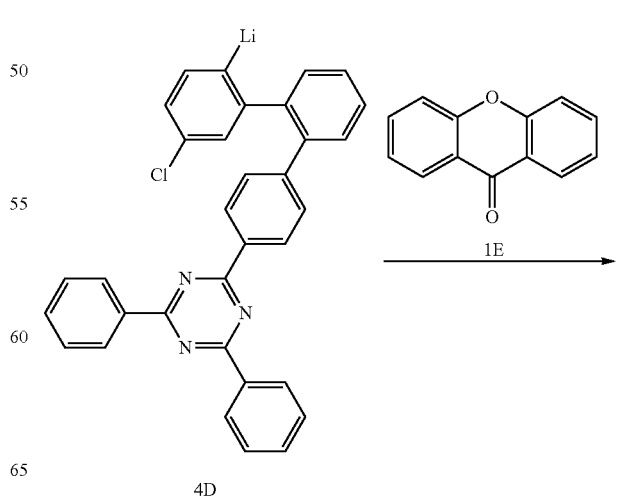

4D

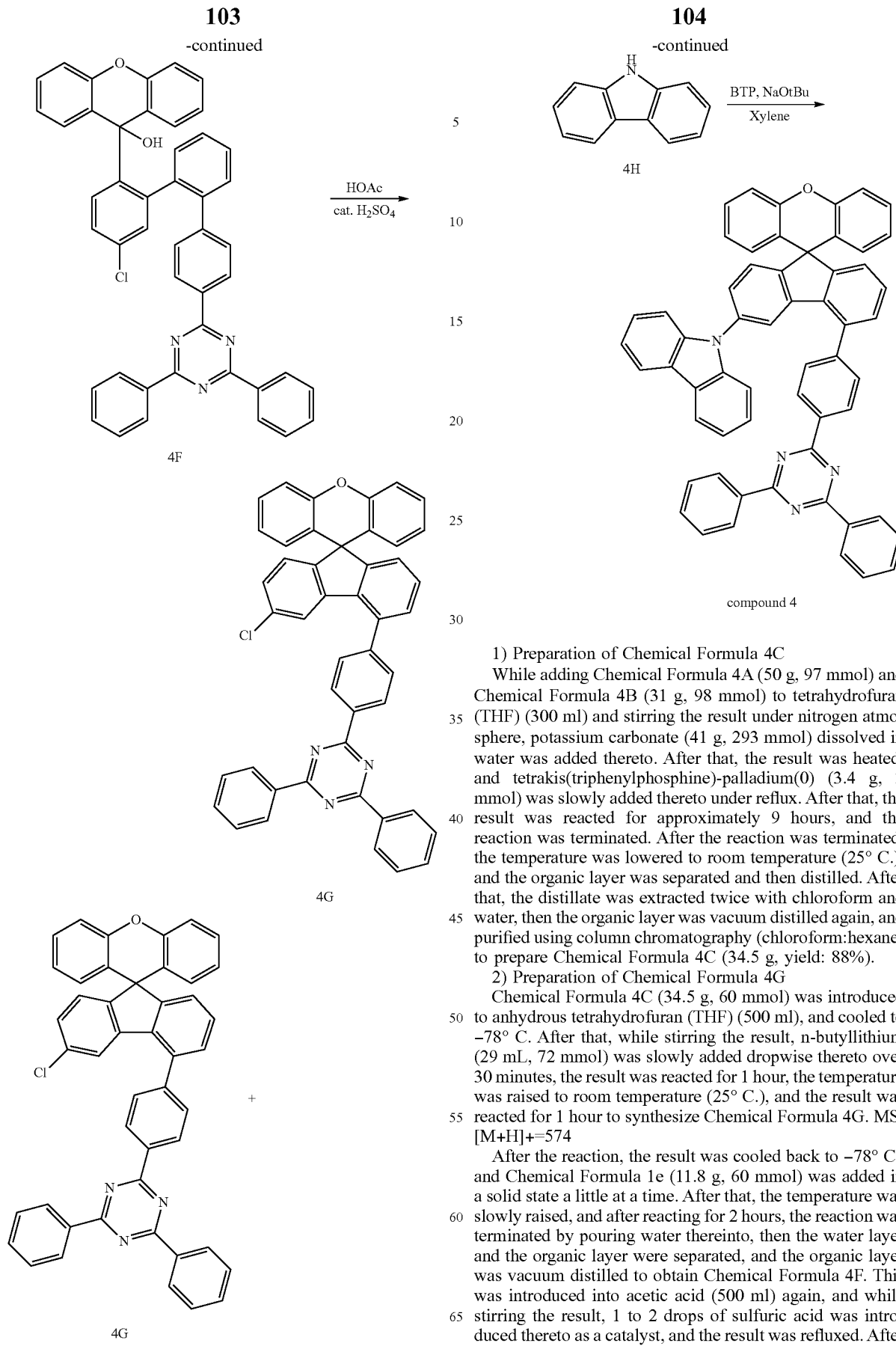

1) Preparation of Chemical Formula 4C

While adding Chemical Formula 4A (50 g, 97 mmol) and Chemical Formula 4B (31 g, 98 mmol) to tetrahydrofuran (THF) (300 ml) and stirring the result under nitrogen atmosphere, potassium carbonate (41 g, 293 mmol) dissolved in water was added thereto. After that, the result was heated, and tetrakis(triphenylphosphine)-palladium(0) (3.4 g, 3 mmol) was slowly added thereto under reflux. After that, the result was reacted for approximately 9 hours, and the reaction was terminated. After the reaction was terminated, the temperature was lowered to room temperature (25° C.), and the organic layer was separated and then distilled. After that, the distillate was extracted twice with chloroform and water, then the organic layer was vacuum distilled again, and purified using column chromatography (chloroform:hexane) to prepare Chemical Formula 4C (34.5 g, yield: 88%).

2) Preparation of Chemical Formula 4G

Chemical Formula 4C (34.5 g, 60 mmol) was introduced to anhydrous tetrahydrofuran (THF) (500 ml), and cooled to −78° C. After that, while stirring the result, n-butyllithium (29 mL, 72 mmol) was slowly added dropwise thereto over 30 minutes, the result was reacted for 1 hour, the temperature was raised to room temperature (25° C.), and the result was reacted for 1 hour to synthesize Chemical Formula 4G. MS: [M+H]+=574

After the reaction, the result was cooled back to −78° C., and Chemical Formula 1e (11.8 g, 60 mmol) was added in a solid state a little at a time. After that, the temperature was slowly raised, and after reacting for 2 hours, the reaction was terminated by pouring water thereinto, then the water layer and the organic layer were separated, and the organic layer was vacuum distilled to obtain Chemical Formula 4F. This was introduced into acetic acid (500 ml) again, and while stirring the result, 1 to 2 drops of sulfuric acid was introduced thereto as a catalyst, and the result was refluxed. After reacting for 2 hours, the produced solids were filtered, the filtered material was dissolved in chloroform again, then neutralized and extracted using water saturated with calcium carbonate, and the organic layer was dried using magnesium sulfate. After that, the organic layer was vacuum distilled, and recrystallized using ethanol. The produced solids were filtered and then dried to prepare Chemical Formula 4G (23.7 g, yield: 66%) MS: [M+H]+=674

3) Preparation of Final Compound 4

Chemical Formula 4G (10 g, 15 mmol) and Chemical Formula 4H (3 g, 17 mmol) were introduced into xylene (100 ml) under nitrogen atmosphere, and the result was stirred and refluxed. After that, sodium tertiary butoxide (3 g, 29 mmol) was introduced thereto, and after sufficiently stirring the result, bis(tritert-butylphosphine)palladium (0.2 g, 0.5 mmol) was introduced thereto. The result was stirred and refluxed for 12 hours. When the reaction was completed, the temperature was lowered to room temperature (25° C.), and then the produced solids were filtered. The filtered solids were dissolved in chloroform, washed twice with water, then the organic material layer was separated, anhydrous magnesium sulfate was added thereto, and the result was stirred, then filtered, and the filtrate was vacuum distilled. The concentrate was purified through silica column using chloroform and hexane to prepare final Compound 4 (7 g, yield: 61%), a white solid compound.

MS: [M+H]+=805

<Synthesis Example 5> Synthesis of Compound 5

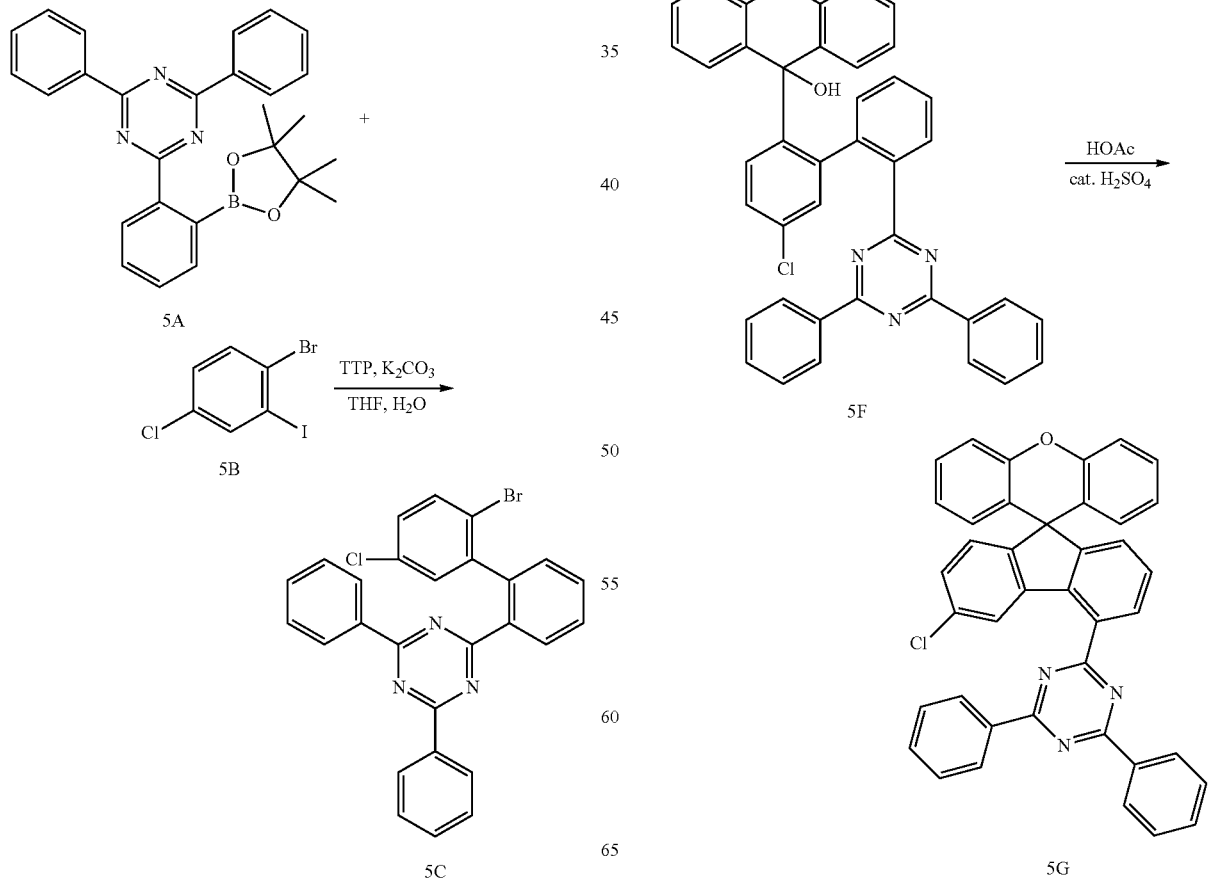

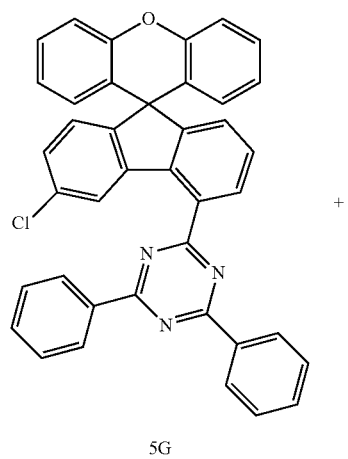

5G

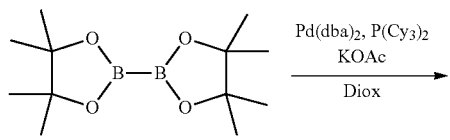
Pd(dba)₂, P(Cy₃)₂
KOAc
Diox

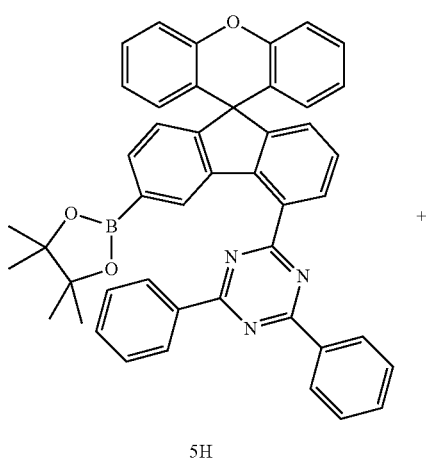

5H

+

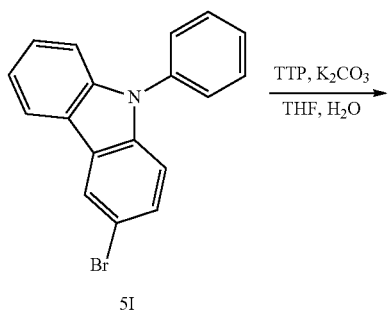

5I

TTP, K₂CO₃
THF, H₂O

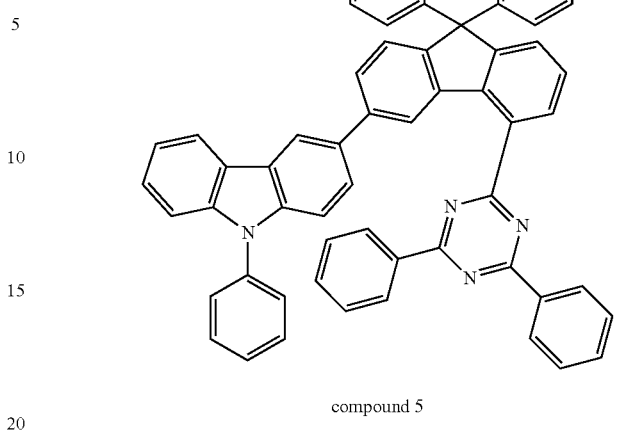

compound 5

1) Preparation of Chemical Formula 5C

While adding Chemical Formula 5A (50 g, 115 mmol) and Chemical Formula 5B (36 g, 115 mmol) to tetrahydrofuran (THF) (300 ml) and stirring the result under nitrogen atmosphere, potassium carbonate (48 g, 345 mmol) dissolved in water was added thereto. After that, the result was heated, and tetrakis(triphenyl-phosphine)palladium(0) (4 g, 3 mmol) was slowly added thereto under reflux. After that, the result was reacted for approximately 9 hours, and the reaction was terminated. After the reaction was terminated, the temperature was lowered to room temperature (25° C.), and the organic layer was separated and then distilled. After that, the distillate was extracted twice with chloroform and water, then the organic layer was vacuum distilled again, and purified using column chromatography (chloroform:hexane) to prepare Chemical Formula 5C (44 g, 77%).

2) Preparation of Chemical Formula 5G

Chemical Formula 5C (30.0 g, 60 mmol) was introduced to anhydrous tetrahydrofuran (THF) (500 ml), and cooled to −78° C. After that, while stirring the result, n-butyllithium (29 mL, 72 mmol) was slowly added dropwise thereto over 30 minutes, the result was reacted for 1 hour, the temperature was raised to room temperature (25° C.), and the result was reacted for 1 hour to synthesize Chemical Formula 5D.

After the reaction, the result was cooled back to −78° C., and Chemical Formula 1e (11.8 g, 60 mmol) was added in a solid state a little at a time. After that, the temperature was slowly raised, and after reacting for 2 hours, the reaction was terminated by pouring water thereinto, then the water layer and the organic layer were separated, and the organic layer was vacuum distilled to synthesize Chemical Formula 5F. This was introduced into acetic acid (500 ml) again, and while stirring the result, 1 to 2 drops of sulfuric acid was introduced thereto as a catalyst, and the result was refluxed. After reacting for 2 hours, the produced solids were filtered, the filtered material was dissolved in chloroform again, then neutralized and extracted using water saturated with calcium carbonate, and the organic layer was dried using magnesium sulfate. After that, the organic layer was vacuum distilled, and recrystallized using ethanol. The produced solids were filtered and then dried to prepare Chemical Formula 5G (21 g, yield: 57%). MS: [M+H]+=598

3) Preparation of Chemical Formula 5H

Under nitrogen atmosphere, Chemical Formula 5G (20 g, 33 mmol), bis(pinacolato)diboron (9.4 g, 37 mmol) and potassium acetate (10 g, 100 mmol) were mixed, added to dioxane (200 ml), and heated while stirring. Under reflux, bis(dibenzylideneacetone)-palladium(0) (1.2 g, 2 mmol) and tricyclohexylphosphine (1.1 g, 4 mmol) were introduced thereto, and the result was heated and stirred for 13 hours. After the reaction was terminated, the temperature was lowered to room temperature (25° C.), and then the result was filtered. Water was poured into the filtrate, the result was extracted with chloroform, and the organic layer was dried with anhydrous magnesium sulfate. The result was vacuum distilled, and then recrystallized with ethanol to prepare Chemical Formula 5H (16 g, yield: 69%). MS: [M+H]+=690

4) Preparation of Final Compound 5

Chemical Formula 5H (10 g, 15 mmol) and Chemical Formula 5I (4.7 g, 15 mmol) were introduced into tetrahydrofuran (THF) (100 ml) under nitrogen atmosphere, and the result was stirred and refluxed. After that, potassium carbonate (6 g, 44 mmol) dissolved in water (20 ml) was introduced thereto, and after sufficiently stirring the result, tetrakistriphenyl-phosphinopalladium (0.5 g, 0.4 mmol) was introduced thereto. After reacting for 8 hours, the temperature was lowered to room temperature (25° C.), and the result was filtered. The filtered material was extracted with chloroform and water, then the organic layer was dried using magnesium sulfate. After that, the organic layer was vacuum distilled, and then recrystallized using ethyl acetate. The produced solids were filtered and then dried to prepare final Compound 5 (7.6 g, yield: 65%).

MS: [M+H]+=805

<Synthesis Example 6> Synthesis of Compound 6

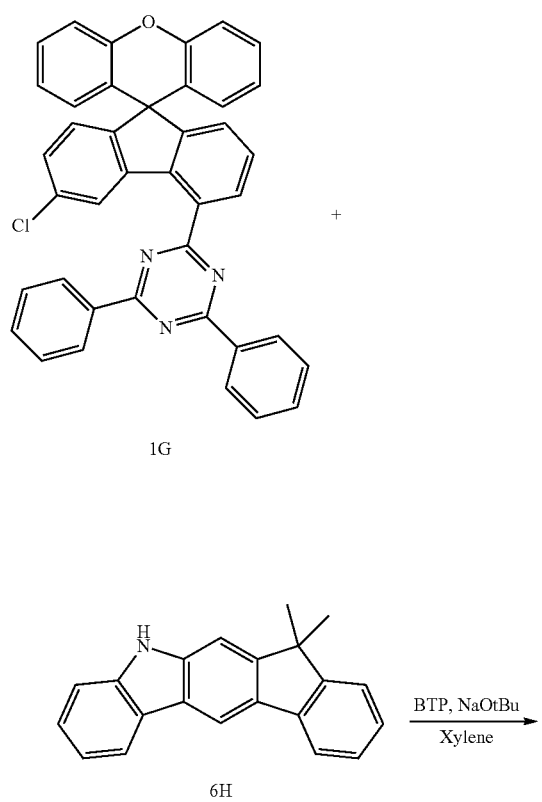

Chemical Formula 1 G (10 g, 17 mmol) synthesized in Synthesis Example 1 and Chemical Formula 6H (5 g, 20 mmol) were introduced into xylene (100 ml) under nitrogen atmosphere, and the result was stirred and refluxed. After that, sodium tertiary butoxide (3 g, 33 mmol) was introduced thereto, and after sufficiently stirring the result, bis(tritert-butylphosphine)palladium (0.3 g, 0.5 mmol) was introduced thereto. The result was stirred and refluxed for 12 hours. When the reaction was completed, the temperature was lowered to room temperature (25° C.), and then the produced solids were filtered. The filtered solids were dissolved in chloroform, washed twice with water, then the organic material layer was separated, anhydrous magnesium sulfate was added thereto, and the result was stirred, then filtered, and the filtrate was vacuum distilled. The concentrate was purified through silica column using chloroform and hexane to prepare Compound 6 (5.5 g, yield: 44%), a white solid compound.

MS: [M+H]+=845

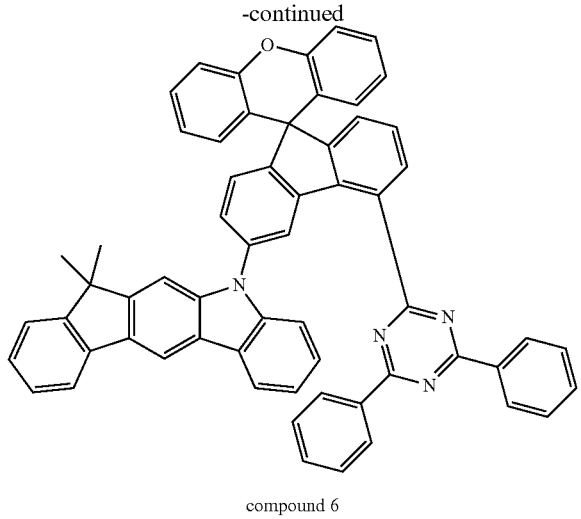

compound 6

EXPERIMENTAL EXAMPLES

Experimental Example 1

A glass substrate on which indium tin oxide (ITO) was coated as a thin film to a thickness of 1,300 Å was placed in distilled water containing dissolved detergent and ultrasonically cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonically cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by thermal vacuum depositing the following HI-1 compound to a thickness of 50 Å. A hole transfer layer was formed on the hole injection layer by thermal vacuum depositing the following HT-1 compound to a thickness of 250 Å, and on the HT-1 deposited film, an electron blocking layer was formed by vacuum depositing the following HT-2 compound to a thickness of 50 Å. On the HT-2 deposited film, a light emitting layer was formed to a thickness of 400 Å by co-depositing Compound 1 prepared above in Synthesis Example 1, the following YGH-1 compound and phosphorescent dopant YGD-1 in a weight ratio of 44:44:12 as the light emitting layer. An electron transfer layer was formed on the light emitting layer by vacuum depositing the following ET-1 compound to a thickness of 250 Å, and on the electron transfer layer, an electron injection layer having a thickness of 100 Å was formed by vacuum depositing the following ET-2 compound and $L_1$ in a weight ratio of 98:2. A cathode was formed on the electron injection layer by depositing aluminum to a thickness of 1000 Å.

HI-1

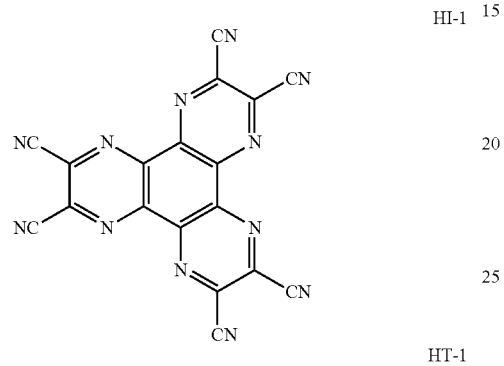

HT-1

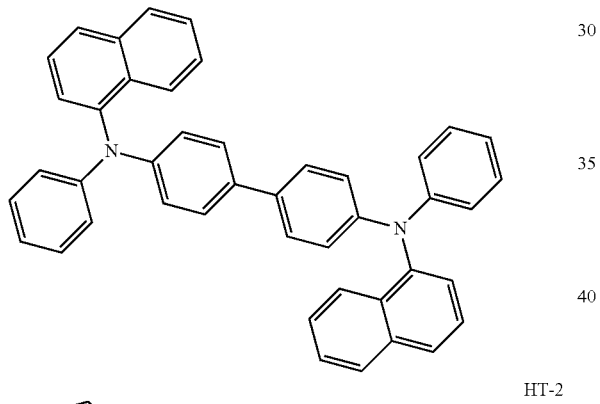

HT-2

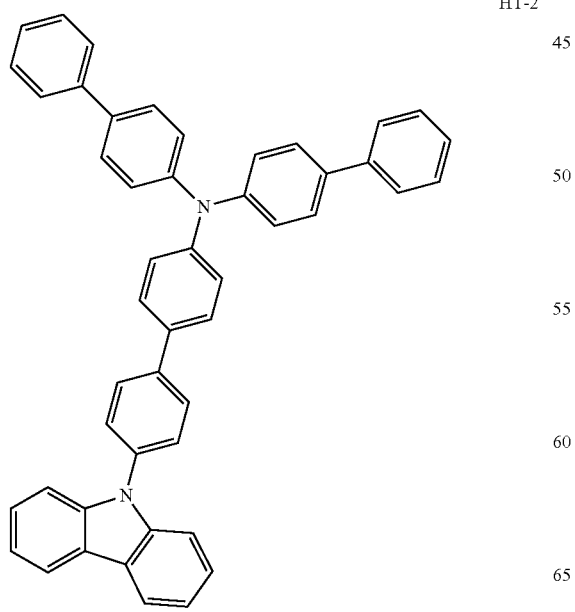

-continued

YGH-1

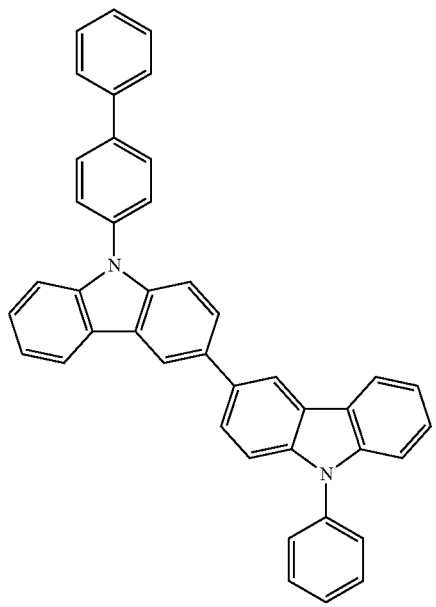

YGD-1

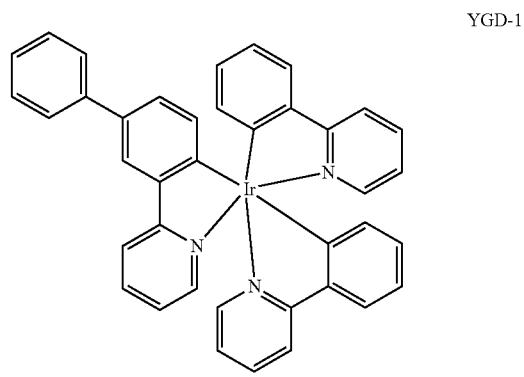

ET-1

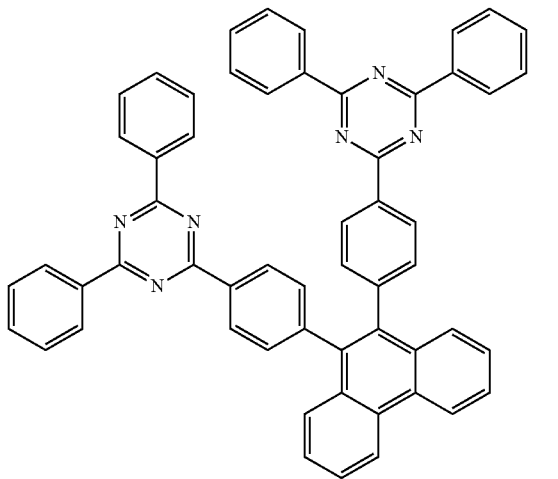

-continued

ET-2

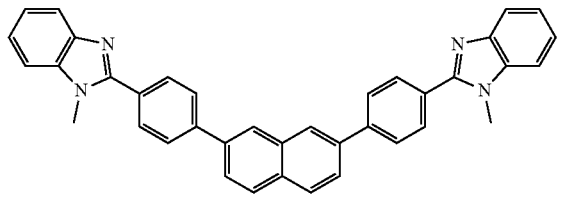

In the above-mentioned processes, the deposition rates of the organic materials were maintained at 0.4 Å/sec to 0.7 Å/sec, the deposition rate of the aluminum was maintained at 2 Å/sec, and the degree of vacuum during the deposition was maintained at $1\times10^{-7}$ torr to $5\times10^{-8}$ torr.

Experimental Examples 2 to 6

Organic light emitting devices were manufactured in the same manner as in Experimental Example 1 except that compounds described in the following Table 1 were each used instead of Compound 1 of Synthesis Example 1 in Experimental Example 1.

Comparative Experimental Examples 1 to 4

Organic light emitting devices were manufactured in the same manner as in Experimental Example 1 except that compounds described in the following Table 1 were each used instead of Compound 1 of Synthesis Example 1 in Experimental Example 1. Compounds of CE1 to CE4 of the following Table 1 are as follows.

CE1

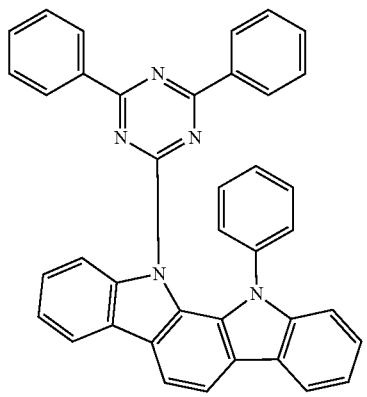

CE2

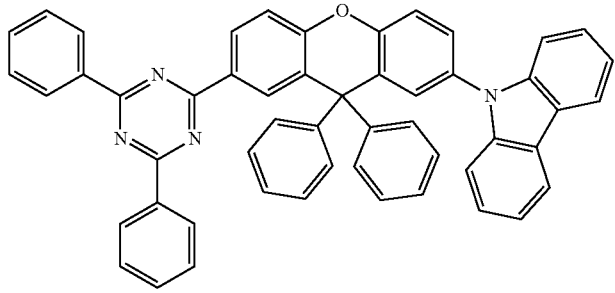

CE3

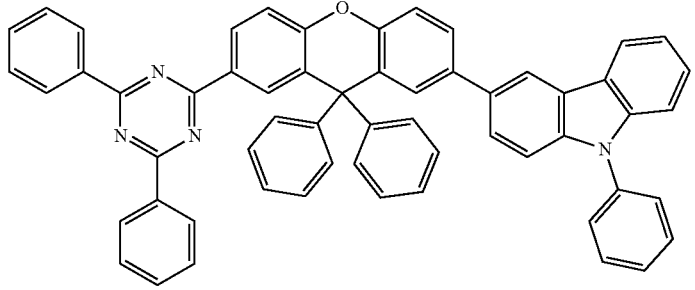

-continued

CE4

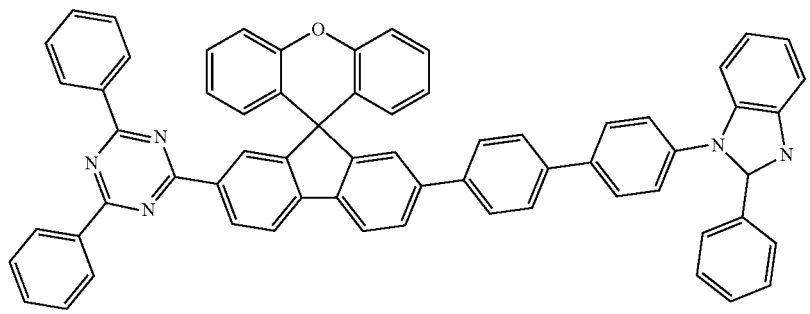

For the organic light emitting devices of the experimental examples and the comparative experimental examples, a voltage and efficiency were measured at current density of 10 mA/cm², and a lifetime was measured at current density of 50 mA/cm², and the results are shown in the following Table 1. Herein, LT95 means times taken to be 95% with respect to initial luminance.

TABLE 1

| Compound | Voltage (V) (@10 mA/cm²) | Efficiency (Cd/A) (@10 mA/cm²) | Color Coordinate (x, y) | Lifetime (h) (LT$_{95}$ at 50 mA/cm²) |
|---|---|---|---|---|
| Experimental Example 1 Compound 1 | 4.1 | 77 | 0.46, 0.54 | 155 |
| Experimental Example 2 Compound 2 | 3.8 | 76 | 0.46, 0.54 | 143 |
| Experimental Example 3 Compound 3 | 3.8 | 79 | 0.46, 0.53 | 126 |
| Experimental Example 4 Compound 4 | 4.0 | 81 | 0.45, 0.52 | 101 |
| Experimental Example 5 Compound 5 | 3.7 | 78 | 0.46, 0.53 | 172 |
| Experimental Example 6 Compound 6 | 3.7 | 77 | 0.45, 0.52 | 180 |
| Comparative Experimental Example 1 CE1 | 4.0 | 70 | 0.46, 0.53 | 90 |
| Comparative Experimental Example 2 CE2 | 4.6 | 75 | 0.44, 0.55 | 12 |
| Comparative Experimental Example 3 CE3 | 4.7 | 71 | 0.46, 0.52 | 15 |
| Comparative Experimental Example 4 CE4 | 4.4 | 51 | 0.46, 0.51 | 7 |

CE1 is a compound having a core structure completely different from Chemical Formula 1, CE2 and CE3 are compounds in which an N-containing monocyclic ring substitutes a benzene ring adjacent to an oxygen atom of the core structure. By the N-containing monocyclic ring of Chemical Formula 1 of the present application substituting a benzene ring that is not adjacent to an oxygen atom of the core structure, excellent efficiency and lifetime properties are obtained. CE4 is a compound substituted with benzimidazole instead of Chemical Formula 2 of Chemical Formula 1.

As shown in Table 1, it was identified that, when using the compound of the present disclosure as a light emitting layer material, excellent properties were obtained in terms of efficiency and lifetime compared to the comparative experimental examples. This indicates that materials between the electron transfer unit and the carbazole have excellent bonding stability through a fluorene group of the xanthene unit, and excellent efficiency and lifetime are obtained in the device.

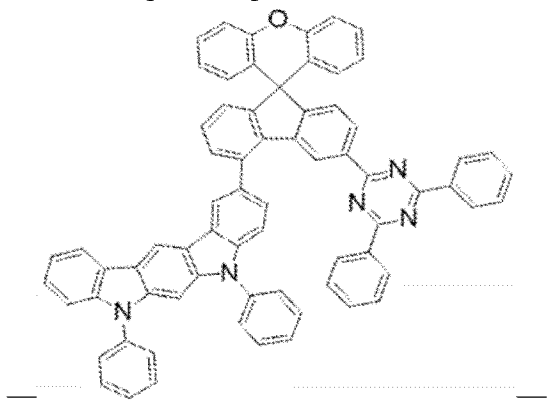

The invention claimed is:

1. A hetero-cyclic compound of Chemical Formula 1:

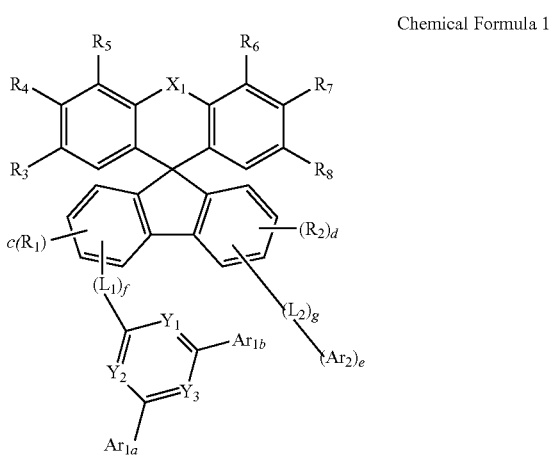

Chemical Formula 1 wherein, in Chemical Formula 1:

$X_1$ is O or S;

$L_1$ and $L_2$ are the same as or different from each other, and each independently is a direct bond, a substituted or unsubstituted $C_6$ to $C_{60}$ arylene group, or a substituted or unsubstituted $C_2$ to $C_{60}$ heteroarylene group;

two or more of $Y_1$ to $Y_3$ are N, and the remaining is $CR_9$;

$Ar_{1a}$ and $Ar_{1b}$ are the same as or different from each other, and each independently is a substituted or unsubstituted $C_6$ to $C_{60}$ aryl group; or a substituted or unsubstituted $C_2$ to $C_{60}$ heteroaryl group;

$Ar_2$ is one of the following Chemical Formula 2 or 3:

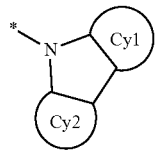

Chemical Formula 2

Chemical Formula 3

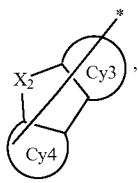

wherein:

Cy1 to Cy4 are the same as or different from each other, and each independently is a substituted or unsubstituted $C_6$ to $C_{60}$ aromatic hydrocarbon ring or a substituted or unsubstituted $C_2$ to $C_{60}$ aromatic heteroring;

$X_2$ is O, S, $NR_{10}$ or $CR_{11}R_{12}$;

$R_1$ to $R_8$ and $R_{10}$ to $R_{12}$ are the same as or different from each other, and each independently is hydrogen, deuterium, a halogen group, a cyano group, a nitro group, an amino group, a substituted or unsubstituted $C_1$ to $C_{60}$ alkyl group, a substituted or unsubstituted $C_1$ to $C_{60}$ haloalkyl group, a substituted or unsubstituted $C_1$ to $C_{60}$ alkoxy group, a substituted or unsubstituted $C_1$ to $C_{60}$ haloalkoxy group, a substituted or unsubstituted $C_3$ to $C_{60}$ cycloalkyl group, a substituted or unsubstituted $C_2$ to $C_{60}$ alkenyl group, a substituted or unsubstituted $C_6$ to $C_{60}$ aryl group, a substituted or unsubstituted $C_6$ to $C_{60}$ aryloxy group, or a substituted or unsubstituted $C_2$ to $C_{60}$ heteroaryl group;

$R_9$ is hydrogen or deuterium;

* is a site bonding to $L_2$ of Chemical Formula 1;

c and d are each an integer of 0 to 3;

e is an integer of 1 or 2;

f and g are each 1;

when c is 2 or greater, the $R_1$s are the same as or different from each other;

when d is 2 or greater, the $R_2$s are the same as or different from each other; and when e is 2, the $Ar_2$s are the same as or different from each other.

2. The hetero-cyclic compound of claim 1, wherein Chemical Formula 2 is any one of the following structural formulae:

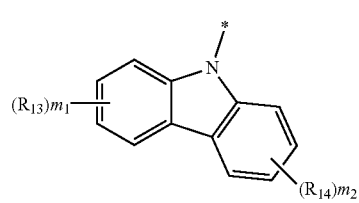

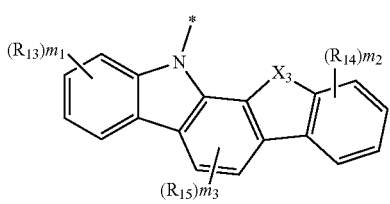

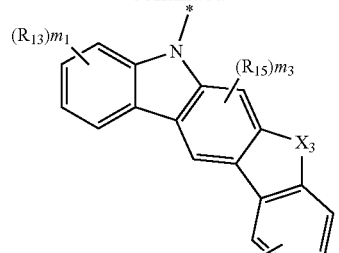

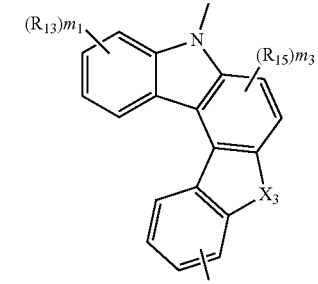

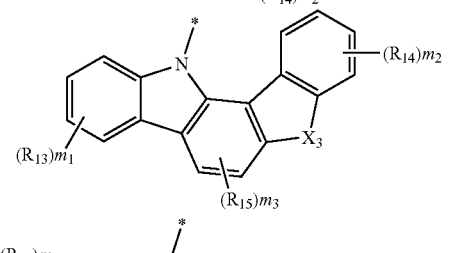

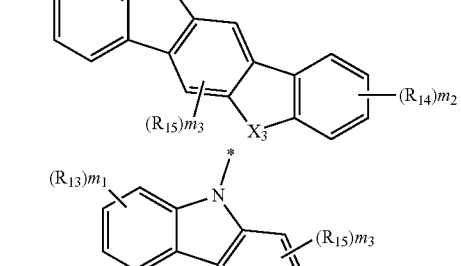

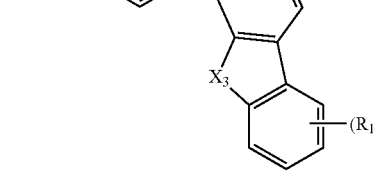

wherein in the structural formulae:
$X_3$ is O, S, $NR_{16}$ or $CR_{17}R_{18}$;
* is a site bonding to $L_2$ of Chemical Formula 1;
$R_{13}$ to $R_{18}$ are the same as or different from each other, and each independently is hydrogen, deuterium, a halogen group, a cyano group, a nitro group, an amino group, a substituted or unsubstituted $C_1$ to $C_{60}$ alkyl group, a substituted or unsubstituted $C_1$ to $C_{60}$ haloalkyl group, a substituted or unsubstituted $C_1$ to $C_{60}$ alkoxy group, a substituted or unsubstituted $C_1$ to $C_{60}$ haloalkoxy group, a substituted or unsubstituted $C_3$ to $C_{60}$ cycloalkyl group, a substituted or unsubstituted $C_2$ to $C_{60}$ alkenyl group, a substituted or unsubstituted $C_6$ to $C_{60}$ aryl group, a substituted or unsubstituted $C_6$ to $C_{60}$ aryloxy group, or a substituted or unsubstituted $C_2$ to $C_{60}$ heteroaryl group;

m1 and m2 are each an integer of 0 to 4;

m3 is an integer of 0 to 2;

when m1 is 2 or greater, the $R_{13}$s are the same as or different from each other;

when m2 is 2 or greater, the $R_{14}$s are the same as or different from each other; and when m3 is 2, the $R_{15}$s are the same as or different from each other.

3. The hetero-cyclic compound of claim 1, wherein Chemical Formula 3 is any one of the following structural formulae:

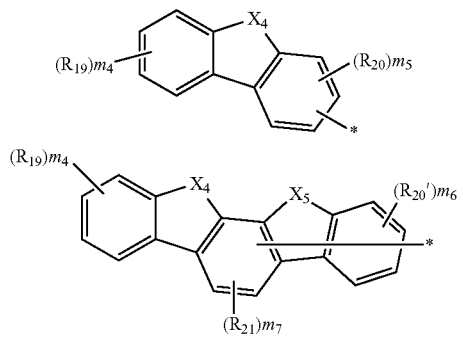
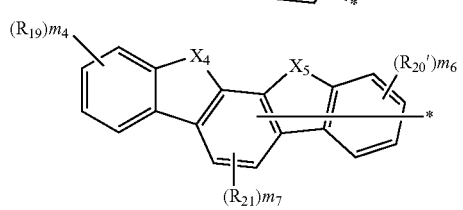
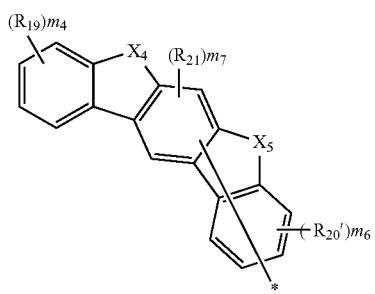
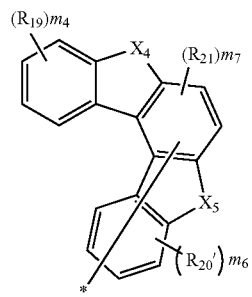
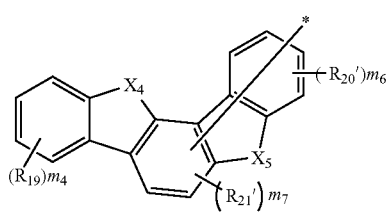
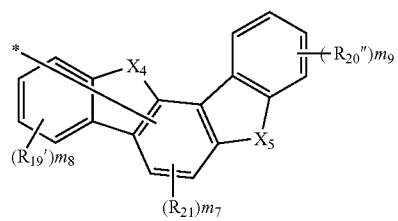
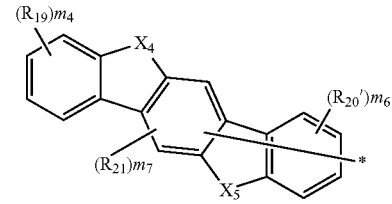
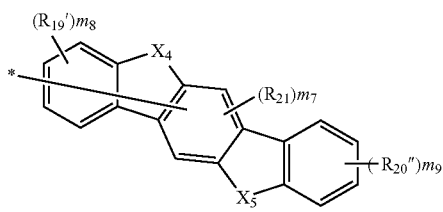
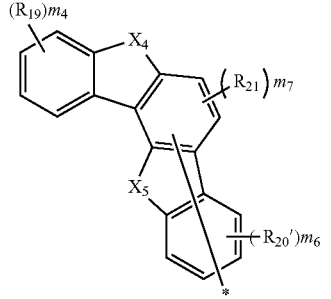
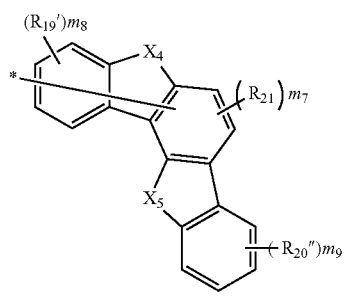

wherein in the structural formulae:

* is a site bonding to $L_2$ of Chemical Formula 1;

$X_4$ and $X_5$ are the same as or different from each other, and each independently is O, S, $NR_{22}$ or $CR_{23}R_{24}$;

$R_{19}$ to $R_{24}$, $R_{19}'$, $R_{20}'$ and $R_{20}''$ are the same as or different from each other, and each independently is hydrogen, deuterium, a halogen group, a cyano group, a nitro group, an amino group, a substituted or unsubstituted $C_1$ to $C_{60}$ alkyl group, a substituted or unsubstituted $C_1$ to $C_{60}$ haloalkyl group, a substituted or unsubstituted $C_1$ to $C_{60}$ alkoxy group, a substituted or unsubstituted $C_1$ to $C_{60}$ haloalkoxy group, a substituted or unsubstituted $C_3$ to $C_{60}$ cycloalkyl group, a substituted or unsubstituted $C_2$ to $C_{60}$ alkenyl group, a substituted or unsubstituted $C_6$ to $C_{60}$ aryl group, a substituted or unsubstituted $C_6$ to $C_{60}$ aryloxy group, or a substituted or unsubstituted $C_2$ to $C_{60}$ heteroaryl group;

m4, m6, m8 and m9 are each an integer of 0 to 4;

m5 is an integer of 0 to 3;

m7 is an integer of 0 to 2;

when m4 is 2 or greater, the $R_{19}$s are the same as or different from each other;

when m5 is 2 or greater, the $R_{20}$s are the same as or different from each other;

when m6 is 2 or greater, the $R_{20}$'s are the same as or different from each other;

when m7 is 2, the $R_{21}$s are the same as or different from each other;

when m8 is 2 or greater, the $R_{19}$'s are the same as or different from each other;

when m9 is 2 or greater, the $R_{20}$"s are the same as or different from each other;

m6+m7≤5; and m7+m8≤5.

4. The hetero-cyclic compound of claim 1, wherein Chemical Formula 1 is any one of the following Chemical Formulae 4 to 11:

Chemical Formula 4

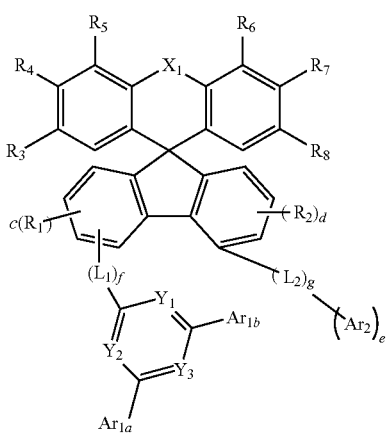

Chemical Formula 5

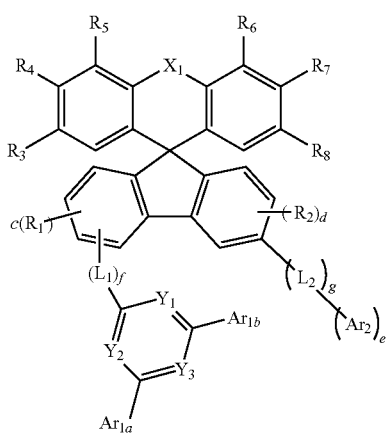

Chemical Formula 6

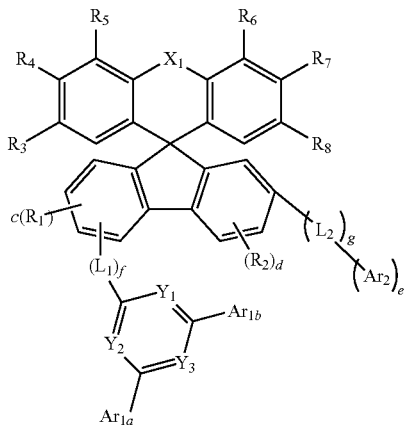

Chemical Formula 7

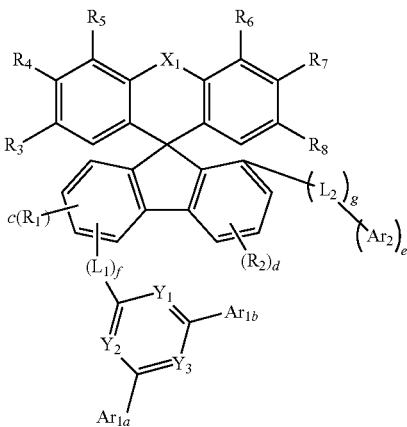

Chemical Formula 8

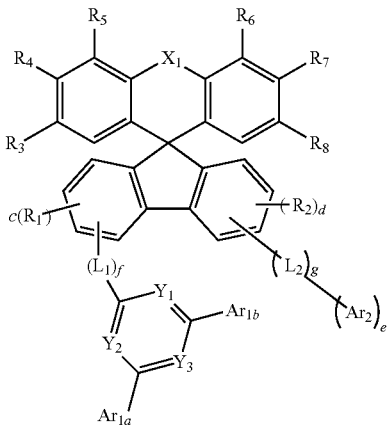

-continued

Chemical Formula 9

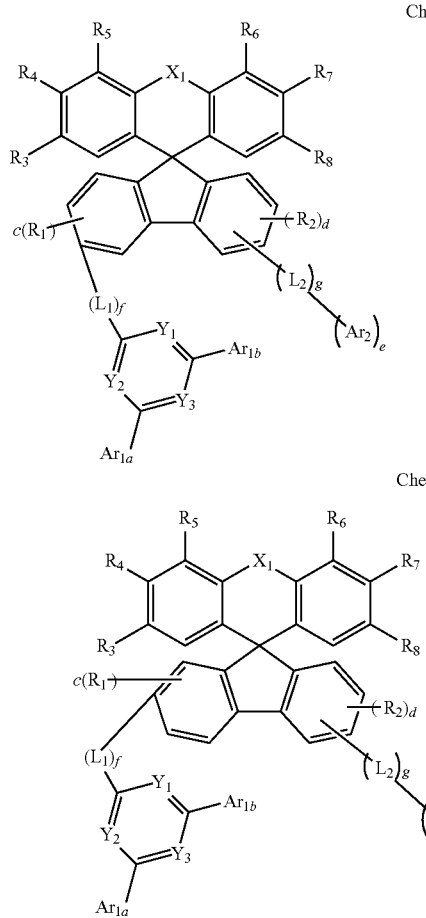

Chemical Formula 10

Chemical Formula 11

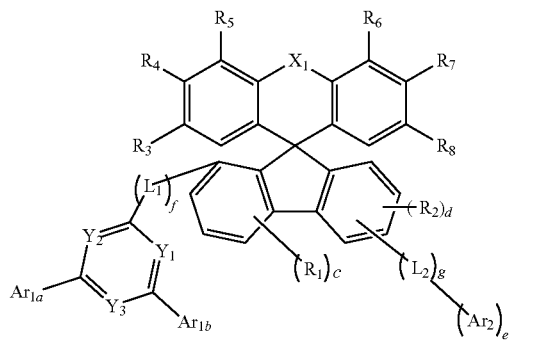

wherein in Chemical Formulae 4 to 11:

$R_1$ to $R_8$, $L_1$, $L_2$, $Ar_{1a}$, $Ar_{1b}$, $Ar_2$, $X_1$, $Y_1$ to $Y_3$ and c to g have the same definitions as in Chemical Formula 1.

5. The hetero-cyclic compound of claim 1, wherein $Ar_{1a}$ and $Ar_{1b}$ are the same as or different from each other, and each independently is a substituted or unsubstituted $C_6$ to $C_{60}$ aryl group.

6. The hetero-cyclic compound of claim 1, wherein Chemical Formula 1 is any one of the following compounds:

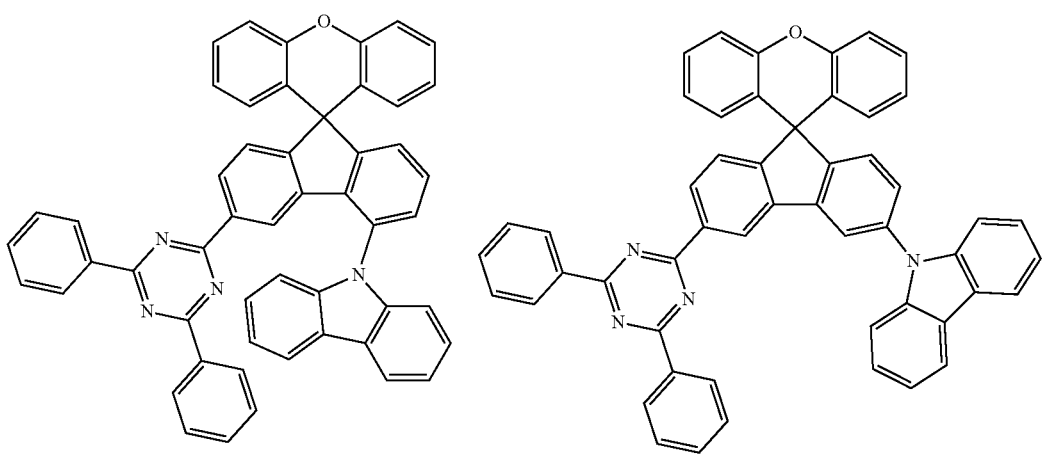

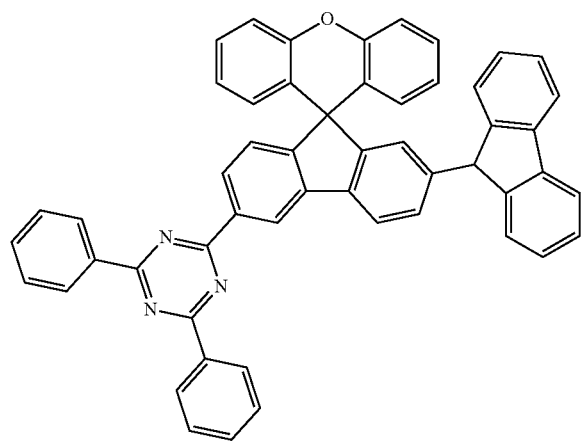
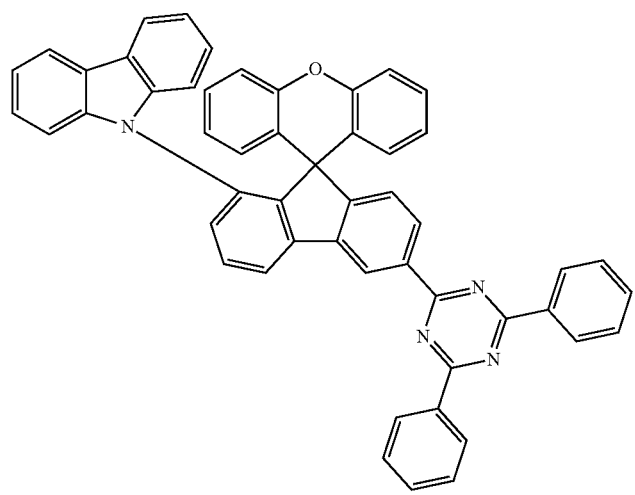
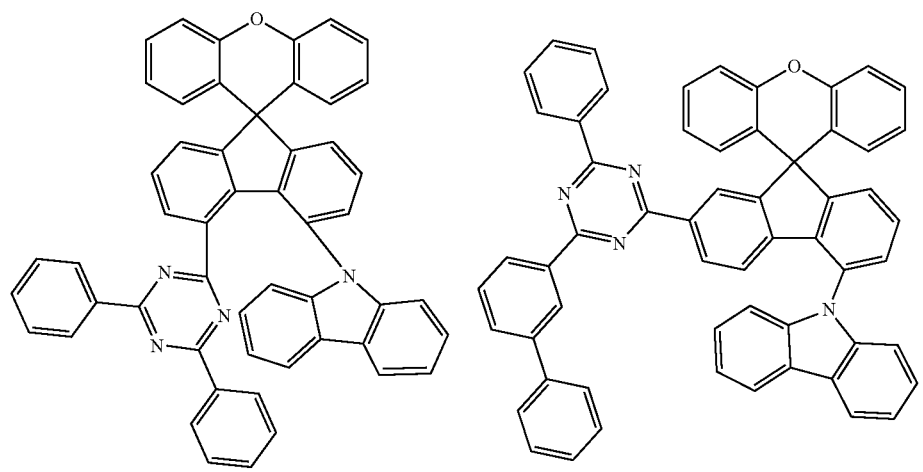

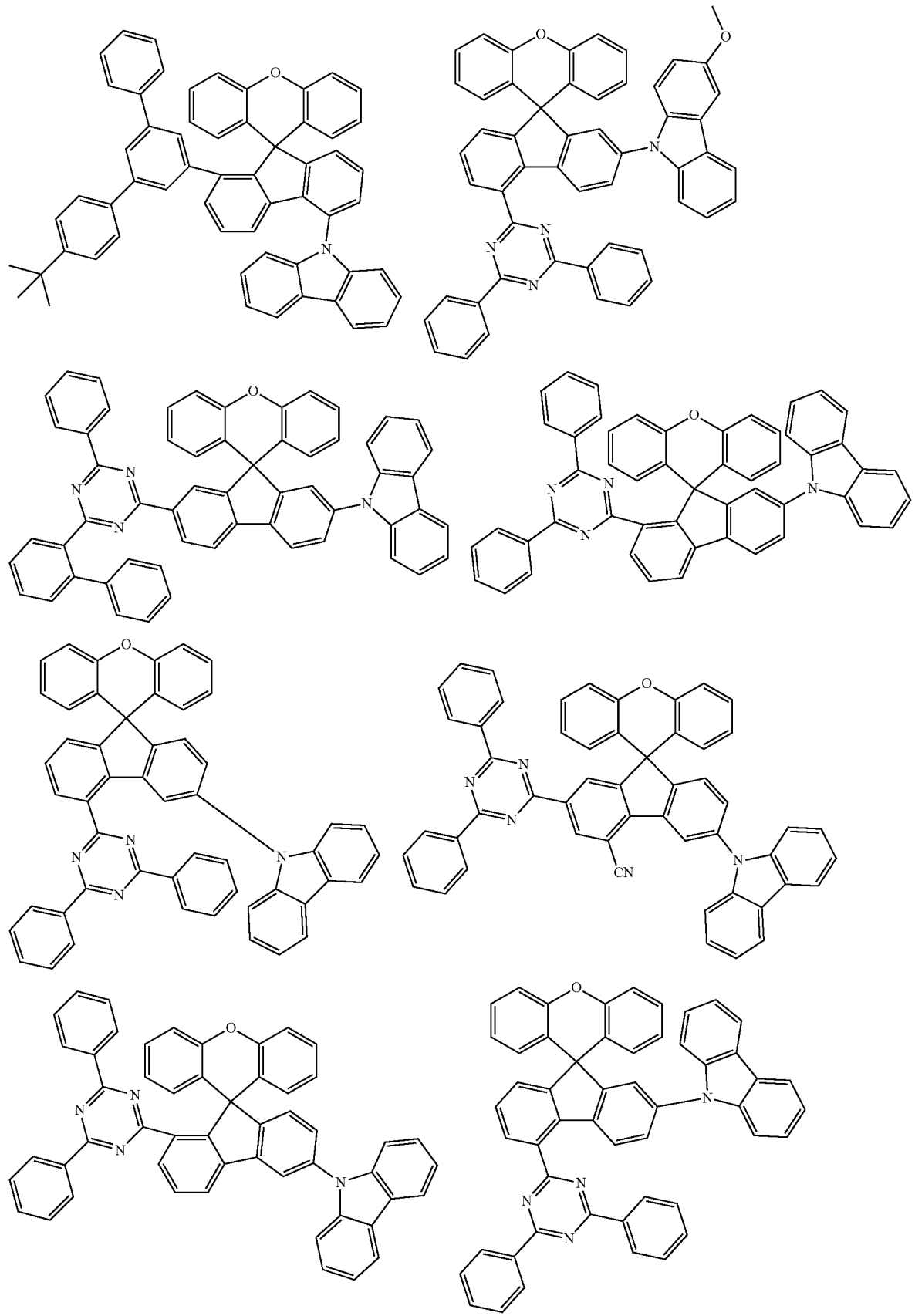

-continued
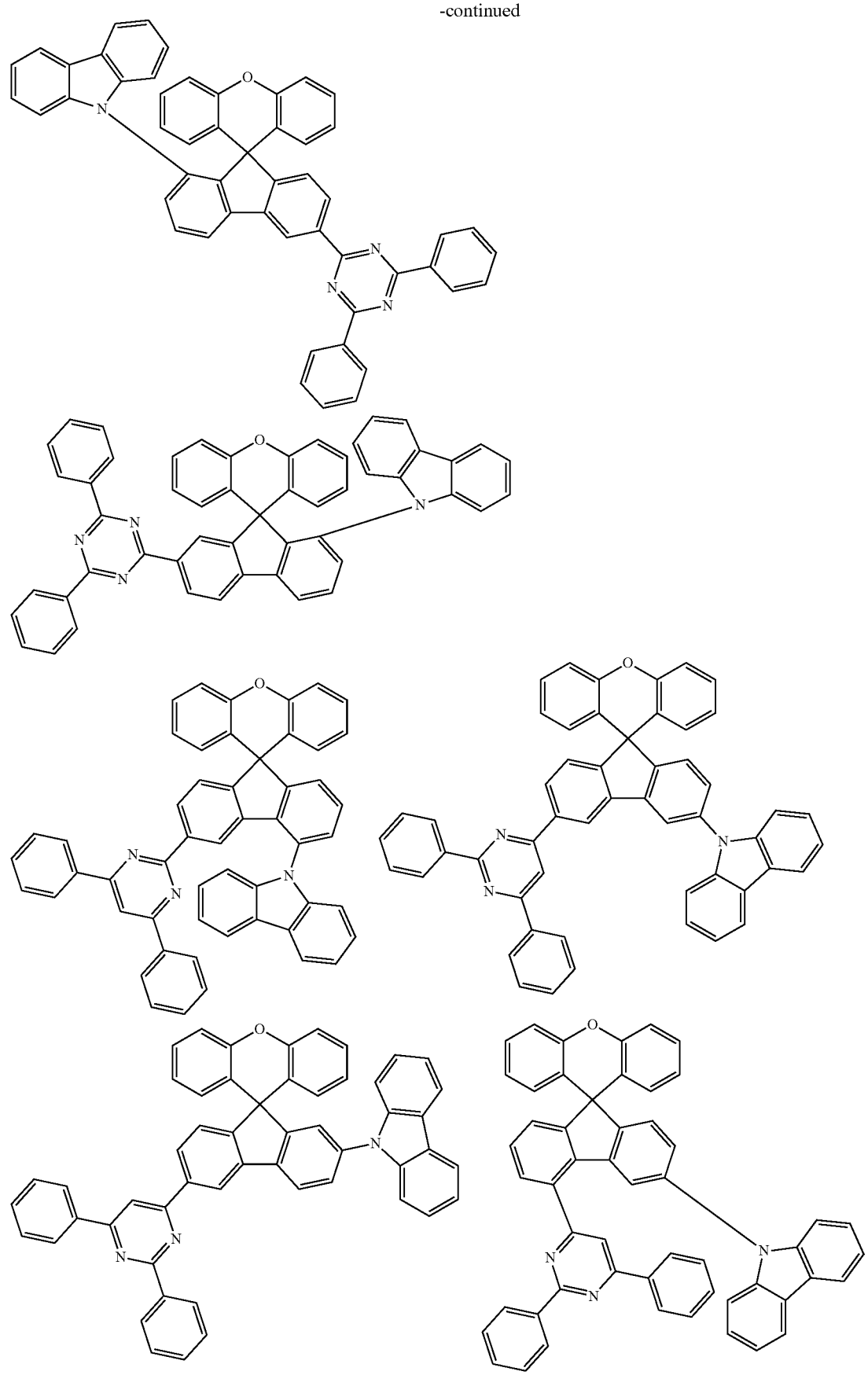

131 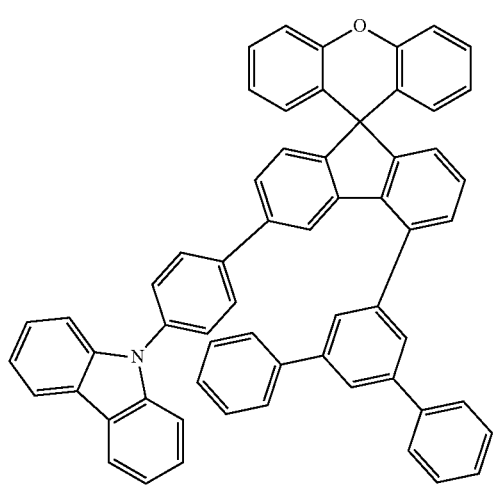 132 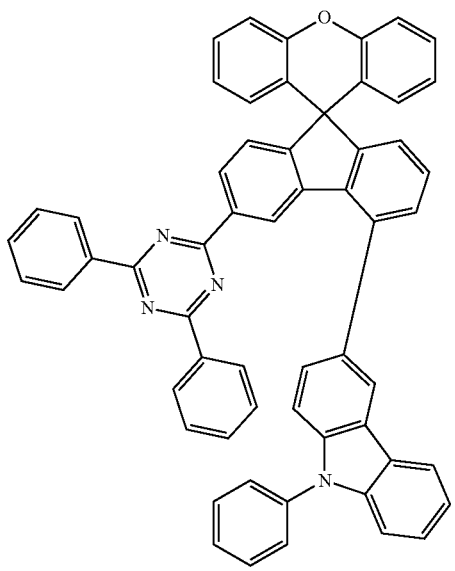
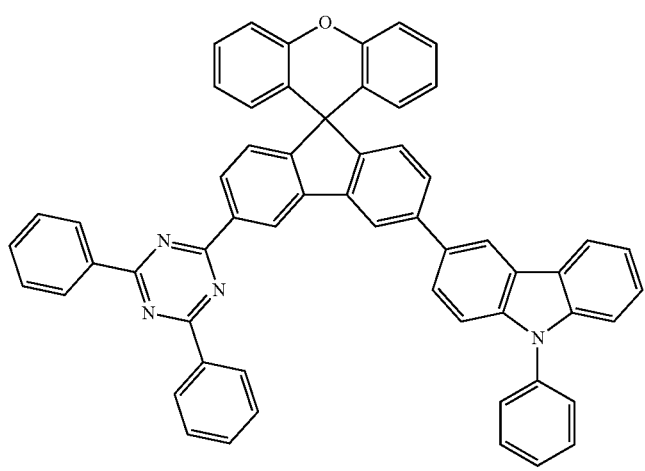
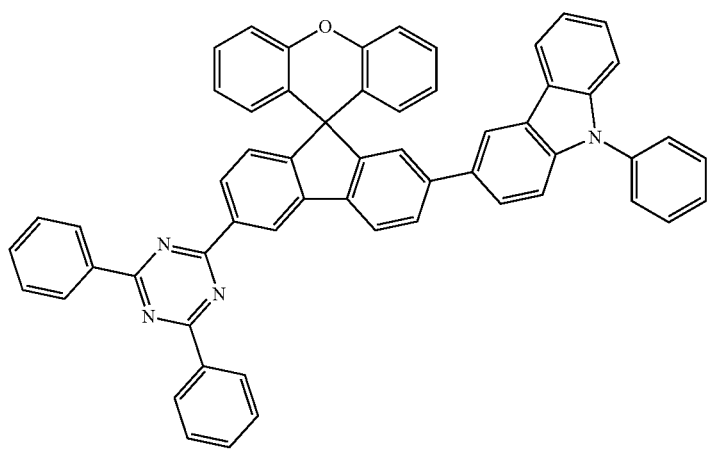

-continued
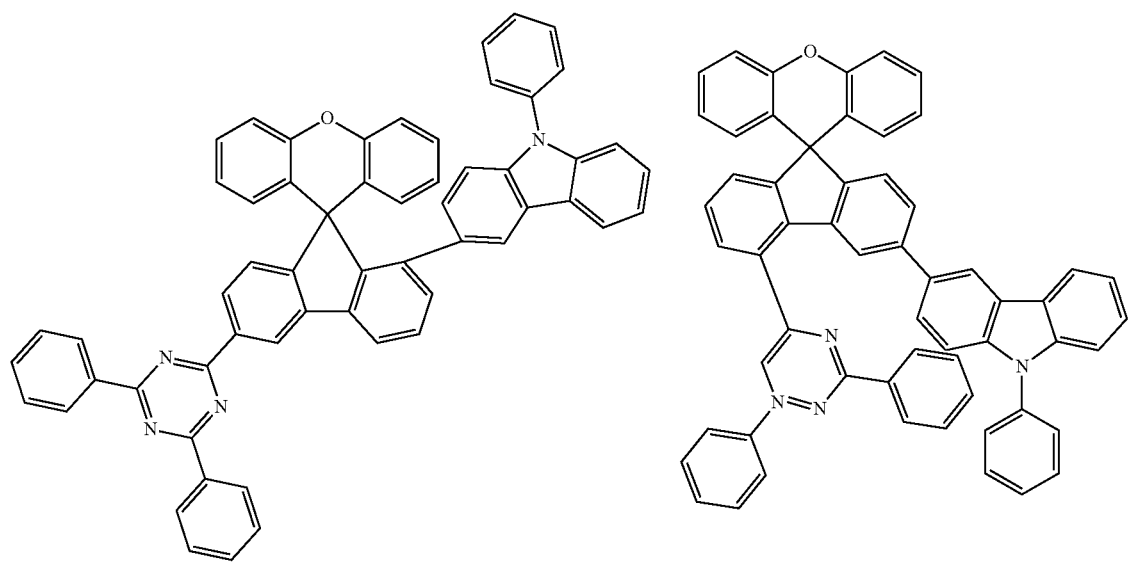
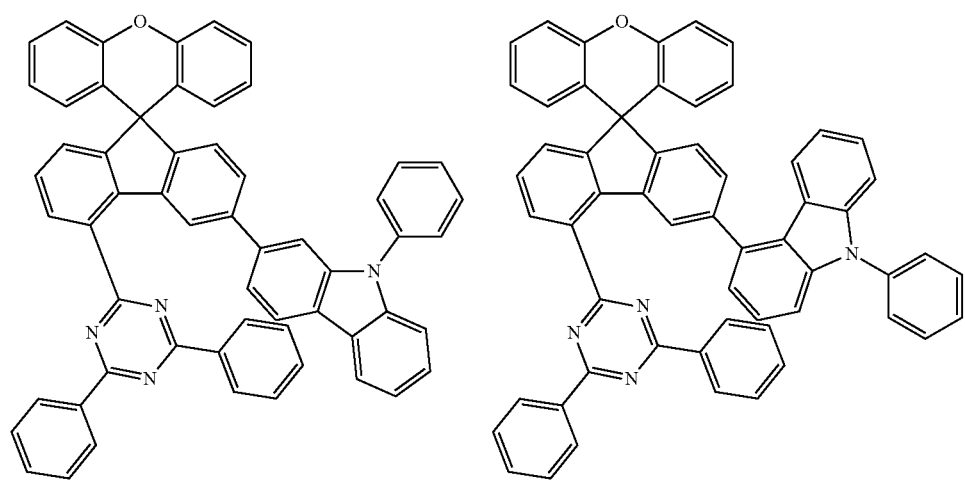
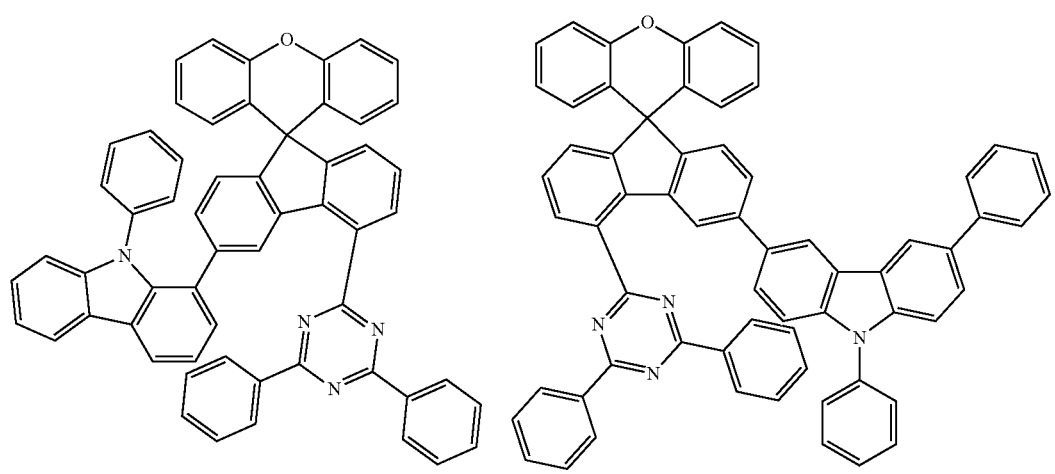

-continued
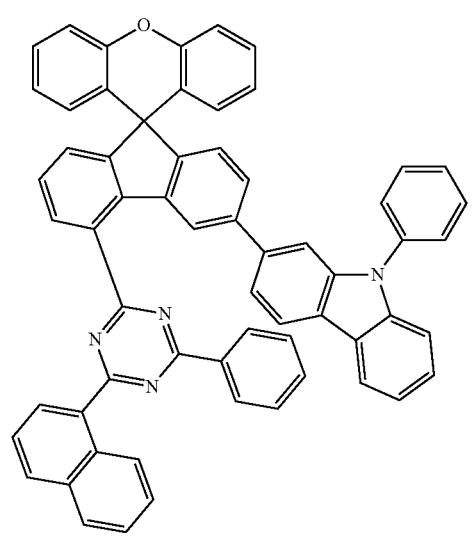
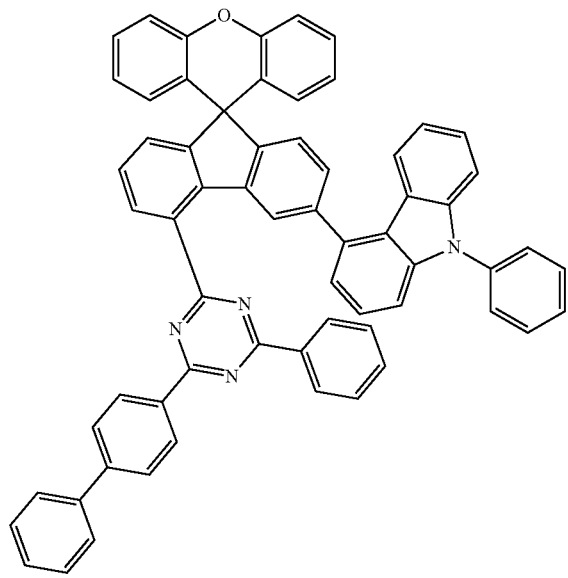
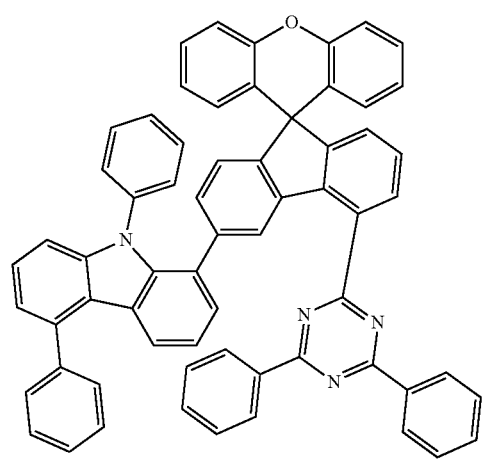
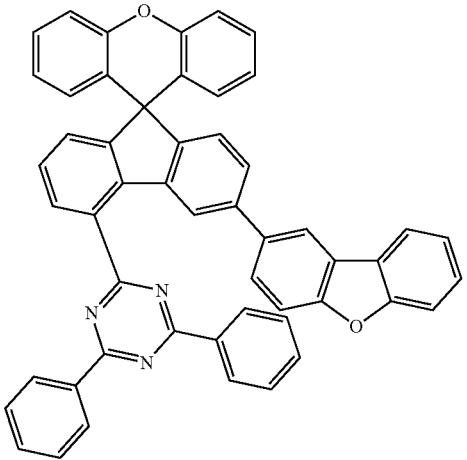
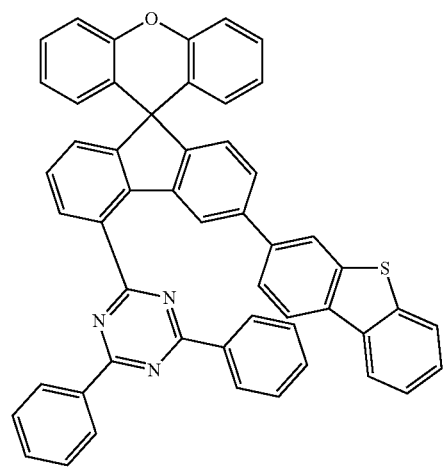
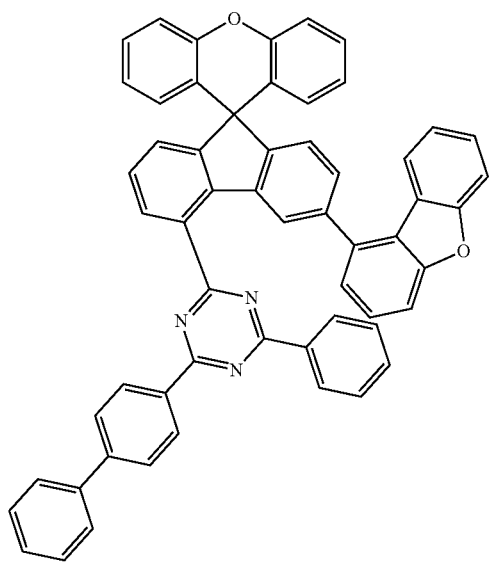

137
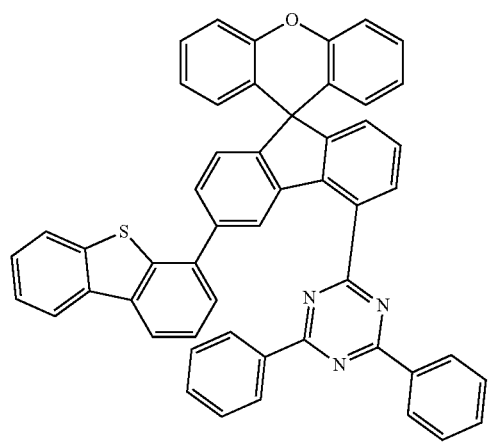
138
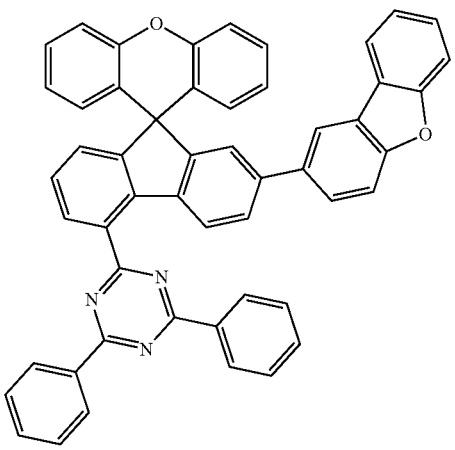
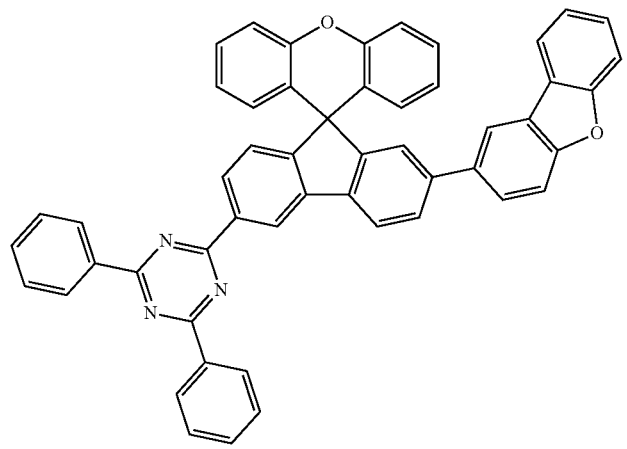
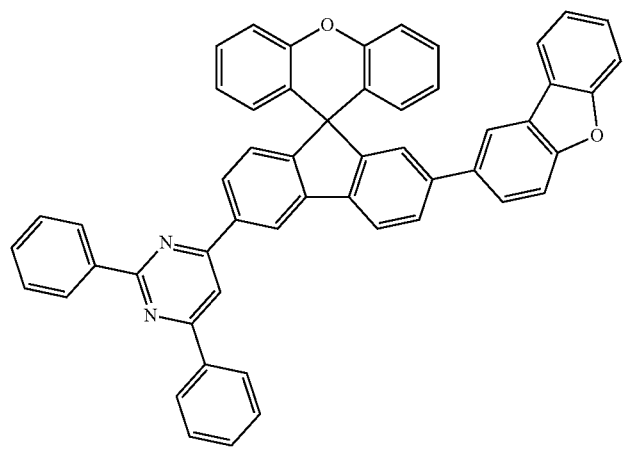

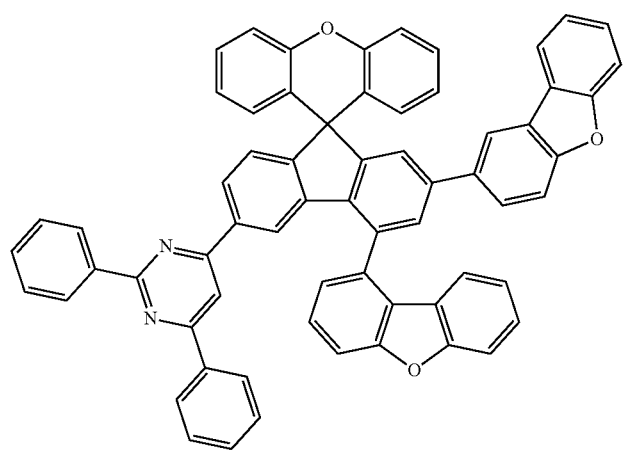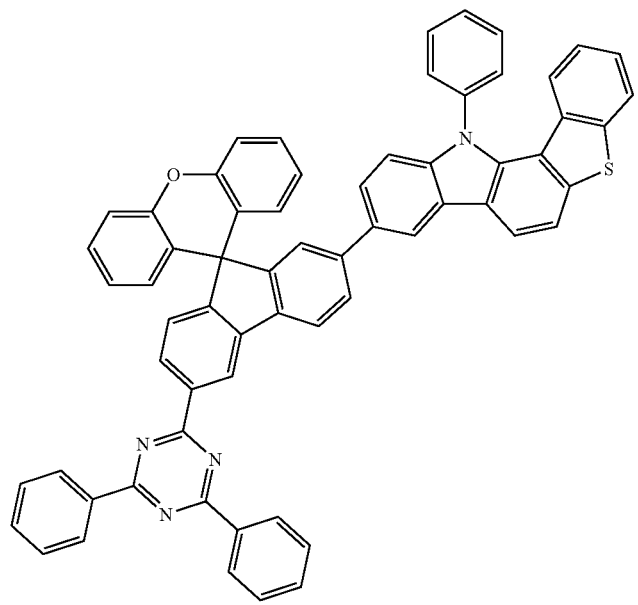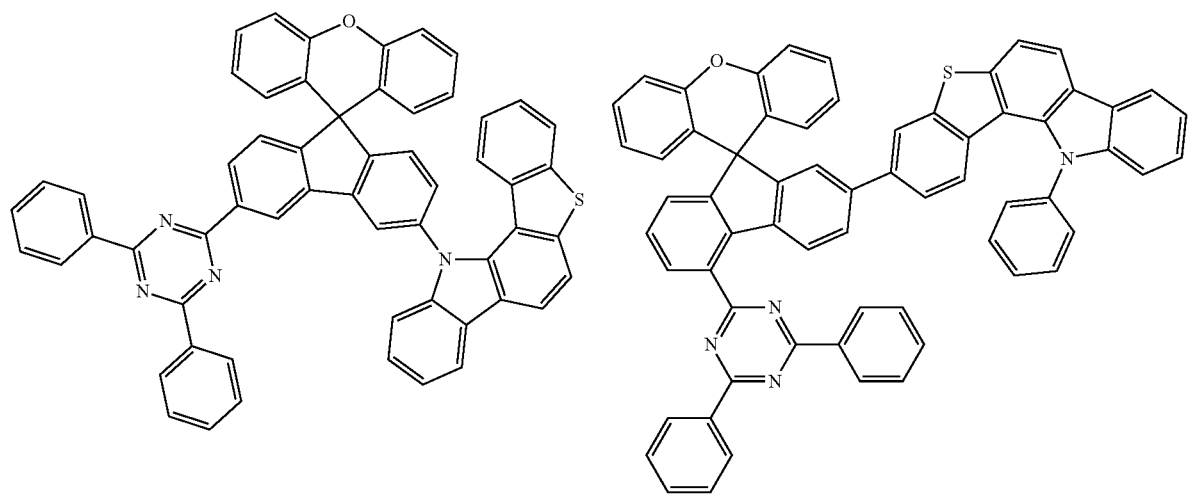

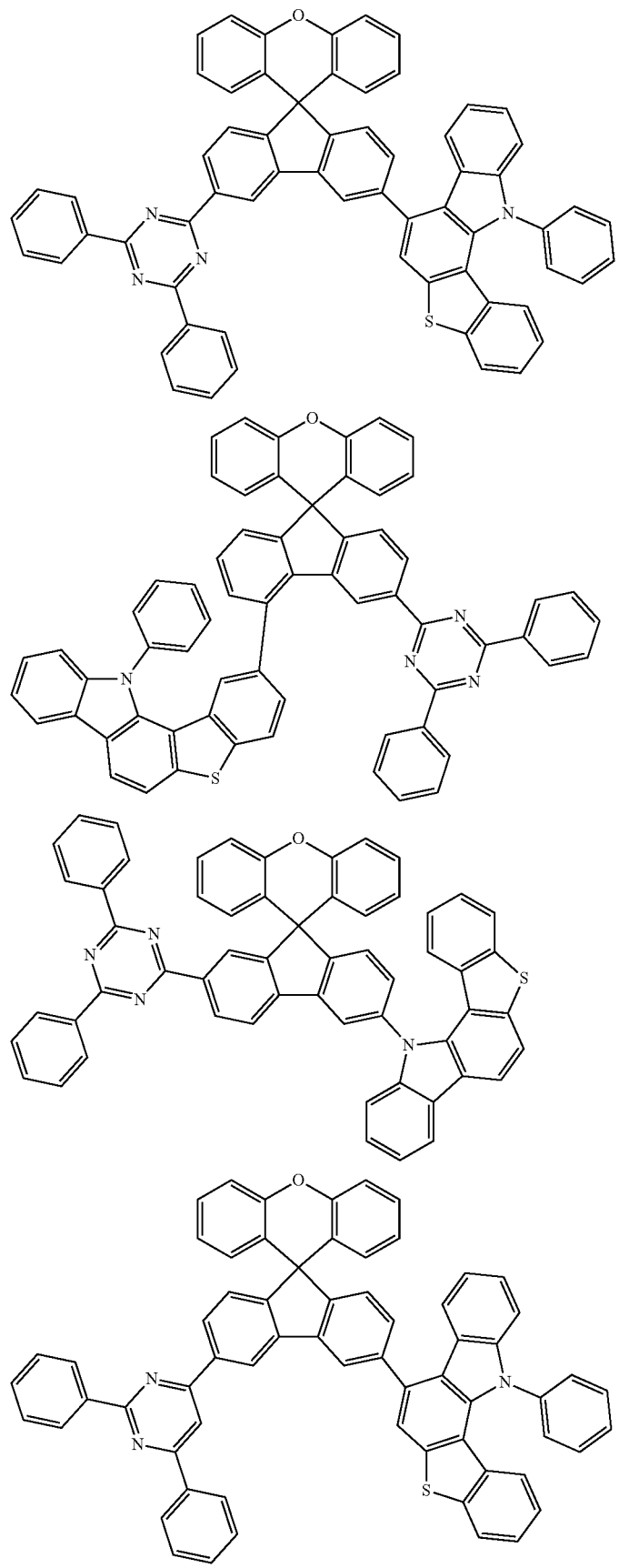

-continued
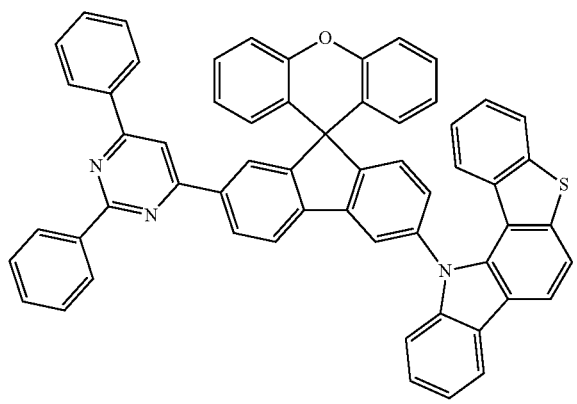
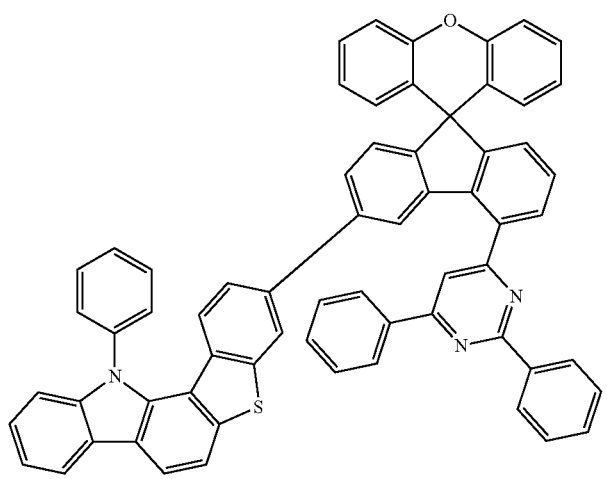
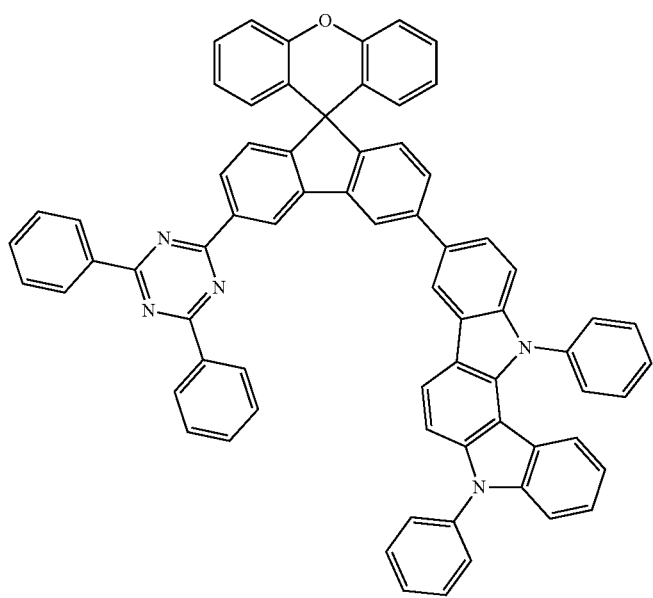

-continued
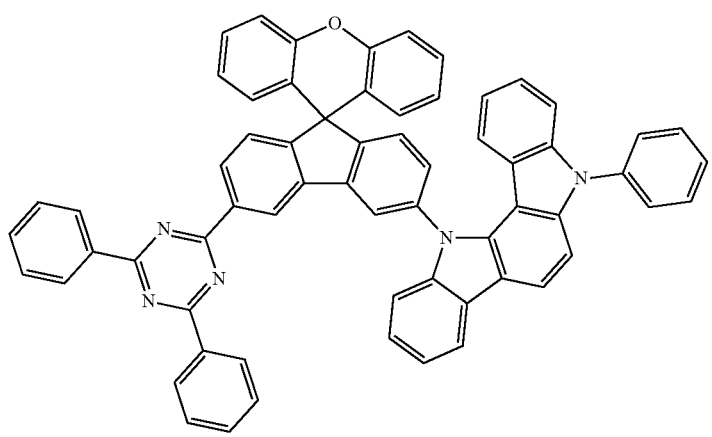
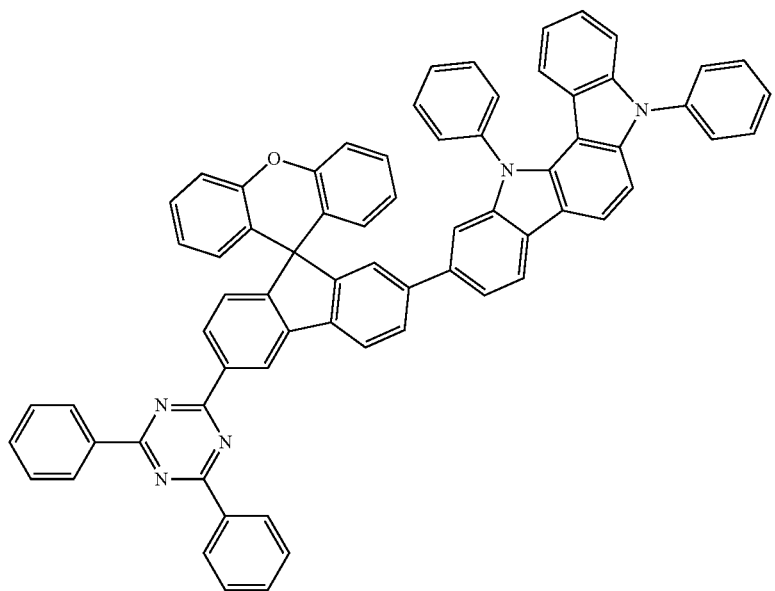
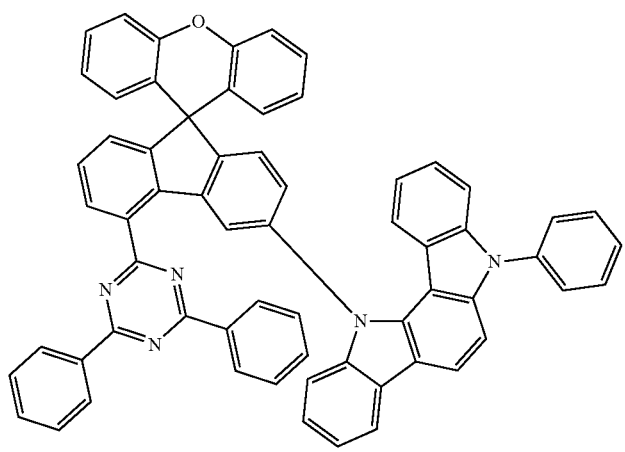

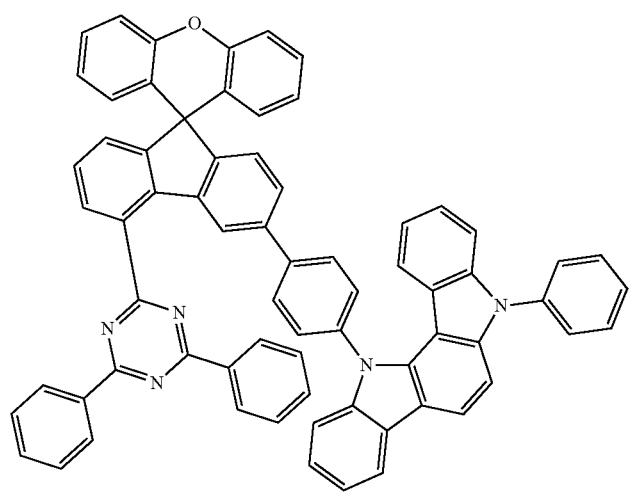
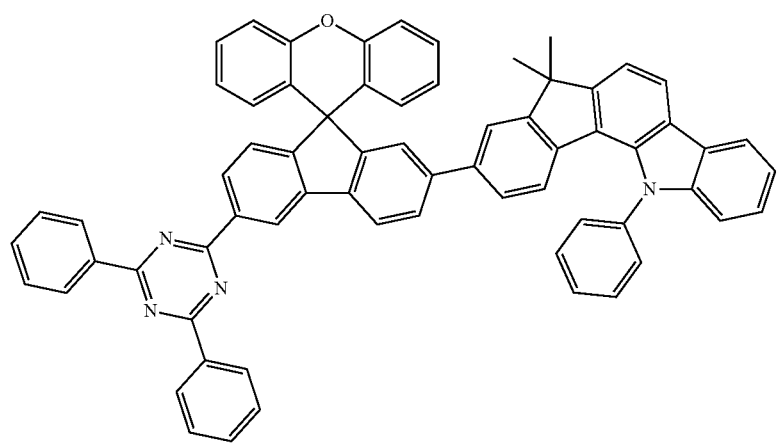
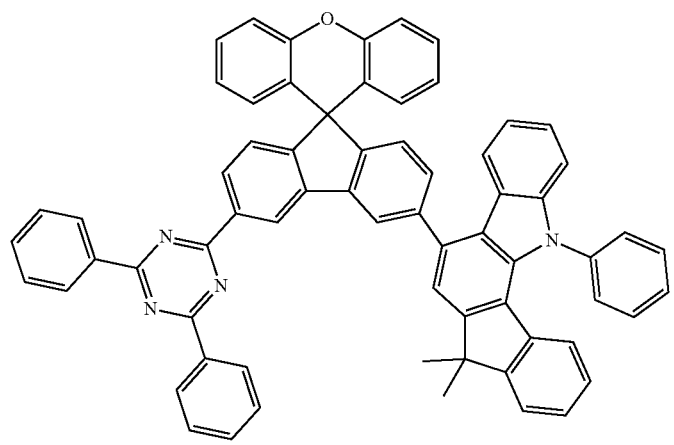

-continued
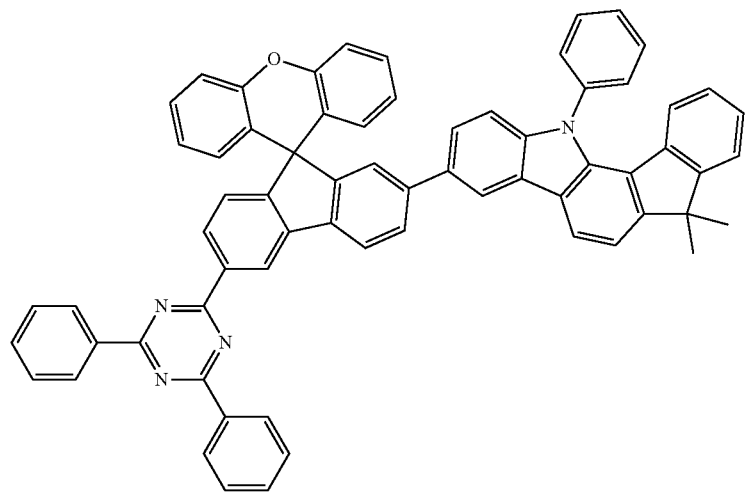
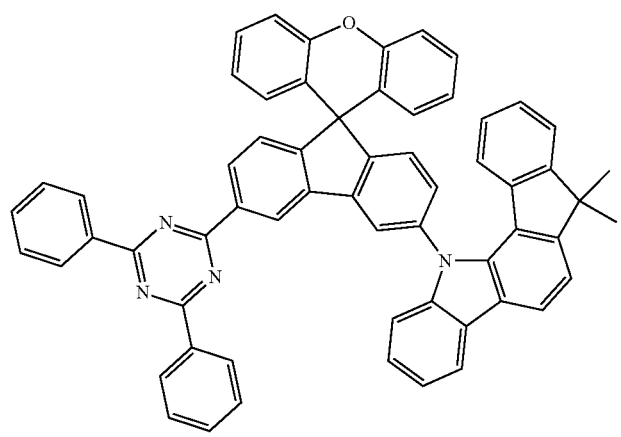
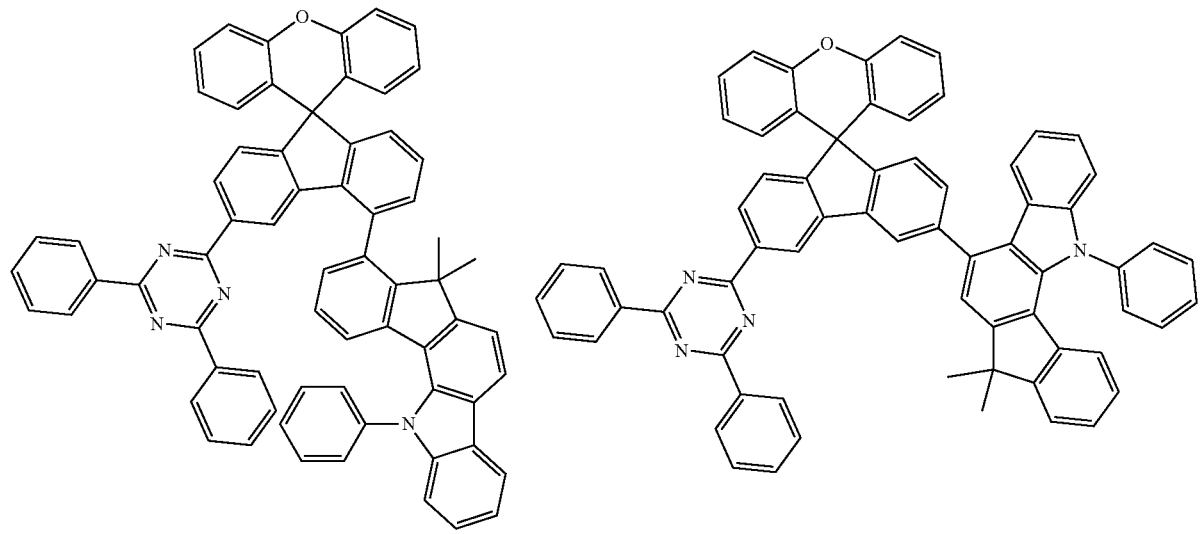

151
152
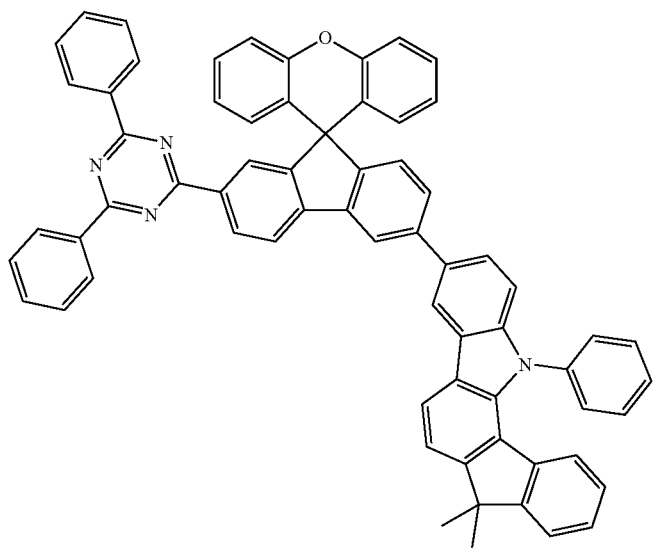
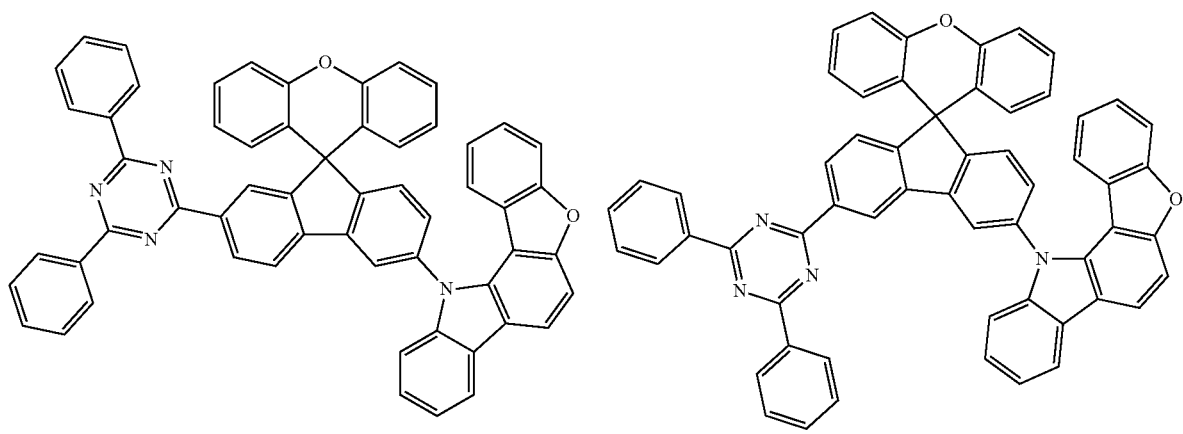
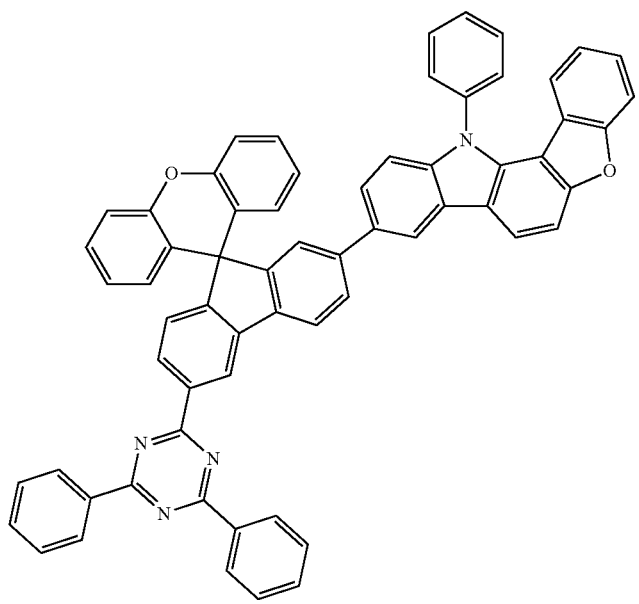

-continued
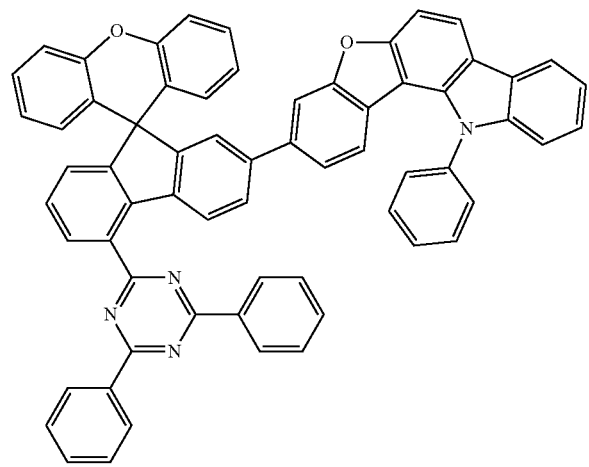
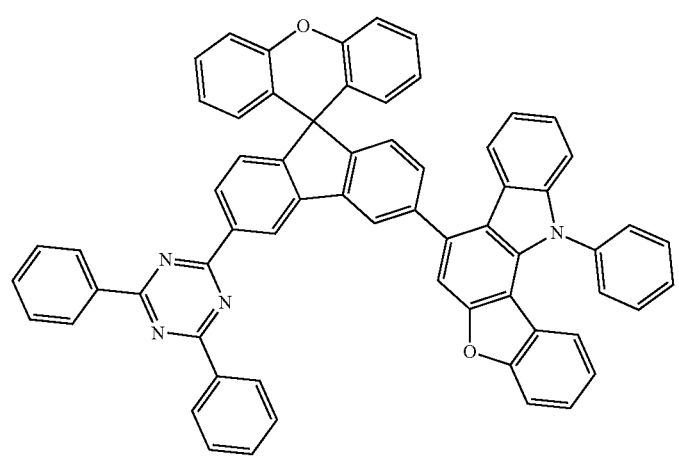
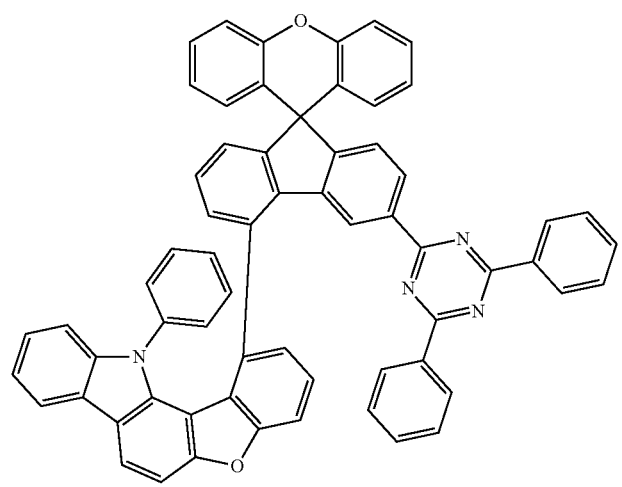

-continued
155
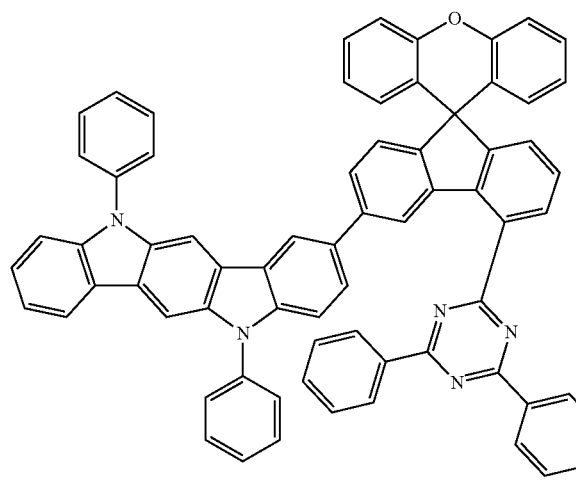
156
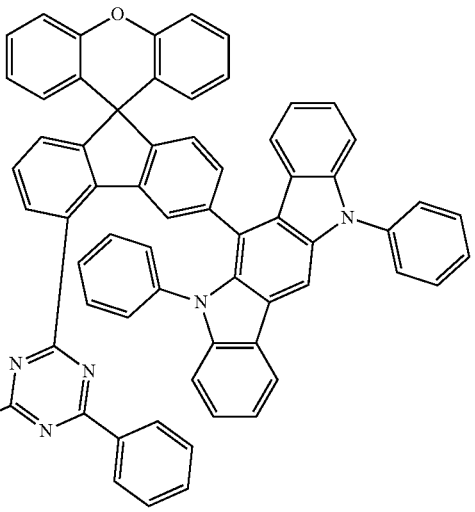
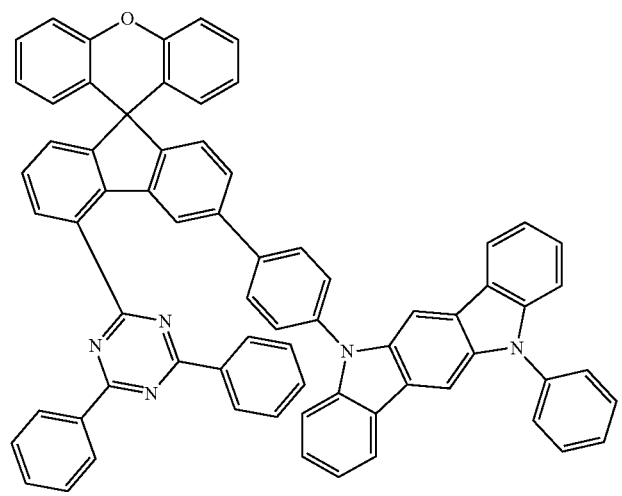
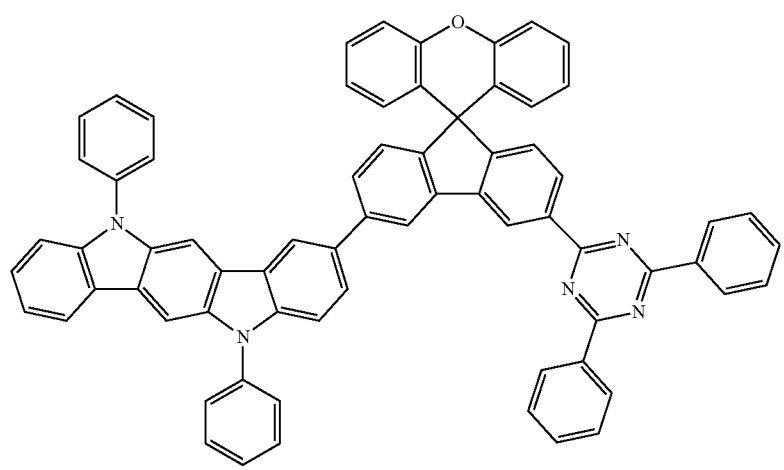

-continued
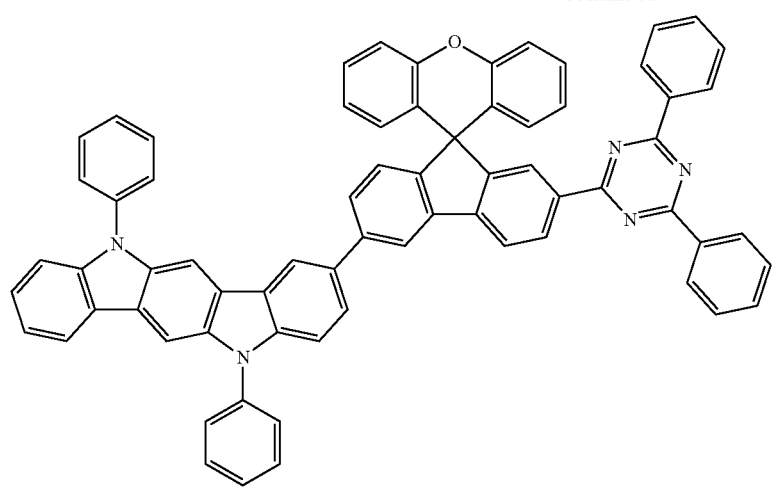
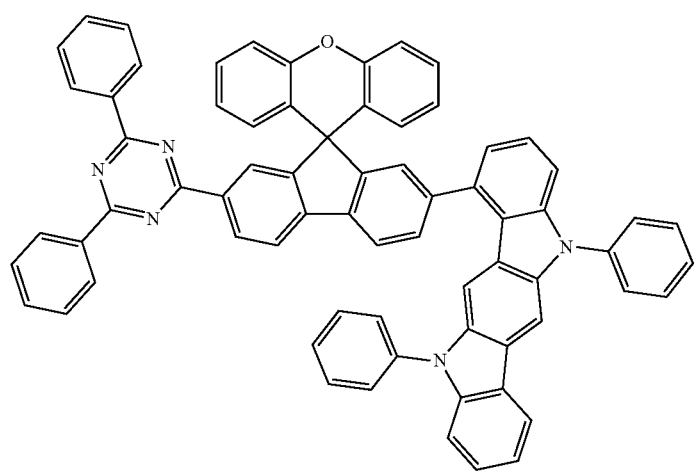
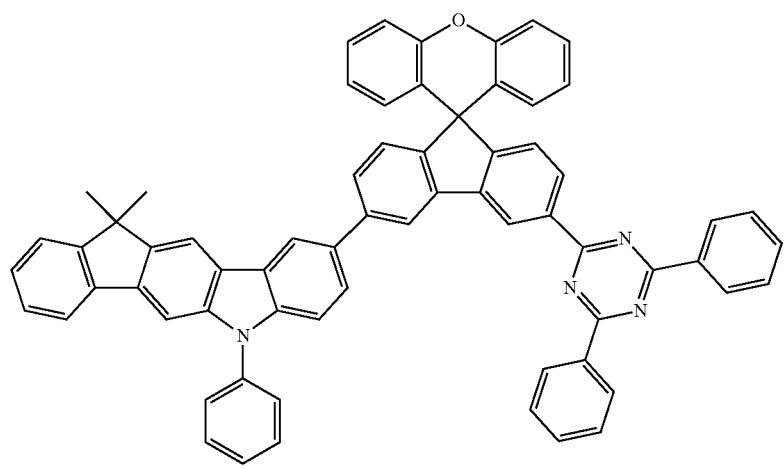

159 160
-continued
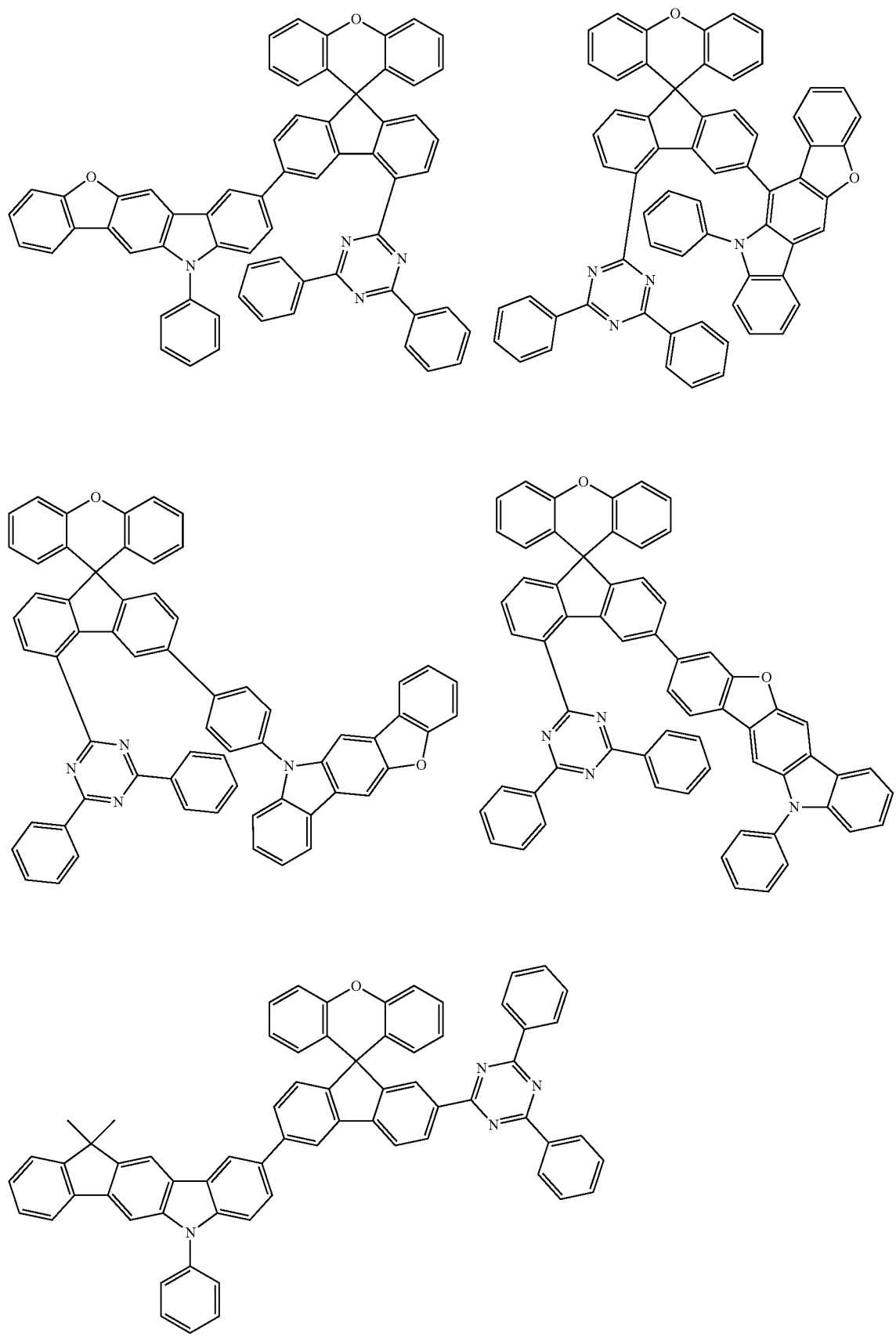

-continued
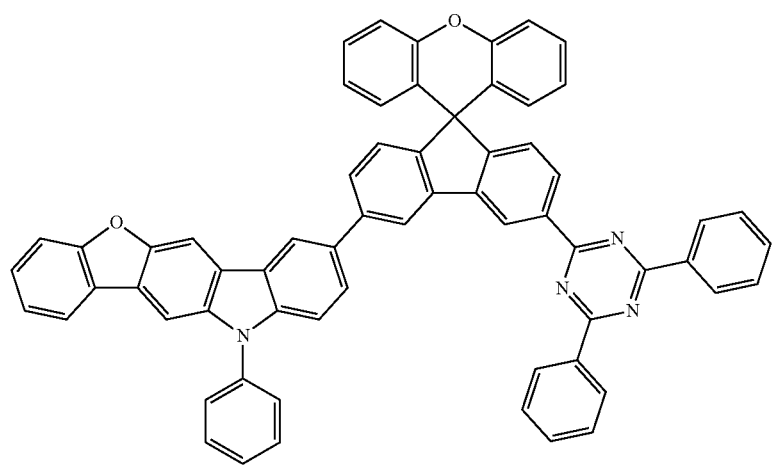
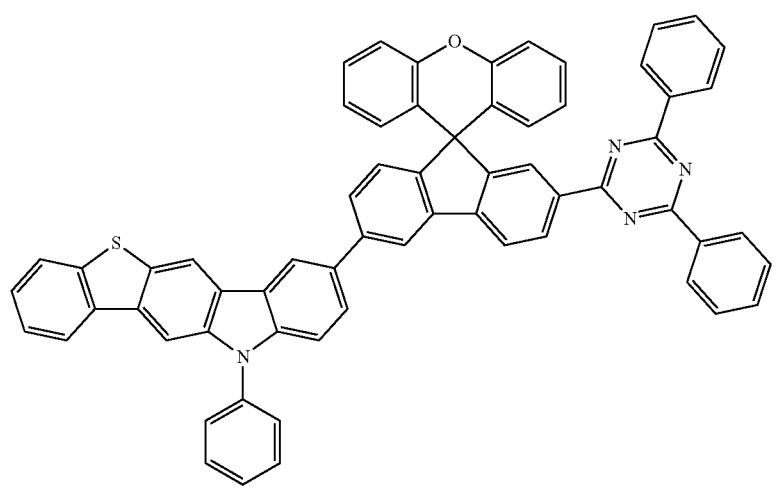
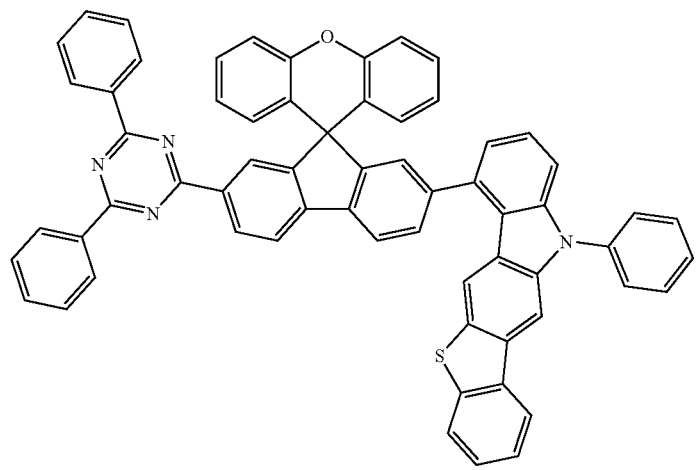

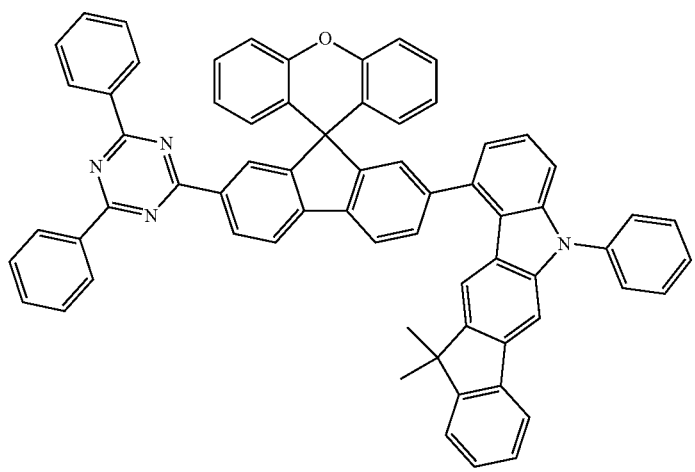
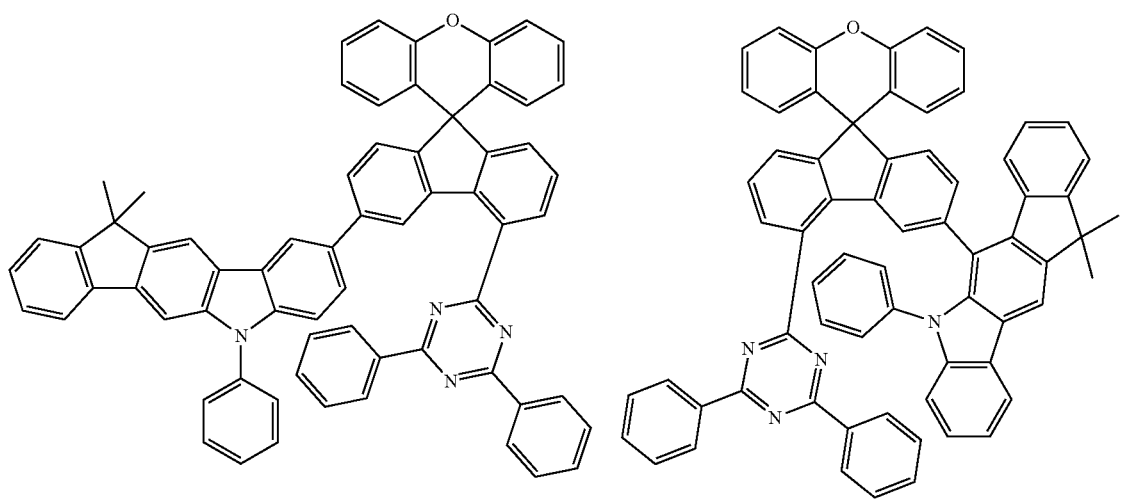
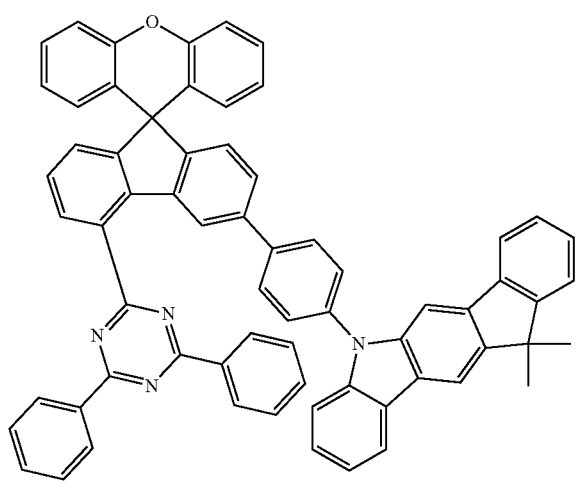

165
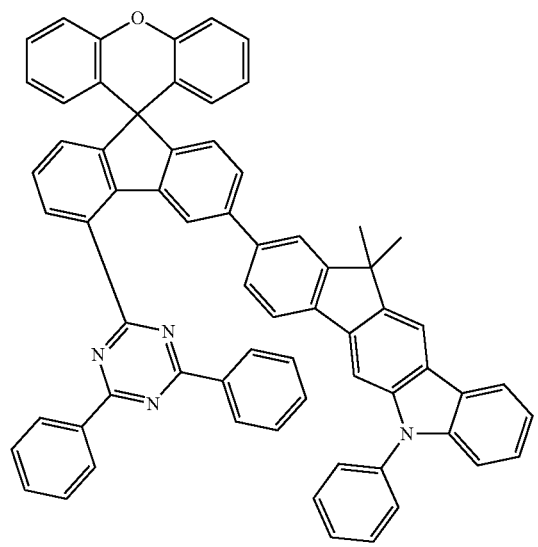
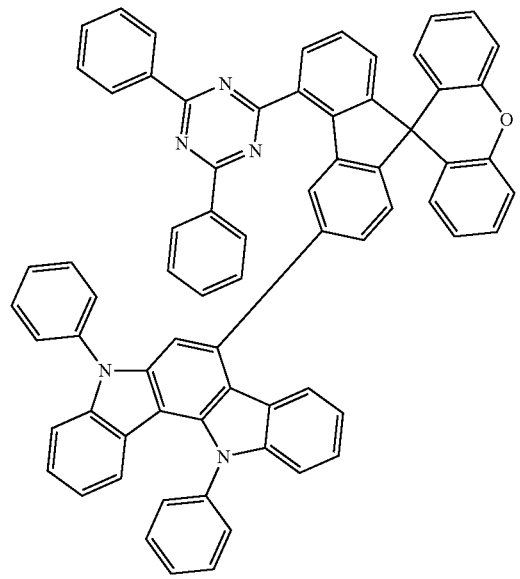
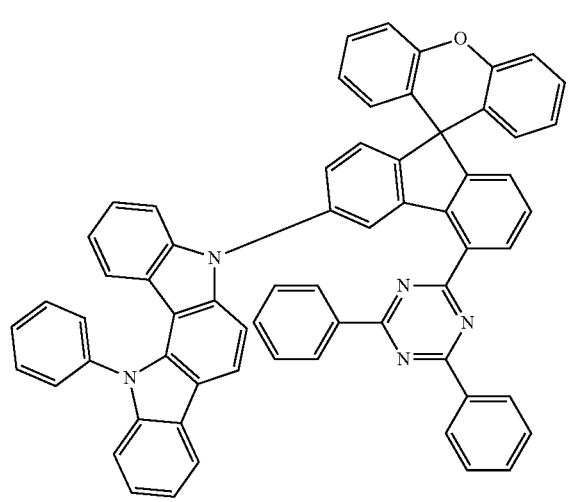
166
-continued
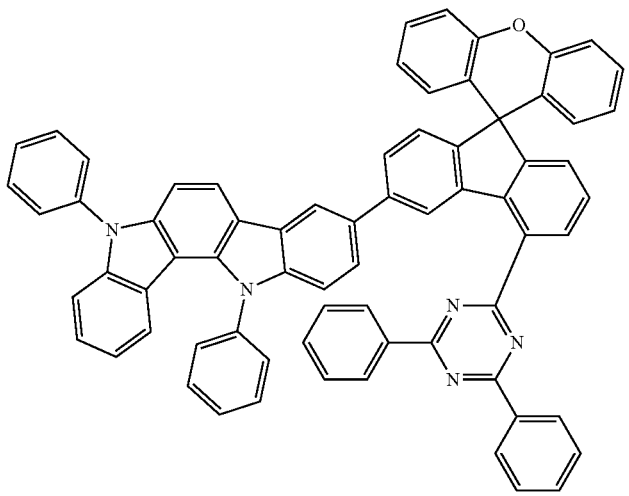
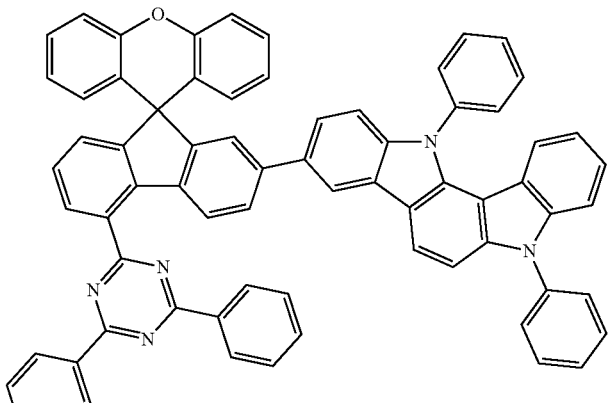
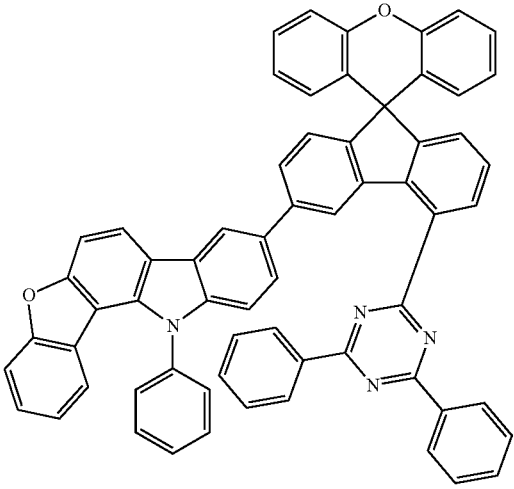

167
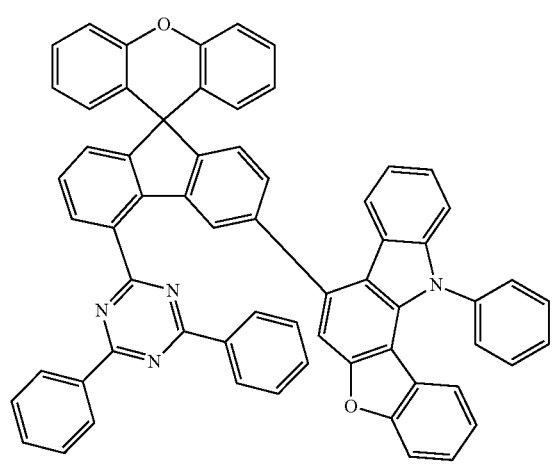
168
-continued
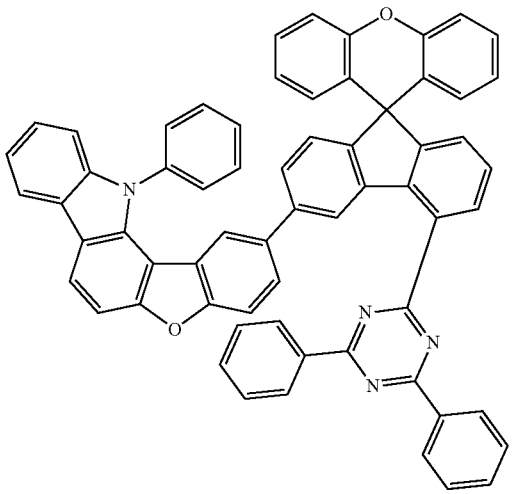
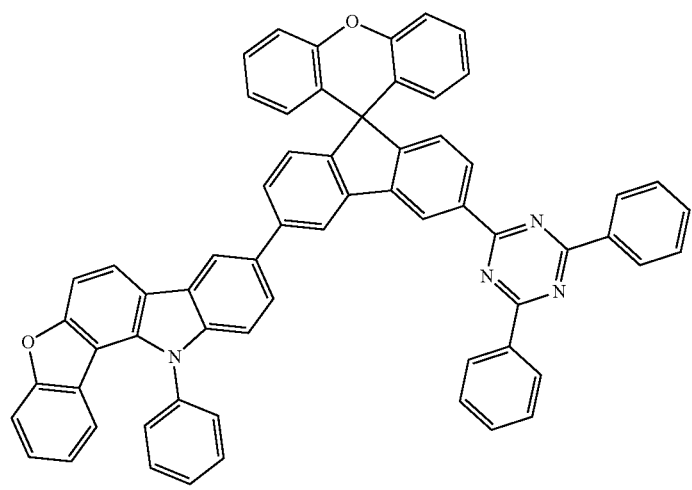
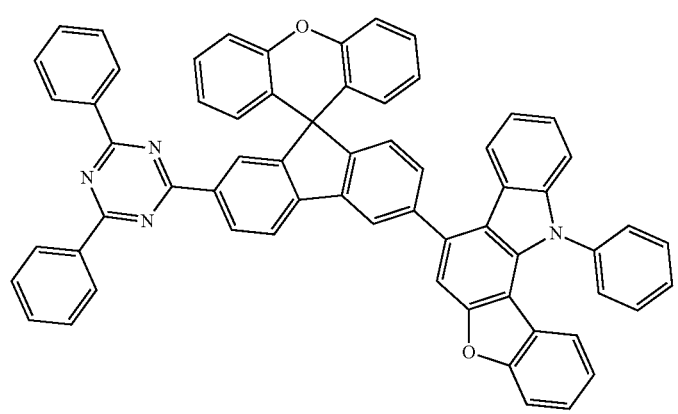

-continued
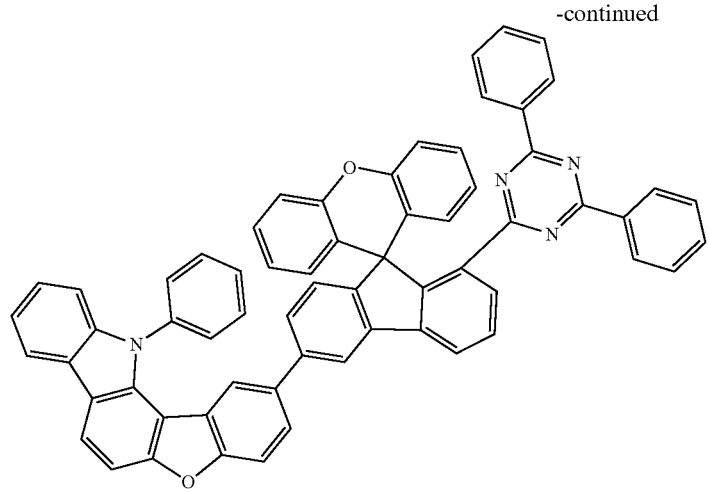
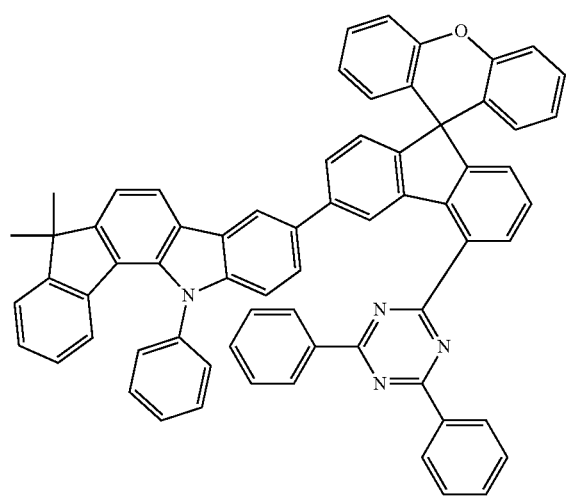
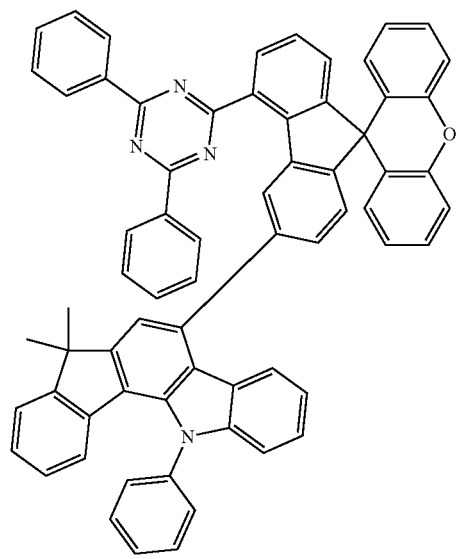

-continued
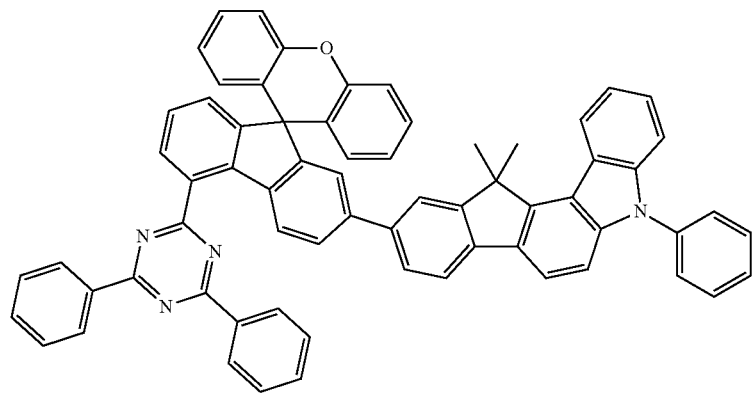
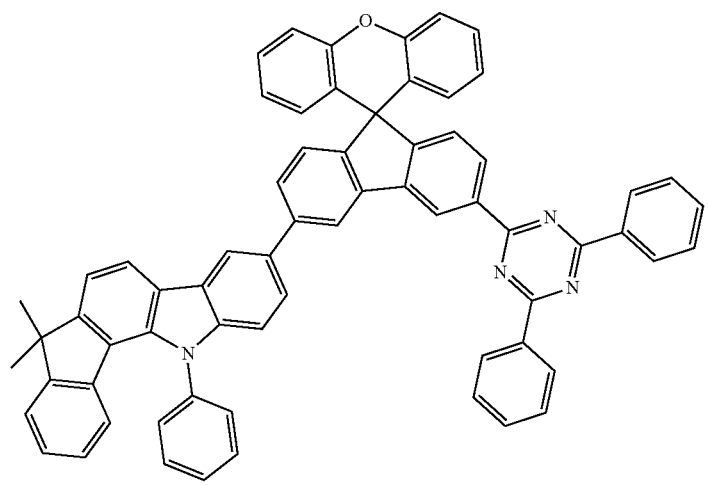
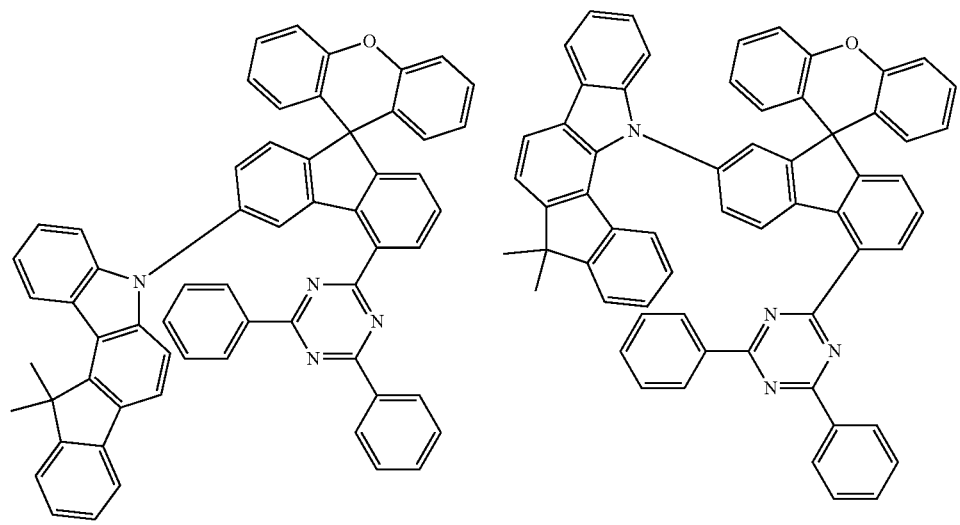

-continued
173 174
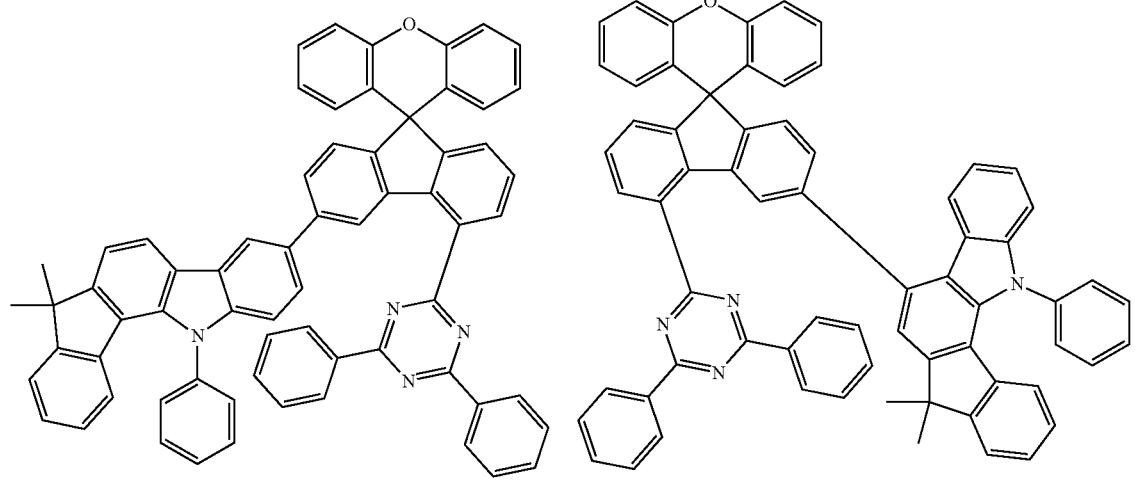
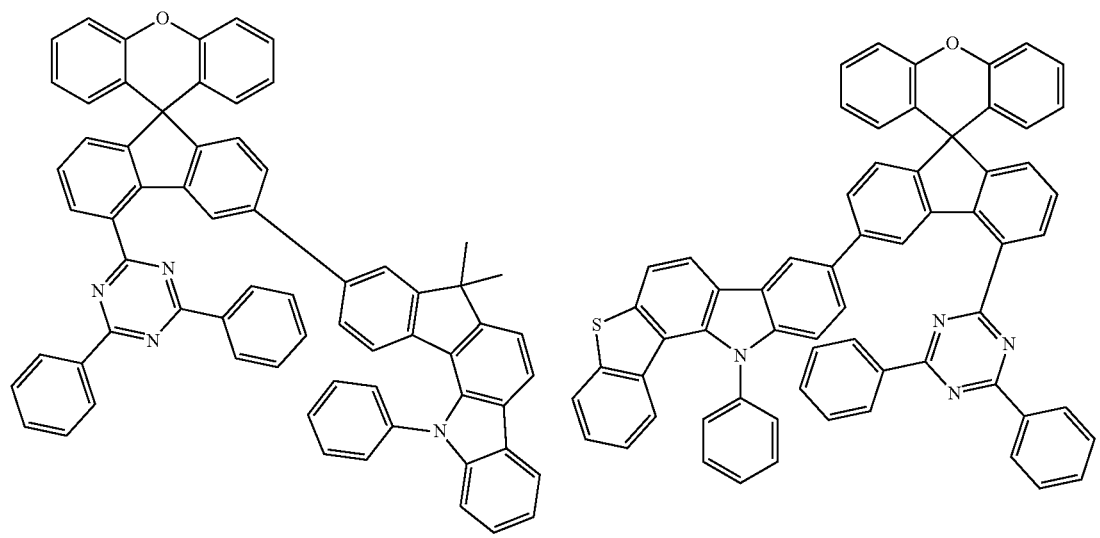
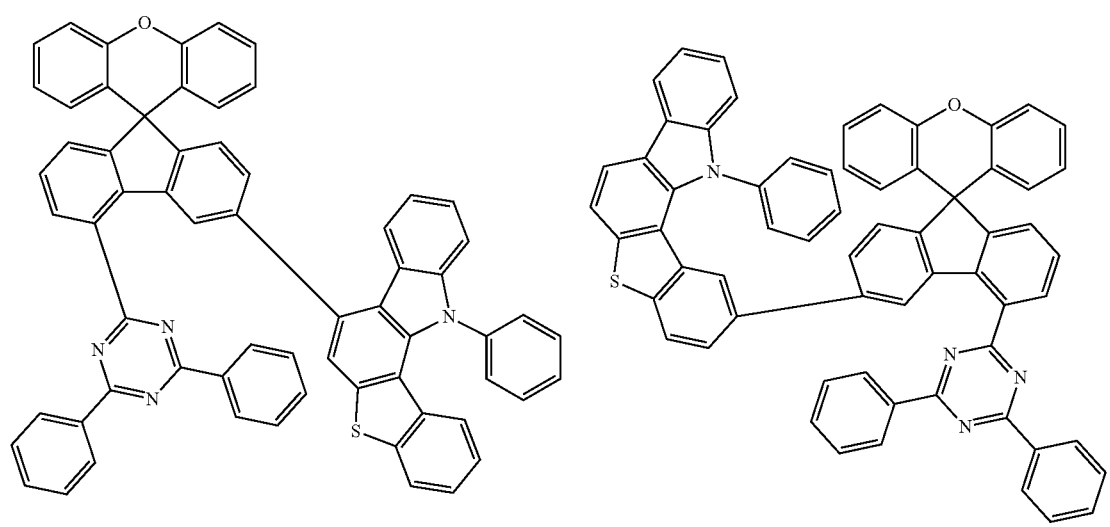

175
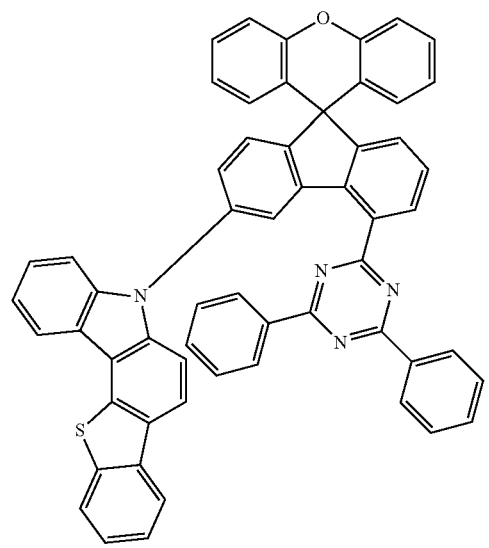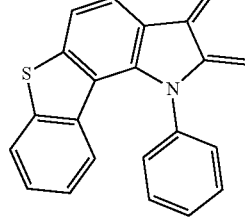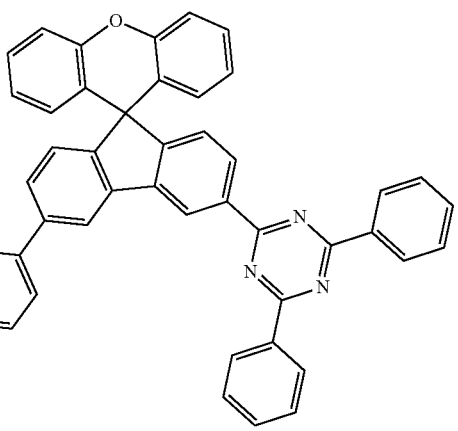
-continued
176
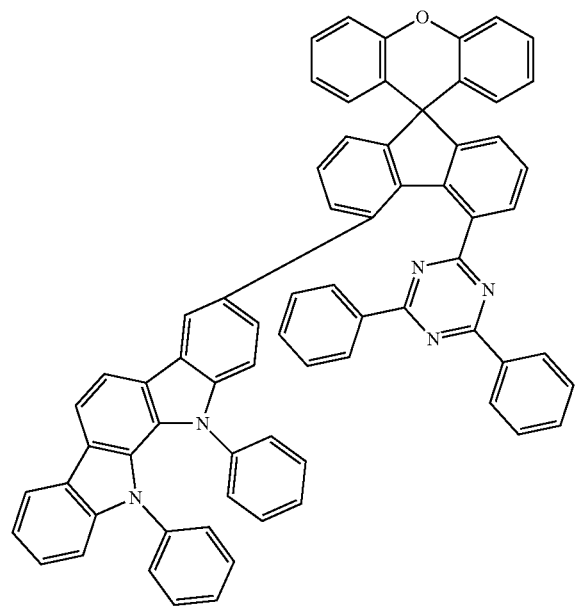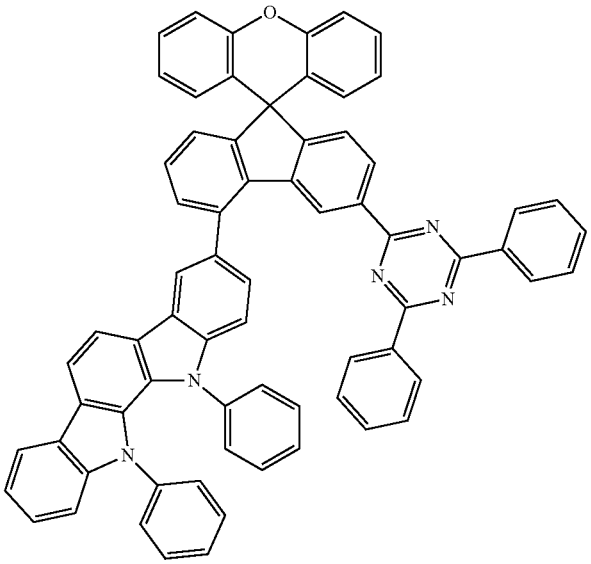

177 178
-continued
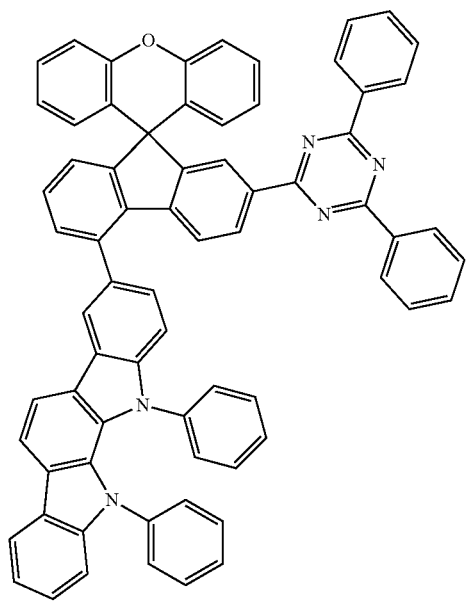
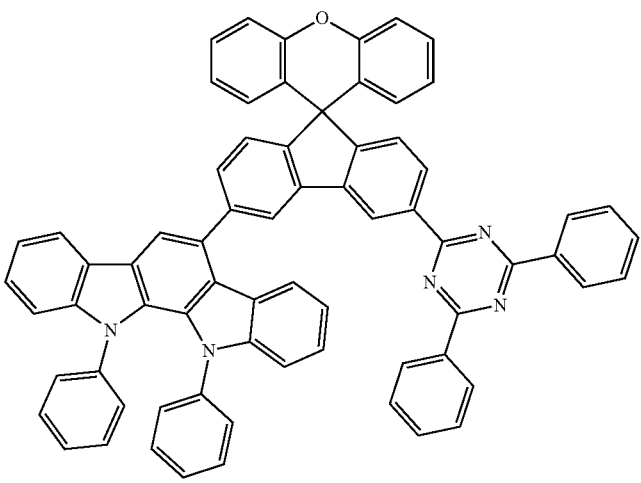
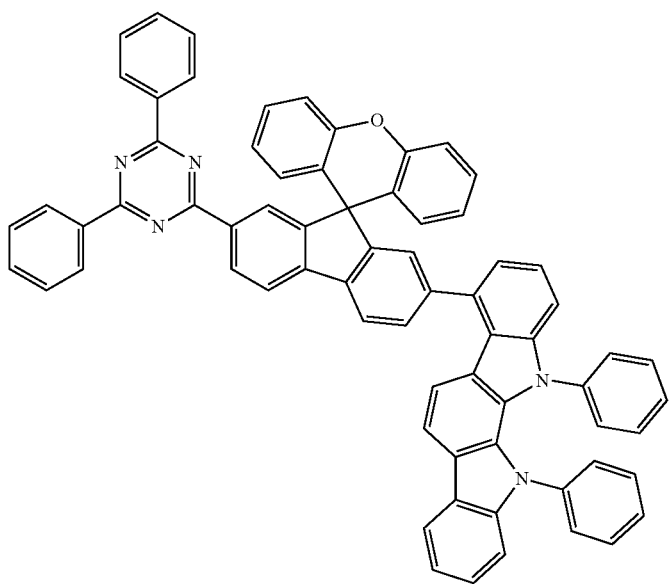

-continued
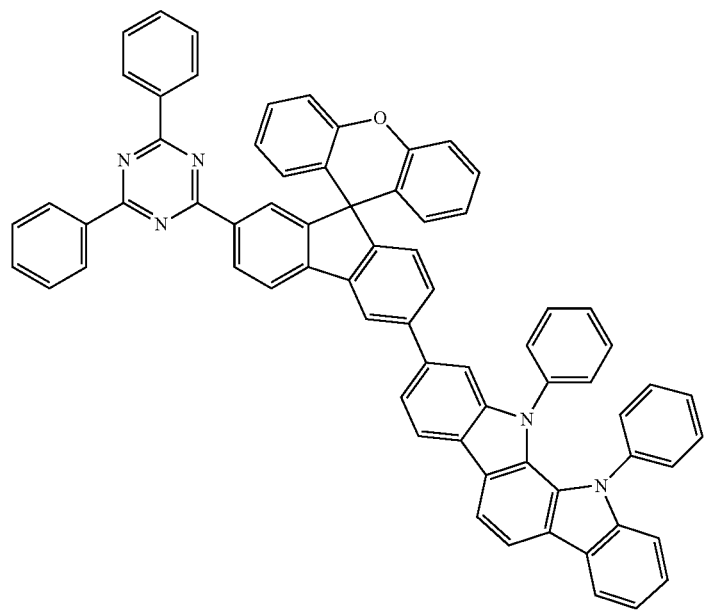
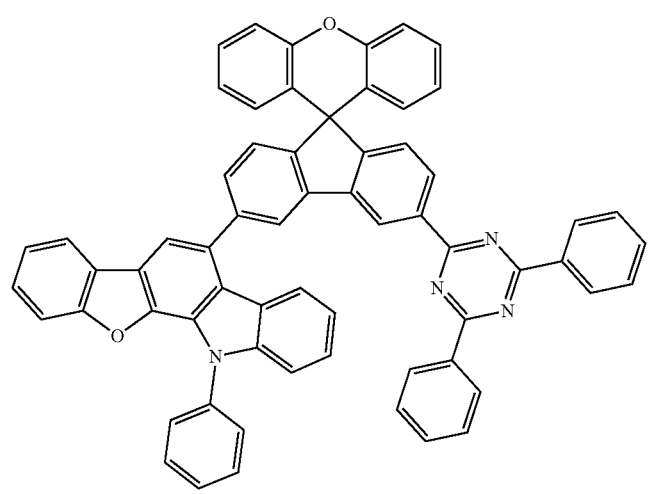
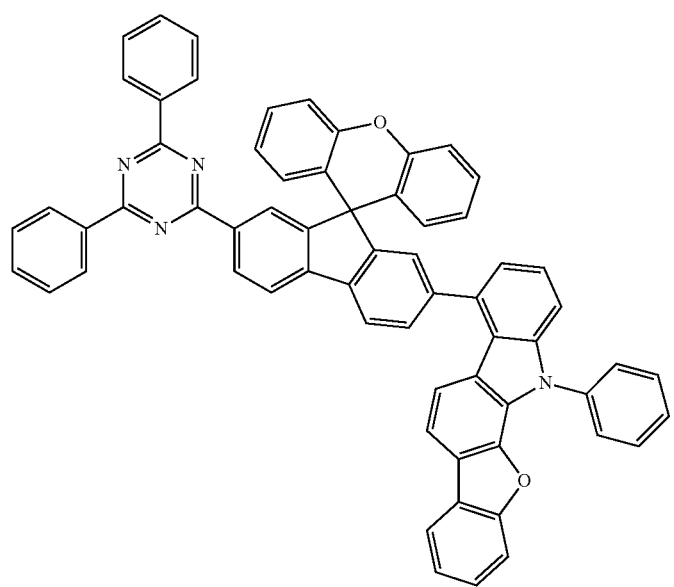

-continued
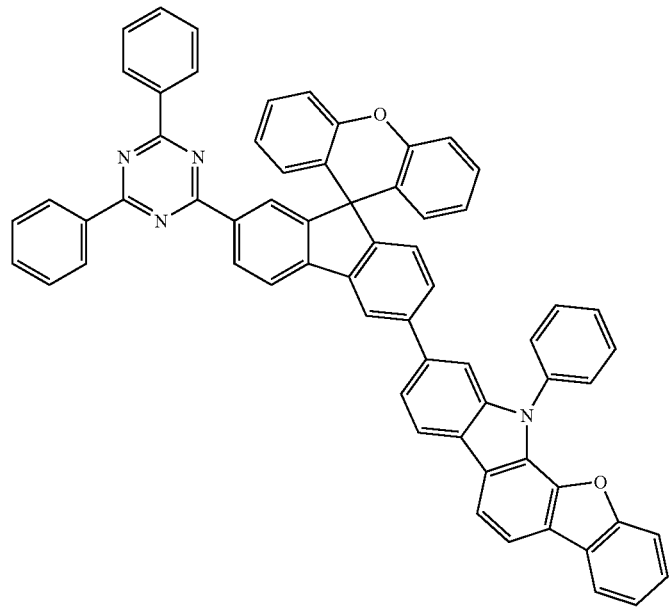
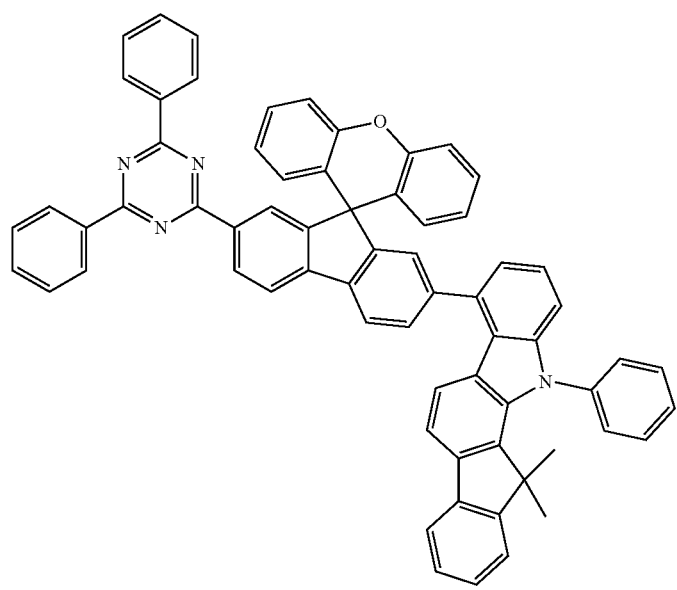

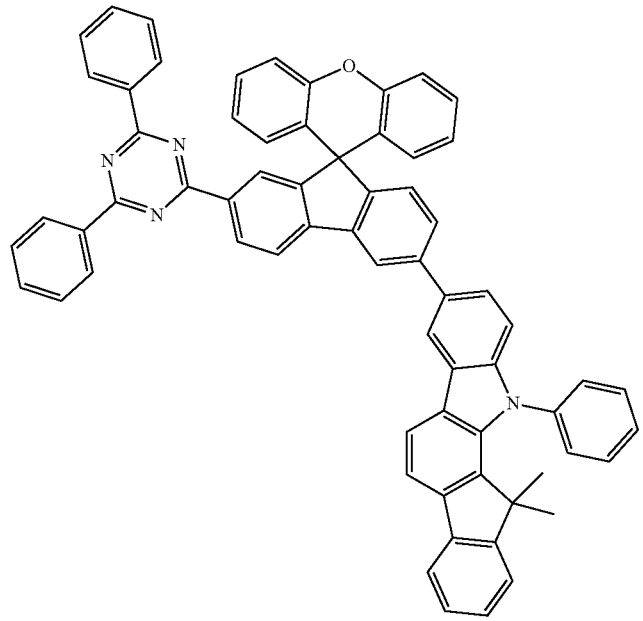
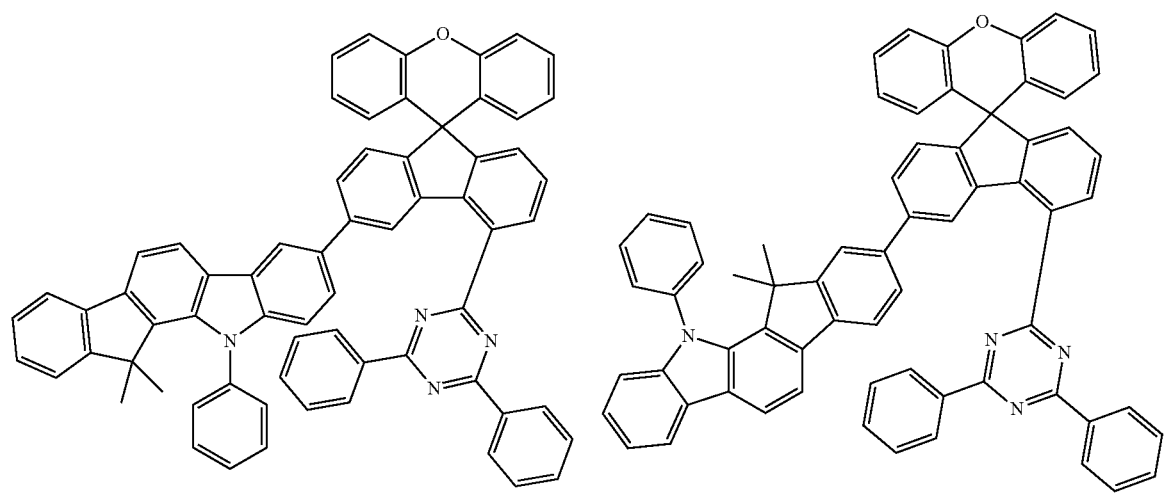

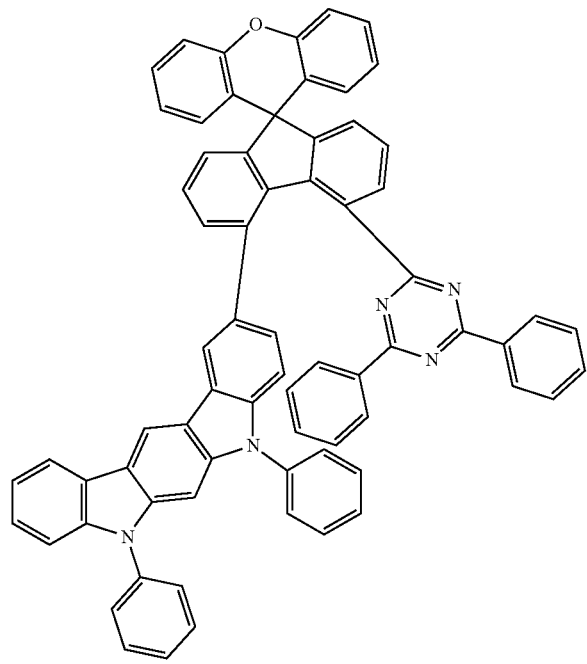
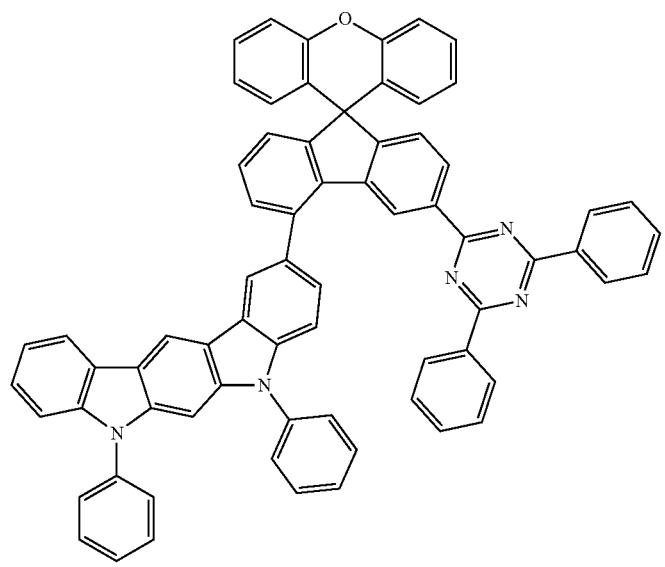

-continued
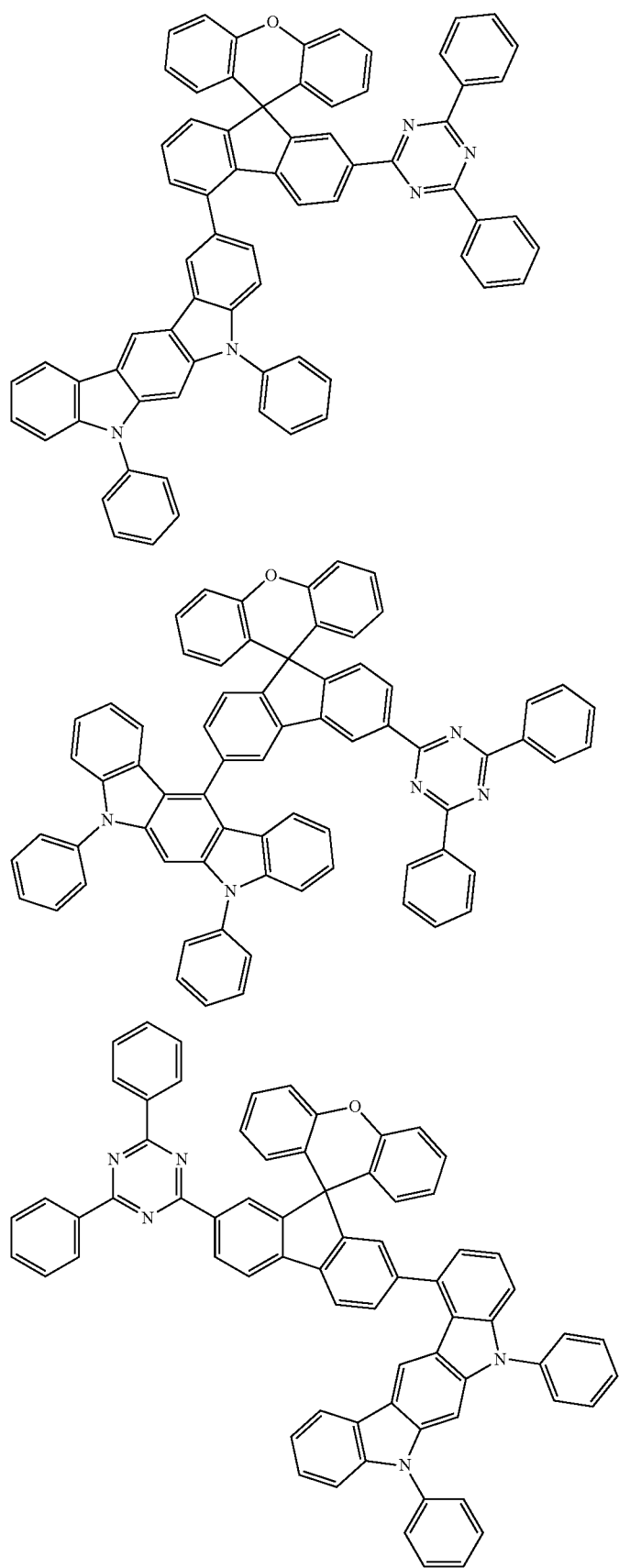

189
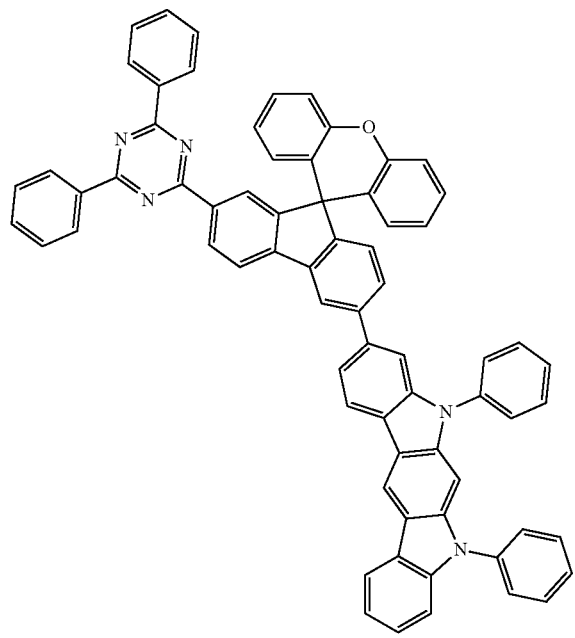
190
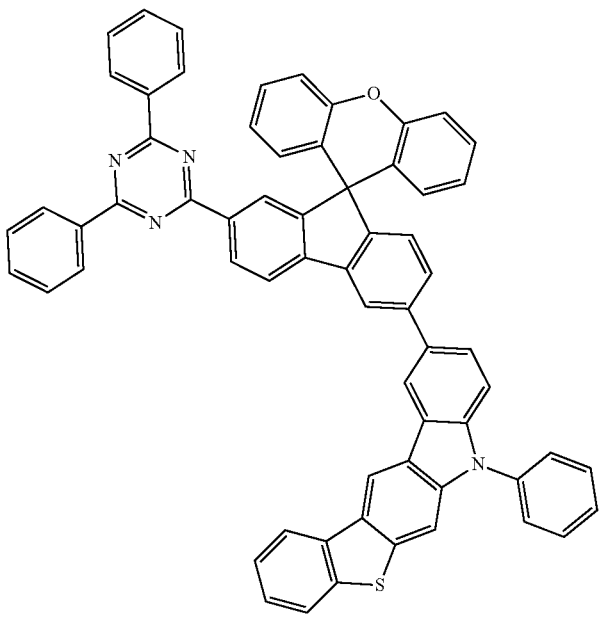
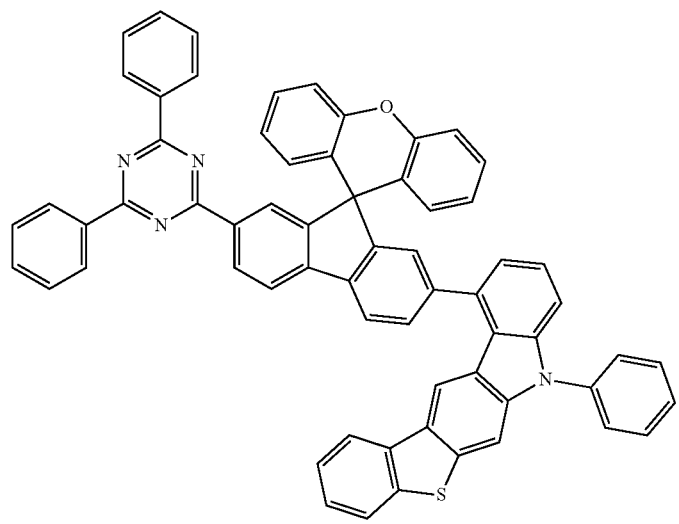
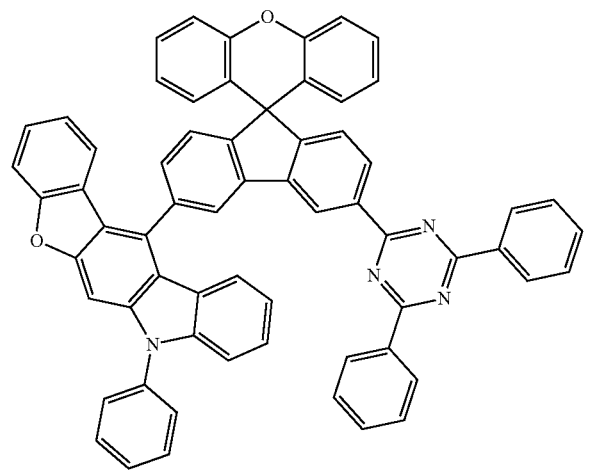

191
-continued
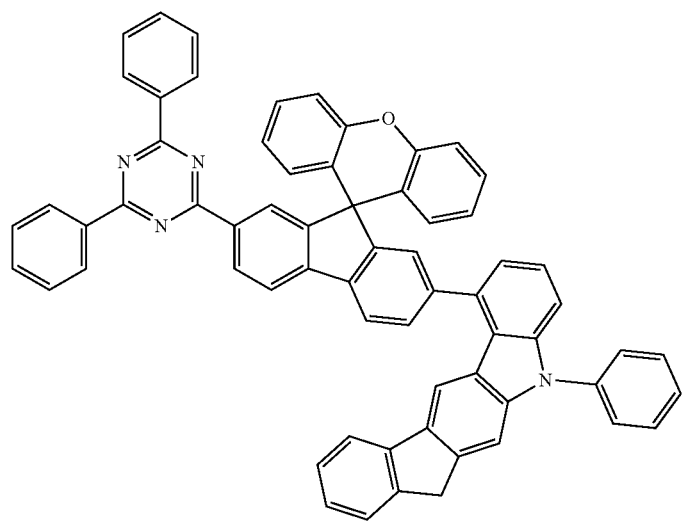
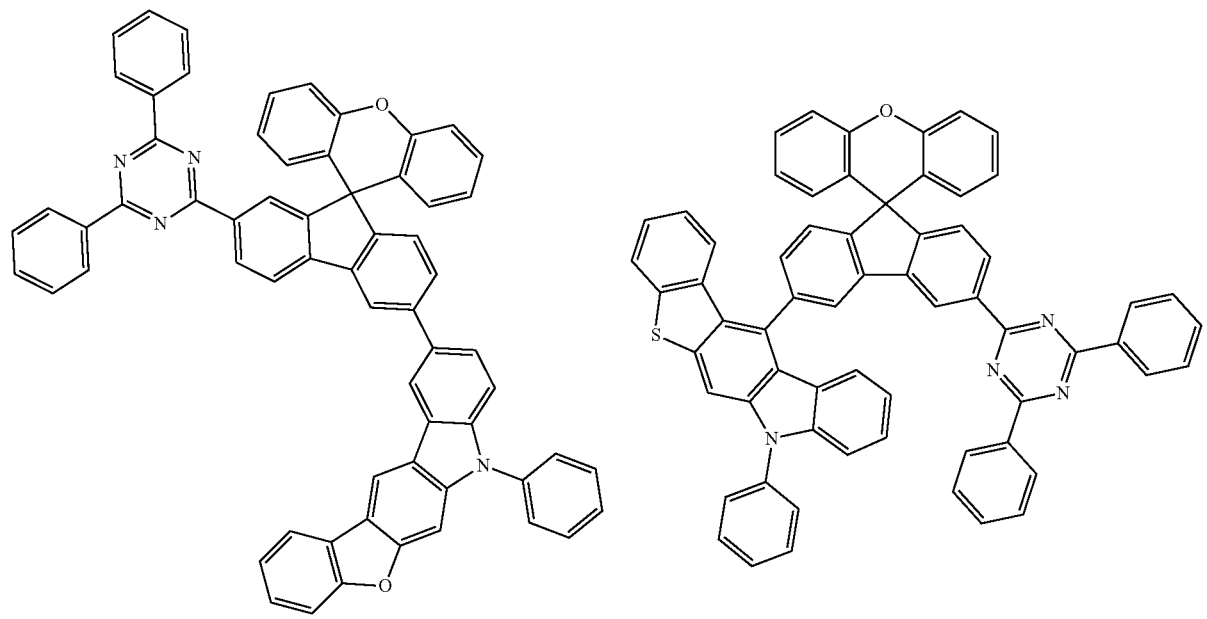
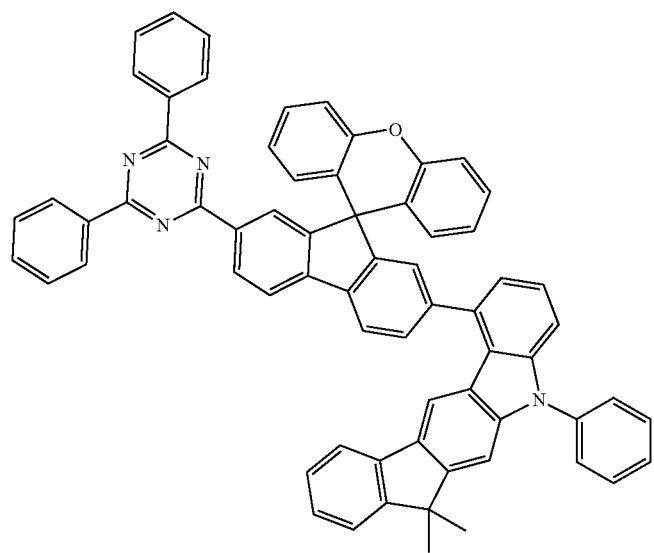

193
194
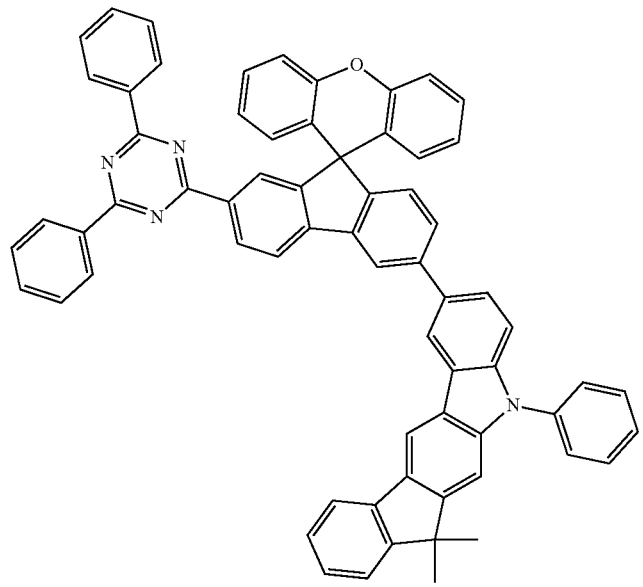
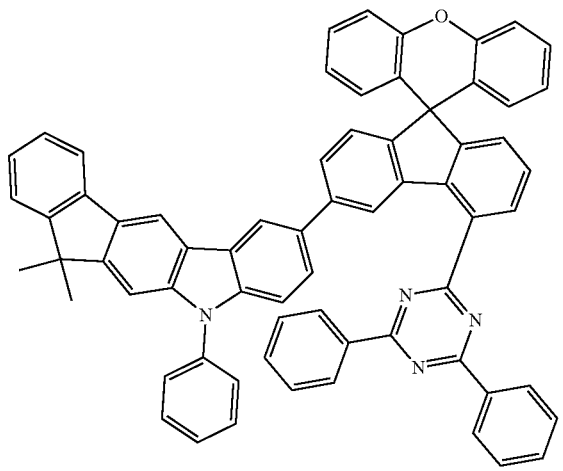
-continued
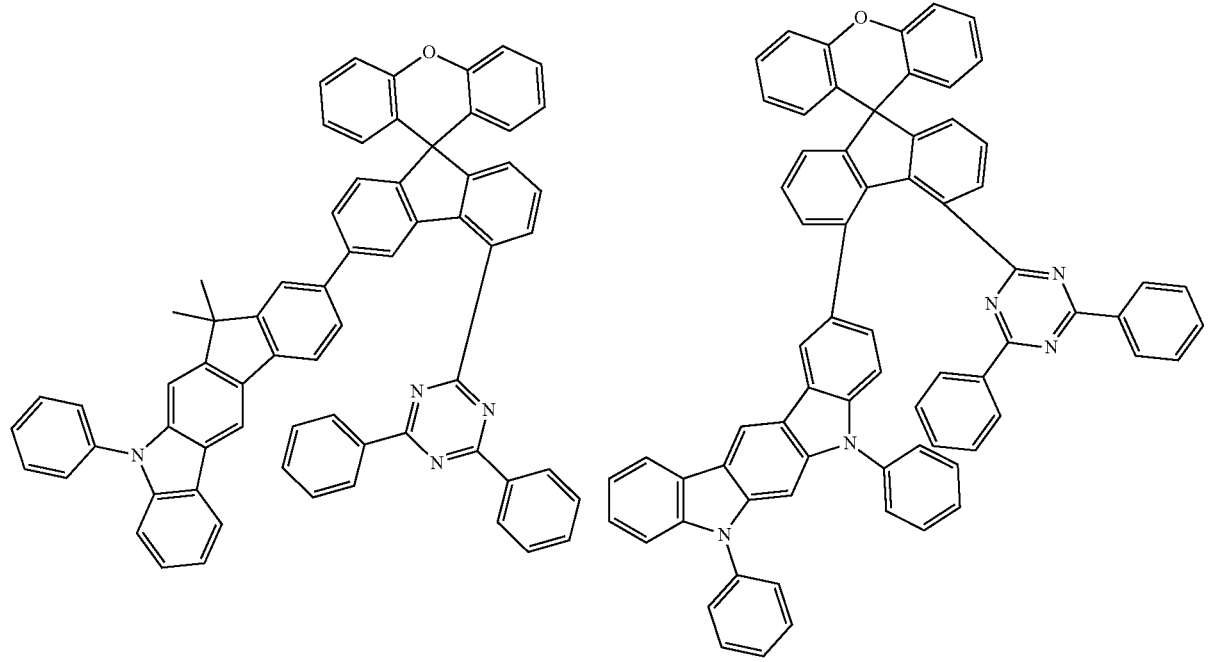

-continued
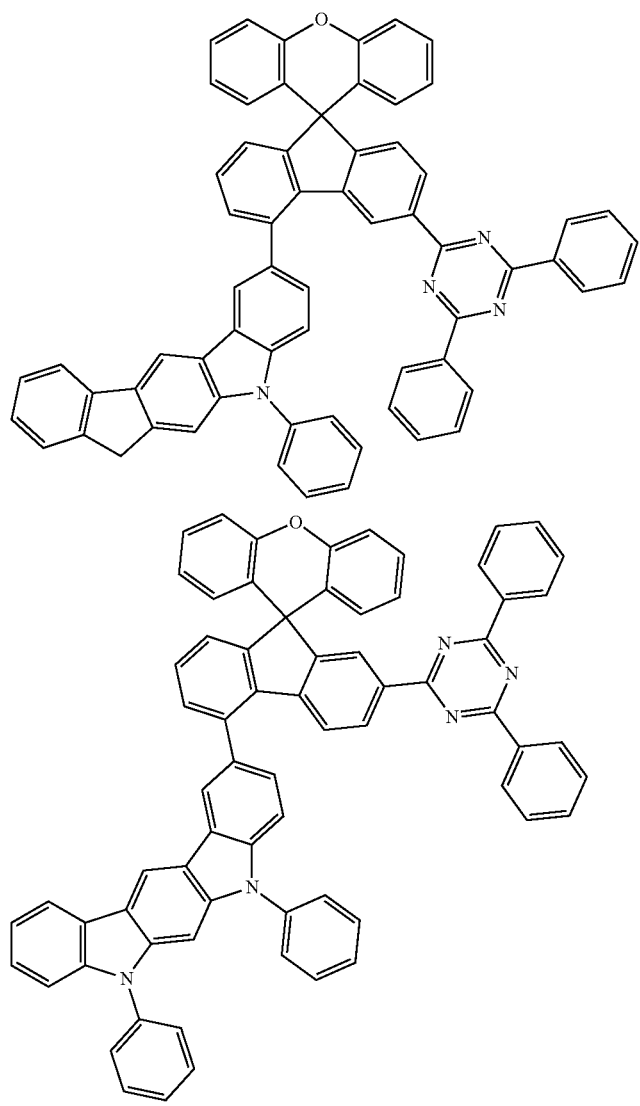
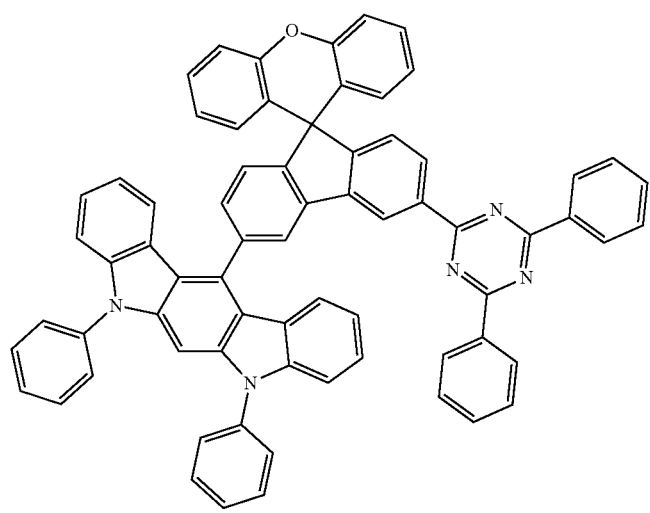

-continued
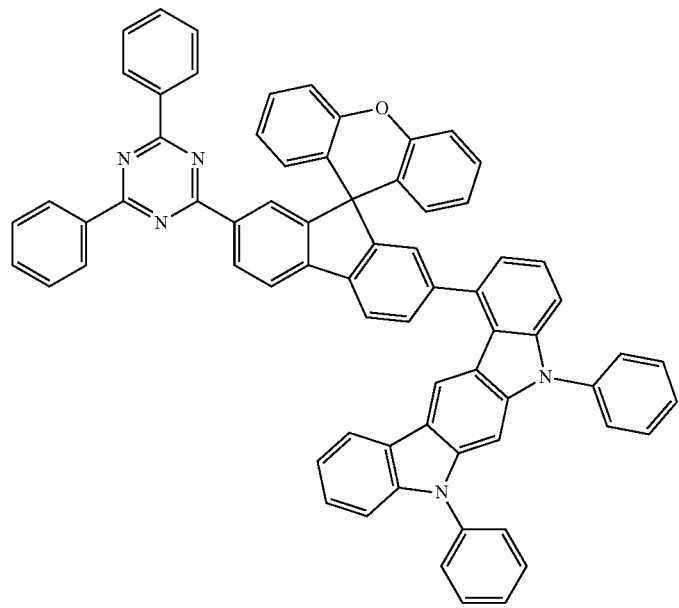
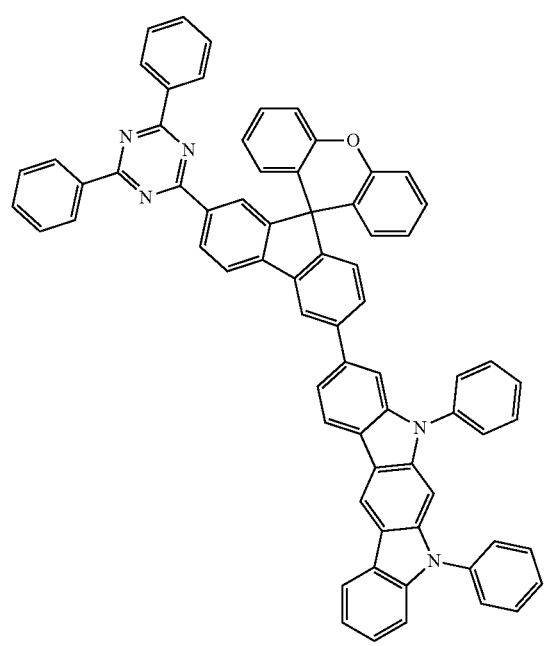

-continued
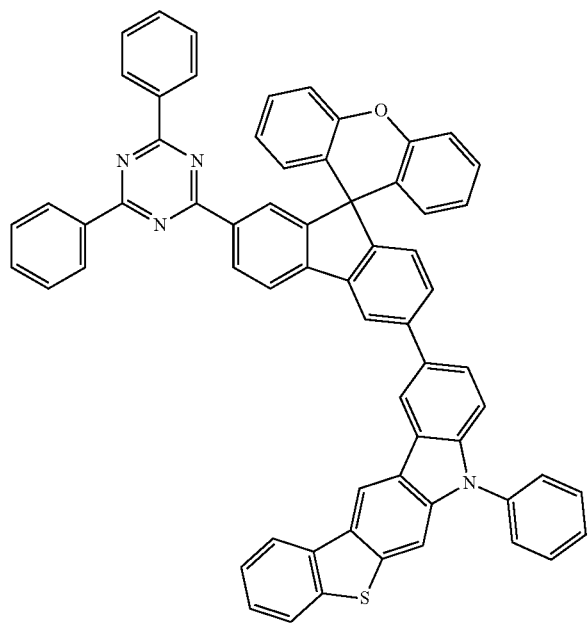
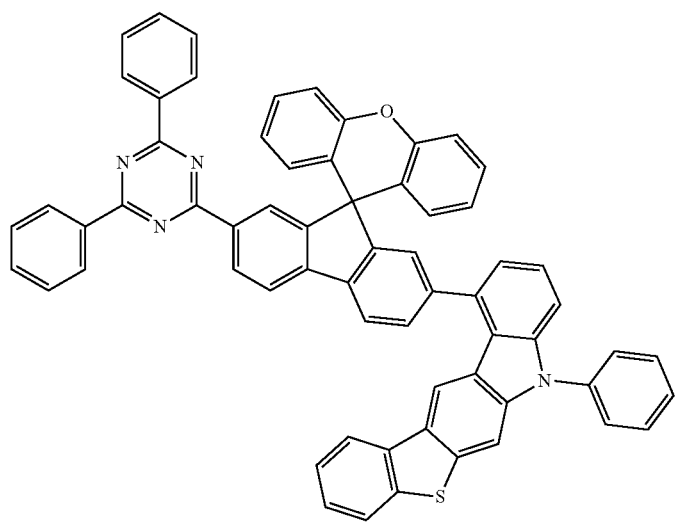
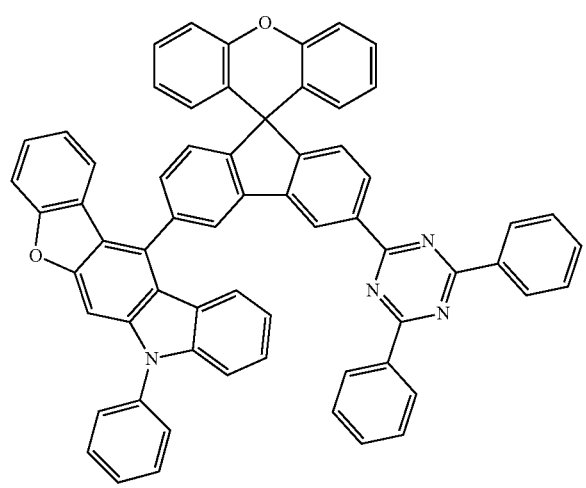

-continued
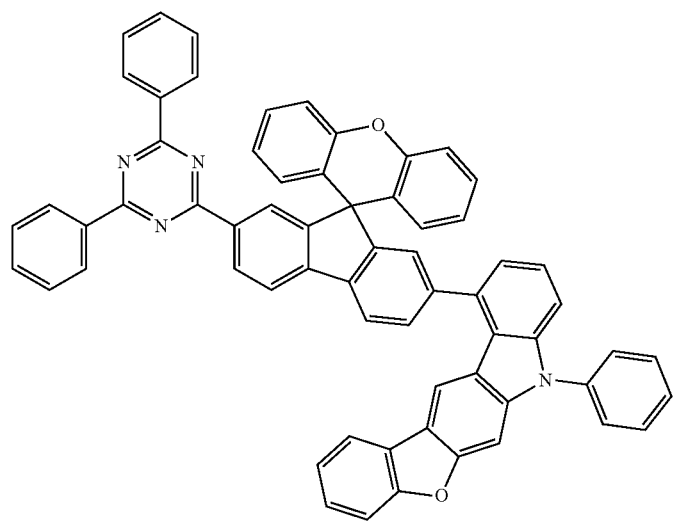
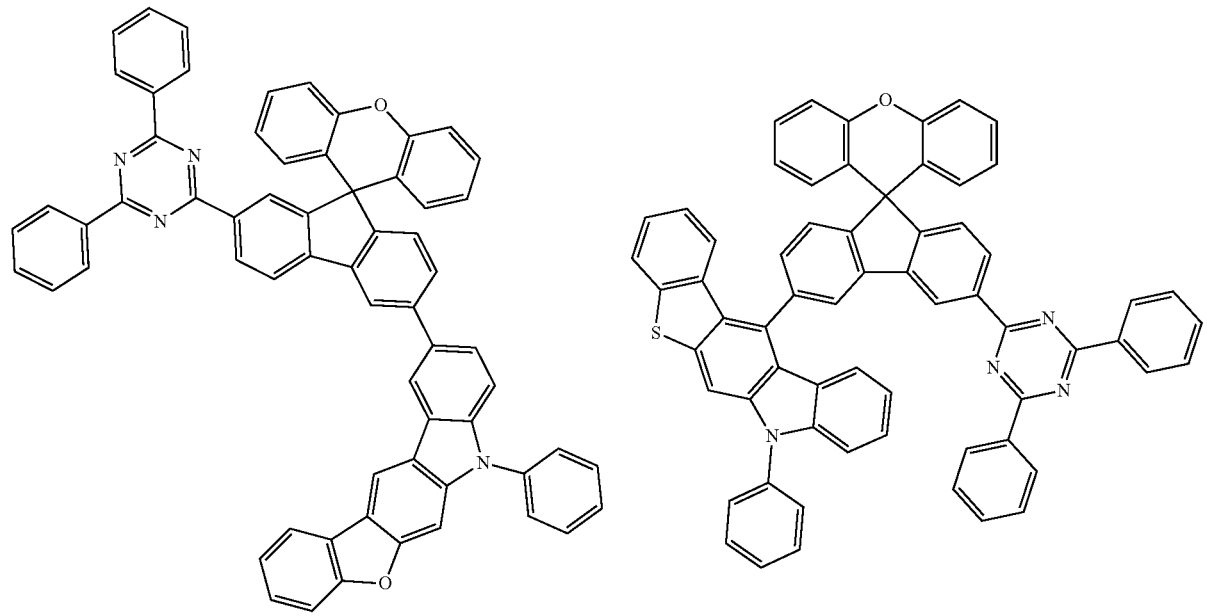
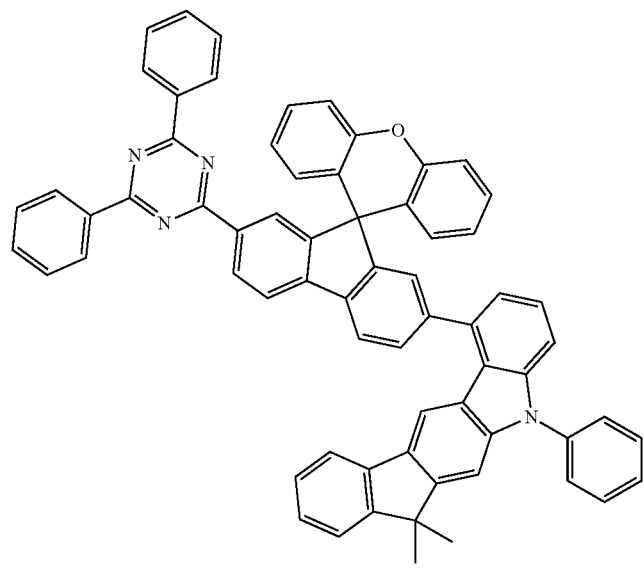

-continued
203
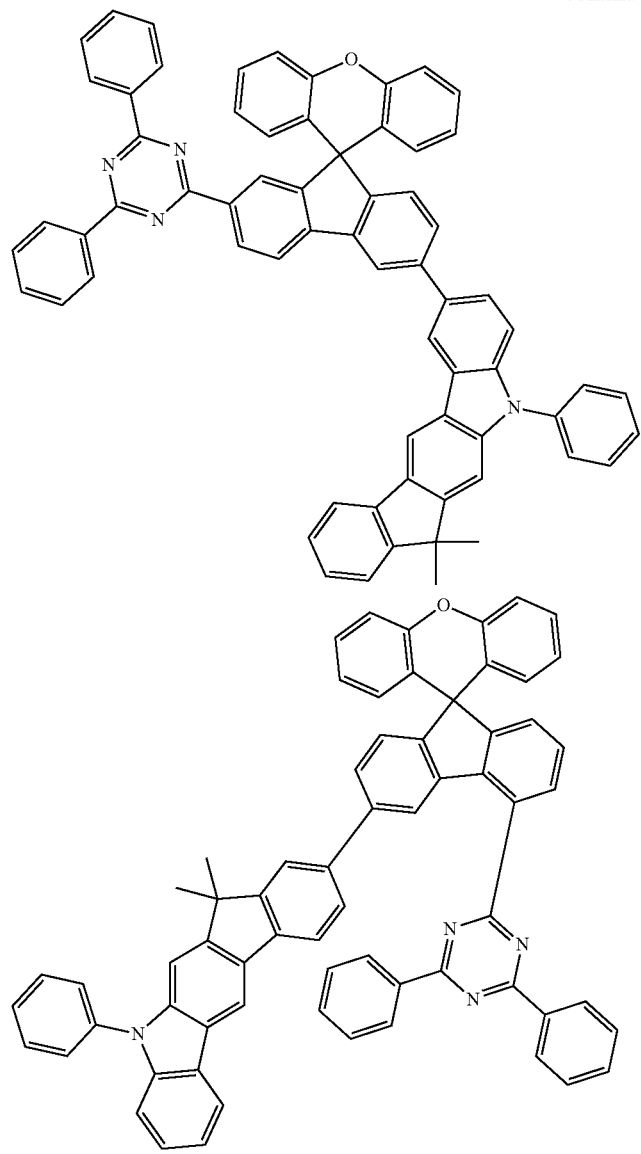
204
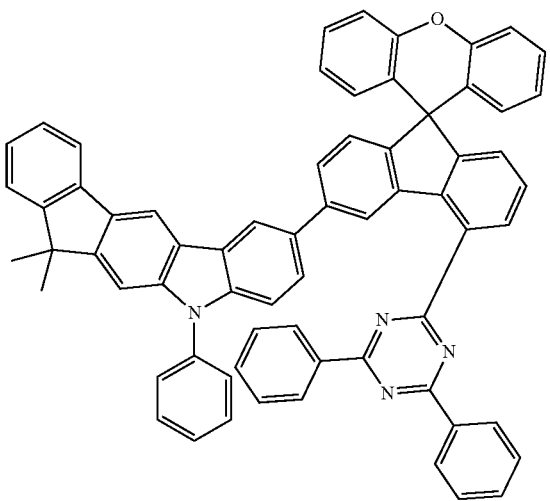
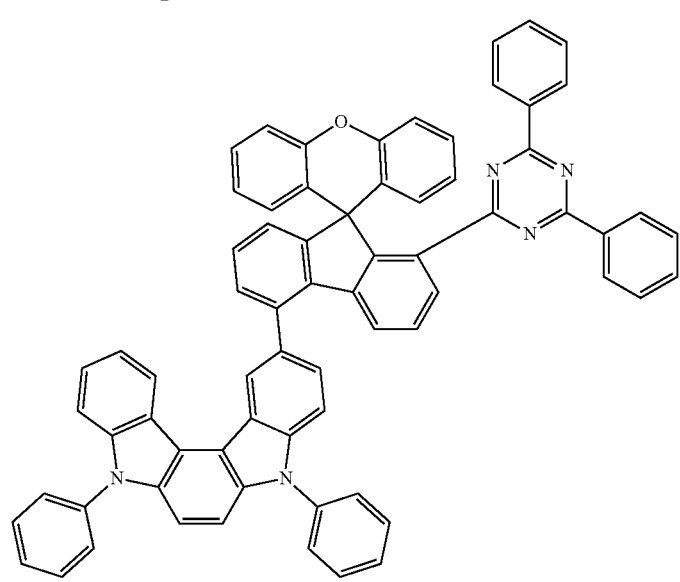

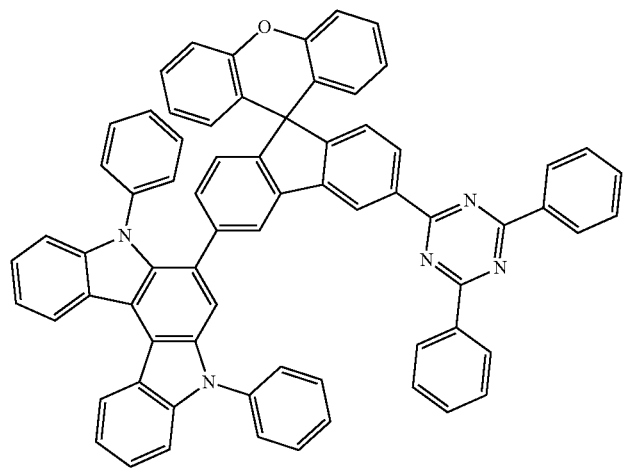
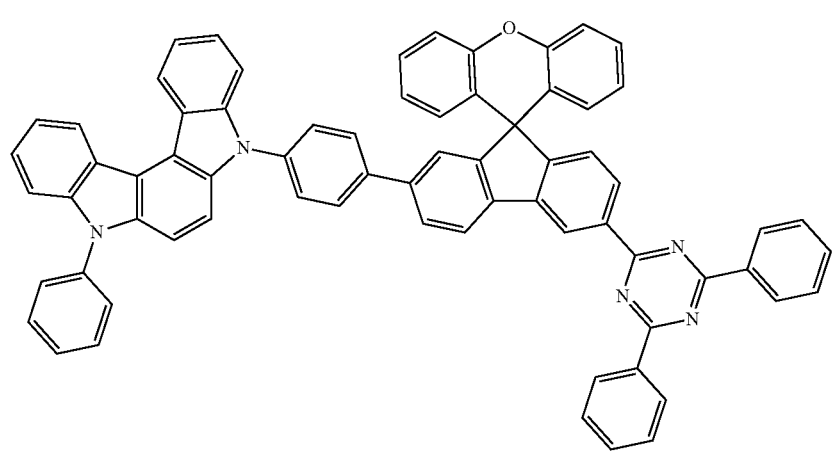
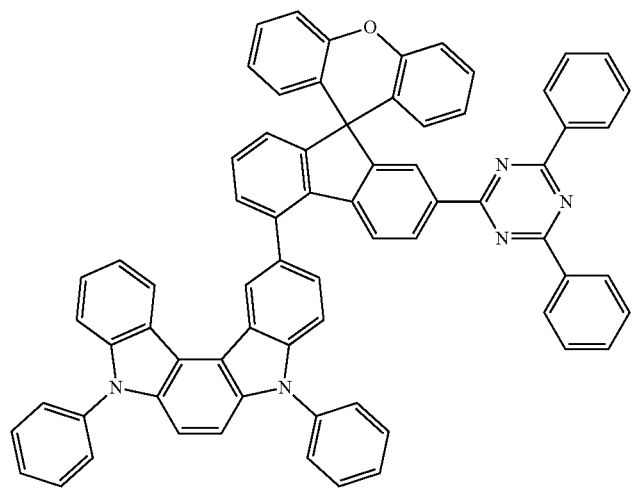

-continued
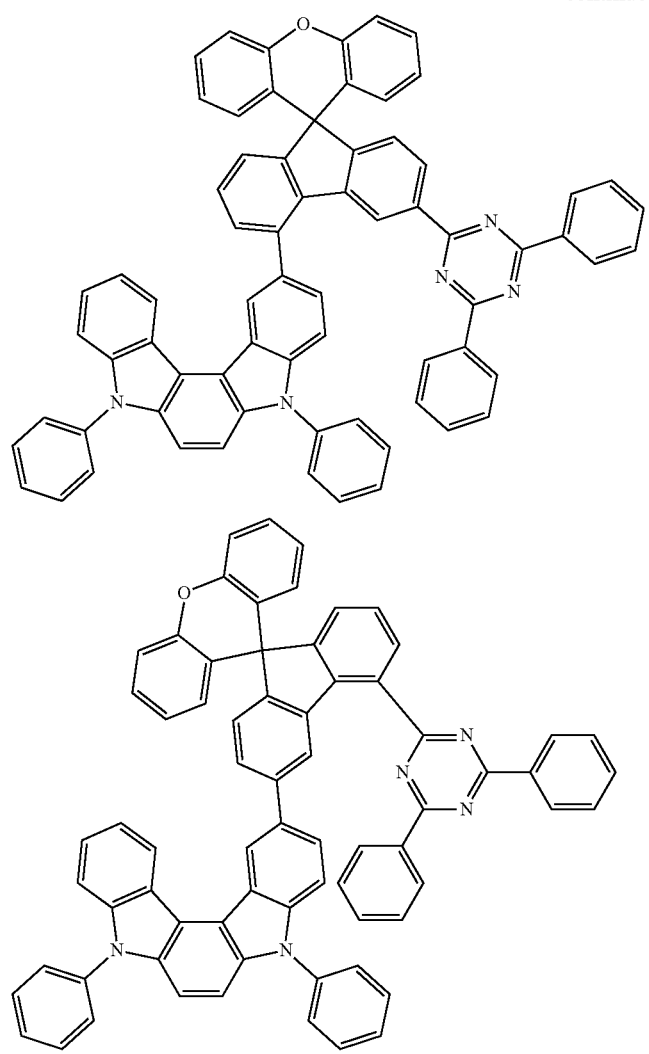
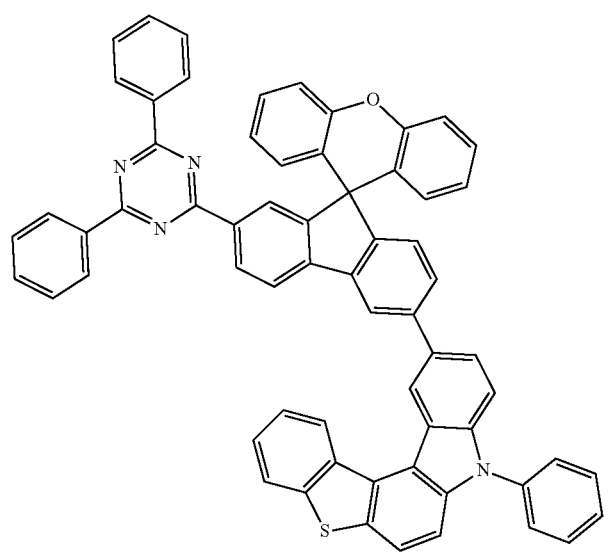

-continued
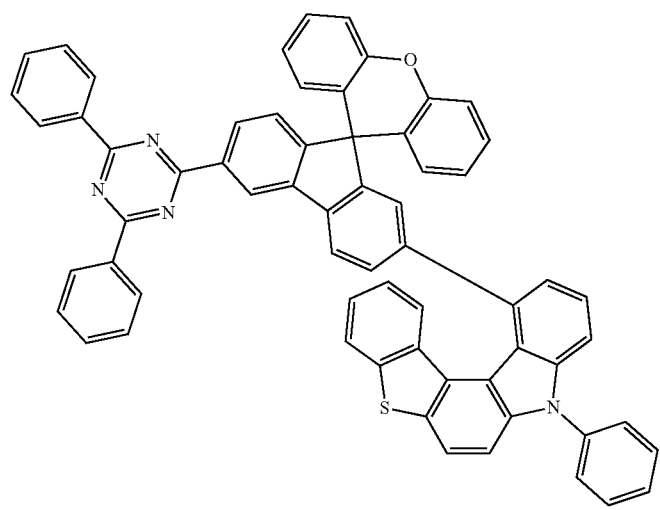
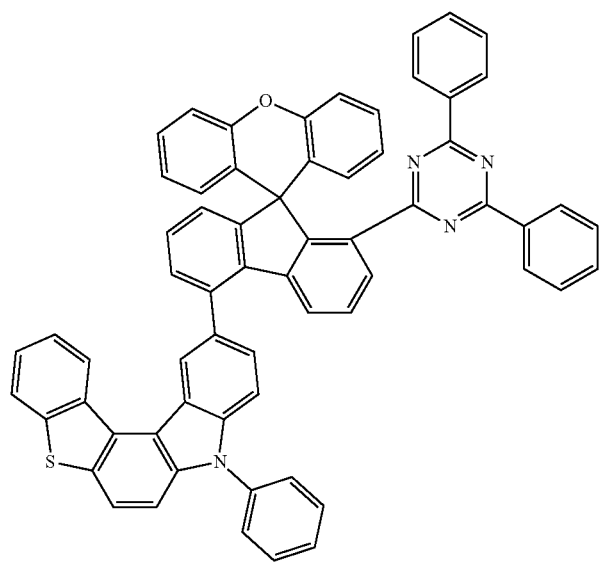
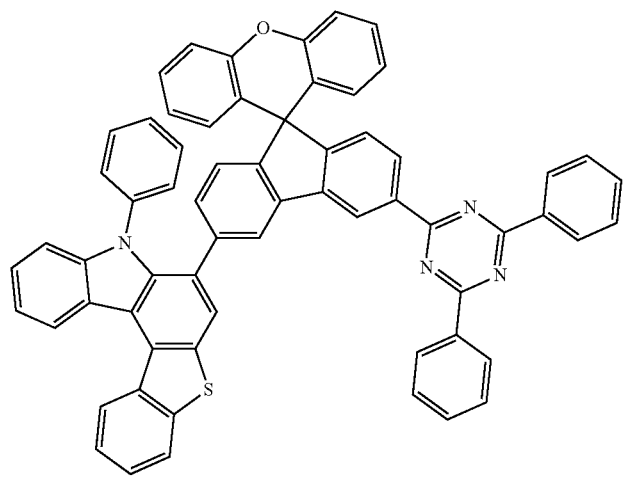

-continued
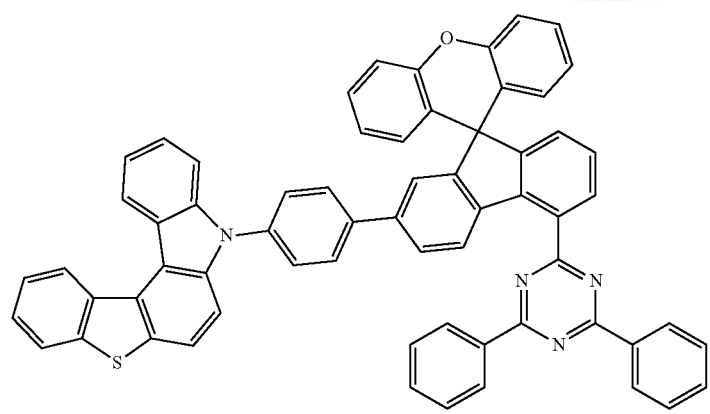
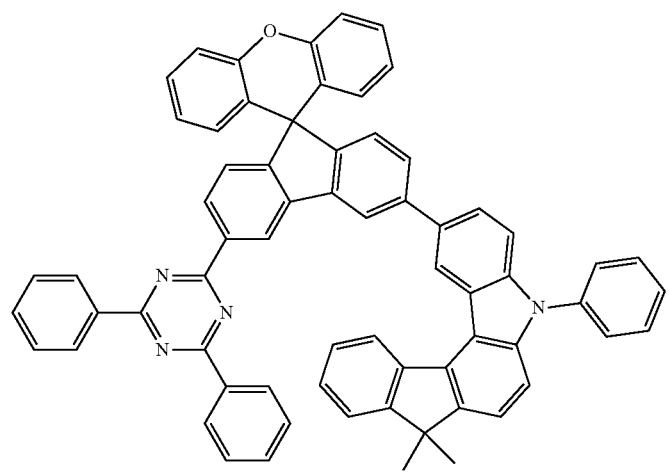
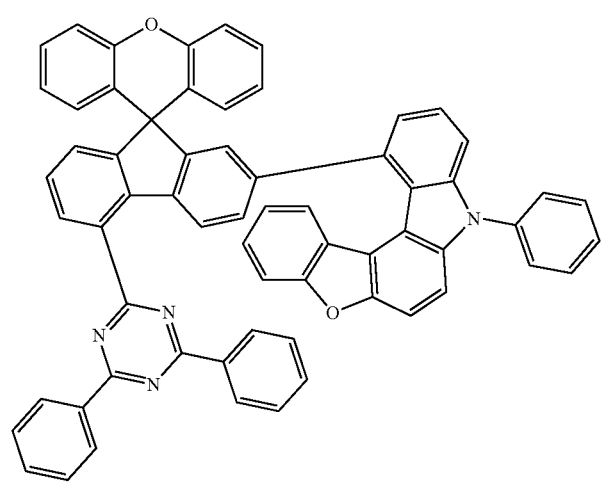

213 214

-continued

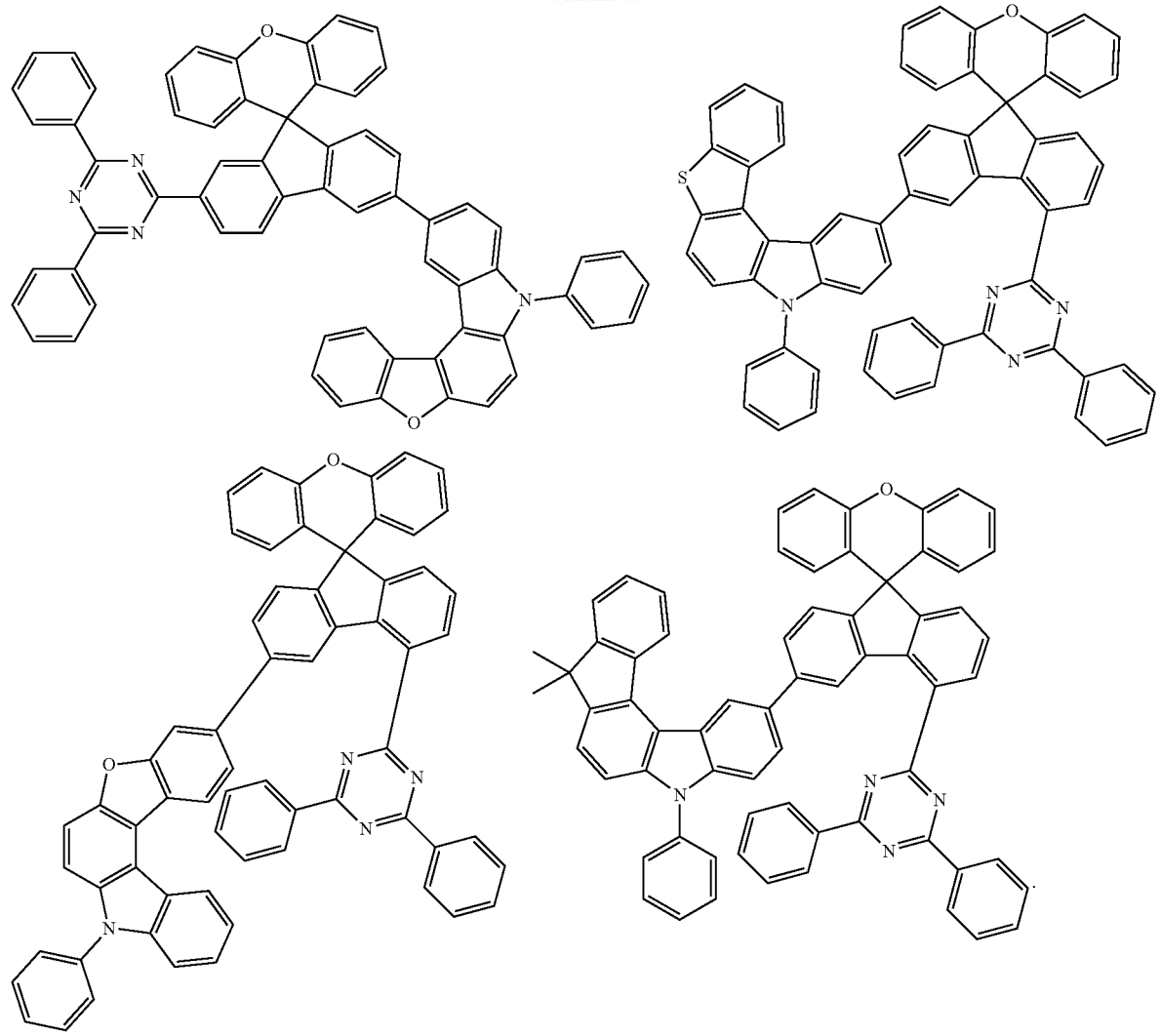

7. An organic light emitting device comprising:
an anode;
a cathode; and
one or more organic material layers provided between the anode and the cathode,
wherein one or more layers of the organic material layers comprise the hetero-cyclic compound of claim 1.

8. The organic light emitting device of claim 7, wherein the organic material layer comprises at least one of a hole blocking layer, an electron injection layer and an electron transfer layer, and at least one of the hole blocking layer, the electron injection layer and the electron transfer layer comprises the hetero-cyclic compound.

9. The organic light emitting device of claim 7, wherein the organic material layer comprises a light emitting layer, and the light emitting layer comprises the hetero-cyclic compound.

* * * * *

UNITED STATES PATENT AND TRADEMARK OFFICE
CERTIFICATE OF CORRECTION

PATENT NO. : 11,634,414 B2
APPLICATION NO. : 16/633538
DATED : April 25, 2023
INVENTOR(S) : Seongmi Cho et al.

Page 1 of 3

It is certified that error appears in the above-identified patent and that said Letters Patent is hereby corrected as shown below:

In the Claims

In Claim 3, at Lines 55-65, please replace the last Chemical Structure appearing in Column 119 with:

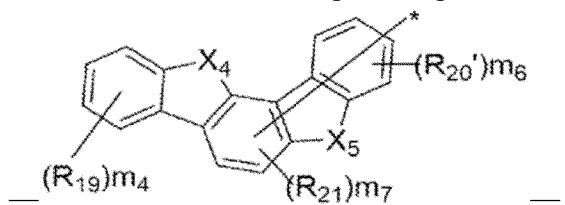

In Claim 4, Column 122 at Lines 50-65, please replace Chemical Formula 8 with:

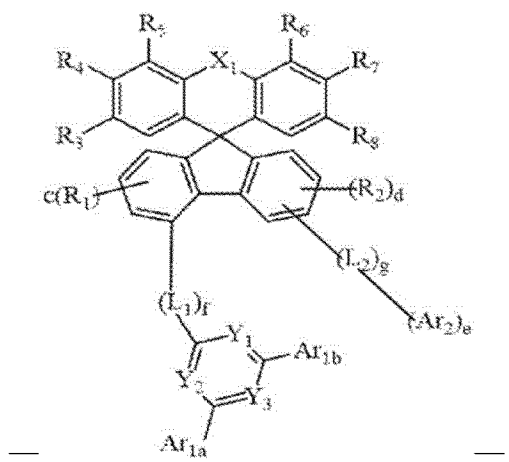

Signed and Sealed this
Twenty-seventh Day of June, 2023

Katherine Kelly Vidal
*Director of the United States Patent and Trademark Office*

In Claim 6, please replace the 1st Chemical Structure appearing in Column 125 with:
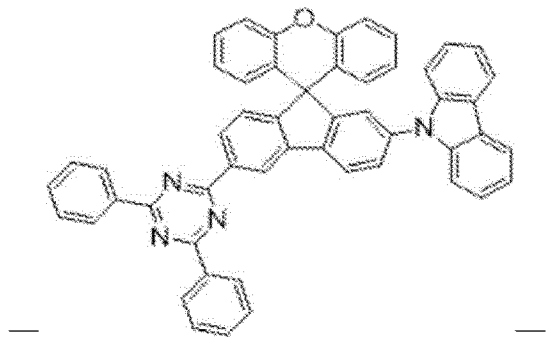
In Claim 6, please replace the 1st Chemical Structure appearing at Column 127 with:
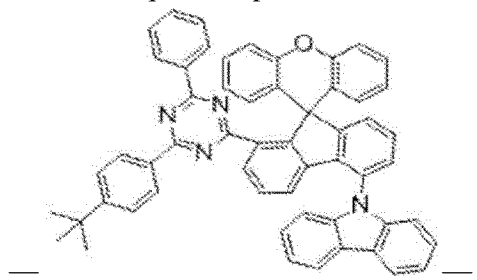
In Claim 6, please replace the 1st Chemical Structure appearing in Column 131 with:
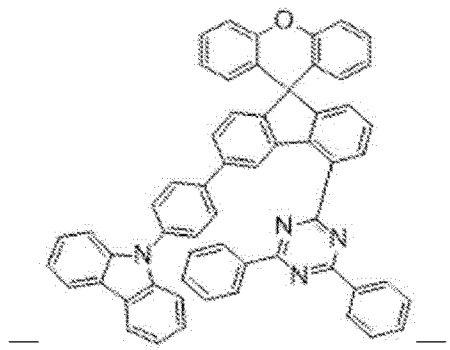
In Claim 6, please replace the 1st Chemical Structure appearing in Column 134 with:
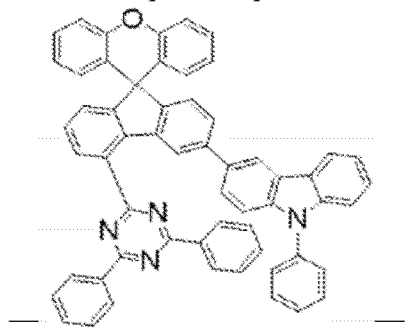

CERTIFICATE OF CORRECTION (continued)
U.S. Pat. No. 11,634,414 B2

In Claim 6, please replace the 1st Chemical Structure appearing in Column 191 with:

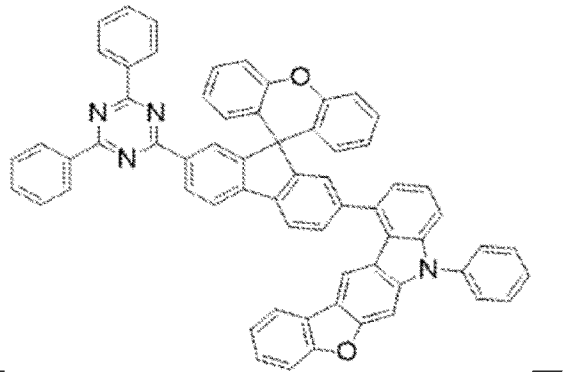

In Claim 6, please replace the 1st Chemical Structure appearing in Column 195 with: